(12) United States Patent
Gelbard et al.

(10) Patent No.: US 9,181,247 B2
(45) Date of Patent: *Nov. 10, 2015

(54) SUBSTITUTED PYRROLO[2,3-B]PYRIDINES AS MLK INHIBITORS

(71) Applicant: The University of Rochester, Rochester, NY (US)

(72) Inventors: Harris A. Gelbard, Pittsford, NY (US); Stephen Dewhurst, Rochester, NY (US); Val S. Goodfellow, Encinitas, CA (US); Colin J. Loweth, San Marcos, CA (US); Torsten Wiemann, Encinitas, CA (US)

(73) Assignee: The University of Rochester, Rochester, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/508,566

(22) Filed: Oct. 7, 2014

(65) Prior Publication Data

US 2015/0105401 A1    Apr. 16, 2015

Related U.S. Application Data

(63) Continuation of application No. 13/131,193, filed as application No. PCT/US2009/065878 on Nov. 25, 2009, now Pat. No. 8,877,772.

(60) Provisional application No. 61/117,950, filed on Nov. 25, 2008, provisional application No. 61/148,755, filed on Jan. 30, 2009, provisional application No. 61/148,778, filed on Jan. 30, 2009.

(51) Int. Cl.
| | |
|---|---|
| *A61K 31/437* | (2006.01) |
| *C07D 471/04* | (2006.01) |
| *A61K 45/06* | (2006.01) |
| *C07D 487/04* | (2006.01) |

(52) U.S. Cl.
CPC ............ *C07D 471/04* (2013.01); *A61K 31/437* (2013.01); *A61K 45/06* (2013.01); *C07D 487/04* (2013.01)

(58) Field of Classification Search
CPC ............................ A61K 31/437; C07D 471/04
USPC ............................................ 514/300; 546/113
See application file for complete search history.

(56) References Cited

U.S. PATENT DOCUMENTS

| 5,296,483 A | 3/1994 | Bodor |
| 5,312,817 A | 5/1994 | Snorrason |
| 5,445,829 A | 8/1995 | Paradissis et al. |
| 5,472,704 A | 12/1995 | Santus et al. |
| 5,672,356 A | 9/1997 | Rault et al. |
| 5,767,128 A | 6/1998 | Guillaumet et al. |
| 6,080,736 A | 6/2000 | Landry et al. |
| 6,150,354 A | 11/2000 | Davis et al. |
| 6,310,177 B1 | 10/2001 | Blaschuk et al. |
| 6,312,717 B1 | 11/2001 | Molinoff et al. |
| 6,319,919 B1 | 11/2001 | Davis et al. |
| 6,350,747 B1 | 2/2002 | Glennon et al. |
| 6,379,696 B1 | 4/2002 | Asmussen et al. |
| 6,403,597 B1 | 6/2002 | Wilson et al. |
| 6,465,006 B1 | 10/2002 | Zhang et al. |
| 6,482,440 B2 | 11/2002 | Zemlan et al. |
| 6,498,176 B1 | 12/2002 | Lackey et al. |
| 6,512,010 B1 | 1/2003 | Gale et al. |
| 6,517,864 B1 | 2/2003 | Orup Jacobsen et al. |
| 6,524,621 B2 | 2/2003 | Adjei et al. |
| 6,528,080 B2 | 3/2003 | Dunn et al. |
| 6,537,579 B1 | 3/2003 | Desai et al. |
| 6,541,020 B1 | 4/2003 | Ding et al. |

(Continued)

FOREIGN PATENT DOCUMENTS

| CN | 101027302 | 8/2007 |
| CN | 101065016 | 10/2007 |
| CN | 101573360 | 11/2009 |
| CN | 101939324 | 1/2011 |
| EP | 0691339 | 1/1996 |
| EP | 2308877 | 4/2011 |
| JP | 2007/108926 | 4/2007 |
| WO | 99/21859 | 5/1999 |
| WO | 00/55159 | 9/2000 |
| WO | 00/56710 | 9/2000 |
| WO | 01/05790 | 1/2001 |
| WO | 03/051366 | 6/2003 |

(Continued)

OTHER PUBLICATIONS

Adams, C., et al., "Mapping the Kinase Domain of Janus Kinase 3," Bioorganic & Medicinal Chemistry Letters, vol. 13, 18, 2003, pp. 3105-3110.

(Continued)

*Primary Examiner* — Douglas M Willis
(74) *Attorney, Agent, or Firm* — Meunier Carlin & Curfman LLC

(57) ABSTRACT

Provided are compounds having an inhibitory effect on Mixed Lineage Kinases. The compounds include substituted pyrrolo [2,3b]pyridines having Formula IX

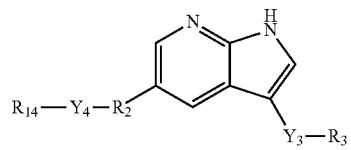

Also provided are pharmaceutical compositions, methods of preparing the compounds, synthetic intermediates, and methods of using the compounds, independently or in combination with other therapeutic agents, for treating diseases and conditions which are affected by Mixed Lineage Kinase inhibition. Also provided are methods of treatment of neuropsychiatric disorders which comprise the inhibition of Mixed Lineage Kinases.

17 Claims, No Drawings

(56) References Cited

U.S. PATENT DOCUMENTS

| | | | |
|---|---|---|---|
| 6,544,548 | B1 | 4/2003 | Siller-Jackson et al. |
| 6,548,084 | B2 | 4/2003 | Leonard et al. |
| 6,562,375 | B1 | 5/2003 | Sako et al. |
| 6,565,883 | B2 | 5/2003 | Ogorka et al. |
| 6,569,463 | B2 | 5/2003 | Patel et al. |
| 6,589,549 | B2 | 7/2003 | Shih et al. |
| 6,589,563 | B2 | 7/2003 | Prokop |
| 6,596,308 | B2 | 7/2003 | Gutierrez-Rocca et al. |
| 6,599,529 | B1 | 7/2003 | Skinhøj et al. |
| 6,607,751 | B1 | 8/2003 | Odidi et al. |
| 6,613,358 | B2 | 9/2003 | Randolph et al. |
| 6,613,361 | B1 | 9/2003 | Lebon et al. |
| 6,624,171 | B1 | 9/2003 | Harris et al. |
| 6,624,200 | B2 | 9/2003 | Bologna et al. |
| 6,635,680 | B2 | 10/2003 | Mulye |
| 6,638,521 | B2 | 10/2003 | Dobrozsi |
| 6,774,132 | B1 | 8/2004 | Claesson et al. |
| 6,815,439 | B2 | 11/2004 | Harris et al. |
| 6,818,632 | B2 | 11/2004 | Glennon et al. |
| 7,129,253 | B2 | 10/2006 | Glennon et al. |
| 7,361,763 | B2 | 4/2008 | Arnold et al. |
| 7,361,764 | B2 | 4/2008 | Arnold et al. |
| 2002/0099071 | A1 | 7/2002 | Glennon et al. |
| 2003/0187026 | A1 | 10/2003 | Li et al. |
| 2003/0199511 | A1 | 10/2003 | Li et al. |
| 2004/0043388 | A1 | 3/2004 | Come et al. |
| 2004/0072836 | A1 | 4/2004 | Harris et al. |
| 2004/0087800 | A1 | 5/2004 | Claesson et al. |
| 2004/0191210 | A1 | 9/2004 | Glennon et al. |
| 2006/0011139 | A1 | 1/2006 | Sterling et al. |
| 2006/0030583 | A1 | 2/2006 | Arnold et al. |
| 2006/0106022 | A1 | 5/2006 | Liu et al. |
| 2007/0043068 | A1 | 2/2007 | Arnold et al. |
| 2007/0287711 | A1 | 12/2007 | Arnold et al. |
| 2008/0064026 | A1 | 3/2008 | Wu et al. |
| 2008/0119500 | A1 | 5/2008 | Jiang et al. |
| 2008/0146561 | A1 | 6/2008 | Muci et al. |
| 2008/0261921 | A1 | 10/2008 | Chen et al. |
| 2009/0143352 | A1 | 6/2009 | Arnold et al. |
| 2011/0236437 | A1 | 9/2011 | Destache |

FOREIGN PATENT DOCUMENTS

| | | |
|---|---|---|
| WO | 2004/078756 | 9/2004 |
| WO | 2004/085409 | 10/2004 |
| WO | 2005/028475 | 3/2005 |
| WO | 2006/015123 | 2/2006 |
| WO | 2006/036883 | 4/2006 |
| WO | 2006/049890 | 5/2006 |
| WO | 2006/063167 | 6/2006 |
| WO | 2006/088836 | 8/2006 |
| WO | 2007/106236 | 9/2007 |
| WO | 2007/149557 | 12/2007 |
| WO | 2008/016669 | 2/2008 |
| WO | 2008/051493 | 5/2008 |
| WO | 2008/119713 | 10/2008 |
| WO | 2008/124848 | 10/2008 |
| WO | 2008/124849 | 10/2008 |
| WO | 2008/129994 | 10/2008 |
| WO | 2009/054941 | 4/2009 |
| WO | 2010/016490 | 2/2010 |
| WO | 2011/149950 | 12/2011 |

OTHER PUBLICATIONS

Bodner, A., et al., "Mixed lineage kinase 3 mediates gp120IIIB-induced neurotoxicity," Journal of Neurochemistry, vol. 82, 2002, pp. 1424-1434.

Conforti, P., et al., Blood level of brain-derived neurotrophic factor mRNA is progressively reduced in rodent models of Huntington's disease: Restoration by the neuroprotective compound CEP-1347, Molecular and Cellular Neuroscience, vol. 39, 2008, pp. 1-7.

Eggert, D., et al., Neuroprotective Activities of CEP-1347 in Models of NeuroAIDS, The Journal of Immunology, vol. 184, 2010, pp. 746-756.

Hackam, D.G., et al., "Translation of Research Evidence From Animals to Humans," JAMA, vol. 296, No. 14, 2006, pp. 1731-1732.

Huang, Y., et al., "Effects of Manufacturing Process Variables on In Vitro Dissolution Characteristics of Extended-Release Tablets Formulated with Hydroxypropyl Methylcellulose," Drug Development and Industrial Pharmacy, vol. 29, No. 1, 2003, pp. 79-88.

Jordan, V.C., "Tamoxifen: A Most Unlikely Pioneering Medicine," Nature reviews: Drug Discovery, vol. 2, 2003, pp. 205-213.

Khanvilkar, K.H., et al., "Influence of Hydroxypropyl Methylcellulose Mixture, Apparent Viscosity, and Tablet Hardness on Drug Release Using a 2³ Full Factorial Design," Drug Development and Industrial Pharmacy, vol. 28, No. 5, 2002, pp. 601-608.

Krishnan, V. et al., "The molecular neurobiology of depression," Nature, vol. 455, 2008, pp. 894-902.

Ma, Q., et al., "Pharmacokinetic interactions of CEP-1347 and atazanavir in HIV-infected patients," Journal of Neurovirology, vol. 19, 2013, pp. 254-260.

Maggi, L., et al. "Photostability of extended-release matrix formulations," European Journal of Pharmaceutics and Biopharmaceutics, Vo. 55, 2003, pp. 55:99-105.

Marie-Claude, V., et al., "Acylation of oxazolo[4,5-b]pyridin-2(3H)-ones, 2-phenyloxazolo[4,5-b]pyridines and pyrrolo[2,3-b]pyridin-2(2H)-ones," Tetrahedron, vol. 53, No. 14, 1997, pp. 5159-5168.

Meanwell, N.A., et al., "Regiospecific Functionalization of 1,3-Dihydro-2H-benzimidazol-2-one and Structurally Related Cyclic Urea Derivatives," J. Org. Chem., vol. 60, 1995, pp. 1565-1582.

Pearnchob, N., et al., "Pharmaceutical Applications of Shellac: Moisture-Protective and Taste-Making Coatings and Extended-Release Matrix Tablets," Drug Development and Industrial Pharmacy, vol. 29, No. 8, 2003, pp. 925-938.

Pratap, R., et al., "A novel synthesis of aryl tethered imidazo[4,5-b]pyrazin-2-ones through in situ ring construction and contraction," Tetrahedron Letters, vol. 48, No. 7, 2007, pp. 1281-1285.

Robinett, R.G., "The discovery of substituted 4-(3-hydroxyanilino)-quinolines as potent RET kinase inhibitors," Bioorganic & Medicinal Chemistry Letters, vol. 17, 2007, pp. 5886-5893.

Schmidt, C., et al., "A multiparticulate drug-delivery system based on pellets incorporated into congealable polyethylene glycol carrier materials," International Journal of Pharmaceuticals, vol. 216, 2001, pp. 9-16.

Sui, Z., et al., "Inhibition of Mixed Lineage Kinase 3 Prevents HIV-1 Tat-Mediated Neurotoxicity and Monocyte Activation," J. Immunol., vol. 177, 2006, pp. 702-711.

Wang, L.H., et al., "Mixed-Lineage Kinase Inhibitors Require the Activation of Trk Receptors to Maintain Long-Term Neuronal Trophism and Survival," The Journal of Pharmacology and Experimental Therapeutics, vol. 312, No. 3, 2005, pp. 1007-1019.

Office Action, dated Apr. 4, 2014, received in connection with corresponding AU Application No. 2009324894.

Office Action, dated Dec. 27, 2013, received in connection with corresponding CN Application No. 200980152665.1. (English Translation).

Office Action, dated May 16, 2013, received in connection with corresponding CN Application No. 200980152665.1.

Office Action, dated Jul. 15, 2014, received in connection with corresponding CN Application No. 200980152665.1. (English Translation).

Office Action, dated Sep. 3, 2014, received in connection with related CN Application No. 201180036376.2. (English Translation).

Office Action, dated Sep. 5, 2014, received in connection with corresponding EP Application No. 09832359.5.

Office Action, dated Nov. 12, 2013, received in connection with corresponding EP Application No. 09832359.5.

Official Action, dated May 24, 2012, received in connection with corresponding EP Application No. 09832359.5.

Search Report, dated Aug. 30, 2012, received in connection with corresponding EP Application No. 09832359.5.

European Search Report, dated Nov. 19, 2013, received in connection with related EP Application No. 11787254.9.

Office Action, dated Jul. 14, 2014, received in connection with corresponding JP Application No. 2011537733. (English Translation).

Office Action, dated Feb. 5, 2014, received in connection with corresponding JP Application No. 2011537733.

(56) References Cited

OTHER PUBLICATIONS

Office Action, dated Jan. 16, 2015, received in connection with corresponding NZ Application No. 614904.
Office Action, dated Sep. 5, 2013, received in connection with corresponding NZ Application No. 614904.
Office Action, dated Aug. 21, 2013, received in connection with corresponding NZ Application No. 594904.
Office Action, dated Oct. 3, 2012, received in connection with corresponding NZ Application No. 594904.
Office Action, dated Feb. 3, 2012, received in connection with corresponding NZ Application No. 594904.
Office Action, dated Jul. 9, 2013, received in connection with related NZ Application No. 603644.
Notice of Allowance, dated May 16, 2014, received in connection with related U.S. Appl. No. 13/698,829.
Office Action, dated Jan. 28, 2014, received in connection with related U.S. Appl. No. 13/698,829.
Restriction Requirement, dated Dec. 17, 2013, received in connection with related U.S. Appl. No. 13/698,829.
International Preliminary Report on Patentability and Written Opinion, dated May 31, 2011, received in connection with corresponding International Application No. PCT/US2009/065878.
International Search Report, dated Jul. 29, 2010, received in connection with corresponding International Application No. PCT/US2009/065878.
International Preliminary Report on Patentability and Written Opinion, dated Nov. 27, 2012, received in connection with related International Application No. PCT/US2011/037758.
International Search Report and Written Opinion, dated Feb. 9, 2012, received in connection with related International Application No. PCT/US2011/037758.
International Search Report and Written Opinion, dated Mar. 14, 2014, received in connection with related International Application No. PCT/US2013/072530.

SUBSTITUTED PYRROLO[2,3-B]PYRIDINES AS MLK INHIBITORS

This application is a continuation of U.S. application Ser. No. 13/131,193, filed Sep. 13, 2011, which is a 371 national phase of International Application No. PCT/US2009/065878, filed Nov. 25, 2009, which claims the benefit of U.S. Provisional Applications No. 61/117,950, filed Nov. 25, 2008, No. 61/148,755 filed Jan. 30, 2009, and No. 61/148,778 filed Jan. 30, 2009, all of which are incorporated by reference as if written herein in their entireties.

STATEMENT REGARDING FEDERALLY SPONSORED RESEARCH OR DEVELOPMENT

This invention was made with government support under Grant No: P01 3MH64570 awarded by the National Institutes of Health. The government has certain rights in this invention.

BACKGROUND

Mammalian protein kinases are involved in the regulation of important cellular functions. Due to the fact that dysfunctions in protein kinase activity have been associated with several diseases and disorders, protein kinases are targets for drug development.

Mixed lineage kinases (MLKs) are MAPK kinase kinases that target JNK and p38 MAPK for activation in response to diverse stimuli that stress cells. As a result, the MLKs regulate a broad range of cellular processes. MLK3 is the most widely expressed MLK family member and is present in neurons. It is activated by GTPases of the Ras superfamily, such as Cdc42 and Rac, which trigger protein dimerization via a leucine zipper interface, resulting in autophosphorylation at Thr277 and Ser281 within the protein activation loop and subsequent activation of the enzyme.

Preclinical studies of the mixed lineage kinase (MLK) inhibitor CEP1347 have shown that this agent can protect neurons against a considerable range of insults, including exposure to the Alzheimer's peptide, Aβ. Studies using the 1-methyl-4-phenyl-1,2,3,6-tetrahydropyridine model of Parkinsonism have demonstrated the efficacy of CEP1347 in treating motor deficits and neuronal degeneration, and CEP1347-mediated neuroprotection has also been observed in an in vitro model for Parkinson's Disease, using methamphetamine-exposed human mesencephalic-derived neurons. This finding suggests that CEP1347 might also be protective in the context of neurologic complications such as HIV-associated dementia (HAD). In fact, Bodner et al. have shown that CEP1347 can protect primary rat hippocampal neurons as well as dorsal root ganglion neurons from the otherwise lethal effects of exposure to HIV-1 gp120. It has been determined that CEP1347 mediates this effect by inhibiting the activity of the mixed lineage kinase (MLK) family.

Maggirwar et al. recently examined the effect of Tat and gp120 on MLK3. Tat and gp120 were shown to induce autophosphorylation of MLK3 in primary rat neurons and this was abolished by the addition of CEP1347. These studies suggest that the normal function of MLK3 is compromised by HIV-1 neurotoxins, resulting in the downstream signaling events that result in neuronal death and monocyte activation (with release of inflammatory cytokines). Most recently, Eggert et al. have demonstrated that CEP1347 is neuroprotective in an in vivo model of HIV-1 infection, reversing microglial activation and restoring normal synaptic architecture, as well as restoring macrophage secretory profiles to a trophic vs. toxic phenotype in response to HIV-1 infection. Eggert, D., Gorantla, S., Poluekova, L., Dou, H., Schifitto, G., Maggirwar, S. B., Dewhurst, S., Gelbard, H. A. and H. E. Gendelman: "Neuroprotective Activities of CEP-1347 in Models of HIV-1 Encephalitis," *J. Immunol.* (in press).]

Recently, MLK3 has been shown to drive the production of the HIV virus. As a result, several lines of evidence now support that an inhibitor of MLK3 could serve as a treatment for numerous neurological conditions, including neuroAIDS. CEP1347 does not have ideal pharmacokinetic properties, which could potentially affect its ability to gain entry to the CNS. Other small molecule MLK3 inhibitors are needed that have improved pharmacokinetic and brain penetrating properties.

An inhibitor of MLK3 could also find use in the treatment of psychological disorders. Depression is a complex disease that has a multifactorial etiology. This may include genetic factors, changes in normal neuronal signaling, and reduced levels of certain neurotrophins (such as brain-derived neurotrophic factor, BDNF) within particular regions of the brain (Krishnan, V., and E. J. Nestler. 2008. Nature 455:894-902). Treatments for depression include drugs such as SSRIs, as well as cognitive and behavioral therapy ("talk therapy") and other inventions such as exercise. Interestingly, SSRIs and exercise share the common property that they promote neurogenesis; this is thought to be related to their anti-depressive effects because of effects on neuronal plasticity and remodeling (Krishnan, supra).

Pharmacologic blockade of mixed lineage kinase 3 (MLK3) has been shown to result in activation of neurotrophin-mediated signaling pathways, and increased expression of neurotrophin receptors—resulting in enhanced responsiveness to endogenous neurotrophins, including BDNF (Wang, L. H., A. J. Paden, and E. M. Johnson, Jr. 2005. J Pharmacol Exp Ther 312:1007-19). MLK3 inhibitors have also been shown to increase production of BDNF itself (Conforti, P. et al. 2008. Mol Cell Neurosci 39:1-7).

Combined treatment with SSRIs and MLK3 inhibitors could result in the synergistic promotion of neurogenesis, due to the neurotrophin-sensitizing effects of MLK3 inhibitors and their ability to directly upregulate BDNF (Wang and Conforti, supra). Increase of the therapeutic effectiveness of SSRIs (and possibly talk therapy and exercise also) could also result if the compounds were coadministered.

Exposure to MLK3 inhibitors may also compensate for lowered BDNF levels in hippocampus of persons with depression, thereby alleviating depression (based on the "BDNF hypothesis") (Krishnan, supra).

SUMMARY

Disclosed herein are compounds having an inhibitory effect on MLK1, MLK2, and MLK3. In a related aspect, also disclosed herein are compounds of Formula I as described below. Thus, provided herein are novel compounds that can be used for therapeutic methods involving modulation of MLKs. Also provided are pharmaceutical compositions, methods of preparing the compounds, synthetic intermediates, and methods of using the compounds, independently or in combination with other therapeutic agents, for treating diseases and conditions affected by MLK inhibition.

In one aspect, the present invention provides for compounds of Formula I:

$$\text{R}_1-\text{Y}_1 \quad \text{R}_{14}-\text{Y}_4-\text{R}_2-\text{Y}_2 \quad X_1 \quad X_2 \quad R_{13} \quad Y_3-R_3 \quad R_5 \quad R_4 \quad \text{I}$$

wherein:
  dashed lines indicate that a second bond may alternatively be present or absent;
  $X_1$ is chosen from CH and N;
  $X_2$ is chosen from C and N;
  $Y_1$ is $-(CR_{6a}R_{6b})_m-Z_1-(CR_{7a}R_{7b})_n-$;
  $Y_2$ is $-(CR_{8a}R_{8b})_p-Z_2-(CR_{9a}R_{9b})_q-$;
  $Y_3$ is $-(CR_{10a}R_{10b})_r-Z_3-(CR_{11a}R_{11b})_s-$;
  $Y_4$ is $-(CH_2)_t-Z_4-$;
  $Z_1$, $Z_2$, and $Z_3$, are each independently chosen from a bond, O, S, S(O), S(O)$_2$, N(R$_{12}$), C(O), C(O)N(R$_{12}$), N(R$_{12}$)C(O), S(O)$_2$N(R$_{12}$), and N(R$_{12}$)S(O)$_2$;
  $Z_4$ is chosen from a bond, O, and N;
  m, n, p, q, r, and s are each independently an integer from 0 to 6;
  t is an integer from 0 to 2;
  $R_1$, $R_2$, and $R_3$ are independently chosen from hydrogen, halo, lower alkyl, lower alkenyl, lower alkynyl, lower haloalkyl, lower cycloalkyl, heterocycloalkyl, aryl, heteroaryl, acyl, amido, amino, alkoxy, hydroxy, cyano, and nitro, any of which may be optionally substituted; or $R_1$ and $R_2$ may each additionally be heteroalkyl, and may be joined together such that $R_1$ and $R_2$ together form an alkylene, alkenylene, or heteroalkyl bridge comprising from 3 to 5 atoms, which may be optionally substituted;
  $R_4$ is chosen from hydrogen, (O), (S), halogen, hydroxy, cyano, nitro, lower alkyl, lower alkenyl, lower alkynyl, lower cycloalkyl, lower cycloalkyloxy, lower thioalkoxy, lower heterocycloalkyl, aryl, lower aralkyl, lower heteroaryl, lower heteroaralkyl, amido, acyl, amino, and lower alkoxy, any of which may be optionally substituted; or $R_3$ and $R_4$ may each additionally be heteroalkyl, and may be joined together such that $R_1$ and $R_2$ together form an alkylene, alkenylene, or heteroalkyl bridge comprising from 3 to 5 atoms, which may be optionally substituted;
  $R_5$ and $R_{13}$ are each independently chosen from hydrogen, halogen, hydroxy, cyano, nitro, lower alkyl, lower alkene, lower alkyne, lower aryl, lower arylalkyl, lower cycloalkyl, lower cycloalkylalkyl, lower heteroaryl, lower heteroarylalkyl, lower heterocycloalkyl, lower heterocycloalkylalkyl, and lower alkoxy, any of which may be optionally substituted; and additionally, $R_{13}$ and $R_3$ may be joined together to form a lower spiro-cycloalkyl or spiro-phenyl comprising from 3 to 6 atoms, which may be optionally substituted;
  $R_{6a}$, $R_{6b}$, $R_{7a}$, $R_{7b}$, $R_{8a}$, $R_{8b}$, $R_{9a}$, $R_{9b}$, $R_{10a}$, $R_{10b}$, $R_{11a}$, $R_{11b}$, and $R_{12}$ are each independently chosen from a bond, hydrogen, halogen, hydroxy, $C_1$-$C_3$ alkoxy and $C_1$-$C_3$ alkyl; and
  $R_{14}$ is chosen from null, lower cycloalkyl, lower heterocycloalkyl, phenyl, and lower heteroaryl, any of which may be optionally substituted.

When, for example, $Y_1$ is $-(CR_{6a}R_{6b})_m-Z_1-(CR_{7a}R_{7b})_n-$, and m and n are both 0, and $Z_1$ is a bond, then $Y_1$ collapses to a direct bond linking the parent ring system with $R_1$. This applies to all similar constructions used herein, including $Y_2$ and $Y_3$. Also, when for example $Y_1$ is $-(CR_{6a}R_{6b})_m-Z_1-(CR_{7a}R_{7b})_n-$, the rightmost portion of $Y_1$ attaches to the parent molecule.

In certain embodiments, $Y_1$, $Y_2$, $Y_3$, and $Y_4$ are no more than 6 atoms in length.

In certain embodiments, $R_4$ is chosen from hydrogen, (O), and (S).

In certain embodiments, $R_4$ is (O), the second bond linking $R_4$ and the fused bicyclic core is present, and the second bond in the five-membered portion of the fused bicyclic core is absent.

In certain embodiments, $R_4$ is hydrogen, the second bond linking $R_4$ and the fused bicyclic core is absent, and the second bond in the five-membered portion of the fused bicyclic core is present.

In certain embodiments,
  $X_1$ is CH; and
  $X_2$ is C.
In certain embodiments,
  $X_1$ is N; and
  $X_2$ is N.
In certain embodiments,
  $X_1$ is CH; and
  $X_2$ is N.
In certain embodiments,
  $X_1$ is N; and
  $X_2$ is C.
In certain embodiments,
  m and n are both 0;
  $Z_1$ is a bond; and
  $R_1$ and $R_5$ are both hydrogen.
In certain embodiments,
  p and r are each independently an integer from 0 to 3;
  q and s are each 0; and
  $Z_2$ and $Z_3$ are each independently chosen from a bond and O.

In certain embodiments, $R_{6a}$, $R_{6b}$, $R_{7a}$, $R_{7b}$, $R_{8a}$, $R_{8b}$, $R_{9a}$, $R_{9b}$, $R_{10a}$, $R_{10b}$, $R_{11a}$, $R_{11b}$, and $R_{12}$ are all hydrogen.

In certain embodiments, compounds have structural Formula II $$\text{R}_1-\text{Y}_1 \quad \text{R}_{14}-\text{Y}_4-\text{R}_2-\text{Y}_2 \quad X_1 \quad X_2 \quad R_{13} \quad Y_3-R_3 \quad R_5 \quad R_4 \quad \text{II}$$

wherein:
  dashed lines indicate that a second bond may alternatively be present or absent;
  $X_1$ is chosen from CH and N;
  $X_2$ is chosen from C and N;
  $Y_1$, $Y_2$, and $Y_3$ are independently chosen from a bond, lower alkyl, lower carboxyl, and lower heteroalkyl;
  $Y_4$ is chosen from $-(CH_2)_m$, C(O), $-(CH_2)_mO-$, and $-(CH_2)_mN-$;
  m is an integer from 0 to 2;
  $R_1$, $R_2$, and $R_3$ are independently chosen from lower alkyl, lower alkenyl, lower alkynyl, lower haloalkyl, lower cycloalkyl, heterocycloalkyl, aryl, heteroaryl, acyl, amido, amino, alkoxy, hydroxy, cyano, and nitro, any of which may be optionally substituted; or $R_1$ and $R_2$ may each additionally be heteroalkyl, and may be joined together such that $R_1$ and $R_2$ together form an alkylene, alkenylene, or heteroalkyl bridge comprising from 3 to 5 atoms, which may be optionally substituted;

$R_4$ is chosen from hydrogen, (O), and (S);

$R_5$ is chosen from hydrogen, hydroxy, cyano, lower alkyl, lower cycloalkyl, and lower alkoxy, any of which may be optionally substituted;

$R_{13}$ is chosen from hydrogen, halogen, hydroxy, cyano, nitro, lower alkyl, lower cycloalkyl, lower cycloalkylalkyl, and lower alkoxy, any of which may be optionally substituted; and additionally, $R_{13}$ and $R_3$ may be joined together to form a lower spiro-cycloalkyl or spiro-phenyl comprising from 3 to 6 atoms, which may be optionally substituted; and $R_{14}$ is chosen from null, lower cycloalkyl, lower heterocycloalkyl, phenyl, and lower heteroaryl, any of which may be optionally substituted.

In certain embodiments, compounds have structural Formula III

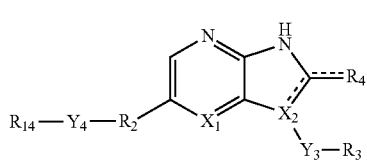

(III)

wherein:
dashed lines indicate that a second bond may alternatively be present or absent;

$X_1$ and $X_2$ are independently chosen from CH and N;

$Y_3$ is chosen from a bond, lower alkyl, lower carboxyl, and lower heteroalkyl;

$Y_4$ is chosen from C(O), —(CH$_2$)$_m$—, —(CH$_2$)$_m$O—, and —(CH$_2$)$_m$N—;

m is an integer from 0 to 1;

$R_2$ and $R_3$ are independently chosen from lower cycloalkyl, heterocycloalkyl, aryl, heteroaryl, any of which may be optionally substituted;

$R_4$ is chosen from hydrogen, (O), and (S);

$R_{13}$ is chosen from hydrogen, lower alkyl, lower cycloalkyl, lower cycloalkylalkyl, and lower alkoxy, any of which may be optionally substituted;

$R_{14}$ is chosen from null, lower cycloalkyl, lower heterocycloalkyl, phenyl, and lower heteroaryl, any of which may be optionally substituted.

In certain embodiments, compounds have a structural Formula chosen from Formula IV and Formula V:

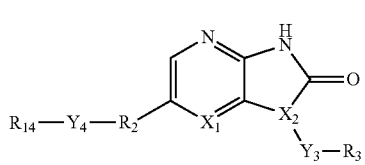

(IV)

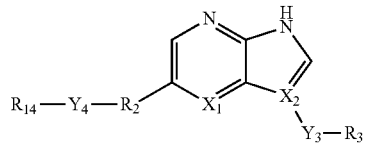

(V)

wherein:
$X_1$ and $X_2$ are independently chosen from CH and N;

$Y_3$ is chosen from a bond, lower alkyl, lower carboxyl, and lower heteroalkyl;

$Y_4$ is chosen from C(O), —(CH$_2$)$_m$—, —(CH$_2$)$_m$O—, and —(CH$_2$)$_m$N—;

m is an integer from 0 to 1;

$R_2$ and $R_3$ are independently chosen from lower cycloalkyl, lower heterocycloalkyl, lower aryl, and lower heteroaryl, any of which may be optionally substituted; and $R_{14}$ is chosen from null, lower cycloalkyl, lower heterocycloalkyl, phenyl, and lower heteroaryl, any of which may be optionally substituted.

In certain embodiments, compounds have a structural Formula chosen from Formula VI, Formula VII, Formula VIII, and Formula IX:

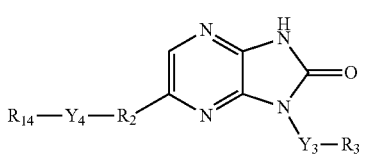

(VI)

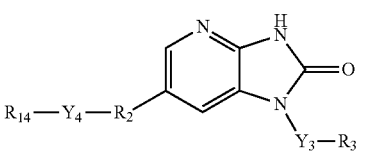

(VII)

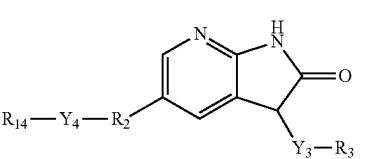

(VIII)

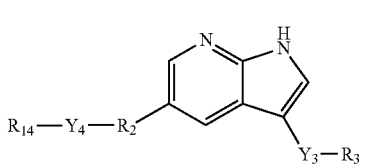

(IX)

wherein
$Y_3$ is chosen from a bond, lower alkyl, lower carboxyl, and lower heteroalkyl;

$Y_4$ is chosen from C(O), —(CH$_2$)$_m$—, —(CH$_2$)$_m$O—, and —(CH$_2$)$_m$N—;

m is an integer from 0 to 1;

$R_2$ is chosen from phenyl, 6-membered monocyclic heteroaryl, and 5/6-fused bicyclic heteroaryl, any of which may be optionally substituted;

$R_3$ is chosen from lower cycloalkyl, phenyl, and lower heteroaryl, any of which may be optionally substituted;

$R_{14}$ is chosen from null, lower cycloalkyl, lower heterocycloalkyl, phenyl, and lower heteroaryl, any of which may be optionally substituted.

In certain embodiments, $R_2$ and $R_3$ are each independently chosen from lower cycloalkyl, lower aryl, and monocyclic or bicyclic heteroaryl, any of which may be optionally substituted.

In certain embodiments, $R_2$ is substituted with one or more substituents chosen from halogen, hydroxy, lower amino, $C_1$-$C_3$ alkoxy and $C_1$-$C_3$ alkyl.

In further embodiments, $R_2$ is chosen from phenyl and lower heteroaryl, any of which may be optionally substituted.

In further embodiments, $R_2$ is chosen from phenyl, 6-membered monocyclic heteroaryl, and 5/6-fused bicyclic heteroaryl, any of which may be optionally substituted.

In further embodiments, $R_2$ is chosen from phenyl, pyridinyl, pyrimidinyl, and indolyl, any of which may be optionally substituted.

In further embodiments, $R_2$ is substituted with one or more substituents chosen from fluorine, hydroxy, $NH_2$, $NH(CH_3)$, $N(CH_3)_2$, methoxy, and methyl.

In further embodiments, $R_2$ is optionally substituted phenyl.

In further embodiments, $R_2$ is chosen from

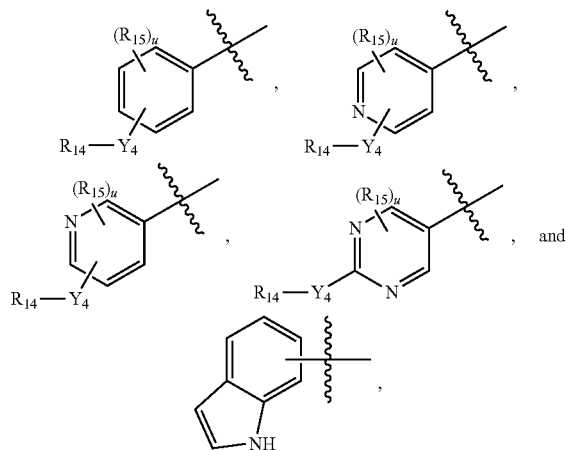

wherein
u is an integer from 0 to 3;
$Y_4$ is chosen from C(O), —$(CH_2)_m$—, —$(CH_2)_m$O—, and —$(CH_2)_m$N—;
m is an integer from 0 to 1;
$R_{14}$ is chosen from null, lower cycloalkyl, lower heterocycloalkyl, phenyl, and lower heteroaryl, any of which may be optionally substituted; and each $R_{15}$ is independently chosen from halogen, hydroxy, $C_1$-$C_4$ alkyl, $C_2$-$C_4$ alkenyl, $C_2$-$C_4$ alkynyl, lower amino, lower amido, lower sulfonamido, and lower sulfonyl.

In certain embodiments, $R_{14}$ is chosen from piperazinyl, morpholinyl, pyrrolyl, and $N(CH_3)_2$.

In certain embodiments, each $R_{15}$ is independently chosen from $R_{15}$ is independently chosen from fluorine, hydroxy, $NH_2$, $NH(CH_3)$, $N(CH_3)_2$, $NS(O)_2CH_3$, methoxy, and methyl.

In certain embodiments,
$Y_4$ is —$(CH_2)_m$—;
m is 0;
$R_{14}$ is null;
u is an integer from 0 to 3; and
$R_{15}$ is independently chosen from $R_{15}$ is independently chosen from fluorine, hydroxy, $NH_2$, $NH(CH_3)$, $N(CH_3)_2$, $NS(O)_2CH_3$, methoxy, and methyl.

In certain embodiments, $Y_4$ is chosen from C(O), O, N, and —$CH_2$—.

In certain embodiments, $Y_4$ is —$CH_2$—.

In certain embodiments, $Y_3$ is chosen from a bond and lower alkyl.

In certain embodiments, $Y_3$ is chosen from a bond and methyl.

In certain embodiments, $Y_3$ is a bond.

In certain embodiments, $R_3$ is chosen from lower cycloalkyl, lower aryl, and monocyclic or bicyclic heteroaryl, any of which may be optionally substituted.

In certain embodiments, $R_3$ is substituted with one or more substituents chosen from halogen, hydroxy, lower amino, lower amido, lower phenylamido, lower phenylalkylamido, lower heterocycloalkyl, lower heterocycloalkyl, lower alkylheterocycloalkyl, $C_1$-$C_3$ alkoxy and $C_1$-$C_3$ alkyl.

In certain embodiments, $R_3$ is chosen from benzothiazolyl, pyrrolopyridinyl, indanyl, cyclopropyl, cyclopentyl, phenyl, pyridinyl, pyrimidinyl, and indolyl, any of which may be optionally substituted.

In certain embodiments, $R_3$ is substituted with one or more substituents chosen from fluorine, chlorine, hydroxy, $NH_2$, $NH(CH_3)$, $N(CH_3)_2$, $C(O)NH_2$, $C(O)NHCH_3$, morpholino, piperazinyl, methylpiperazinyl, acetamido, methylacetamido, methylpropionamido, phenylacetamidomethylene, benzamidomethylene, phenylpropanamidomethylene, methoxy and methyl.

In certain embodiments are provided a compound of structural Formula III

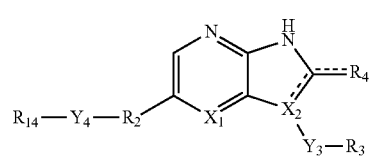

or a salt thereof, wherein:
dashed lines indicate that a second bond may alternatively be present or absent;
$X_1$ and $X_2$ are independently chosen from CH and N;
$Y_3$ is a bond;
$Y_4$ is chosen from C(O), $CH_2$, CHF, and $CF_2$;
$R_2$ is chosen from phenyl and 6-membered monocyclic heteroaryl, either of which may be optionally substituted;
$R_3$ is optionally substituted bicyclic heteroaryl;
$R_4$ is chosen from hydrogen, (O), and (S);
$R_{14}$ is optionally substituted monocyclic heterocycloalkyl.

In certain embodiments, $R_3$ is an optionally substituted 5/6-fused bicyclic heteroaryl.

In certain embodiments, wherein $Y_4$ is $CH_2$.

In certain embodiments, $R_{14}$ is optionally substituted piperazinyl.

In certain embodiments, $R_2$ is chosen from hydrogen, halo, hydroxy, $C_1$-$C_4$ alkyl, $C_3$-$C_{10}$ cycloalkyl, $C_1$-$C_4$ alkyloxy, $C_3$-$C_{10}$ cycloalkyloxy, aryl, cyano or nitro.

In certain embodiments, $R_1$ and $R_2$ together form a butadienylene bridge.

In certain embodiments,
m and n are both 0;
$Z_1$ is a bond;
$R_1$, $R_5$, and $R_4$ are hydrogen; and
$R_2$ and $R_3$ are each independently chosen from aryl and heteroaryl, either of which may be optionally substituted.

In certain embodiments,
m and n are both 0;
$Z_1$ is a bond;
$R_1$, $R_5$, and $R_4$ are hydrogen;
$R_2$ is selected from the group consisting of aryl and heteroaryl, either of which may be optionally substituted; and
$R_3$ is chosen from 5-substituted-1H-indole, 5-substituted pyridine-2-amine, and 5-substituted pyrimidine-2-amine.

In certain embodiments,
m is 0 or 1
n is 0;
$Z_1$ is a bond;
$R_1$, $R_5$, and $R_4$ are hydrogen; and
$R_1$ is chosen from 5-substituted-1H-indole, 5-substituted pyridine-2-amine, and 5-substituted pyrimidine-2-amine; and
$R_2$ is chosen from 5-substituted-1,2,3-trimethoxybenzene, 4-substituted-1,2-dimethoxyphenyl, 5-substituted pyridine-2-amine, and 5-substituted pyrimidine-2-amine.

In certain embodiments,
$R_1$, $R_5$, and $R_4$ are hydrogen; and
$R_2$ and $R_3$ are each independently chosen from aryl and heteroaryl, either of which may be optionally substituted.

In certain embodiments of Formula I,
m and n are both 0;
$Z_1$ is a bond;
$R_1$, $R_5$, and $R_4$ are hydrogen,
$R_2$ is chosen from aryl and heteroaryl, either of which may be optionally substituted; and
$R_3$ is chosen from 5-substituted-1H-indole, 5-substituted pyridine-2-amine, and 5-substituted pyrimidine-2-amine, any of which may be optionally substituted.

In certain embodiments of Formula I,
m and n are both 0;
$Z_1$ is a bond;
$R_1$, $R_5$, and $R_4$ represent hydrogen,
$R_3$ is chosen from 5-substituted-1H-indole, 5-substituted pyridine-2-amine, and 5-substituted pyrimidine-2-amine; and
$R_2$ is chosen from 5-substituted-1,2,3-trimethoxybenzene, 4-substituted-1,2-dimethoxybenzene, 5-substituted pyridine-2-amine, and 5-substituted pyrimidine-2-amine.

In certain embodiments,
$R_4$ is (O), the second bond linking $R_4$ and the fused bicyclic core is present, and the second bond in the five-membered portion of the fused bicyclic core is absent;
m and n are both 0;
$Z_1$ is a bond;
$R_1$ and $R_5$ are each hydrogen; and
$R_2$ and $R_3$ are each independently chosen from aryl and heteroaryl, either of which may be optionally substituted.

In certain embodiments,
$R_4$ is (O), the second bond linking $R_4$ and the fused bicyclic core is present, and the second bond in the five-membered portion of the fused bicyclic core is absent;
m and n are both 0;
$Z_1$ is a bond;
$R_1$ and $R_5$ are each hydrogen; and
$R_2$ is chosen from aryl and heteroaryl, either of which may be optionally substituted; and
$R_3$ is chosen from 5-substituted-1H-indole, 5-substituted pyridine-2-amine, and 5-substituted pyrimidine-2-amine.

In certain embodiments,
$R_4$ is (O), the second bond linking $R_4$ and the fused bicyclic core is present, and the second bond in the five-membered portion of the fused bicyclic core is absent;
m and n are both 0;
$Z_1$ is a bond;
$R_1$ and $R_5$ are each hydrogen;
$R_3$ is chosen from 5-substituted-1H-indole, 5-substituted pyridine-2-amine, or 5-substituted pyrimidine-2-amine; and
$R_2$ is chosen from 5-substituted-1,2,3-trimethoxybenzene, 4-substituted-1,2-dimethoxybenzene, 5-substituted pyridine-2-amine, and 5-substituted pyrimidine-2-amine.

In certain embodiments, optionally substituted groups are substituted with one or more substituent chosen from halogen, hydroxy, $C_1$-$C_3$ alkoxy and $C_1$-$C_3$ alkyl.

In certain embodiments, $R_4$ is mono- or poly-substituted with fluorine.

In certain embodiments, $R_5$ is mono- or poly-substituted with fluorine.

In certain embodiments is provided a compound chosen from Examples 1 to 167.

Also provided herein is a compound as disclosed herein for use as a medicament.

Also provided herein is a compound as disclosed herein for use as a medicament for the treatment of an MLK-mediated disease.

Also provided herein is the use of a compound as disclosed herein in the manufacture of a medicament for the treatment of an MLK-mediated disease.

Also provided herein is a pharmaceutical composition comprising a compound of Formula I together with a pharmaceutically acceptable carrier.

Also provided is a pharmaceutical composition comprising a compound chosen from Examples 1 to 167.

Also provided herein is a method of inhibition of MLK comprising contacting MLK with a compound of Formula I.

In certain embodiments, said MLK is MLK3.

In certain embodiments, said inhibition is selective over other kinases.

Also provided herein is a method of treatment of a MLK-mediated disease comprising the administration of a therapeutically effective amount of a compound of Formula I to a patient in need thereof.

In certain embodiments, said disease is an inflammatory disease or a metabolic disease.

In certain embodiments, said disease is chosen from diabetes mellitus, hyperglycemia, retinopathy, nephropathy, neuropathy, ulcers, micro- and macroangiopathies, gout and diabetic foot disease, insulin resistance, metabolic syndrome, hyperinsulinemia, hypertension, hyperuricemia, obesity, edema, dyslipidemia, chronic heart failure, atherosclerosis, peripheral inflammation, and HIV dementia.

Also provided herein is a method of treatment of a MLK-mediated disease comprising the administration of:
a) a therapeutically effective amount of a compound of Formula I; and
b) another therapeutic agent.

In certain embodiments, said disorder a psychological disorder.

In certain embodiments, said disease is chosen from depression, bipolar disorder, and post-traumatic stress disorder (PTSD).

In certain embodiments, said disorder is a traumatic brain injury.

In certain embodiments, said traumatic brain injury is stroke.

In certain embodiments, said disorder is chosen from Alzheimer's Disease (AD), Parkinson's Disease, HIV dementia and HIV associated neurocognitive disorder (HAND).

In certain embodiments, said disorder is a neurologic disorder of hearing or vision.

In certain embodiments, said disorder is chosen from ototoxicity, hearing loss, acute injury to the inner ear, acoustic trauma, and injury resulting from blast noise.

In certain embodiments the methods of treatment disclosed herein additionally comprise the administration of a second therapeutic agent, as part of a therapeutic regimen. The compounds may be delivered in the same dosage form or separately, and further may be taken concurrently or one subsequent to the other.

In certain embodiments, said second therapeutic agent is a selective serotonin reuptake inhibitor (SSRI).

In certain embodiments, said second therapeutic agent is CEP1347.

Also provided herein is a method of treatment of a MLK-mediated disease comprising the administration of:
a) a therapeutically effective amount of a an MKL inhibitor; and
b) another therapeutic agent.

In certain embodiments, said second therapeutic agent is a selective serotonin reuptake inhibitor (SSRI).

In certain embodiments, said second therapeutic agent is CEP1347.

Also provided herein is a method of achieving an effect in a patient comprising the administration of a therapeutically effective amount of a compound as disclosed herein to a patient, wherein the effect is chosen from:
increased survival of cells of the nervous system, cochlear cells, vestibular cells or retinal cells;
increased survival of heart cells;
promotion of neurogenesis;
promotion of synaptogenesis;
prevention or reduction of neuronal damage;
restoration or improvement of neuronal function;
suppression of neuroinflammation or peripheral inflammation;
suppression of activation of immune cells;
suppression of proliferation of hepatocytes following injury; and
suppression of proliferation of cancer cells.

In certain embodiments, the effect is chosen from:
increased survival of heart cells;
suppression of neuroinflammation or peripheral inflammation;
suppression of activation of immune cells;
suppression of proliferation of hepatocytes following injury; and
suppression of proliferation of cancer cells.

In certain embodiments, said immune cells are chosen from monocytes, macrophages and microglia.

In certain embodiments, the effect is chosen from:
increased survival of cells of the nervous system, cochlear cells, vestibular cells or retinal cells;
increased survival of heart cells;
promotion of neurogenesis;
promotion of synaptogenesis;
prevention or reduction of neuronal damage;
restoration or improvement of neuronal function;
suppression of neuroinflammation or peripheral inflammation;
suppression of activation of immune cells;
suppression of proliferation of hepatocytes following injury; and
suppression of proliferation of cancer cells.

In certain embodiments, said immune cells are chosen from monocytes, macrophages and microglia.

In certain embodiments, the effect is chosen from:
increased survival of cells of the nervous system, cochlear cells, vestibular cells or retinal cells;
promotion of neurogenesis;
promotion of synaptogenesis;
prevention or reduction of neuronal damage; and
restoration or improvement of neuronal function.

DETAILED DESCRIPTION

As used herein, the terms below have the meanings indicated.

When ranges of values are disclosed, and the notation "from $n_1$ ... to $n_2$" is used, where $n_1$ and $n_2$ are the numbers, then unless otherwise specified, this notation is intended to include the numbers themselves and the range between them. This range may be integral or continuous between and including the end values. By way of example, the range "from 2 to 6 carbons" is intended to include two, three, four, five, and six carbons, since carbons come in integer units. Compare, by way of example, the range "from 1 to 3 µM (micromolar)," which is intended to include 1 µM, 3 µM, and everything in between to any number of significant figures (e.g., 1.255 µM, 2.1 µM, 2.9999 µM, etc.).

The term "about," as used herein, is intended to qualify the numerical values which it modifies, denoting such a value as variable within a margin of error. When no particular margin of error, such as a standard deviation to a mean value given in a chart or table of data, is recited, the term "about" should be understood to mean that range which would encompass the recited value and the range which would be included by rounding up or down to that figure as well, taking into account significant figures.

The term "acyl," as used herein, alone or in combination, refers to a carbonyl attached to an alkenyl, alkyl, aryl, cycloalkyl, heteroaryl, heterocycle, or any other moiety were the atom attached to the carbonyl is carbon. An "acetyl" group refers to a —C(O)CH$_3$ group. An "alkylcarbonyl" or "alkanoyl" group refers to an alkyl group attached to the parent molecular moiety through a carbonyl group. Examples of such groups include methylcarbonyl and ethylcarbonyl. Examples of acyl groups include formyl, alkanoyl and aroyl.

The term "alkenyl," as used herein, alone or in combination, refers to a straight-chain or branched-chain hydrocarbon radical having one or more double bonds and containing from 2 to 20 carbon atoms. In certain embodiments, said alkenyl will comprise from 2 to 6 carbon atoms. The term "alkenylene" refers to a carbon-carbon double bond system attached at two or more positions such as ethenylene [(—CH=CH—),(—C::C—)]. Examples of suitable alkenyl radicals include ethenyl, propenyl, 2-propenyl, 2-methylpropenyl, butenyl, isobutenyl, 1,4-butadienyl, isoprenyl, vinyl, and the like. Unless otherwise specified, the term "alkenyl" may include "alkenylene" groups.

The term "alkoxy," as used herein, alone or in combination, refers to an alkyl ether radical, wherein the term alkyl is as defined below. Examples of suitable alkyl ether radicals include methoxy, ethoxy, n-propoxy, isopropoxy, n-butoxy, iso-butoxy, sec-butoxy, tert-butoxy, and the like.

The term "alkyl," as used herein, alone or in combination, refers to a straight-chain or branched-chain alkyl radical containing from 1 to 20 carbon atoms. In certain embodiments, said alkyl will comprise from 1 to 10 carbon atoms. In further embodiments, said alkyl will comprise from 1 to 6 carbon atoms. Alkyl groups may be optionally substituted as defined herein. Examples of alkyl radicals include methyl, ethyl, n-propyl, isopropyl, n-butyl, isobutyl, sec-butyl, tert-butyl, pentyl, iso-amyl, hexyl, octyl, noyl and the like. The term "alkylene," as used herein, alone or in combination, refers to a saturated aliphatic group derived from a straight or branched chain saturated hydrocarbon attached at two or more positions, such as methylene (—$CH_2$—). Unless otherwise specified, the term "alkyl" may include "alkylene" groups.

The term "alkylamino," as used herein, alone or in combination, refers to an alkyl group attached to the parent molecular moiety through an amino group. Suitable alkylamino groups may be mono- or dialkylated, forming groups such as, for example, N-methylamino, N-ethylamino, N,N-dimethylamino, N,N-ethylmethylamino and the like.

The term "alkylidene," as used herein, alone or in combination, refers to an alkenyl group in which one carbon atom of the carbon-carbon double bond belongs to the moiety to which the alkenyl group is attached.

The term "alkylthio," as used herein, alone or in combination, refers to an alkyl thioether (R—S—) radical wherein the term alkyl is as defined above and wherein the sulfur may be singly or doubly oxidized. Examples of suitable alkyl thioether radicals include methylthio, ethylthio, n-propylthio, iso-propylthio, n-butylthio, iso-butylthio, sec-butylthio, tert-butylthio, methanesulfonyl, ethanesulfinyl, and the like.

The term "alkynyl," as used herein, alone or in combination, refers to a straight-chain or branched chain hydrocarbon radical having one or more triple bonds and containing from 2 to 20 carbon atoms. In certain embodiments, said alkynyl comprises from 2 to 6 carbon atoms. In further embodiments, said alkynyl comprises from 2 to 4 carbon atoms. The term "alkynylene" refers to a carbon-carbon triple bond attached at two positions such as ethynylene (—C:::C—, —C≡C—). Examples of alkynyl radicals include ethynyl, propynyl, hydroxypropynyl, butyn-1-yl, butyn-2-yl, pentyn-1-yl, 3-methylbutyn-1-yl, hexyn-2-yl, and the like. Unless otherwise specified, the term "alkynyl" may include "alkynylene" groups.

The terms "amido" and "carbamoyl," as used herein, alone or in combination, refer to an amino group as described below attached to the parent molecular moiety through a carbonyl group, or vice versa. The term "C-amido" as used herein, alone or in combination, refers to a —C(O)N(RR) group with R and R' as defined herein or as defined by the specifically enumerated "R" groups designated. The term "N-amido" as used herein, alone or in combination, refers to a RC(O)N(R')— group, with R and R' as defined herein or as defined by the specifically enumerated "R" groups designated. The term "acylamino" as used herein, alone or in combination, embraces an acyl group attached to the parent moiety through an amino group. An example of an "acylamino" group is acetylamino ($CH_3$C(O)NH—).

The term "amino," as used herein, alone or in combination, refers to —NRR', wherein R and R' are independently chosen from hydrogen, alkyl, acyl, heteroalkyl, aryl, cycloalkyl, heteroaryl, and heterocycloalkyl, any of which may themselves be optionally substituted. Additionally, R and R' may combine to form heterocycloalkyl, either of which may be optionally substituted.

The term "aryl," as used herein, alone or in combination, means a carbocyclic aromatic system containing one, two or three rings wherein such polycyclic ring systems are fused together. The term "aryl" embraces aromatic groups such as phenyl, naphthyl, anthracenyl, and phenanthryl.

The term "arylalkenyl" or "aralkenyl," as used herein, alone or in combination, refers to an aryl group attached to the parent molecular moiety through an alkenyl group.

The term "arylalkoxy" or "aralkoxy," as used herein, alone or in combination, refers to an aryl group attached to the parent molecular moiety through an alkoxy group.

The term "arylalkyl" or "aralkyl," as used herein, alone or in combination, refers to an aryl group attached to the parent molecular moiety through an alkyl group.

The term "arylalkynyl" or "aralkynyl," as used herein, alone or in combination, refers to an aryl group attached to the parent molecular moiety through an alkynyl group.

The term "arylalkanoyl" or "aralkanoyl" or "aroyl," as used herein, alone or in combination, refers to an acyl radical derived from an aryl-substituted alkanecarboxylic acid such as benzoyl, naphthoyl, phenylacetyl, 3-phenylpropionyl (hydrocinnamoyl), 4-phenylbutyryl, (2-naphthyl)acetyl, 4-chlorohydrocinnamoyl, and the like.

The term aryloxy as used herein, alone or in combination, refers to an aryl group attached to the parent molecular moiety through an oxy.

The terms "benzo" and "benz," as used herein, alone or in combination, refer to the divalent radical $C_6H_4$=derived from benzene. Examples include benzothiophene and benzimidazole.

The term "carbamate," as used herein, alone or in combination, refers to an ester of carbamic acid (—NRC(O)O—) which may be attached to the parent molecular moiety from either the nitrogen or acid end, and which may be optionally substituted as defined herein. The term "O-carbamyl" as used herein, alone or in combination, refers to a —OC(O)NRR' group; and the term "N-carbamyl" as used herein, alone or in combination, refers to a ROC(O)NR'— group. R and R' are as defined herein, or as defined by the specifically enumerated "R" groups designated.

The term "carbonyl," as used herein, when alone includes formyl [—C(O)H] and in combination is a —C(O)— group.

The term "carboxyl" or "carboxy," as used herein, refers to —C(O)OH or the corresponding "carboxylate" anion, such as is in a carboxylic acid salt. An "O-carboxy" group refers to a RC(O)O— group, where R is as defined herein. A "C-carboxy" group refers to a —C(O)OR groups where R is as defined herein.

The term "cyano," as used herein, alone or in combination, refers to —CN.

The term "cycloalkyl," or, alternatively, "carbocycle," as used herein, alone or in combination, refers to a saturated or partially saturated monocyclic, bicyclic or tricyclic alkyl group wherein each cyclic moiety contains from 3 to 12 carbon atom ring members and which may optionally be a benzo fused ring system which is optionally substituted as defined herein. In certain embodiments, said cycloalkyl will comprise from 5 to 7 carbon atoms. Examples of such cycloalkyl groups include cyclopropyl, cyclobutyl, cyclopentyl, cyclohexyl, cycloheptyl, tetrahydronaphthyl, indanyl, octahydronaphthyl, 2,3-dihydro-1H-indenyl, adamantyl and the like. "Bicyclic" and "tricyclic" as used herein are intended to include both fused ring systems, such as decahydronaphthalene, octahydronaphthalene as well as the multicyclic (multicentered) saturated or partially unsaturated type. The latter type of isomer is exemplified in general by, bicyclo[1,1,1]pentane, camphor, adamantane, and bicyclo[3,2,1]octane.

The term "ester," as used herein, alone or in combination, refers to a carboxy group bridging two moieties linked at carbon atoms.

The term "ether," as used herein, alone or in combination, refers to an oxy group bridging two moieties linked at carbon atoms.

The term "halo," or "halogen," as used herein, alone or in combination, refers to fluorine, chlorine, bromine, or iodine.

The term "haloalkoxy," as used herein, alone or in combination, refers to a haloalkyl group attached to the parent molecular moiety through an oxygen atom. Haloalkoxy includes perhaloalkoxy. The term "perhaloalkoxy" refers to an alkoxy group where all of the hydrogen atoms are replaced by halogen atoms. An example of perhaloalkoxy is perfluoromethoxy.

The term "haloalkyl," as used herein, alone or in combination, refers to an alkyl radical having the meaning as defined above wherein one or more hydrogens are replaced with a halogen. Specifically embraced are monohaloalkyl, dihaloalkyl, polyhaloalkyl, and perhaloalkyl radicals. A monohaloalkyl radical, for one example, may have an iodo, bromo, chloro or fluoro atom within the radical. Dihalo and polyhaloalkyl radicals may have two or more of the same halo atoms or a combination of different halo radicals. Examples of haloalkyl radicals include fluoromethyl, difluoromethyl, trifluoromethyl, chloromethyl, dichloromethyl, trichloromethyl, pentafluoroethyl, heptafluoropropyl, difluorochloromethyl, dichlorofluoromethyl, difluoroethyl, difluoropropyl, dichloroethyl and dichloropropyl. "Haloalkylene" refers to a haloalkyl group attached at two or more positions. Examples of haloalkyl radicals include fluoromethyl, difluoromethyl, trifluoromethyl, chloromethyl, dichloromethyl, trichloromethyl, pentafluoroethyl, heptafluoropropyl, difluorochloromethyl, dichlorofluoromethyl, difluoroethyl, difluoropropyl, dichloroethyl and dichloropropyl. "Haloalkylene" refers to a haloalkyl group attached at two or more positions. Examples include fluoromethylene (—CFH—), difluoromethylene (—CF$_2$—), chloromethylene (—CHCl—) and the like. The term "perhaloalkyl" as used herein, alone or in combination, refers to an alkyl group where all of the hydrogen atoms are replaced by halogen atoms. Examples include perfluoromethyl.

The term "heteroalkyl," as used herein, alone or in combination, refers to a stable straight or branched chain, or cyclic hydrocarbon radical, or combinations thereof, fully saturated or containing from 1 to 3 degrees of unsaturation, consisting of the stated number of carbon atoms and from one to three heteroatoms chosen from O, N, and S, and wherein the nitrogen and sulfur atoms may optionally be oxidized and the nitrogen heteroatom may optionally be quaternized. The heteroatom(s) O, N and S may be placed at any interior position of the heteroalkyl group. Up to two heteroatoms may be consecutive, such as, for example, —CH$_2$—NH—OCH$_3$.

The term "heteroaryl," as used herein, alone or in combination, refers to a 3 to 15 membered unsaturated heteromonocyclic ring, or a fused monocyclic, bicyclic, or tricyclic ring system in which at least one of the fused rings is aromatic, which contains at least one atom chosen from O, S, and N. Additionally, a heteroaryl may contain one or two C(O), S(O), or S(O)$_2$ groups as ring members. In certain embodiments, said heteroaryl will comprise from 5 to 10 atoms. In certain embodiments, said heteroaryl will comprise from 5 to 7 atoms. In certain embodiments, said heteroaryl will comprise from 1 to 4 heteroatoms as ring members. In further embodiments, said heteroaryl will comprise from 1 to 2 heteroatoms as ring members. The term also embraces fused polycyclic groups wherein heterocyclic rings are fused with aryl rings, wherein heteroaryl rings are fused with other heteroaryl rings, wherein heteroaryl rings are fused with heterocycloalkyl rings, or wherein heteroaryl rings are fused with cycloalkyl rings. Examples of heteroaryl groups include pyrrolyl, pyrrolinyl, imidazolyl, pyrazolyl, pyridyl, pyrimidinyl, pyrazinyl, pyridazinyl, imidazolyl, triazinyl, triazolyl, tetrazolyl, pyranyl, furyl, thienyl, oxazolyl, isoxazolyl, oxadiazolyl, thiazolyl, thiadiazolyl, isothiazolyl, indolyl, isoindolyl, indolizinyl, benzimidazolyl, quinolyl, isoquinolyl, quinoxalinyl, quinazolinyl, indazolyl, benzotriazolyl, benzodioxolyl, benzopyranyl, benzoxazolyl, benzoxadiazolyl, benzothiazolyl, benzothiadiazolyl, benzofuryl, benzothienyl, chromonyl, coumarinyl, benzopyranyl, tetrahydroquinolinyl, tetrazolopyridazinyl, tetrahydroisoquinolinyl, thienopyridinyl, furopyridinyl, pyrrolopyridinyl and the like. Exemplary tricyclic heterocyclic groups include carbazolyl, benzidolyl, phenanthrolinyl, dibenzofuranyl, acridinyl, phenanthridinyl, xanthenyl and the like.

The terms "heterocycloalkyl" and, interchangeably, "heterocycle," as used herein, alone or in combination, each refer to a saturated, partially unsaturated, or fully unsaturated monocyclic, bicyclic, or tricyclic heterocyclic group containing at least one heteroatom as a ring member, wherein each said heteroatom may be independently chosen from N, O, and S. Additionally, a heterocycloalkyl may contain one or two C(O), S(O), or S(O)$_2$ groups as ring members. In certain embodiments, said hetercycloalkyl will comprise from 1 to 4 heteroatoms as ring members. In further embodiments, said hetercycloalkyl will comprise from 1 to 2 heteroatoms as ring members. In certain embodiments, said hetercycloalkyl will comprise from 3 to 8 ring members in each ring. In further embodiments, said hetercycloalkyl will comprise from 3 to 7 ring members in each ring. In yet further embodiments, said hetercycloalkyl will comprise from 5 to 6 ring members in each ring. "Heterocycloalkyl" and "heterocycle" are intended to include sulfones, sulfoxides, N-oxides of tertiary nitrogen ring members, and carbocyclic fused and benzo fused ring systems; additionally, both terms also include systems where a heterocycle ring is fused to an aryl group, as defined herein, or an additional heterocycle group. Examples of heterocycle groups include aziridinyl, azetidinyl, 1,3-benzodioxolyl, dihydroisoindolyl, dihydroisoquinolinyl, dihydrocinnolinyl, dihydrobenzodioxinyl, dihydro[1,3]oxazolo[4,5-b]pyridinyl, benzothiazolyl, dihydroindolyl, dihy-dropyridinyl, 1,3-dioxanyl, 1,4-dioxanyl, 1,3-dioxolanyl, isoindolinyl, morpholinyl, piperazinyl, pyrrolidinyl, tetrahydropyridinyl, piperidinyl, thiomorpholinyl, and the like. The heterocycle groups may be optionally substituted unless specifically prohibited.

The term "hydroxy," as used herein, alone or in combination, refers to —OH.

The term "lower," as used herein, alone or in a combination, where not otherwise specifically defined, means containing from 1 to and including 6 carbon atoms.

The term "lower alkyl," as used herein, alone or in a combination, means $C_1$-$C_6$ straight or branched chain alkyl. The term "lower alkenyl" means $C_2$-$C_6$ straight or branched chain alkenyl. The term "lower alkynyl" means $C_2$-$C_6$ straight or branched chain alkynyl.

The term "lower aryl," as used herein, alone or in combination, means phenyl or naphthyl, either of which may be optionally substituted as provided.

The term "lower heteroaryl," as used herein, alone or in combination, means either 1) monocyclic heteroaryl comprising five or six ring members, of which between one and four said members may be heteroatoms chosen from O, S, and N, or 2) bicyclic heteroaryl, wherein each of the fused rings comprises five or six ring members, comprising between them one to four heteroatoms chosen from O, S, and N.

The term "lower cycloalkyl," as used herein, alone or in combination, means a monocyclic cycloalkyl having between three and six ring members. Lower cycloalkyls may be unsaturated. Examples of lower cycloalkyl include cyclopropyl, cyclobutyl, cyclopentyl, and cyclohexyl.

The term "lower heterocycloalkyl," as used herein, alone or in combination, means a monocyclic heterocycloalkyl having between three and six ring members, of which between one and four may be heteroatoms chosen from O, S, and N. Examples of lower heterocycloalkyls include pyrrolidinyl, imidazolidinyl, pyrazolidinyl, piperidinyl, piperazinyl, and morpholinyl. Lower heterocycloalkyls may be unsaturated.

The term "lower amino," as used herein, alone or in combination, refers to —NRR', wherein R and R' are independently chosen from hydrogen, lower alkyl, and lower heteroalkyl, any of which may be optionally substituted. Additionally, the R and R' of a lower amino group may combine to form a five- or six-membered heterocycloalkyl, either of which may be optionally substituted.

The term "nitro," as used herein, alone or in combination, refers to —NO$_2$.

The terms "oxy" or "oxa," as used herein, alone or in combination, refer to —O—.

The term "oxo," as used herein, alone or in combination, refers to =O.

The term "perhaloalkoxy" refers to an alkoxy group where all of the hydrogen atoms are replaced by halogen atoms.

The term "perhaloalkyl" as used herein, alone or in combination, refers to an alkyl group where all of the hydrogen atoms are replaced by halogen atoms.

The terms "sulfonate," "sulfonic acid," and "sulfonic," as used herein, alone or in combination, refer the —SO$_3$H group and its anion as the sulfonic acid is used in salt formation.

The term "N-sulfonamido" refers to a RS(=O)$_2$NR'— group with R and R' as defined herein or as defined by the specifically enumerated "R" groups designated.

The term "S-sulfonamido" refers to a —S(=O)$_2$NRR', group, with R and R' as defined herein or as defined by the specifically enumerated "R" groups designated.

The terms "thia" and "thio," as used herein, alone or in combination, refer to a —S— group or an ether wherein the oxygen is replaced with sulfur. The oxidized derivatives of the thio group, namely sulfinyl and sulfonyl, are included in the definition of thia and thio. The term "sulfanyl," as used herein, alone or in combination, refers to —S—. The term "sulfinyl," as used herein, alone or in combination, refers to —S(O)—. The term "sulfonyl," as used herein, alone or in combination, refers to —S(O)$_2$—.

The term "thiol," as used herein, alone or in combination, refers to an —SH group.

The term "thiocarbonyl," as used herein, when alone includes thioformyl —C(S)H and in combination is a —C(S)— group.

Any definition herein may be used in combination with any other definition to describe a composite structural group. By convention, the trailing element of any such definition is that which attaches to the parent moiety. For example, the composite group alkylamido would represent an alkyl group attached to the parent molecule through an amido group, and the term alkoxyalkyl would represent an alkoxy group attached to the parent molecule through an alkyl group.

When a group is defined to be "null," what is meant is that said group is absent.

The term "optionally substituted" means the anteceding group may be substituted or unsubstituted. When substituted, the substituents of an "optionally substituted" group may include, without limitation, one or more substituents independently selected from the following groups or a particular designated set of groups, alone or in combination: lower alkyl, lower alkenyl, lower alkynyl, lower alkanoyl, lower heteroalkyl, lower heterocycloalkyl, lower halo alkyl, lower haloalkenyl, lower haloalkynyl, lower perhaloalkyl, lower perhaloalkoxy, lower cycloalkyl, phenyl, aryl, aryloxy, lower alkoxy, lower haloalkoxy, oxo, lower acyloxy, carbonyl, carboxyl, lower alkylcarbonyl, lower carboxyester, lower carboxamido, cyano, hydrogen, halogen, hydroxy, amino, lower alkylamino, arylamino, amido, nitro, thiol, lower alkylthio, lower haloalkylthio, lower perhaloalkylthio, arylthio, sulfonate, sulfonic acid, trisubstituted silyl, N3, SH, SCH3, C(O)CH3, CO2CH3, CO2H, pyridinyl, thiophene, furanyl, lower carbamate, and lower urea. Two substituents may be joined together to form a fused five-, six-, or seven-membered carbocyclic or heterocyclic ring comprising zero to three heteroatoms, for example forming methylenedioxy or ethylenedioxy. An optionally substituted group may be unsubstituted (e.g., —CH2CH3), fully substituted (e.g., —CF2CF3), monosubstituted (e.g., —CH2CH2F) or substituted at a level anywhere in-between fully substituted and monosubstituted (e.g., —CH2CF3). Where substituents are recited without qualification as to substitution, both substituted and unsubstituted forms are encompassed. Where a substituent is qualified as "substituted," the substituted form is specifically intended. Additionally, different sets of optional substituents to a particular moiety may be defined as needed; in these cases, the optional substitution will be as defined, often immediately following the phrase, "optionally substituted with."

The term R or the term R, appearing by itself and without a number designation, unless otherwise defined, refers to a moiety chosen from hydrogen, alkyl, cycloalkyl, heteroalkyl, aryl, heteroaryl and heterocycloalkyl, any of which may be optionally substituted. Such R and R' groups should be understood to be optionally substituted as defined herein. Whether an R group has a number designation or not, every R group, including R, R' and R" where n=(1, 2, 3, ... n), every substituent, and every term should be understood to be independent of every other in terms of selection from a group. Should any variable, substituent, or term (e.g. aryl, heterocycle, R, etc.) occur more than one time in a formula or generic structure, its definition at each occurrence is independent of the definition at every other occurrence. Those of skill in the art will further recognize that certain groups may be attached to a parent molecule or may occupy a position in a chain of elements from either end as written. Thus, by way of example only, an unsymmetrical group such as —C(O)N(R)— may be attached to the parent moiety at either the carbon or the nitrogen.

Asymmetric centers exist in the compounds disclosed herein. These centers are designated by the symbols "R" or "S," depending on the configuration of substituents around the chiral carbon atom. It should be understood that the invention encompasses all stereochemical isomeric forms, including diastereomeric, enantiomeric, and epimeric forms, as well as d-isomers and l-isomers, and mixtures thereof. Individual stereoisomers of compounds can be prepared synthetically from commercially available starting materials which contain chiral centers or by preparation of mixtures of enantiomeric products followed by separation such as conversion to a mixture of diastereomers followed by separation or recrystallization, chromatographic techniques, direct separation of enantiomers on chiral chromatographic columns, or any other appropriate method known in the art. Compounds can be prepared using diastereomers, enantiomers or racemic mixtures as starting materials. Starting compounds of particular stereochemistry are either commercially available or can be made and resolved by techniques known in the art. Furthermore, diastereomer and enantiomer products can be separated by chromatography, fractional crystallization or other methods known to those of skill in the art. Additionally, the compounds disclosed herein may exist as geometric isomers. The present invention includes all cis, trans, syn, anti, entgegen (E), and zusammen (Z) isomers as well as the appropriate mixtures thereof. Additionally, compounds may exist as tautomers; all tautomeric isomers are provided by this invention. Solvates, hydrates, isomorphs, polymorphs are also provided. Additionally, the compounds disclosed herein can exist in unsolvated as well as solvated forms with pharmaceutically acceptable solvents such as water, ethanol, and the like. In general, the solvated forms are considered equivalent to the unsolvated forms.

The term "bond" refers to a covalent linkage between two atoms, or two moieties when the atoms joined by the bond are considered to be part of larger substructure. A bond may be single, double, or triple unless otherwise specified. A dashed line between two atoms in a drawing of a molecule indicates that an additional bond may be present or absent at that position. When, for example, $Y_1$ is —$(CR_{6a}R_{6b})_m$—$Z_1$—$(CR_{7a}R_{7b})_n$—, and m and n are both 0, and $Z_1$ is a bond, then $Y_1$ collapses to a direct bond linking the parent ring system with $R_1$. This applies to all similar constructions used herein, including $Y_2$ and $Y_3$. Or, for example, when either of $R_{6a}$ and $R_{6b}$ of $(CR_{6a}R_{6b})_m$ are designated to be "a bond," and $m \geq 1$, then an additional bond forms between a C of $(CR_{6a}R_{6b})$ and an adjacent atom. When $m \geq 2$, then $(CR_{6a}R_{6b})_m$ may form an alkene (alkenylene) or alkyne (alkynylene).

As used herein, the terms "treating" and "treatment" refer to delaying the onset of, retarding or reversing the progress of, or alleviating or preventing either the disease or condition to which the term applies, or one or more symptoms of such disease or condition.

The term "patient" (and, equivalently, "subject") means all mammals including humans. Examples of patients include humans, cows, dogs, cats, goats, sheep, pigs, and rabbits. Preferably, the patient is a human.

The term "disease" as used herein is intended to be generally synonymous, and is used interchangeably with, the terms "disorder," "syndrome," and "condition" (as in medical condition), in that all reflect an abnormal condition of the human or animal body or of one or more of its parts that impairs normal functioning, is typically manifested by distinguishing signs and symptoms, and/or causes the human or animal to have a reduced duration or quality of life.

The term "neuropsychiatric disorder" includes, without limitation, psychological, psychiatric, and neurological disorders.

The term "HIV associated neurocognitive disorder (HAND)" is related to, and is intended to be substantially synonymous with, the terms HIV dementia, AIDS dementia, HIV encephalopathy, and NeuroAIDS.

The term "combination therapy" means the administration of two or more therapeutic agents to treat a therapeutic condition or disorder described in the present disclosure. Such administration encompasses co-administration of these therapeutic agents in a substantially simultaneous manner, such as in a single capsule having a fixed ratio of active ingredients or in multiple, separate capsules for each active ingredient. In addition, such administration also encompasses use of each type of therapeutic agent in a sequential manner. In either case, the treatment regimen will provide beneficial effects of the drug combination in treating the conditions or disorders described herein.

As used herein, the term "administering" means oral administration, administration as a suppository, topical contact, intravenous, intraperitoneal, intramuscular, intralesional, intranasal or subcutaneous administration, or the implantation of a slow-release device, e.g., a mini-osmotic pump, to a subject. Administration is by any route including parenteral, and transmucosal (e.g., oral, nasal, vaginal, rectal, or transdermal). Parenteral administration includes, e.g., intravenous, intramuscular, intra-arteriole, intradermal, subcutaneous, intraperitoneal, intraventricular, and intracranial. Other modes of delivery include, but are not limited to, the use of liposomal formulations, intravenous infusion, transdermal patches, and the like.

As used herein, the term "prodrug" refers to a precursor compound that, following administration, releases the biologically active compound in vivo via some chemical or physiological process (e.g., a prodrug on reaching physiological pH or through enzyme action is converted to the biologically active compound).

The terms "controlled release," "sustained release," "extended release," and "timed release" are intended to refer interchangeably to any drug-containing formulation in which release of the drug is not immediate, i.e., with a "controlled release" formulation, oral administration does not result in immediate release of the drug into an absorption pool. The terms are used interchangeably with "nonimmediate release" as defined in Remington: The Science and Practice of Pharmacy, 21$^{st}$ Ed., Gennaro, Ed., Lippencott Williams & Wilkins (2003). As discussed therein, immediate and nonimmediate release can be defined kinetically by reference to the following equation:

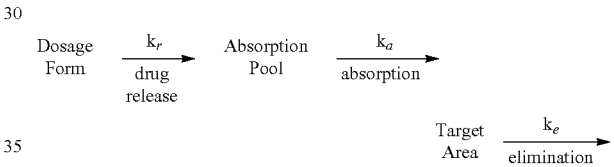

The "absorption pool" represents a solution of the drug administered at a particular absorption site, and $k_r$, $k_a$ and $k_e$ are first-order rate constants for (1) release of the drug from the formulation, (2) absorption, and (3) elimination, respectively. For immediate release dosage forms, the rate constant for drug release $k_r$ is far greater than the absorption rate constant $k_a$. For controlled release formulations, the opposite is true, i.e., $k_r \ll k_a$, such that the rate of release of drug from the dosage form is the rate-limiting step in the delivery of the drug to the target area.

The terms "sustained release" and "extended release" are used in their conventional sense to refer to a drug formulation that provides for gradual release of a drug over an extended period of time, for example, 12 hours or more, and that preferably, although not necessarily, results in substantially constant blood levels of a drug over an extended time period.

As used herein, the term "delayed release" refers to a pharmaceutical preparation that passes through the stomach intact and dissolves in the small intestine.

"MLK3 inhibitor" is used herein to refer to a compound that exhibits an IC$_{50}$ with respect to MLK3 activity of no more than about 100 μM and more typically not more than about 50 μM, as measured in the MLK3 (assay name) described generally hereinbelow. "IC$_{50}$" is that concentration of inhibitor which reduces the activity and/or expression of an enzyme (e.g., MLK or MLK3) to half-maximal level. Certain compounds disclosed herein have been discovered to exhibit inhibition against MLK3. In certain embodiments, compounds will exhibit an IC50 with respect to MLK3 of no more than about 10 μM; in further embodiments, compounds will exhibit an $IC_{50}$ with respect to MLK3 of no more than about 5 μM; in yet further embodiments, compounds will exhibit an $IC_{50}$ with respect to MLK3 of not more than about 1 μM; in yet further embodiments, compounds will exhibit an $IC_{50}$ with respect to MLK3 of not more than about 200 nM, as measured in the MLK3 assay described herein.

The phrase "therapeutically effective" is intended to qualify the amount of active ingredients used in the treatment of a disease or disorder. This amount will achieve the goal of reducing or eliminating the said disease or disorder.

The term "therapeutically acceptable" refers to those compounds (or salts, prodrugs, tautomers, zwitterionic forms, etc.) which are suitable for use in contact with the tissues of patients without undue toxicity, irritation, and allergic response, are commensurate with a reasonable benefit/risk ratio, and are effective for their intended use.

The term "prodrug" refers to a compound that is made more active in vivo. Certain compounds disclosed herein may also exist as prodrugs, as described in *Hydrolysis in Drug and Prodrug Metabolism: Chemistry, Biochemistry, and Enzymology* (Testa, Bernard and Mayer, Joachim M. Wiley-VHCA, Zurich, Switzerland 2003). Prodrugs of the compounds described herein are structurally modified forms of the compound that readily undergo chemical changes under physiological conditions to provide the compound. Additionally, prodrugs can be converted to the compound by chemical or biochemical methods in an ex vivo environment. For example, prodrugs can be slowly converted to a compound when placed in a transdermal patch reservoir with a suitable enzyme or chemical reagent. Prodrugs are often useful because, in some situations, they may be easier to administer than the compound, or parent drug. They may, for instance, be bioavailable by oral administration whereas the parent drug is not. The prodrug may also have improved solubility in pharmaceutical compositions over the parent drug. A wide variety of prodrug derivatives are known in the art, such as those that rely on hydrolytic cleavage or oxidative activation of the prodrug. An example, without limitation, of a prodrug would be a compound which is administered as an ester (the "prodrug"), but then is metabolically hydrolyzed to the carboxylic acid, the active entity. Additional examples include peptidyl derivatives of a compound.

Prodrugs of compounds of Formula I are provided herein. Prodrugs of compounds provided herein include, but are not limited to, carboxylate esters, carbonate esters, hemi-esters, phosphorus esters, nitro esters, sulfate esters, sulfoxides, amides, carbamates, azo compounds, phosphamides, glycosides, ethers, acetals, and ketals. Prodrug esters and carbonates may be formed, for example, by reacting one or more hydroxyl groups of compounds of Formula I or Formula II with alkyl, alkoxy or aryl substituted acylating reagents using methods known to those of skill in the art to produce methyl carbonates, acetates, benzoates, pivalates and the like. Illustrative examples of prodrug esters of the compounds provided herein include, but are not limited to, compounds of Formula I having a carboxyl moiety wherein the free hydrogen is replaced by $C_1$-$C_4$ alkyl, $C_1$-$C_7$ alkanoyloxymethyl, 1-(($C_1$-$C_5$)alkanoyloxy)ethyl, 1-methyl-1-(($C_1$-$C_5$)alkanoyloxy)ethyl, $C_1$-$C_5$ alkoxycarbonyloxymethyl, 1-(($C_1$-$C_5$)alkoxycarbonyloxy)ethyl, 1-methyl-1-(($C_1$-$C_5$)alkoxycarbonyloxy)ethyl, N—(($C_1$-$C_5$)alkoxycarbonyl)aminomethyl, 1-(N—(($C_1$-$C_5$)alkoxycarbonyl)amino)ethyl, 3-phthalidyl, 4-crotonolactonyl, gamma-butyrolacton-4-yl, di-N,N—($C_1$-$C_2$)alkylamino($C_2$-$C_3$)alkyl (e.g., beta-dimethylaminoethyl), carbamoyl-($C_1$-$C_2$)alkyl, N,N-di($C_1$-$C_2$)alkylcarbamoyl-($C_1$-$C_2$)alkyl and piperidino-, pyrrolidino- or morpholino ($C_2$-$C_3$)alkyl. Oligopeptide modifications and biodegradable polymer derivatives (as described, for example, in Int. J. Pharm. 115, 61-67, 1995) are within the scope of the present disclosure. Methods for selecting and preparing suitable prodrugs are provided, for example, in the following: T. Higuchi and V. Stella, "Prodrugs as Novel Delivery Systems," Vol. 14, ACS Symposium Series, 1975; H. Bundgaard, "Design of Prodrugs," Elsevier, 1985; and "Bioreversible Carriers in Drug Design," ed. Edward Roche, American Pharmaceutical Association and Pergamon Press, 1987.

The compounds disclosed herein can exist as therapeutically acceptable salts. The present invention includes compounds disclosed herein in the form of salts, including acid addition salts. Suitable salts include those formed with both organic and inorganic acids. Such acid addition salts will normally be pharmaceutically acceptable. However, salts of non-pharmaceutically acceptable salts may be of utility in the preparation and purification of the compound in question. Basic addition salts may also be formed and be pharmaceutically acceptable. For a more complete discussion of the preparation and selection of salts, refer to *Pharmaceutical Salts: Properties, Selection, and Use* (Stahl, P. Heinrich. Wiley-VCHA, Zurich, Switzerland, 2002).

The term "therapeutically acceptable salt," as used herein, represents salts or zwitterionic forms of the compounds disclosed herein which are water or oil-soluble or dispersible and therapeutically acceptable as defined herein. The salts can be prepared during the final isolation and purification of the compounds or separately by reacting the appropriate compound in the form of the free base with a suitable acid. Representative acid addition salts include acetate, adipate, alginate, L-ascorbate, aspartate, benzoate, benzenesulfonate (besylate), bisulfate, butyrate, camphorate, camphorsulfonate, citrate, digluconate, formate, fumarate, gentisate, glutarate, glycerophosphate, glycolate, hemisulfate, heptanoate, hexanoate, hippurate, hydrochloride, hydrobromide, hydroiodide, 2-hydroxyethansulfonate (isethionate), lactate, maleate, malonate, DL-mandelate, mesitylenesulfonate, methanesulfonate, naphthylenesulfonate, nicotinate, 2-naphthalenesulfonate, oxalate, pamoate, pectinate, persulfate, 3-phenylproprionate, phosphonate, picrate, pivalate, propionate, pyroglutamate, succinate, sulfonate, tartrate, L-tartrate, trichloroacetate, trifluoroacetate, phosphate, glutamate, bicarbonate, para-toluenesulfonate (p-tosylate), and undecanoate. Also, basic groups in the compounds disclosed herein can be quaternized with methyl, ethyl, propyl, and butyl chlorides, bromides, and iodides; dimethyl, diethyl, dibutyl, and diamyl sulfates; decyl, lauryl, myristyl, and steryl chlorides, bromides, and iodides; and benzyl and phenethyl bromides. Examples of acids which can be employed to form therapeutically acceptable addition salts include inorganic acids such as hydrochloric, hydrobromic, sulfuric, and phosphoric, and organic acids such as oxalic, maleic, succinic, and citric. Salts can also be formed by coordination of the compounds with an alkali metal or alkaline earth ion. Hence, the present invention contemplates sodium, potassium, magnesium, and calcium salts of the compounds disclosed herein, and the like.

Basic addition salts can be prepared during the final isolation and purification of the compounds by reacting a carboxy group with a suitable base such as the hydroxide, carbonate, or bicarbonate of a metal cation or with ammonia or an organic primary, secondary, or tertiary amine. The cations of therapeutically acceptable salts include lithium, sodium, potassium, calcium, magnesium, and aluminum, as well as nontoxic quaternary amine cations such as ammonium, tetramethylammonium, tetraethylammonium, methylamine, dimethylamine, trimethylamine, triethylamine, diethylamine, ethylamine, tributylamine, pyridine, N,N-dimethylaniline, N-methylpiperidine, N-methylmorpholine, dicyclohexylamine, procaine, dibenzylamine, N,N-dibenzylphenethylamine, 1-ephenamine, and N,N-dibenzylethylenediamine. Other representative organic amines useful for the formation of base addition salts include ethylenediamine, ethanolamine, diethanolamine, piperidine, and piperazine.

Also provided herein are isotopically-substituted or -labeled compounds of Formula I, wherein one or more atoms are replaced by one or more atoms having specific atomic mass or mass numbers. Examples of isotopes that can be incorporated into compounds disclosed herein include, but are not limited to, isotopes of hydrogen, carbon, nitrogen, oxygen, fluorine, sulfur, and chlorine (such as $^2$H, $^3$H, $^{13}$C, $^{14}$C, $^{15}$N, $^{18}$O, $^{17}$O, $^{18}$F, $^{35}$S and $^{36}$Cl). Isotopically-labeled compounds of Formula I and prodrugs thereof, as well as isotopically-labeled, pharmaceutically acceptable salts of compounds of Formula I and prodrugs thereof, are herein disclosed. Isotopically-labeled compounds are useful in assays of the tissue distribution of the compounds and their prodrugs and metabolites; preferred isotopes for such assays include $^3$H and $^{14}$C. In addition, in certain circumstances substitution with heavier isotopes, such as deuterium ($^2$H), can provide increased metabolic stability, which offers therapeutic advantages such as increased in vivo half-life or reduced dosage requirements. Isotopically-labeled compounds and prodrugs thereof can generally be prepared according to the methods described herein by substituting an isotopically-labeled reagent for a non-isotopically labeled reagent.

In other aspects, provided herein are intermediates and processes useful for preparing the intermediates below as well as the compounds of Formula I, and pharmaceutically acceptable salts and prodrugs thereof.

In a similar manner, the present invention provides methods of preparing compounds of Formula I, that are based on the synthetic protocols outlined in Schemes 1 through 21 as well as methods well known by persons skilled in the art, and the more detailed particular examples presented below in the experimental section describing the examples. By following the general preparative methods discussed below, or employing variations or alternative methods, the compounds can be readily prepared by the use of chemical reactions and procedures known to those of skill in the art. Unless otherwise specified, the variables (e.g., R groups) denoting groups in the general methods described below have the meanings as hereinbefore defined.

Those of skill in the art will recognize that compounds with each described functional group are generally prepared using slight variations of the below-listed general methods. Within the scope of each method, functional groups which are suitable to the reaction conditions are used. Functional groups which might interfere with certain reactions are presented in protected forms where necessary, and the removal of such protective groups is completed at appropriate stages by methods well known to those skilled in the art.

In certain cases compounds can be prepared from other compounds disclosed herein by elaboration, transformation, exchange and the like of the functional groups present. Such elaboration includes, but is not limited to, hydrolysis, reduction, oxidation, alkylation, acylation, esterification, amidation and dehydration. Such transformations can in some instances require the use of protecting groups by the methods disclosed in T. W. Greene and P. G. M. Wuts, *Protective Groups in Organic Synthesis*; Wiley: New York, (1999), and incorporated herein by reference. Such methods would be initiated after synthesis of the desired compound or at another place in the synthetic route that would be readily apparent to one skilled in the art.

In another aspect, provided herein are synthetic intermediates useful for preparing the compounds of Formula I, and pharmaceutically acceptable salts and prodrugs thereof, according to the general preparative methods discussed below and other processes known to those of skill in the art.

When the following abbreviations and acronyms are used throughout the disclosure, they have the following meanings: CDCl$_3$, chloroform-d; CH$_2$Cl$_2$, methylene chloride; CH$_3$CN, acetonitrile; DIPEA, N,N-diisopropylethylamine; DMAP, 4-dimethylaminopyridine; DMF, N,N-dimethylformamide; DMSO, dimethylsulfoxide; Et, ethyl; Et$_3$N, triethylamine; EtOAc (or AcOEt), ethyl acetate; EtOH, ethanol; h, hour; HCl, hydrochloric acid; $^1$H NMR, proton nuclear magnetic resonance; H$_2$SO$_4$, sulfuric acid; HPLC, high performance liquid chromatography; K$_2$CO$_3$, potassium carbonate; KOH, potassium hydroxide; LC-MS, liquid chromatography—mass spectroscopy; Me, methyl; MeOH, methanol; min, minute; MS ESI, mass spectroscopy with electrospray ionization; MsOH, methanesulfonic acid; NaH, sodium hydride; NaHCO$_3$, sodium bicarbonate; NaOH, sodium hydroxide; Na$_2$SO$_4$, sodium sulfate; NBS, N-bromosuccinimide; NCS, N-chlorosuccinimide; NH$_3$, ammonia; NIS, N-iodosuccinimide; Pd/C, palladium on carbon; Pd(PPh$_3$)$_4$, tetrakis(triphenylphosphine)palladium(0); R$_f$, retention factor; TBAF, tetrabutylammonium fluoride; TBAI, tetrabutylammonium iodide; TBDMS, t-butyldimethylsilyl; Tf$_2$O, trifluoromethanesulfonic anhydride; TFA, trifluoroacetic acid; THF, tetrahydrofuran; TLC, thin layer chromatography; TMS, trimethylsilyl; TMSCN, trimethylsilyl cyanide; TsOH, toluenesulfonic acid.

While it may be possible for compounds to be administered as the raw chemical, it is also possible to present them as a pharmaceutical formulation. Accordingly, provided herein are pharmaceutical formulations which comprise one or more of certain compounds disclosed herein, or one or more pharmaceutically acceptable salts, esters, prodrugs, amides, or solvates thereof, together with one or more pharmaceutically acceptable carriers thereof and optionally one or more other therapeutic ingredients. The carrier(s) must be "acceptable" in the sense of being compatible with the other ingredients of the formulation and not deleterious to the recipient thereof. Proper formulation is dependent upon the route of administration chosen. Any of the well-known techniques, carriers, and excipients may be used as suitable and as understood in the art; e.g., in *Remington: The Science and Practice of Pharmacy,* 21$^{st}$ Ed., Gennaro, Ed., Lippencott Williams & Wilkins (2003). The pharmaceutical compositions disclosed herein may be manufactured in any manner known in the art, e.g., by means of conventional mixing, dissolving, granulating, dragee-making, levigating, emulsifying, encapsulating, entrapping or compression processes.

A compound as provided herein can be incorporated into a variety of formulations for therapeutic administration, including solid, semi-solid, liquid or gaseous forms. The formulations include those suitable for oral, parenteral (including subcutaneous, intradermal, intramuscular, intravenous, intraarticular, and intramedullary), intraperitoneal, transmucosal, transdermal, rectal and topical (including dermal, buccal, sublingual and intraocular) administration although the most suitable route may depend upon for example the condition and disorder of the recipient. The formulations may conveniently be presented in unit dosage form and may be prepared by any of the methods well known in the art of pharmacy. Typically, these methods include the step of bringing into association a compound or a pharmaceutically acceptable salt, ester, amide, prodrug or solvate thereof ("active ingredient") with the carrier which constitutes one or more accessory ingredients. In general, the formulations are prepared by uniformly and intimately bringing into association the active ingredient with liquid carriers or finely divided solid carriers or both and then, if necessary, shaping the product into the desired formulation.

Formulations of the compounds disclosed herein suitable for oral administration may be presented as discrete units such as capsules, cachets or tablets each containing a predetermined amount of the active ingredient; as a powder or granules; as a solution or a suspension in an aqueous liquid or a non-aqueous liquid; or as an oil-in-water liquid emulsion or a water-in-oil liquid emulsion. The active ingredient may also be presented as a bolus, electuary or paste.

Pharmaceutical preparations which can be used orally include tablets, push-fit capsules made of gelatin, as well as soft, sealed capsules made of gelatin and a plasticizer, such as glycerol or sorbitol. Tablets may be made by compression or molding, optionally with one or more accessory ingredients. Compressed tablets may be prepared by compressing in a suitable machine the active ingredient in a free-flowing form such as a powder or granules, optionally mixed with binders, inert diluents, or lubricating, surface active or dispersing agents. Molded tablets may be made by molding in a suitable machine a mixture of the powdered compound moistened with an inert liquid diluent. The tablets may optionally be coated or scored and may be formulated so as to provide slow or controlled release of the active ingredient therein. All formulations for oral administration should be in dosages suitable for such administration. The push-fit capsules can contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols. In addition, stabilizers may be added.

Dragee cores are provided with suitable coatings. For this purpose, concentrated sugar solutions may be used, which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of active compound doses. Also provided are oral formulations in the form of powders and granules containing one or more compounds disclosed herein.

The compounds may be formulated for parenteral administration by injection, e.g., by bolus injection or continuous infusion. Formulations for injection may be presented in unit dosage form, e.g., in ampoules or in multi-dose containers, with an added preservative. The compositions may take such forms as suspensions, solutions or emulsions in oily or aqueous vehicles, and may contain formulatory agents such as suspending, stabilizing and/or dispersing agents. The formulations may be presented in unit-dose or multi-dose containers, for example sealed ampoules and vials, and may be stored in powder form or in a freeze-dried (lyophilized) condition requiring only the addition of the sterile liquid carrier, for example, saline or sterile pyrogen-free water, immediately prior to use. Extemporaneous injection solutions and suspensions may be prepared from sterile powders, granules and tablets of the kind previously described.

Formulations for parenteral administration include aqueous and non-aqueous (oily) sterile injection solutions of the active compounds which may contain antioxidants, buffers, bacteriostats and solutes which render the formulation isotonic with the blood of the intended recipient; and aqueous and non-aqueous sterile suspensions which may include suspending agents and thickening agents. Suitable lipophilic solvents or vehicles include fatty oils such as sesame oil, or synthetic fatty acid esters, such as ethyl oleate or triglycerides, or liposomes. Aqueous injection suspensions may contain substances which increase the viscosity of the suspension, such as sodium carboxymethyl cellulose, sorbitol, or dextran. Optionally, the suspension may also contain suitable stabilizers or agents which increase the solubility of the compounds to allow for the preparation of highly concentrated solutions.

In addition to the formulations described previously, the compounds may also be formulated as a depot preparation. Such long acting formulations may be administered by implantation (for example subcutaneously or intramuscularly) or by intramuscular injection. Thus, for example, the compounds may be formulated with suitable polymeric or hydrophobic materials (for example as an emulsion in an acceptable oil) or ion exchange resins, or as sparingly soluble derivatives, for example, as a sparingly soluble salt.

For buccal or sublingual administration, the compositions may take the form of tablets, lozenges, pastilles, or gels formulated in conventional manner. Such compositions may comprise the active ingredient in a flavored basis such as sucrose and *acacia* or tragacanth.

The compounds may also be formulated in rectal compositions such as suppositories or retention enemas, e.g., containing conventional suppository bases such as cocoa butter, polyethylene glycol, or other glycerides.

Certain compounds disclosed herein may be administered topically, that is by non-systemic administration. This includes the application of a compound disclosed herein externally to the epidermis or the buccal cavity and the instillation of such a compound into the ear, eye and nose, such that the compound does not significantly enter the blood stream. In contrast, systemic administration refers to oral, intravenous, intraperitoneal and intramuscular administration.

Formulations suitable for topical administration include liquid or semi-liquid preparations suitable for penetration through the skin to the site of inflammation such as gels, liniments, lotions, creams, ointments or pastes, and drops suitable for administration to the eye, ear or nose. The active ingredient for topical administration may comprise, for example, from 0.001% to 10% w/w (by weight) of the formulation. In certain embodiments, the active ingredient may comprise as much as 10% w/w. In other embodiments, it may comprise less than 5% w/w. In certain embodiments, the active ingredient may comprise from 2% w/w to 5% w/w. In other embodiments, it may comprise from 0.1% to 1% w/w of the formulation.

For administration by inhalation, compounds may be conveniently delivered from an insufflator, nebulizer pressurized packs or other convenient means of delivering an aerosol spray. Pressurized packs may comprise a suitable propellant such as dichlorodifluoromethane, trichlorofluoromethane, dichlorotetrafluoroethane, carbon dioxide or other suitable gas. In the case of a pressurized aerosol, the dosage unit may be determined by providing a valve to deliver a metered amount. Alternatively, for administration by inhalation or insufflation, the compounds may take the form of a dry powder composition, for example a powder mix of the compound and a suitable powder base such as lactose or starch. The powder composition may be presented in unit dosage form, in for example, capsules, cartridges, gelatin or blister packs from which the powder may be administered with the aid of an inhalator or insufflator.

In one embodiment, a compound is prepared for delivery in a sustained-release, controlled release, extended-release, timed-release or delayed-release formulation, for example, in semipermeable matrices of solid hydrophobic polymers containing the therapeutic agent. Various types of sustained-release materials have been established and are well known by those skilled in the art. Current extended-release formulations include film-coated tablets, multiparticulate or pellet systems, matrix technologies using hydrophilic or lipophilic materials and wax-based tablets with pore-forming excipients (see, for example, Huang, et al. *Drug Dev. Ind. Pharm.* 29:79 (2003); Pearnchob, et al. *Drug Dev. Ind. Pharm.* 29:925 (2003); Maggi, et al. *Eur. J. Pharm. Biopharm.* 55:99 (2003); Khanvilkar, et al., *Drug Dev. Ind. Pharm.* 228:601 (2002); and Schmidt, et al., *Int. J. Pharm.* 216:9 (2001)). Sustained-release delivery systems can, depending on their design, release the compounds over the course of hours or days, for instance, over 4, 6, 8, 10, 12, 16, 20, 24 hours or more. Usually, sustained release formulations can be prepared using naturally-occurring or synthetic polymers, for instance, polymeric vinyl pyrrolidones, such as polyvinyl pyrrolidone (PVP); carboxyvinyl hydrophilic polymers; hydrophobic and/or hydrophilic hydrocolloids, such as methylcellulose, ethylcellulose, hydroxypropylcellulose, and hydroxypropylmethylcellulose; and carboxypolymethylene.

The sustained or extended-release formulations can also be prepared using natural ingredients, such as minerals, including titanium dioxide, silicon dioxide, zinc oxide, and clay (see, U.S. Pat. No. 6,638,521, herein incorporated by reference). Exemplified extended release formulations that can be used in delivering a compound include those described in U.S. Pat. Nos. 6,635,680; 6,624,200; 6,613,361; 6,613,358, 6,596,308; 6,589,563; 6,562,375; 6,548,084; 6,541,020; 6,537,579; 6,528,080 and 6,524,621, each of which is hereby incorporated herein by reference. Controlled release formulations of particular interest include those described in U.S. Pat. Nos. 6,607,751; 6,599,529; 6,569,463; 6,565,883; 6,482,440; 6,403,597; 6,319,919; 6,150,354; 6,080,736; 5,672,356; 5,472,704; 5,445,829; 5,312,817 and 5,296,483, each of which is hereby incorporated herein by reference. Those skilled in the art will readily recognize other applicable sustained release formulations.

Systemic administration can also be by transmucosal or transdermal means. For transmucosal or transdermal administration, penetrants appropriate to the barrier to be permeated are used in the formulation. For topical administration, the agents can be formulated into ointments, creams, salves, powders or gels. In one embodiment, the transdermal delivery agent can be DMSO. Transdermal delivery systems can include, e.g., patches. For transmucosal administration, penetrants appropriate to the barrier to be permeated are used in the formulation. Such penetrants are generally known in the art. Exemplified transdermal delivery formulations that can find use with the compounds disclosed herein include those described in U.S. Pat. Nos. 6,589,549; 6,544,548; 6,517,864; 6,512,010; 6,465,006; 6,379,696; 6,312,717 and 6,310,177, each of which are hereby incorporated herein by reference.

The precise amount of compound administered to a patient will be the responsibility of the attendant physician. The specific dose level for any particular patient will depend upon a variety of factors including the activity of the specific compound employed, the age, body weight, general health, sex, diets, time of administration, route of administration, rate of excretion, drug combination, the precise disorder being treated, and the severity of the indication or condition being treated. Also, the route of administration may vary depending on the condition and its severity. The dosage can be increased or decreased over time, as required by an individual patient. A patient initially may be given a low dose, which is then increased to an efficacious dosage tolerable to the patient. Typically, a useful dosage for adults may be from 5 to 2000 mg, but have been known to range from 0.1 to 500 mg/kg per day. By way of example, a dose may range from 1 to 200 mg, when administered by oral route; or from 0.1 to 100 mg or, in certain embodiments, 1 to 30 mg, when administered by intravenous route; in each case administered, for example, from 1 to 4 times per day. When a compound is administered in combination with another therapeutic agent, a useful dosage of the combination partner may be from 20% to 100% of the normally recommended dose, since, as discussed below, even doses of a given drug which would be subtherapeutic if administered on its own may be therapeutic when used in combination with another agent.

Dosage amount and interval can be adjusted individually to provide plasma levels of the active compounds which are sufficient to maintain therapeutic effect. In certain embodiments, therapeutically effective serum levels will be achieved by administering single daily doses, but efficacious multiple daily dose schedules may be used as well. In cases of local administration or selective uptake, the effective local concentration of the drug may not be related to plasma concentration. One having skill in the art will be able to optimize therapeutically effective local dosages without undue experimentation. Additionally, applicable methods for determining an appropriate dose and dosing schedule for administration of compounds such as those disclosed herein are described, for example, in *Goodman and Gilman's The Pharmacological Basis of Therapeutics*, 11$^{th}$ Ed., Brunton, Lazo and Parker, Eds., McGraw-Hill (2006), and in *Remington: The Science and Practice of Pharmacy*, 21$^{st}$ Ed., Gennaro, Ed., Lippencott Williams & Wilkins (2003), both of which are hereby incorporated herein by reference.

In certain instances, it may be appropriate to administer at least one of the compounds described herein (or a pharmaceutically acceptable salt, ester, or prodrug thereof) in combination with another therapeutic agent. By way of example only, if one of the side effects experienced by a patient upon receiving one of the compounds herein is hypertension, then it may be appropriate to administer an anti-hypertensive agent in combination with the initial therapeutic agent. Or, by way of example only, the therapeutic effectiveness of one of the compounds described herein may be enhanced by administration of an adjuvant (i.e., by itself the adjuvant may only have minimal therapeutic benefit, but in combination with another therapeutic agent, the overall therapeutic benefit to the patient is enhanced). Or, by way of example only, the benefit of experienced by a patient may be increased by administering one of the compounds described herein with another therapeutic agent (which also includes a therapeutic regimen) that also has therapeutic benefit. By way of example only, in a treatment for HIV dementia involving administration of one of the compounds described herein, increased therapeutic benefit may result by also providing the patient with another therapeutic agent for dementia or inflammation. In any case, regardless of the disease, disorder or condition being treated, the overall benefit experienced by the patient may simply be additive of the two therapeutic agents or the patient may experience a synergistic benefit.

Specific, non-limiting examples of possible combination therapies include use of certain compounds disclosed herein with compounds used for treating diseases and conditions which can be affected by SGLT inhibition, such as antidiabetic agents, lipid-lowering/lipid-modulating agents, agents for treating diabetic complications, anti-obesity agents, antihypertensive agents, antihyperuricemic agents, and agents for treating chronic heart failure, atherosclerosis or related disorders.

In any case, the multiple therapeutic agents (at least one of which is a compound disclosed herein) may be administered in any order or even simultaneously. If simultaneously, the multiple therapeutic agents may be provided in a single, unified form, or in multiple forms (by way of example only, either as a single pill or as two separate pills). One of the therapeutic agents may be given in multiple doses, or both may be given as multiple doses. If not simultaneous, the timing between the multiple doses may be any duration of time ranging from a few minutes to four weeks.

Examples of agents to be used in combination with compounds disclosed herein include lithium, valproate and other agents used in neuroprotection, PAF receptor antagonists, antioxidants including mitochondrially-targeted antioxidants, activators of SIRT1 and other sirtuins, inhibitors of indoleamine 2,3 dehydrogenase (IDO), agents which enhance trans-blood brain barrier (BBB) uptake of drugs, including compounds that inhibit drug pumps at the BBB such as, for example, ritonavir; HAART drugs and other agents for use in HIV treatment; agents for the treatment of cardiovascular, heart, and metabolic disorders, such as HMG-CoA reductase inhibitors including statins, insulin and insulin mimetics, and glycogen synthase kinase-3 beta (GSK3β) inhibitors; agents which "normalize" mitochondrial function; antiinflammatory agents including PAF receptor antagonists or PAF acetylhydrolase, cyclooxygenase inhibitors (including COX-2 selective and nonselective) such as aspirin, ibuprofen, naproxen, and celecoxib; and agents for blocking liver cell proliferation, such as JNK inhibitors.

Also provided are combinations of multiple agents, such as lithium plus a GSK3β blocker, to be used in combination with the compounds provided herein.

Additionally, agents for neuroprotection and/or neurogenesis include selective serotonin reuptake inhibitors SSRIs and small molecule agonists of neurotrophin receptors.

Any of the aforementioned agents may be combined with viral vectors that express genes intended to induce neural progenitor cells, as well.

Treatment with the compounds disclosed here in may also be effective when delivered along with deep-brain stimulation, such as in Parkinsonism and HIV-associated dementia/HIV-associated neurocognitive disorder.

Thus, in another aspect, certain embodiments provide methods for treating MLK3-mediated disorders in a human or animal subject in need of such treatment comprising administering to said subject an amount of a compound disclosed herein effective to reduce or prevent said disorder in the subject, in combination with at least one additional agent for the treatment of said disorder that is known in the art. In a related aspect, certain embodiments provide therapeutic compositions comprising at least one compound disclosed herein in combination with one or more additional agents for the treatment of MLK3-mediated disorders.

Specific diseases to be treated by the compounds, compositions, and methods disclosed herein include: metabolic diseases such as type 1 and type 2 diabetes mellitus, hyperglycemia, diabetic complications (such as retinopathy, nephropathy, neuropathy, ulcers, micro- and macroangiopathies, gout and diabetic foot disease), insulin resistance, metabolic syndrome (Syndrome X), hyperinsulinemia, hypertension, hyperuricemia, obesity, edema, dyslipidemia, hepatic steatosis, non-alcoholic steatohepatitis (NASH), chronic heart failure, and atherosclerosis.

Compounds disclosed herein may also be useful for the treatment of inflammatory diseases such as bacterial sepsis, otitis media, endotoxemia, mucosal hyperplasia, inflammatory bowel disease, Crohn's disease, irritable bowel syndrome, and ulcerative colitis; and respiratory diseases and conditions such as asthma, chronic obstructive pulmonary disease (COPD), and acute inhalation-induced lung injury.

Compounds disclosed herein may also be useful for the treatment of autoimmune diseases such as multiple sclerosis, rheumatoid arthritis, lupus and Crohn's disease.

Compounds disclosed herein may also be useful for the treatment of proliferative disorders including cancers such as liver cancer. Furthermore, Compounds disclosed herein may also be useful for the treatment of hepatitis, including viral hepatitis, and non-alcoholic steatohepatitis (NASH).

Compounds disclosed herein may also be useful for the treatment of ischemic injury, including stroke, cerebral ischemia/reperfusion, myocardial infarction, and ischemic heart disease.

Compounds disclosed herein may also be useful for the treatment of diseases and disorders of the nervous system such as Alzheimer's Disease (AD), Parkinson's Disease, HIV dementia, HIV associated neurocognitive disorder (HAND), neuroinflammatory diseases, and neuropathies including drug-induced peripheral neuropathy, and diabetic neuropathy, and HIV-associated neuropathy, ototoxicity and hearing loss, acute insults to the inner ear, including acoustic trauma, blast noise (for example, as experienced by military personnel), exposure to ototoxic chemotherapeutic agents for cancer therapy (such as cisplatin) and treatment with aminoglycoside antibiotics. Compounds disclosed herein may also be useful for the treatment of traumatic brain injury including stroke.

Compounds disclosed herein may also be useful for the treatment of pain including inflammatory pain, neuropathic pain, back pain including discogenic pain, the pain of arthritis and autoimmune disorders such as rheumatoid arthritis, and cancer pain including pain due to bone metastasis.

Compounds disclosed herein may also be useful for the treatment of psychological disorders including depression or major depressive disorder (MDD), bipolar disorder, and post-traumatic stress disorder.

Compounds disclosed herein may also be useful for enhancement of stem-cell based therapies in the central nervous system (CNS).

All publications and patent applications cited in this specification are herein incorporated by reference as if each individual publication or patent application were specifically and individually indicated to be incorporated by reference. Although the foregoing has been described in some detail by way of illustration and example for purposes of clarity of understanding, it will be readily apparent to those of ordinary skill in the art in light of the teachings of this invention that certain changes and modifications can be made thereto without departing from the spirit or scope of the invention.

EXAMPLES

The invention is further illustrated by the following examples, which are offered for illustrative purposes, and are not intended to limit the invention in any manner. Those of skill in the art will readily recognize a variety of noncritical parameters, which can be changed or modified to yield essentially the same results.

The structures of compounds synthesized in the examples below were confirmed using the following procedures. LC-MS/UV/ELS analysis was performed on instrumentation consisting of Shimadzu LC-10AD vp series HPLC pumps and dual wavelength UV detector, a Gilson 215 autosampler, a Sedex 75c evaporative light scattering (ELS) detector, and a PE/Sciex API 150EX mass spectrometer. The ELS detector was set to a temperature of 40° C., a gain setting of 7, and a N2 pressure of 3.3 atm. The Turbo IonSpray source was employed on the API 150 with an ion spray voltage of 5 kV, a temperature of 300° C., and orifice and ring voltages of 5 V and 175 V respectively. Positive ions were scanned in Q1 from 160 to 650 m/z. 5.0 μL injections were performed for each sample, on a Phenomenex Gemini 5 μm C18 column. Mobile phases consisted of 0.05% formic acid in both HPLC grade water (A) and HPLC grade acetonitrile (B). 5.0 μL injections were performed for each sample, using gradient elution from 5% B to 100% B in 4 min at a flow rate of 2.0 mL/min with a final hold at 100% B of 1.8 min. UV and ELS data is collected for 4.5 min. Routine one-dimensional NMR spectroscopy was performed on a 300 MHz Varian Mercury-Plus spectrometer. The samples were dissolved in deuterated solvents obtained from Cambridge Isotope Laboratories, Inc., and transferred to 5 mm ID NMR tubes. The spectra were acquired at 293 K. The chemical shifts were recorded on the ppm scale and were referenced to the appropriate solvent signals, such as 2.49 ppm for DMSO-d6, 1.93 ppm for CD$_3$CN, 3.30 ppm for CD$_3$OD, 5.32 ppm for CD$_2$Cl$_2$ and 7.26 ppm for CDCl$_3$ for $^1$H spectra.

Other equipment and techniques standard in the art of chemical analysis and characterization may be used.

Example 1

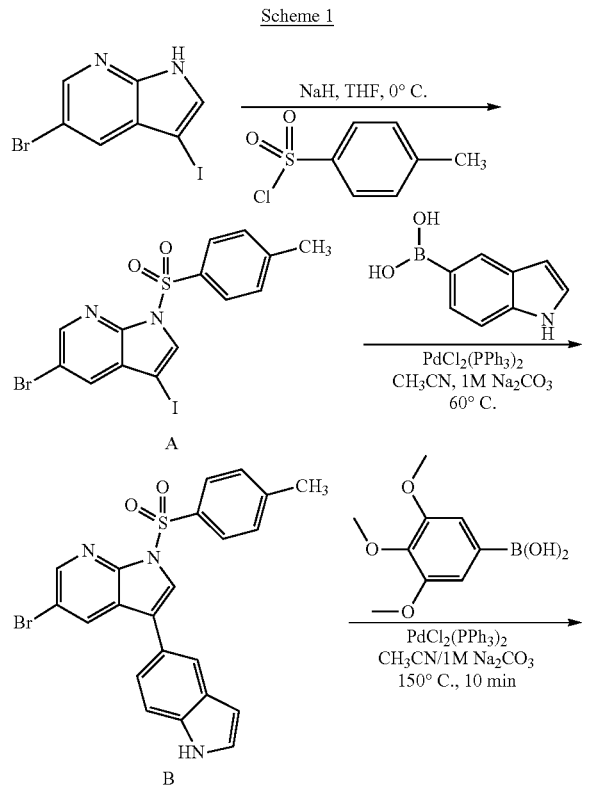

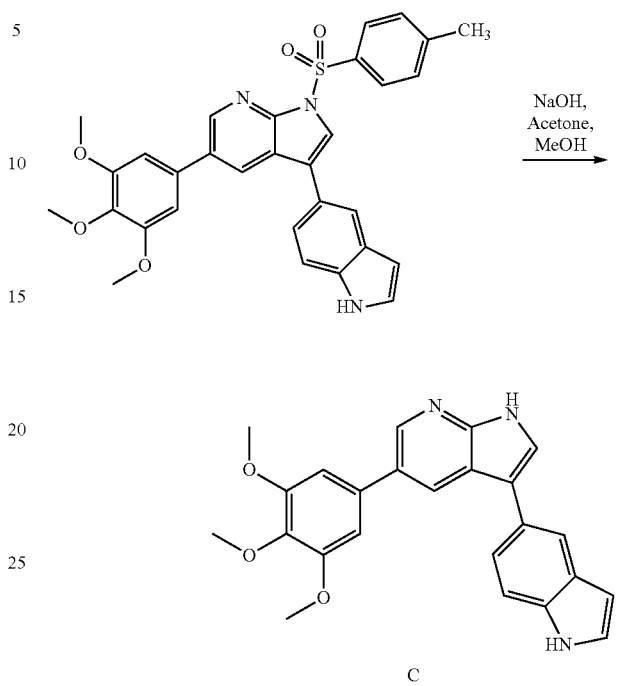

Preparation of
5-bromo-3-iodo-1-tosyl-1H-pyrrolo[2,3-b]pyridine
(Intermediate A)

To a stirred solution of 5-bromo-3-iodo-1H-pyrrolo[2,3-b]pyridine (0.70 g, 2.2 mmol) in 15 mL of anhydrous THF cooled to 0° C. with an ice bath was added NaH [60% dispersion in mineral oil] (0.13 g, 3.3 mmol). The reaction mixture was stirred for 20 min at 0° C., after which p-toluenesulfonyl chloride (0.47 g, 2.4 mmol) was added. The resulting mixture was stirred at 0° C. for 1.5 hr, after which cold 0.5 M HCl (20 mL) was added. The mixture was partitioned between EtOAc and 0.5 M HCl, after which the organic layer was separated, dried over MgSO$_4$, filtered, and evaporated in vacuo to yield a residue that was triturated with 20% CH$_2$Cl$_2$ in hexanes to yield the title compound (0.84 g, 81%) as a light yellow powder. $^1$H NMR (DMSO-d6, 300 MHz) δ 8.51 (d, J=2.1 Hz, 1H), 8.22 (s, 1H), 8.02 (d, J=1.2 Hz, 1H), 8.00 (d, J=5.1 Hz, 2H), 7.44 (dd, J=8.7 Hz, 0.6 Hz, 2H), 2.35 (s, 3H); MS ESI (m/z): 477.0/479.0 (M+1)$^+$, calc. 476.

Preparation of 5-bromo-3-(1H-indol-5-yl)-1-tosyl-
1H-pyrrolo[2,3-b]pyridine (Intermediate B)

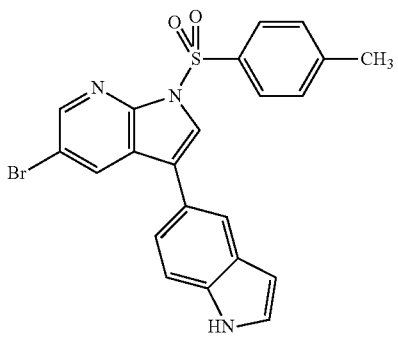 [SMILES: Cc1ccc(S(=O)(=O)n2cc(-c3ccc4[nH]ccc4c3)c3cc(Br)cnc32)cc1]

To a stirred suspension of 5-bromo-3-iodo-1-tosyl-1H-pyrrolo[2,3-b]pyridine (0.35 g, 0.73 mmol) and 1H-indol-5-ylboronic acid (0.14 mg, 0.88 mmol) in $CH_3CN$ (10 mL) was added 1 M $Na_2CO_3$ (10 mL) followed by bis(triphenylphosphine)palladium(II) dichloride (0.050 g, 0.071 mmol). The resulting mixture was stirred overnight at 60° C. After the mixture was evaporated to dryness in vacuo, it was dissolved in DMF (3 mL), absorbed onto Celite, and dried. The residue was purified via silica gel chromatography using $CH_2Cl_2$ as the eluent to obtain the title compound (0.26 g, 76%). $^1$H NMR ($CDCl_3$, 300 MHz): δ 8.48 (d, J=2.1 Hz, 1H), 8.27 (bs, 1H), 8.26 (d, J=2.4 Hz, 1H), 8.08 (d, J=8.1 Hz, 1H), 7.85 (s, 1H), 7.81 (m, 1H), 7.50 (d, J=8.7 Hz, 1 H), 7.37 (dd, J=1.8, 8.4 Hz), 7.30 (m, 3H), 6.63 (m, 1 H), 2.39 (s, 3H); MS ESI (m/z): 466.2/468.2 (M+1)$^+$, calc. 465.

Preparation of 3-(1H-indol-5-yl)-5-(3,4,5-trimethoxyphenyl)-1H-pyrrolo[2,3-b]pyridine (Compound C)

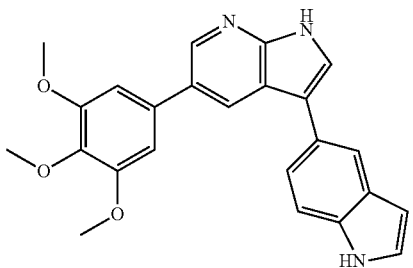 [SMILES: COc1cc(-c2cnc3[nH]cc(-c4ccc5[nH]ccc5c4)c3c2)cc(OC)c1OC]

To a solution of 5-bromo-3-(1H-indol-5-yl)-1-tosyl-1H-pyrrolo[2,3-b]pyridine (65 mg, 0.14 mmol) in $CH_3CN$ (1 mL) in a Personal Chemistry microwave reaction vial was added 3,4,5-trimethoxyphenylboronic acid (30 mg, 0.14 mmol), bis(triphenylphosphine)-palladium(II) dichloride (7.0 mg, 0.010 mmol), and 1 μM $Na_2CO_3$ (1 mL). The resulting mixture was de-gassed with Ar for 10 min, after which it was heated at 150° C. for 10 min in a Personal Chemistry Optimizer. The organic layer was separated, filtered, and concentrated in vacuo. The residue was dissolved in MeOH (3 mL) and acetone (2 mL), and 2 M NaOH (1.5 mL) was added. The resulting mixture was stirred at 65° C. for 30 min, after which it was partitioned between EtOAc and 1 M NaOH. The organic layer was separated, dried over $MgSO_4$, filtered, and stripped to give a residue purified via preparatory HPLC to give the title compound as a white solid. $^1$H NMR (DMSO-d6, 300 MHz): δ 11.78 (s, 1H), 11.03 (s, 1 H), 8.51 (d, J=2.1 Hz, 1H), 8.36 (d, J=1.8 Hz, 1H), 7.86 (s, 1H), 7.72 (d, J=2.4 Hz, 1H), 7.45 (s, 2H), 7.32 (m, 1H), 6.92 (s, 2H), 6.45 (m, 1 H), 3.85 (s, 6H), 3.70 (s, 3H); HPLC retention time: 2.04 minutes; MS ESI (m/z): 400.4 (M+1)$^+$, calc. 399.

Example 2

Preparation of 5-(3,4-dimethoxyphenyl)-3-(1H-indol-5-yl)-1H-pyrrolo[2,3-b]pyridine (Compound D)

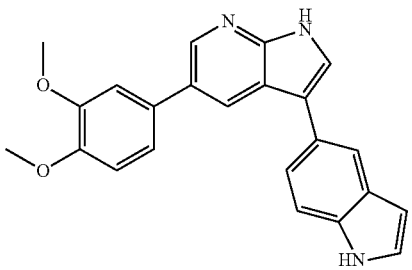 [SMILES: COc1ccc(-c2cnc3[nH]cc(-c4ccc5[nH]ccc5c4)c3c2)cc1OC]

Compound D was prepared by a method analogous to that described in Example 1 by substituting 3,4-dimethoxyphenylboronic acid for 3,4,5-trimethoxyphenylboronic acid in the reaction with intermediate B. HPLC retention time: 2.33 minutes. MS ESI (m/z): 370.2 (M+H)$^+$, calc. 369.

Example 3

Preparation of N-(4-(3-(1H-indol-5-yl)-1H-pyrrolo[2,3-b]pyridin-5-yl)phenyl)acetamide (Compound E)

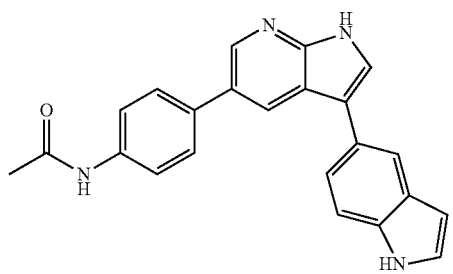 [SMILES: CC(=O)Nc1ccc(-c2cnc3[nH]cc(-c4ccc5[nH]ccc5c4)c3c2)cc1]

Compound E was prepared by a method analogous to that described in Example 1 by substituting 4-acetamidophenylboronic acid for 3,4,5-trimethoxyphenylboronic acid in the reaction with intermediate B. HPLC retention time: 1.86 minutes. MS ESI (m/z): 367.4 (M+H)$^+$, calc. 366.

Example 4

Preparation of 5-(3-(1H-indol-5-yl)-1H-pyrrolo[2,3-b]pyridin-5-yl)pyridin-2-amine (Compound F)

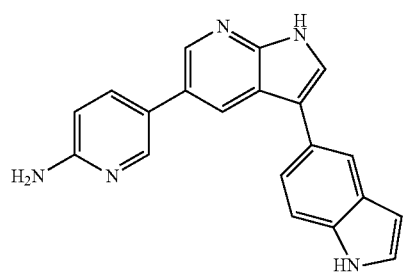 [SMILES: Nc1ccc(-c2cnc3[nH]cc(-c4ccc5[nH]ccc5c4)c3c2)cn1]

Compound F was prepared by a method analogous to that described in Example 1 by substituting 5-(4,4,5,5-tetramethyl-1,3,2-dioxaborolan-2-yl)pyridin-2-amine for 3,4,5-trimethoxyphenylboronic acid in the reaction with intermediate B. $^1$H NMR (DMSO-d6, 300 MHz): δ 11.73 (d, J=1.8 Hz, 1H), 11.05 (s, 1 H), 8.43 (d, J=2.4 Hz, 1H), 8.29 (d, J=1.8 Hz, 1H), 8.27 (d, J=2.1 Hz, 1H), 7.88 (s, 1H), 7.76 (dd, J=2.4, 8.4

Hz, 1H), 7.46 (s, 2H), 7.33 (m, 1H), 6.55 (dd, J=0.6, 8.7 Hz, 1H), 6.46 (m, 1 H), 5.99 (s, 2H). HPLC retention time: 1.10 minutes. MS ESI (m/z): 326.2 (M+H)+, calc. 325.

Example 5

Preparation of 4-(3-(1H-indol-5-yl)-1H-pyrrolo[2,3-b]pyridin-5-yl)-2-methoxyaniline (Compound G)

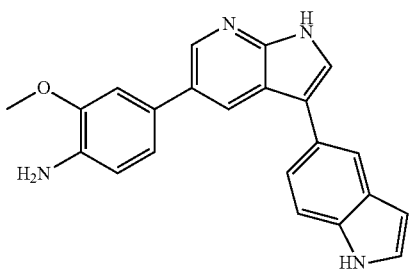 [SMILES: COc1cc(-c2cnc3[nH]cc(-c4ccc5[nH]ccc5c4)c3c2)ccc1N]

Compound G was prepared by a method analogous to that described in Example 1 by substituting 4-amino-3-methoxyphenylboronic acid for 3,4,5-trimethoxyphenylboronic acid in the reaction with intermediate B. HPLC retention time: 1.54 minutes. MS ESI (m/z): 355.4 (M+H)+, calc. 354.

Example 6

Preparation of 3-(1H-indol-5-yl)-5-(6-methoxypyridin-3-yl)-1H-pyrrolo[2,3-b]pyridine (Compound H)

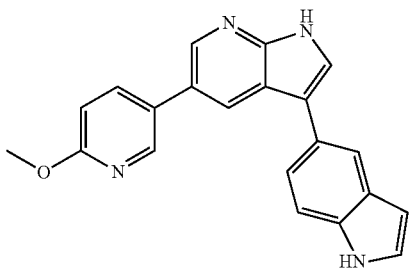 [SMILES: COc1ccc(-c2cnc3[nH]cc(-c4ccc5[nH]ccc5c4)c3c2)cn1]

Compound H was prepared by a method analogous to that described in Example 1 by substituting 6-methoxypyridin-3-ylboronic acid for 3,4,5-trimethoxyphenylboronic acid in the reaction with intermediate B. HPLC retention time: 2.16 minutes. MS ESI (m/z): 341.4 (M+H)+, calc. 340.

Example 7

Preparation of 3-(1H-indol-5-yl)-5-(2-(4-methylpiperazin-1-yl)pyridin-4-yl)-1H-pyrrolo[2,3-b]pyridine (Compound I)

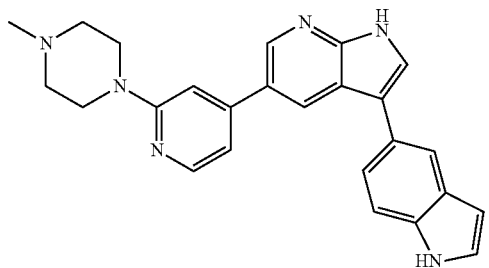 [SMILES: CN1CCN(c2cc(-c3cnc4[nH]cc(-c5ccc6[nH]ccc6c5)c4c3)ccn2)CC1]

Compound I was prepared by a method analogous to that described in Example 1 by substituting 2-(4-methylpiperazin-1-yl)pyridin-4-ylboronic acid for 3,4,5-trimethoxyphenylboronic acid in the reaction with intermediate B. HPLC retention time: 1.37 minutes. MS ESI (m/z): 409.4 (M+H)+, calc. 408.

Example 8

Preparation of 4-(3-(1H-indol-5-yl)-1H-pyrrolo[2,3-b]pyridin-5-yl)aniline (Compound J)

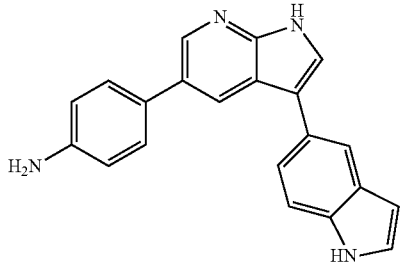 [SMILES: Nc1ccc(-c2cnc3[nH]cc(-c4ccc5[nH]ccc5c4)c3c2)cc1]

Compound J was prepared by a method analogous to that described in Example 1 by substituting 4-aminophenylboronic acid for 3,4,5-trimethoxyphenylboronic acid in the reaction with intermediate B. HPLC retention time: 1.47 minutes. MS ESI (m/z): 325.4 (M+H)+, calc. 324.

Example 9

Preparation of 5-(3-(1H-indol-5-yl)-1H-pyrrolo[2,3-b]pyridin-5-yl)pyrimidin-2-amine (Compound K)

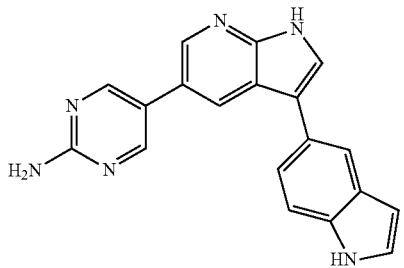

Compound K was prepared by a method analogous to that described in Example 1 by substituting 2-aminopyrimidin-5-ylboronic acid for 3,4,5-trimethoxyphenylboronic acid in the reaction with intermediate B. HPLC retention time: 1.81 minutes. MS ESI (m/z): 327.2 (M+H)+, calc. 326.

Example 10

Preparation of 3-(1H-indol-5-yl)-5-(6-(piperazin-1-yl)pyridin-3-yl)-1H-pyrrolo[2,3-b]pyridine (Compound L)

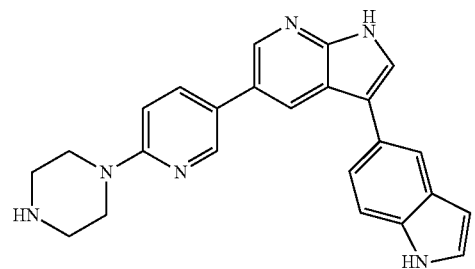 [SMILES: c1cc2cc(-c3c[nH]c4ncc(-c5ccc(N6CCNCC6)nc5)cc34)ccc2[nH]1]

Compound L was prepared by a method analogous to that described in Example 1 by substituting 6-(piperazin-1-yl)pyridin-3-ylboronic acid for 3,4,5-trimethoxyphenylboronic acid acid in the reaction with intermediate B. HPLC retention time: 1.15 minutes. MS ESI (m/z) 395.4 (M+H)+, calc. 394.

Example 11

Preparation of N-(4-(3-(1H-indol-5-yl)-1H-pyrrolo[2,3-b]pyridin-5-yl)phenyl)methanesulfonamide (Compound M)

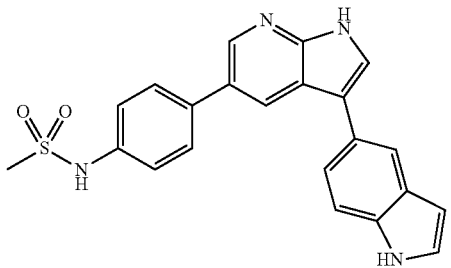 [SMILES: CS(=O)(=O)Nc1ccc(-c2cnc3[nH]cc(-c4ccc5[nH]ccc5c4)c3c2)cc1]

Compound M was prepared by a method analogous to that described in Example 1 by substituting 4-(methylsulfonamido)phenylboronic acid for 3,4,5-trimethoxyphenylboronic acid in the reaction with intermediate B. HPLC retention time: 1.99 minutes. MS ESI (m/z): 403.4 (M+H)+, calc. 402.

Example 12

Preparation of 3,5-di(1H-indol-5-yl)-1H-pyrrolo[2,3-b]pyridine (Compound N)

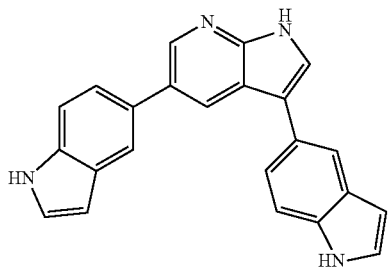 [SMILES: c1cc2cc(-c3cnc4[nH]cc(-c5ccc6[nH]ccc6c5)c4c3)ccc2[nH]1]

Compound N was prepared by a method analogous to that described in Example 1 by substituting 1H-indol-5-ylboronic acid for 3,4,5-trimethoxyphenylboronic acid in the reaction with intermediate B. HPLC retention time: 2.01 minutes. MS ESI (m/z): 349.2 (M+H)+, calc. 348.

Example 13

Preparation of 5-(3-(1H-indol-5-yl)-1H-pyrrolo[2,3-b]pyridin-5-yl)-N,N-dimethylpyridin-2-amine (Compound O)

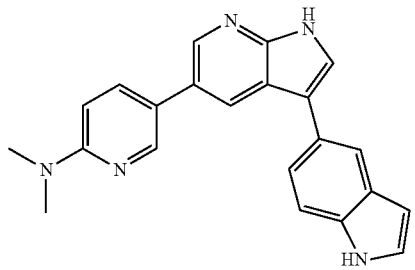 [SMILES: CN(C)c1ccc(-c2cnc3[nH]cc(-c4ccc5[nH]ccc5c4)c3c2)cn1]

Compound O was prepared by a method analogous to that described in Example 1 by substituting 6-(dimethylamino)pyridin-3-ylboronic acid for 3,4,5-trimethoxyphenylboronic acid in the reaction with intermediate B. HPLC retention time: 1.58 minutes. MS ESI (m/z): 354.4 (M+H)+, calc. 353.

Example 14

Preparation of 3-(1H-indol-5-yl)-5-phenyl-1H-pyrrolo[2,3-b]pyridine (Compound P)

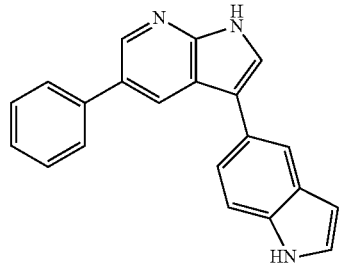 [SMILES: c1ccc(-c2cnc3[nH]cc(-c4ccc5[nH]ccc5c4)c3c2)cc1]

Compound P was prepared by a method analogous to that described in Example 1 by substituting phenylboronic acid for 3,4,5-trimethoxyphenylboronic acid in the reaction with intermediate B. HPLC retention time: 2.49 minutes. MS ESI (m/z): 310.2 (M+H)+, calc. 309.

Example 15

Preparation of 4-(5-(3,4,5-trimethoxyphenyl)-1H-pyrrolo[2,3-b]pyridin-3-yl)aniline (Compound Q)

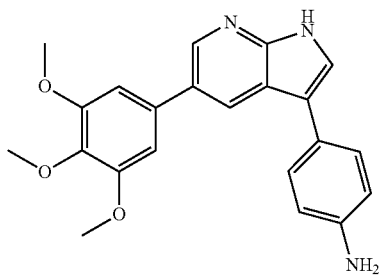 [SMILES: COc1cc(-c2cnc3[nH]cc(-c4ccc(N)cc4)c3c2)cc(OC)c1OC]

Compound Q was prepared by a method analogous to that described in Example 1 by substituting 4-aminophenylboronic acid for 1H-indol-5-ylboronic acid in the reaction with Intermediate A. HPLC retention time: 1.45 minutes. MS ESI (m/z): 376.4 (M+H)+, calc. 375.

Example 16

Preparation of N-(4-(5-(3,4,5-trimethoxyphenyl)-1H-pyrrolo[2,3-b]pyridin-3-yl)phenyl)acetamide (Compound R)

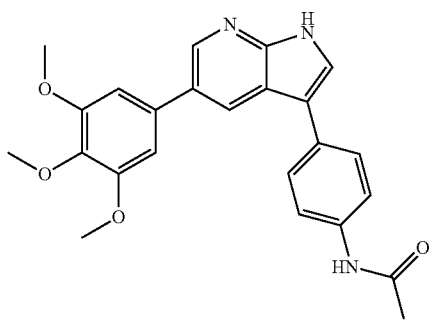 [SMILES: COc1cc(-c2cnc3[nH]cc(-c4ccc(NC(C)=O)cc4)c3c2)cc(OC)c1OC]

Compound R was prepared by a method analogous to that described in Example 1 by substituting 4-acetamidophenylboronic acid for 1H-indol-5-ylboronic acid in the reaction with Intermediate A. HPLC retention time: 1.98 minutes. MS ESI (m/z): 418.6 (M+H)+, calc. 417.

Example 17

Preparation of 5-(5-(3,4,5-trimethoxyphenyl)-1H-pyrrolo[2,3-b]pyridin-3-yl)pyrimidin-2-amine (Compound S)

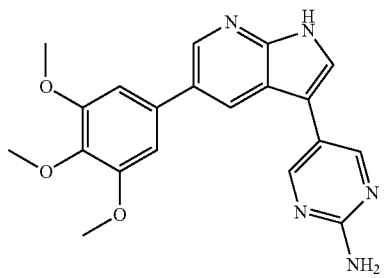 [SMILES: COc1cc(-c2cnc3[nH]cc(-c4cnc(N)nc4)c3c2)cc(OC)c1OC]

Compound S was prepared by a method analogous to that described in Example 1 by substituting 2-aminopyrimidin-5-ylboronic acid for 1H-indol-5-ylboronic acid in the reaction with Intermediate A. HPLC retention time: 1.98 minutes. MS ESI (m/z): 378.4 (M+H)$^+$, calc. 377.

Example 18

Preparation of 5-(5-(3,4,5-trimethoxyphenyl)-1H-pyrrolo[2,3-b]pyridin-3-yl)pyridin-2-amine (Compound T)

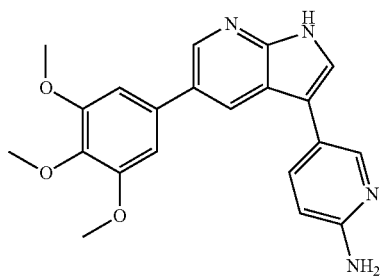 [SMILES: COc1cc(-c2cnc3[nH]cc(-c4ccc(N)nc4)c3c2)cc(OC)c1OC]

Compound T was prepared by a method analogous to that described in Example 1 by substituting 5-(4,4,5,5-tetramethyl-1,3,2-dioxaborolan-2-yl)pyridin-2-amine for 1H-indol-5-ylboronic acid in the reaction with Intermediate A. $^1$H NMR (DMSO-d6, 300 MHz): δ 11.82 (s, 1H), 8.53 (d, J=1.8 Hz, 1H), 8.31 (d, J=1.8, 1 H), 8.28 (d, J=1.5 Hz), 7.76 (dd, J=2.1, 8.4 Hz, 1 H), 7.70 (d, J=2.4 Hz, 1H), 6.95 (s, 2H), 6.54 (d, J=8.4 Hz, 1 H), 5.87 (s, 2H), 3.86 (s, 6H), 3.68 (s, 3H); HPLC retention time: 1.10 minutes. MS ESI (m/z): 377.4 (M+H)$_+$, calc. 376.

Example 19

Preparation of N,N-dimethyl-5-(5-(3,4,5-trimethoxyphenyl)-1H-pyrrolo[2,3-b]pyridin-3-yl)pyridin-2-amine (Compound U)

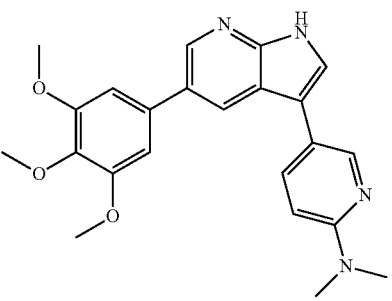

Compound U was prepared by a method analogous to that described in Example 1 by substituting 6-(dimethylamino)pyridin-3-ylboronic acid for 1H-indol-5-ylboronic acid in the reaction with Intermediate A. HPLC retention time: 1.43 minutes. MS ESI (m/z): 405.6 (M+H)$^+$, calc. 404.

Example 20

Preparation of 5,5'-(1H-pyrrolo[2,3-b]pyridine-3,5-diyl)dipyrimidin-2-amine (Compound W)

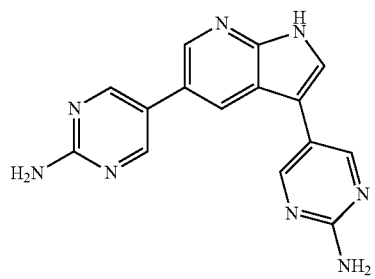 [SMILES: Nc1ncc(-c2cnc3[nH]cc(-c4cnc(N)nc4)c3c2)cn1]

Compound W was prepared by a method analogous to that described in Example 1 by substituting 2-aminopyrimidin-5-ylboronic acid for 1H-indol-5-ylboronic acid in the reaction with Intermediate A and 2-aminopyrimidin-5-ylboronic acid for 3,4,5-trimethoxyphenylboronic acid in the reaction with Intermediate B. HPLC retention time: 1.17 minutes. MS ESI (m/z): 305.2 (M+H)$^+$, calc. 304.

Example 21

Preparation of 5,5'-(1H-pyrrolo[2,3-b]pyridine-3,5-diyl)bis(N,N-dimethylpyridin-2-amine) (Compound X)

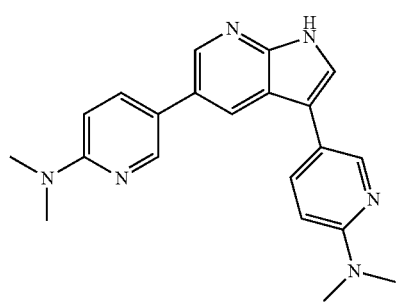

Compound X was prepared by a method analogous to that described in Example 1 by substituting 6-(dimethylamino)pyridin-3-ylboronic acid for 1H-indol-5-ylboronic acid in the reaction with Intermediate A and 6-(dimethylamino)pyridin-3-ylboronic acid for 3,4,5-trimethoxyphenylboronic acid in the reaction with Intermediate B. HPLC retention time: 1.17 minutes. MS ESI (m/z): 359.4 (M+H)$^+$, calc. 358.

Example 22

Preparation of 5-(3-(3-chloro-4-fluorophenyl)-1H-pyrrolo[2,3-b]pyridin-5-yl)-N,N-dimethylpyridin-2-amine (Compound Y)

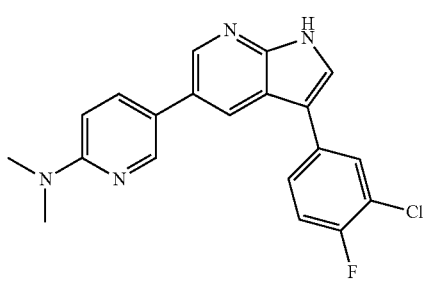 [SMILES: CN(C)c1ccc(-c2cnc3[nH]cc(-c4ccc(F)c(Cl)c4)c3c2)cn1]

Compound Y was prepared by a method analogous to that described in Example 1 by substituting 3-chloro-4-fluorophenylboronic acid for 1H-indol-5-ylboronic acid in the reaction with Intermediate A and 6-(dimethylamino)pyridin-3-ylboronic acid for 3,4,5-trimethoxyphenylboronic acid in the reaction with Intermediate B. HPLC retention time: 1.73 minutes. MS ESI (m/z): 367.2 (M+H)+, calc. 366.

Example 23

Preparation of 5-(3-(4-aminophenyl)-1H-pyrrolo[2,3-b]pyridin-5-yl)pyridin-2-amine (Compound Z)

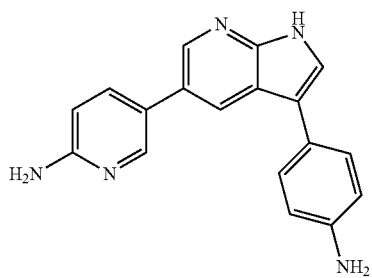 [SMILES: Nc1ccc(-c2c[nH]c3ncc(-c4ccc(N)nc4)cc23)cc1]

Compound Z was prepared by a method analogous to that described in Example 1 by substituting 4-aminophenylboronic acid for 1H-indol-5-ylboronic acid in the reaction with Intermediate A and 6-aminopyridin-3-ylboronic acid for 3,4,5-trimethoxyphenylboronic acid in the reaction with Intermediate B. HPLC retention time: 0.68 minutes. MS ESI (m/z): 302.4 (M+H)+, calc. 301.

Example 24

Preparation of 3-(1-methyl-1H-indol-5-yl)-5-(3,4,5-trimethoxyphenyl)-1H-pyrrolo[2,3-b]pyridine (Compound AA)

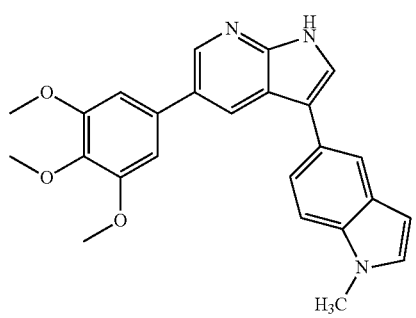 [SMILES: COc1cc(-c2cnc3[nH]cc(-c4ccc5c(ccn5C)c4)c3c2)cc(OC)c1OC]

Compound AA was prepared by a method analogous to that described in Example 1 by substituting 1-methyl-1H-indol-5-ylboronic acid for 1H-indol-5-ylboronic acid in the reaction with Intermediate A. HPLC retention time: 2.29 minutes. MS ESI (m/z): 414.4 (M+H)+, calc. 413.

Example 25

Preparation of 4-(5-(3,4,5-trimethoxyphenyl)-1H-pyrrolo[2,3-b]pyridin-3-yl)benzamide (Compound AB)

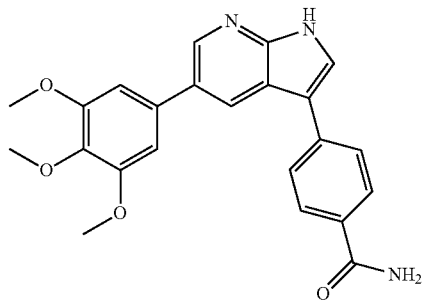 [SMILES: COc1cc(-c2cnc3[nH]cc(-c4ccc(C(N)=O)cc4)c3c2)cc(OC)c1OC]

Compound AB was prepared by a method analogous to that described in Example 1 by substituting 4-carbamoylphenylboronic acid for 1H-indol-5-ylboronic acid in the reaction with Intermediate A. HPLC retention time: 1.64 minutes. MS ESI (m/z): 404.6 (M+H)+, calc. 403.

Example 26

Preparation of 4-(5-(3,4-dimethoxyphenyl)-1H-pyrrolo[2,3-b]pyridin-3-yl)benzamide (Compound AC)

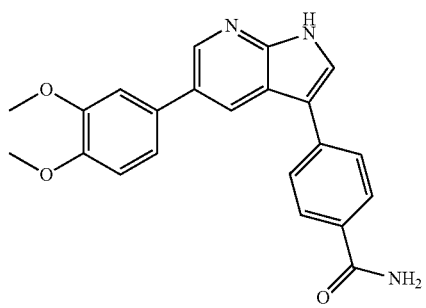 [SMILES: COc1ccc(-c2cnc3[nH]cc(-c4ccc(C(N)=O)cc4)c3c2)cc1OC]

Compound AC was prepared by a method analogous to that described in Example 1 by substituting 4-carbamoylphenylboronic acid for 1H-indol-5-ylboronic acid in the reaction with Intermediate A and 3,4-dimethoxyphenylboronic acid for 3,4,5-trimethoxyphenylboronic acid in the reaction with Intermediate B. HPLC retention time: 1.60 minutes. MS ESI (m/z): 374.2 (M+H)+, calc. 373.

Example 27

Preparation of 4-(5-(4-amino-3-methoxyphenyl)-1H-pyrrolo[2,3-b]pyridin-3-yl)benzamide (Compound AD)

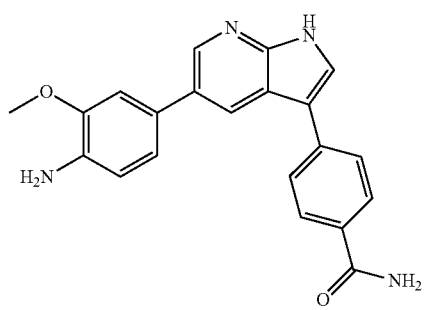 [SMILES: COc1cc(-c2cnc3[nH]cc(-c4ccc(C(N)=O)cc4)c3c2)ccc1N]

Compound AD was prepared by a method analogous to that described in Example 1 by substituting 4-carbamoylphenylboronic acid for 1H-indol-5-ylboronic acid in the reaction with Intermediate A and 4-amino-3-methoxyphenylboronic acid for 3,4,5-trimethoxyphenylboronic acid in the reaction with Intermediate B. HPLC retention time: 1.46 minutes. MS ESI (m/z): 359.2 (M+H)+, calc. 358.

Example 28

Preparation of 4-(5-(6-aminopyridin-3-yl)-1H-pyrrolo[2,3-b]pyridin-3-yl)benzamide (Compound AE)

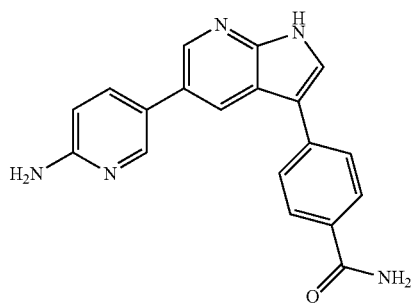 [SMILES: NC(=O)c1ccc(-c2c[nH]c3ncc(-c4ccc(N)nc4)cc23)cc1]

Compound AE was prepared by a method analogous to that described in Example 1 by substituting 4-carbamoylphenylboronic acid for 1H-indol-5-ylboronic acid in the reaction with Intermediate A and 5-(4,4,5,5-tetramethyl-1,3,2-dioxaborolan-2-yl)pyridin-2-amine for 3,4,5-trimethoxyphenylboronic acid in the reaction with Intermediate B. HPLC retention time: 1.13 minutes. MS ESI (m/z): 330.4 (M+H)+, calc. 329.

Example 29

Preparation of 5-(3-(3-chloro-4-fluorophenyl)-1H-pyrrolo[2,3-b]pyridin-5-yl)pyridin-2-amine (Compound AF)

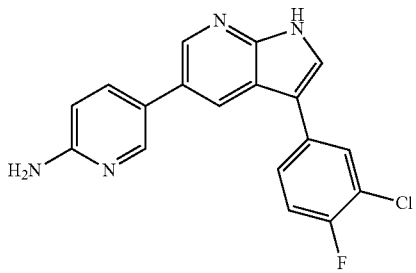 [SMILES: Nc1ccc(-c2cnc3[nH]cc(-c4ccc(F)c(Cl)c4)c3c2)cn1]

Compound AF was prepared by a method analogous to that described in Example 1 by substituting 3-chloro-4-fluorophenylboronic acid for 1H-indol-5-ylboronic acid in the reaction with Intermediate A and 5-(4,4,5,5-tetramethyl-1,3,2-dioxaborolan-2-yl)pyridin-2-amine for 3,4,5-trimethoxyphenylboronic acid in the reaction with Intermediate B. HPLC retention time: 1.47 minutes. MS ESI (m/z): 339.4 (M+H)+, calc. 338.

Example 30

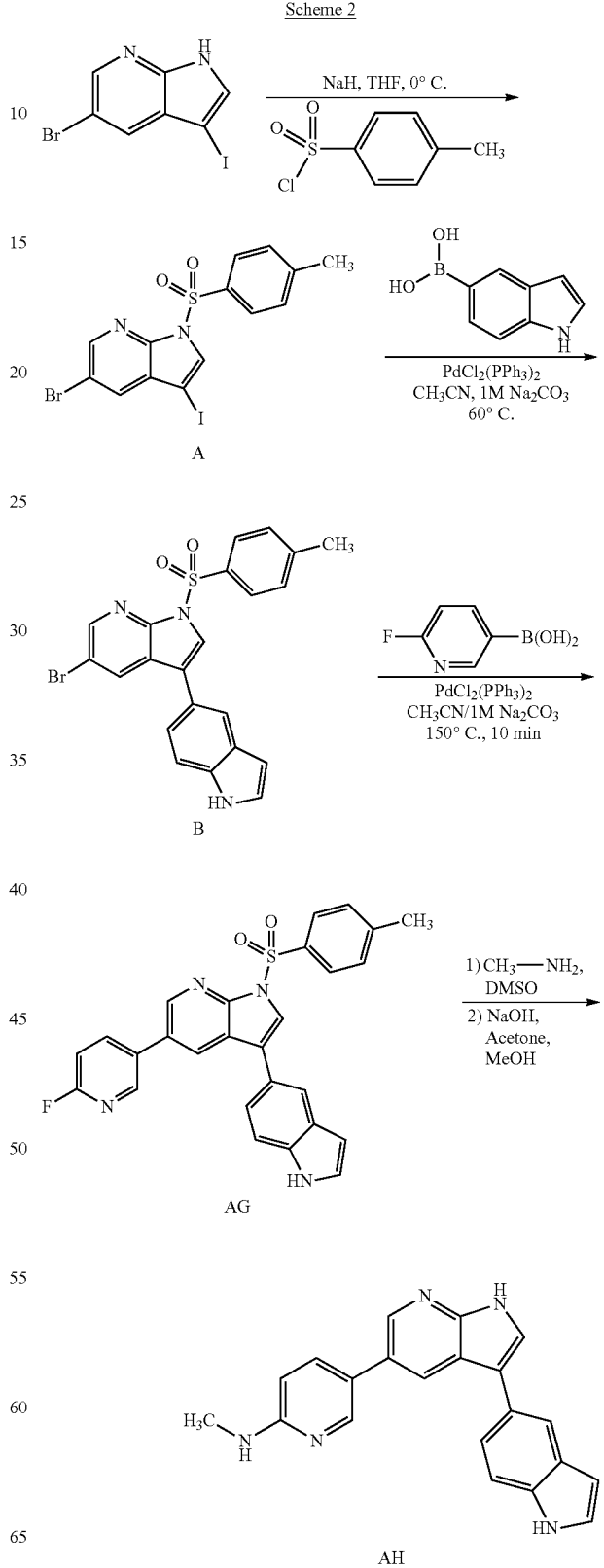

45

Preparation of 5-(3-(1H-indol-5-yl)-1H-pyrrolo[2,3-b]pyridin-5-yl)-N-methylpyridin-2-amine (Compound AH)

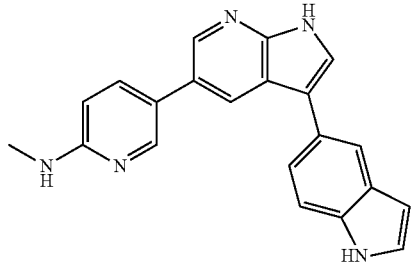 [SMILES: CNc1ccc(-c2cnc3[nH]cc(-c4ccc5[nH]ccc5c4)c3c2)cn1]

To a solution of 5-bromo-3-(1H-indol-5-yl)-1-tosyl-1H-pyrrolo[2,3-b]pyridine (40 mg, 0.09 mmol) in CH$_3$CN (1 mL) in a Personal Chemistry microwave reaction vial was added 6-fluoropyridin-3-ylboronic acid (12 mg, 0.09 mmol), bis(triphenylphosphine)-palladium(II) dichloride (5.0 mg, 0.007 mmol), and 1 M Na$_2$CO$_3$ (1 mL). The resulting mixture was de-gassed with Ar for 10 min, after which it was heated at 150° C. for 10 min in a Personal Chemistry Optimizer. The organic layer was separated, filtered, and concentrated in vacuo to give intermediate Q. The residue was dissolved in DMSO (0.5 mL) and methylamine hydrochloride salt (29 mg, 0.43 mmol), and K$_2$CO$_3$ (95 mg, 0.70 mmol) were added. The resulting mixture was stirred at 80° C. for 48 hr, after which it was diluted with DMF (0.5 mL), filtered, and subjected to preparative HPLC to yield the title compound (6.0 mg, 21%). $^1$H NMR (DMSO-d6, 300 MHz): δ 11.77 (s, 1H), 11.07 (s, 1 H), 8.46 (d, J=2.1 Hz, 1H), 8.34 (dd, J=2.4, 9.3 Hz, 1H), 7.90 (s, 1H), 7.86 (m, 1H), 7.74 (d, J=2.7 Hz, 1 H), 7.47 (s, 2H), 7.35 (s, 1 H), 6.80 (s, 1 H), 6.63 (d, J=8.4 Hz, 1 H), 6.48 (m, 1H), 2.84 (d, J=4.5 Hz, 1 H). HPLC retention time: 1.10 minutes; HPLC retention time: 1.56 minutes; MS ESI (m/z): 340.2 (M+1)$^+$, calc. 339.

Example 31

Preparation of 5-(3-(1H-indol-5-yl)-1H-pyrrolo[2,3-b]pyridin-5-yl)-N-(2-(pyrrolidin-1-yl)ethyl)pyridin-2-amine (Compound AI)

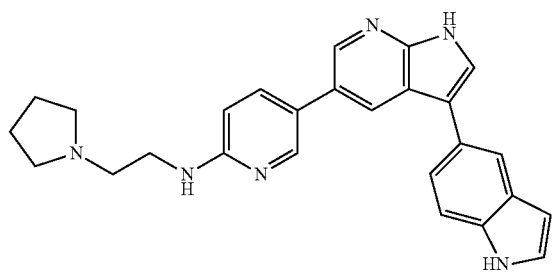 [SMILES: c1cc2cc(-c3c[nH]c4ncc(-c5ccc(NCCN6CCCC6)nc5)cc34)ccc2[nH]1]

Compound AI was prepared by a method analogous to that described in Example 15 by substituting 2-(pyrrolidin-1-yl)ethanamine for methylamine hydrochloride salt in the reaction with intermediate Q. HPLC retention time: 1.58 minutes. MS ESI (m/z): 354.4 (M+H)$^+$, calc. 353.

46

Example 32

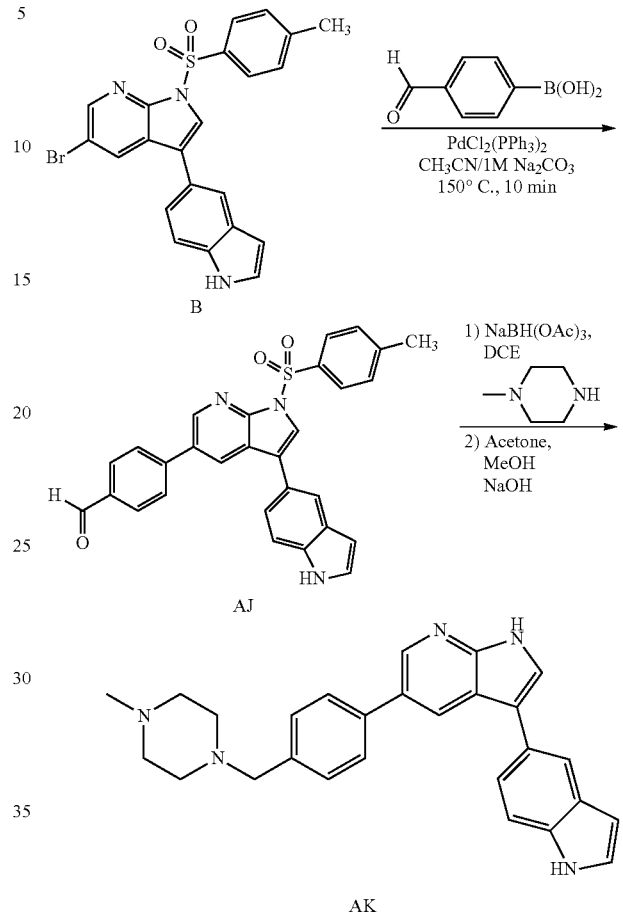

Preparation of 4-(3-(1H-indol-5-yl)-1-tosyl-1H-pyrrolo[2,3-b]pyridin-5-yl)benzaldehyde (Intermediate AJ)

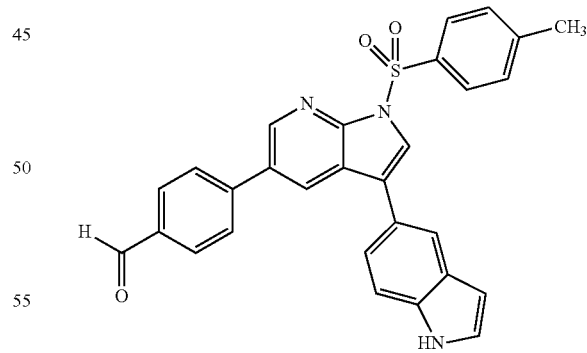

To a solution of 5-bromo-3-(1H-indol-5-yl)-1-tosyl-1H-pyrrolo[2,3-b]pyridine [Intermediate B] (0.20 g, 0.43 mmole) in CH$_3$CN (4 mL) in a Personal Chemistry microwave reaction vial was added 4-formylphenylboronic acid (64 mg, 0.43 mmol), bis(triphenylphosphine)-palladium(II) dichloride (40 mg, 0.057 mmol), and 1 M Na$_2$CO$_3$ (2 mL). The resulting mixture was de-gassed with Ar for 10 min, after which it was heated at 150° C. for 10 min in a Personal Chemistry Optimizer. The organic layer was separated, filtered, and partitioned between EtOAc and brine. The organic layer was dried over MgSO$_4$, filtered, and concentrated in vacuo to give Intermediate AJ. HPLC retention time: 3.01 minutes. MS ESI (m/z): 492.4 (M+H)+, calc. 491.

Preparation of 3-(1H-indol-5-yl)-5-(4-((4-methylpiperazin-1-yl)methyl)phenyl)-1H-pyrrolo[2,3-b]pyridine (Compound AK)

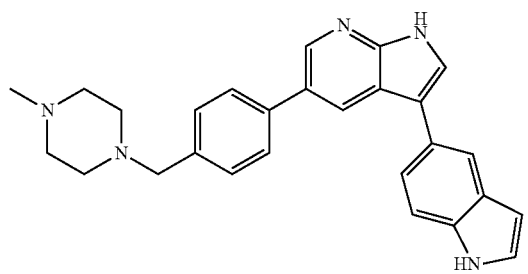 [SMILES: CN1CCN(Cc2ccc(-c3cnc4[nH]cc(-c5ccc6[nH]ccc6c5)c4c3)cc2)CC1]

To a solution of 4-(3-(1H-indol-5-yl)-1-tosyl-1H-pyrrolo[2,3-b]pyridin-5-yl)benzaldehyde [Intermediate AJ] (0.11 g, 0.214 mmol) in CH$_2$Cl$_2$ (3 mL) was added 1-methylpiperazine (40 μL, 0.40 mmol) and sodium triacetoxyborohydride (68 mg, 0.32 mmol). The reaction mixture was stirred for 1 hr at room temperature, after which it was partitioned between CH$_2$Cl$_2$ and 1 M NaOH. The organic layer was separated, dried over MgSO$_4$, and concentrated in vacuo. The residue was dissolved in 3:2 MeOH:acetone (5 mL), and 2 M NaOH (1.5 mL) was added. The resulting mixture was stirred at 65° C. for 30 min, after which it was partitioned between EtOAc and 1 M NaOH. The organic layer was separated, dried over MgSO$_4$, filtered, and stripped to provide a residue that was subjected to preparatory HPLC to yield the title compound. HPLC retention time: 1.63 minutes; MS ESI (m/z) 422.4 (M+1)+, calc. 421.

Example 33

Preparation of 1-(4-(3-(1H-indol-5-yl)-1H-pyrrolo[2,3-b]pyridin-5-yl)phenyl)-N,N-dimethylmethanamine (Compound AL)

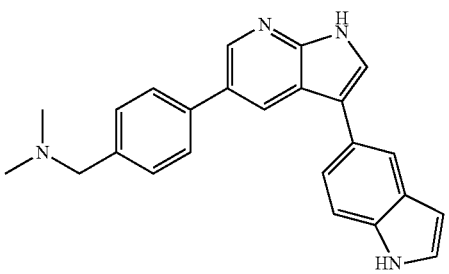 [SMILES: CN(C)Cc1ccc(-c2cnc3[nH]cc(-c4ccc5[nH]ccc5c4)c3c2)cc1]

Compound AL was prepared by a method analogous to that described in Example 33 by substituting dimethylamine (2 M solution in THF) for 1-methylpiperazine in the reaction with intermediate T. HPLC retention time: 1.66 minutes. MS ESI (m/z): 367.4 (M+H)+, calc. 366.

Example 34

Scheme 4

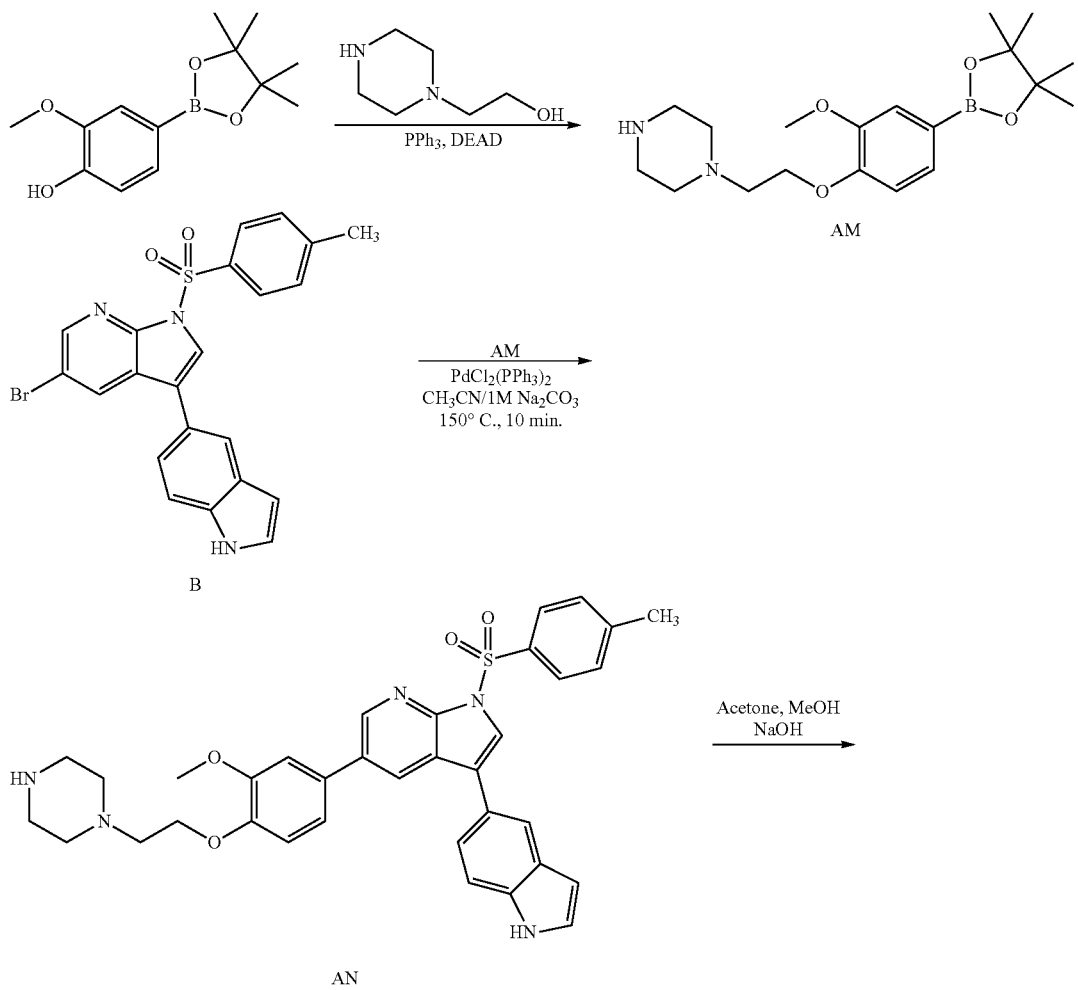

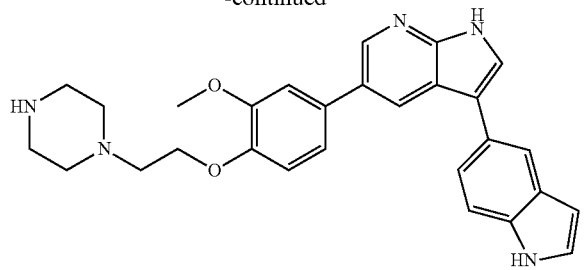

AO

Preparation of 1-(2-(2-methoxy-4-(4,4,5,5-tetramethyl-,3,2-dioxaborolan-2-yl)phenoxy)ethyl)piperazine (Intermediate AM)

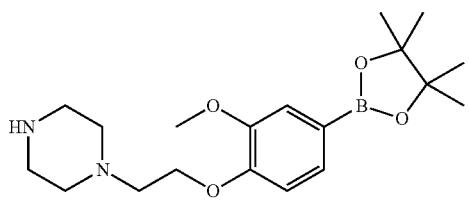 [SMILES: COc1cc(B2OC(C)(C)C(C)(C)O2)ccc1OCCN1CCNCC1]

To a solution of 2-(piperazin-1-yl)ethanol (0.78 mL, 6.0 mmol) and triphenylphosphine (1.6 g, 6.0 mmol) in anhydrous THF (20 mL) at 0° C. was added diethyl azodicarboxylate (0.95 mL, 6.0 mmol), followed by 2-methoxy-4-(4,4,5,5-tetramethyl-1,3,2-dioxaborolan-2-yl)phenol (1.0 g, 4.0 mmol). After stirring for 4 h at rt, additional triphenylphosphine (1.6 g, 6.0 mmol) and diethyl azodicarboxylate (0.95 mL, 6.0 mmol) were added. After stirring for an additional 2 h, the resulting mixture was evaporated to dryness in vacuo and the residue was purified via silica gel chromatography eluting with 15% MeOH in $CH_2Cl_2$ to yield a yellow oil (1.89 g) which contained approximately 60% of the title compound by HPLC analysis. HPLC retention time: 1.01 minutes. MS ESI (m/z): 363.6 (M+H)$^+$, calc. 362.

Preparation of 3-(1H-indol-5-yl)-5-(3-methoxy-4-(2-(piperazin-1-yl)ethoxy)phenyl)-1H-pyrrolo[2,3-b]pyridine (Compound AO)

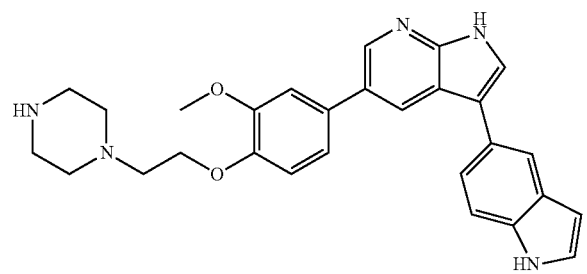 [SMILES: COc1cc(-c2cnc3[nH]cc(-c4ccc5[nH]ccc5c4)c3c2)ccc1OCCN1CCNCC1]

To a solution of 5-bromo-3-(1H-indol-5-yl)-1-tosyl-1H-pyrrolo[2,3-b]pyridine (Intermediate B) (92 mg, 0.20 mmol) in $CH_3CN$ (2 mL) in a Personal Chemistry microwave reaction vial was added 1-(2-(2-methoxy-4-(4,4,5,5-tetramethyl-1,3,2-dioxaborolan-2-yl)phenoxy)ethyl)piperazine (Intermediate AM) (72 mg, 0.20 mmol), bis(triphenylphosphine)-palladium(II) dichloride (20 mg, 0.028 mmol), and 1 M $Na_2CO_3$ (2 mL). The resulting mixture was de-gassed with Ar for 10 min, after which it was heated at 150° C. for 25 min in a Personal Chemistry Optimizer. The organic layer was separated, filtered, and concentrated in vacuo to give Intermediate AN. The residue was dissolved in MeOH (3 mL) and acetone (2 mL), and 2 M NaOH (1.5 mL) was added. The resulting mixture was stirred at 50° C. for 2 h, after which it was partitioned between EtOAc and 1 M NaOH. The organic layer was separated, dried over $MgSO_4$, filtered, and stripped to give a residue that was subjected to preparatory HPLC to yield the title compound. HPLC retention time: 1.29 minutes; MS ESI (m/z) 468.6 (M+1)$^+$, calc. 467.

Example 35

Preparation of 2-(4-(3-(1H-indol-5-yl)-1H-pyrrolo[-2,3-b]pyridin-5-yl)-2-methoxyphenoxy)-N,N-dimethylethanamine (Compound AP)

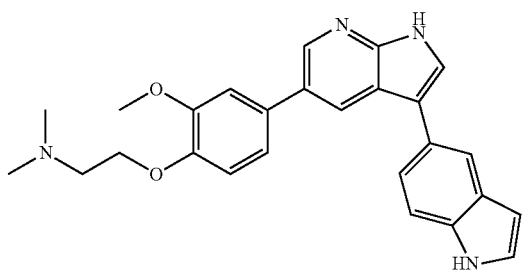 [SMILES: COc1cc(-c2cnc3[nH]cc(-c4ccc5[nH]ccc5c4)c3c2)ccc1OCCN(C)C]

Compound AP was prepared by a method analogous to that described in Example 36 by substituting 2-(dimethylamino)ethanol for 2-(piperazin-1-yl)ethanol in the reaction with 2-methoxy-4-(4,4,5,5-tetramethyl-1,3,2-dioxaborolan-2-yl)phenol. HPLC retention time: 1.20 minutes. MS ESI (m/z): 427.2 (M+H)$_+$, calc. 426.

Example 36

Scheme 5

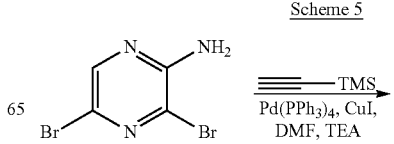

-continued

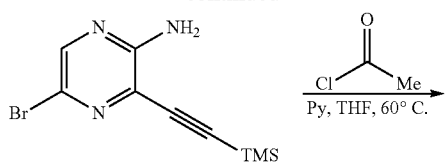

AQ

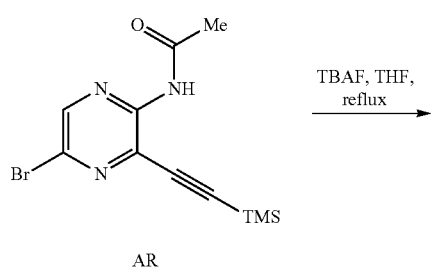

AR

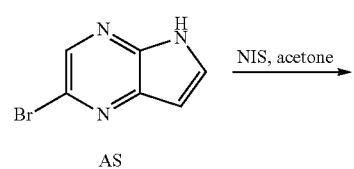

AS

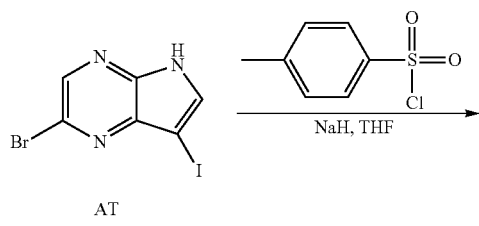

AT

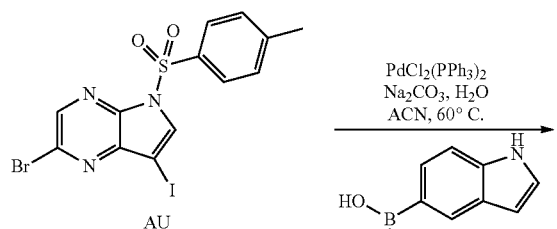

AU

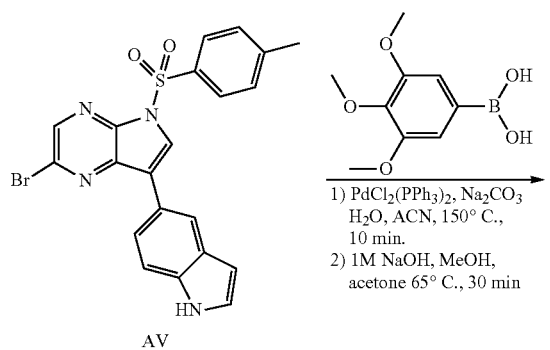

AV

-continued

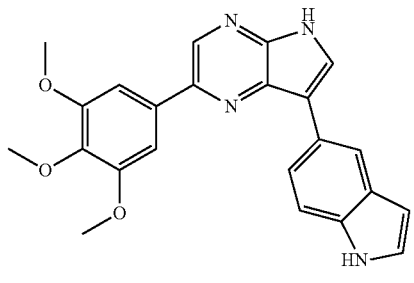

AW

Preparation of 5-bromo-3-((trimethylsilyl)ethynyl)pyrazin-2-amine (Intermediate AQ)

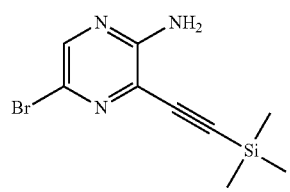

To a solution of 3,5-dibromopyrazin-2-amine (10 g, 40 mmol), copper(I) iodide (0.91 g, 4.7 mmol), diisopropylethylamine (53 mL, 0.55 mol), and tetrakis(triphenylphosphine)palladium(0) (2.3 g, 1.9 mmol) in DMF (120 mL) that was de-gassed with Ar was added trimethylsilylacetylene (6.7 mL, 48 mmol). The resulting mixture was stirred under an Ar atmosphere for 1 h at 120° C., after which it was evaporated to dryness in vacuo. The residue was subjected to silica gel chromatography eluting with 35% EtOAc in hexanes to give a brown oil that was triturated with hexanes to give the title compound (5.0 g, 47%). $^1$H NMR (CDCl$_3$, 300 MHz): δ 8.04 (s, 1H), 5.10 (s, 2 H), 0.28 (s, 9H). HPLC retention time: 2.75 minutes. MS ESI (m/z): 270.0, 272.0 (M+H)$_+$, calc. 269.

Preparation of N-(5-bromo-3-((trimethylsilyl)ethynyl)pyrazin-2-yl)acetamide (Intermediate AR)

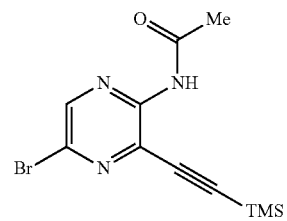 [SMILES: CC(=O)Nc1ncc(Br)nc1C#C[Si](C)(C)C]

To a solution of 5-bromo-3-((trimethylsilyl)ethynyl)pyrazin-2-amine (5.0 g, 19 mmol) and pyridine (3.8 mL, 46 mmol) in anhydrous THF (75 mL) was added acetyl chloride (1.6 mL, 23 mmol) in a drop-wise manner. After stirring for 48 hr at rt, additional acetyl chloride (0.4 mL, 6 mmol) was added and the mixture was stirred for an additional 48 hr at rt. The solvent was removed in vacuo, and the residue was diluted with 30% EtOAc in hexanes. The mixture was filtered, and the filtrate was purified via silica gel chromatography eluting with 30% EtOAc in hexanes to give a yellow-brown solid (1.8 g, 31%). $^1$H NMR (CDCl$_3$, 300 MHz): δ 8.34 (s, 1H), 8.08 (s, 1 H), 2.46 (s, 3 H), 0.32 (s, 9H). HPLC retention time: 2.29 minutes. MS ESI (m/z): 312.2, 314.2 (M+H)+, calc. 311.

Preparation of 2-bromo-5H-pyrrolo[3,2-b]pyrazine (Intermediate AS)

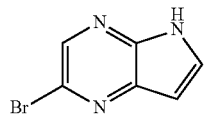

A solution of N-(5-bromo-3-((trimethylsilyl)ethynyl)pyrazin-2-yl)acetamide [Intermediate AR] (2.6 g, 8.4 mmol) and tetrabutylammonium fluoride [1 M in THF] (18 mL, 18 mmol) in anhydrous THF (26 mL) was heated at 75° C. for 20 h, after which it was partitioned between EtOAc and H₂O. The organic layer was washed with brine, dried over Na₂SO₄, and evaporated in vacuo to yield a residue that was purified via silica gel chromatography eluting with 30% EtOAc in hexanes to give the title compound as a tan solid (0.69 g, 42%). ¹H NMR (CDCl₃, 300 MHz): δ 8.88 (bs, 1H), 8.34 (s, 1 H), 7.62 (t, J=3.3 Hz, 1 H), 6.71 (dd, J=3.6 Hz, 3.9 Hz, 1 H). HPLC retention time: 1.73 minutes. MS ESI (m/z): 198.2, 200.2 (M+H)+, calc. 197.

Preparation of 2-bromo-7-iodo-5H-pyrrolo[3,2-b]pyrazine (Intermediate AT)

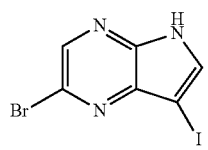 [SMILES: Brc1cnc2[nH]cc(I)c2n1]

To a solution of 2-bromo-5H-pyrrolo[3,2-b]pyrazine [Intermediate AS](0.68 g, 3.4 mmol) in acetone (17 mL) was added N-iodosuccinimide (0.82 g, 3.6 mmol) and the resulting mixture was stirred for 4 h at rt. The mixture was evaporated in vacuo to yield a residue that was purified via silica gel chromatography eluting with 40% THF in hexanes to give the title compound as a yellow solid (0.99 g, 89%). ¹H NMR (DMSO-d6, 300 MHz): δ 12.82 (s, 1H), 8.42 (s, 1 H), 8.20 (s, 1 H). HPLC retention time: 2.23 minutes. MS ESI (m/z): 324.0, 326.0 (M+H)+, calc. 323.

Preparation of 2-bromo-7-iodo-5-tosyl-5H-pyrrolo[3,2-b]pyrazine (Intermediate AU)

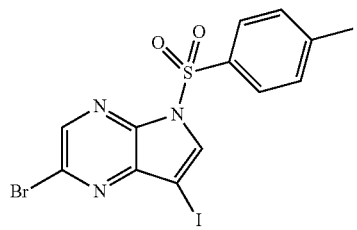 [SMILES: Cc1ccc(S(=O)(=O)n2cc(I)c3nc(Br)cnc32)cc1]

To a stirred solution of 2-bromo-7-iodo-5H-pyrrolo[3,2-b]pyrazine [Intermediate AT] (1.1 g, 3.5 mmol) in anhydrous THF (20 mL) cooled to 0° C. was added NaH [60% dispersion in mineral oil] (0.17 g, 4.3 mmol). The reaction mixture was stirred for 20 min at 0° C., after which p-toluenesulfonyl chloride (0.73 g, 3.8 mmol) in THF (8 mL) was added. The resulting mixture was stirred at rt for 3 hr, after which it was diluted with EtOAc and washed with H₂O and brine. The organic layer was separated, dried over Na₂SO₄, filtered, and evaporated in vacuo to yield a residue that was triturated with hexanes to yield the title compound (1.6 g, 94%) as a light yellow powder. ¹H NMR (DMSO-d6, 300 MHz) δ 8.62 (d, J=7.5 Hz, 2 H), 8.03 (s, 1 H), 8.00 (s, 1H), 7.47 (d, J=8.1 Hz, 2 H), 2.37 (s, 3H). HPLC retention time: 2.84 minutes. MS ESI (m/z): 478.0/480.0 (M+H)+, calc. 477.

Preparation of 2-bromo-7-(1H-indol-5-yl)-5-tosyl-5H-pyrrolo[3,2-b]pyrazine (Intermediate AV)

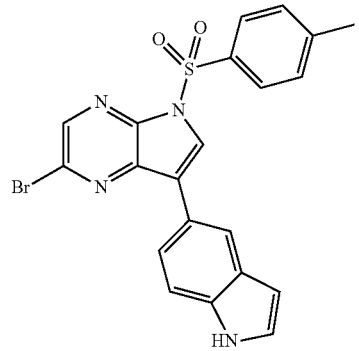 [SMILES: Cc1ccc(S(=O)(=O)n2cc(-c3ccc4[nH]ccc4c3)c3nc(Br)cnc32)cc1]

To a stirred suspension of 2-bromo-7-iodo-5-tosyl-5H-pyrrolo[3,2-b]pyrazine [Intermediate AU] (0.25 g, 0.52 mmol) and 1H-indol-5-ylboronic acid (0.10 mg, 0.62 mmol) in CH₃CN (20 mL) was added 1 M Na₂CO₃ (20 mL) followed by bis(triphenylphosphine)-palladium(II) dichloride (60 mg, 0.086 mmol). The resulting mixture was stirred for 2 h at 60° C. The title compound was isolated as a yellow solid via filtration from the CH₃CN layer (0.23 g, 94%). HPLC retention time: 3.23 minutes. MS ESI (m/z): 467.2/469.2 (M+H)+, calc. 466.

Preparation of 7-(1H-indol-5-yl)-2-(3,4,5-trimethoxyphenyl)-5H-pyrrolo[3,2-b]pyrazine (Compound AW)

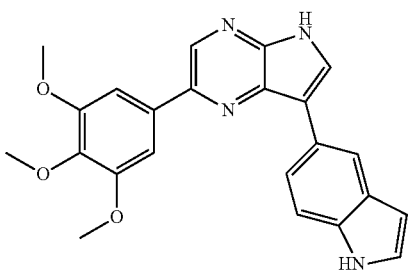 [SMILES: COc1cc(-c2cnc3[nH]cc(-c4ccc5[nH]ccc5c4)c3n2)cc(OC)c1OC]

To a solution of 2-bromo-7-(1H-indol-5-yl)-5-tosyl-5H-pyrrolo[3,2-b]pyrazine [Intermediate AV] (65 mg, 0.14 mmol) in CH₃CN (1 mL) in a Personal Chemistry microwave reaction vial was added 3,4,5-trimethoxyphenylboronic acid (30 mg, 0.14 mmol), bis(triphenylphosphine)-palladium(II) dichloride (7.0 mg, 0.010 mmol), and 1 M Na₂CO₃ (1 mL). The resulting mixture was de-gassed with Ar for 10 min, after which it was heated at 150° C. for 10 min in a Personal Chemistry Optimizer. The organic layer was separated, filtered, and concentrated in vacuo. The residue was dissolved in MeOH (3 mL) and acetone (2 mL), and 2 M NaOH (1.5 mL) was added. The resulting mixture was stirred at 65° C. for 30 min, after which it was partitioned between EtOAc and 1 M NaOH. The organic layer was separated, dried over MgSO$_4$, filtered, and stripped to give a residue which was purified by preparatory HPLC to give the title compound as a yellow solid. HPLC retention time: 2.25 minutes; MS ESI (m/z) 401.2 (M+1)$^+$, calc. 400.

Example 37

Preparation of 2-(3,4-dimethoxyphenyl)-7-(1H-indol-5-yl)-5H-pyrrolo[3,2-b]pyrazine (Compound AX)

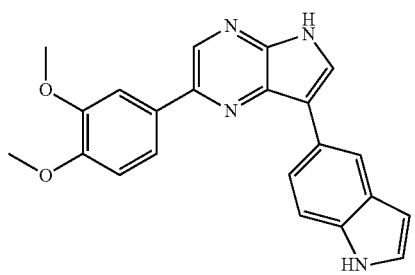 [SMILES: COc1ccc(-c2cnc3[nH]cc(-c4ccc5[nH]ccc5c4)c3n2)cc1OC]

Compound AX was prepared by a method analogous to that described in Example 38 by substituting 3,4-dimethoxyboronic acid for 3,4,5-trimethoxyphenylboronic acid in the reaction with intermediate AV. HPLC retention time: 2.45 minutes. MS ESI (m/z): 371.2 (M+H)$^+$, calc. 370.

Example 38

Preparation of 4-(7-(1H-indol-5-yl)-5H-pyrrolo[3,2-b]pyrazin-2-yl)-2-methoxyaniline (Compound AY)

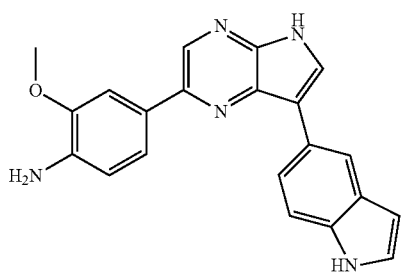 [SMILES: COc1cc(-c2cnc3[nH]cc(-c4ccc5[nH]ccc5c4)c3n2)ccc1N]

Compound AY was prepared by a method analogous to that described in Example 38 by substituting 4-amino-3-methoxyphenylboronic acid for 3,4,5-trimethoxyphenylboronic acid in the reaction with intermediate AV. HPLC retention time: 2.07 minutes. MS ESI (m/z): 356.4 (M+H)$^+$, calc. 355.

Example 39

Preparation of 4-(2-(4-(7-(1H-indol-5-yl)-5H-pyrrolo[3,2-b]pyrazin-2-yl)-2-methoxyphenoxy)ethyl)morpholine (Compound AZ)

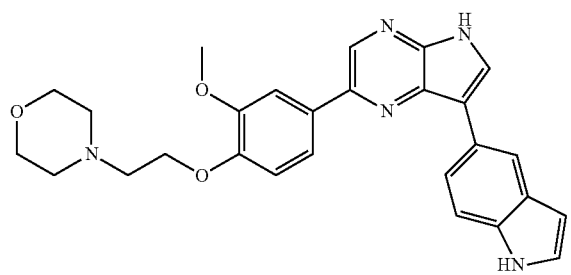 [SMILES: COc1cc(-c2cnc3[nH]cc(-c4ccc5[nH]ccc5c4)c3n2)ccc1OCCN1CCOCC1]

Compound AZ was prepared by a method analogous to that described in Example 36 by substituting 4-(2-(2-methoxy-4-(4,4,5,5-tetramethyl-1,3,2-dioxaborolan-2-yl)phenoxy)ethyl)morpholine for 1-(2-(2-methoxy-4-(4,4,5,5-tetramethyl-1,3,2-dioxaborolan-2-yl)phenoxy)ethyl)piperazine and 2-bromo-7-(1H-indol-5-yl)-5-tosyl-5H-pyrrolo[3,2-b]pyrazine for intermediate B. HPLC retention time: 1.59 minutes. MS ESI (m/z): 470.4 (M+H)$^+$, calc. 469.

Example 40

Scheme 6

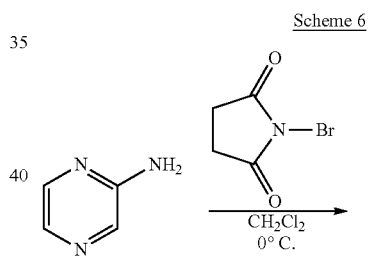

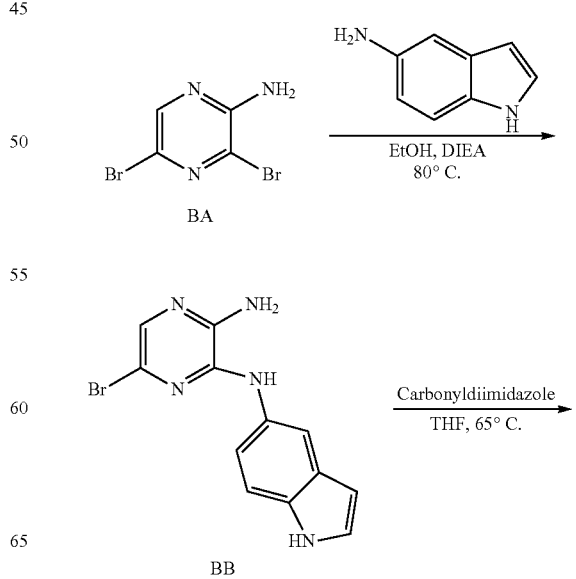

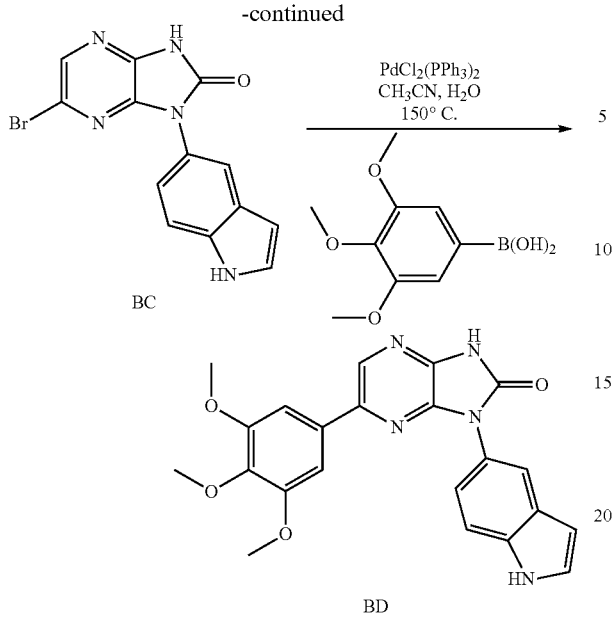

Preparation of 3,5-dibromopyrazin-2-amine (Intermediate BA)

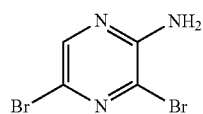

To a stirred solution of aminopyrazine (8.21 g, 86.4 mmol) in anhydrous methylene chloride (215 mL) cooled to 0° C. was added N-bromosuccinimide (32.3 g, 181 mmol) in portions over a six hour period, during which time the temperature of the reaction was kept below 0° C. The resulting mixture was stored at 4° C. overnight, after which it was stirred vigorously and quenched with H$_2$O (100 mL). The organic layer was separated, after which it was washed with saturated aqueous NaHCO$_3$, washed with brine, dried over MgSO$_4$, filtered, and evaporated in vacuo to yield a residue that was triturated with 20% EtOAc in hexanes to yield the title compound (10.3 g, 47%) as a yellow/brown powder. $^1$H NMR (CDCl$_3$, 300 MHz) δ 8.02 (s, 1H), 5.05 (bs, 2H); HPLC retention time: 1.99 minutes; MS ESI (m/z): 252.0/254.0/256.2 (M+1)$^+$, calc. 251.

Preparation of 6-bromo-N$^2$-(1H-indol-5-yl)pyrazine-2,3-diamine (Intermediate BB)

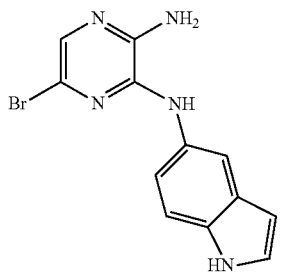 [SMILES: Nc1ncc(Br)nc1Nc1ccc2[nH]ccc2c1]

To a stirred suspension of 3,5-dibromopyrazin-2-amine (3.48 g, 13.7 mmol) and 1H-indol-5-amine (2.00 g, 15.0 mmol) in EtOH (3.5 mL) was added diisopropylethylamine [DIEA] (2.60 mL, 15.0 mmol). The resulting mixture was stirred for 48 hr at 80° C., after which it was partitioned between EtOAc and H$_2$O. The organic layer was separated, after which it was washed with brine, dried over Na$_2$SO$_4$, filtered, and evaporated in vacuo to yield a residue that was purified via silica gel chromatography eluting with 1:1 EtOAc:hexanes to yield the title compound (1.75 g, 42%) as a red/brown solid. $^1$H NMR (DMSO-d6, 300 MHz): δ 10.98 (s, 1H), 8.22 (s, 1H), 7.83 (s, 1H), 7.31-7.28 (m, 3H), 7.19 (d, J=8.7 Hz, 1H), 6.43 (s, 2H), 6.36 (s, 1H); HPLC retention time: 2.07 minutes; MS ESI (m/z): 304.2/306.2 (M+1)$^+$, calc. 303.

Preparation of 6-bromo-1-(1H-indol-5-yl)-1H-imidazo[4,5-b]pyrazin-2(3H)-one (Intermediate BC)

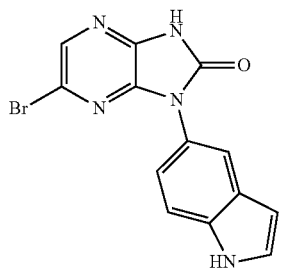 [SMILES: O=c1[nH]c2ncc(Br)nc2n1-c1ccc2[nH]ccc2c1]

To a solution of 6-bromo-N$^2$-(1H-indol-5-yl)pyrazine-2,3-diamine (0.450 g, 1.48 mmol) in THF (5 mL) was added carbonyldiimidazole (1.20 g, 7.40 mmol). The resulting mixture was heated at 65° C. for 48 hr, after which it was concentrated in vacuo and partitioned between EtOAc and H$_2$O. The organic layer was separated, dried over MgSO$_4$, filtered, and concentrated in vacuo to yield a residue that was purified via silica gel chromatography eluting with EtOAc to yield the title compound (0.20 g, 41%). HPLC retention time: 2.07 minutes; MS ESI (m/z): 330.2/332.2 (M+1)$^+$, calc. 329.

Preparation of 1-(1H-indol-5-yl)-6-(3,4,5-trimethoxyphenyl)-1H-imidazo[4,5-b]pyrazin-2(3H)-one (Compound BD)

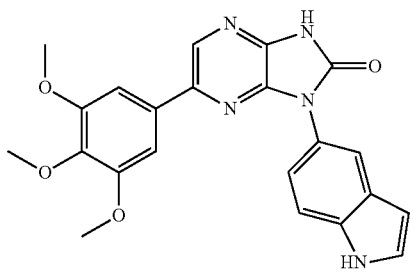 [SMILES: COc1cc(-c2cnc3[nH]c(=O)n(-c4ccc5[nH]ccc5c4)c3n2)cc(OC)c1OC]

To a solution of 6-bromo-1-(1H-indol-5-yl)-1H-imidazo[4,5-b]pyrazin-2(3H)-one (27 mg, 0.08 mmol) in CH$_3$CN (1 mL) in a Personal Chemistry microwave reaction vial was added 3,4,5-trimethoxyphenylboronic acid (17 mg, 0.08 mmol), bis(triphenylphosphine)-palladium(II) dichloride (6.0 mg, 0.008 mmol), and 1 M Na$_2$CO$_3$ (1 mL). The resulting mixture was de-gassed with Ar for 10 min, after which it was heated at 150° C. for 10 min in a Personal Chemistry Optimizer. The organic layer was separated, filtered, and concentrated in vacuo. The residue was purified by preparatory HPLC to yield the title compound (6.5 mg, 19%). ¹H NMR (DMSO-d6, 300 MHz): δ 12.18 (s, 1H), 11.28 (s, 1H), 8.57 (s, 1H), 7.83 (d, J=1.8 Hz, 1H), 7.52 (d, J=8.4 Hz, 1H), 7.42 (m, 1H), 7.37 (dd, J=1.8, 8.4 Hz, 1H), 7.20 (s, 2H), 6.51 (m, 1H), 3.78 (s, 6H), 3.66 (s, 3H); HPLC retention time: 2.30 minutes; MS ESI (m/z): 418.4 (M+1)⁺, calc. 417.

Example 41

Preparation of 1-(1-methyl-1H-indol-5-yl)-6-(3,4,5-trimethoxyphenyl)-1H-imidazo[4,5-b]pyrazin-2(3H)-one (Compound BE)

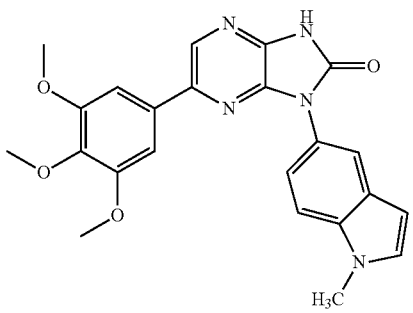 [SMILES: COc1cc(-c2cnc3[nH]c(=O)n(-c4ccc5c(ccn5C)c4)c3n2)cc(OC)c1OC]

Compound BE was prepared by a method analogous to that described in Example 1 by substituting 1-methyl-1H-indol-5-amine for 1H-indol-5-amine in the reaction with Intermediate BA. 4.0 mg recovered. ¹H NMR (DMSO-d6, 300 MHz): δ 12.22 (s, 1H), 8.57 (s, 1H), 7.85 (d, J=1.8 Hz, 1H), 7.57 (d, J=8.7 Hz, 1H), 7.45 (d, J=1.8 Hz), 7.41 (m, 2H), 7.20 (s, 2H), 6.50 (d, J=3.0 Hz, 1H), 3.84 (s, 3H), 3.78 (s, 6H), 3.66 (s, 3H); HPLC retention time: 2.50 minutes. MS ESI (m/z): 432.4 (M+H)⁺, calc. 431.

Example 42

Preparation of 6-(4-hydroxyphenyl)-1-(1-methyl-1H-indol-5-yl)-1H-imidazo[4,5-b]pyrazin-2(3H)-one (Compound BF)

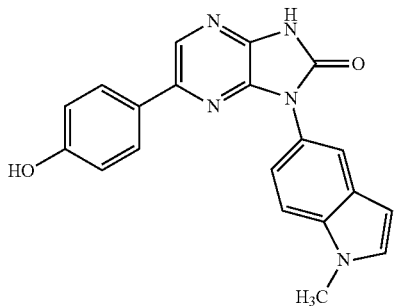 [SMILES: Cn1ccc2cc(-n3c(=O)[nH]c4ncc(-c5ccc(O)cc5)nc43)ccc21]

Compound BE was prepared by a method analogous to that described in Example 1 by substituting 1-methyl-1H-indol-5-amine for 1H-indol-5-amine in the reaction with Intermediate BA to prepare 6-bromo-1-(1-methyl-1H-indol-5-yl)-1H-imidazo[4,5-b]pyrazin-2(3H)-one. In a procedure similar to that used to synthesize Compound D, 4-hydroxyphenylboronic acid was substituted for 3,4,5-trimethoxyphenylboronic acid and 6-bromo-1-(1-methyl-1H-indol-5-yl)-1H-imidazo[4,5-b]pyrazin-2(3H)-one was substituted for 6-bromo-1-(1H-indol-5-yl)-1H-imidazo[4,5-b]pyrazin-2(3H)-one to obtain the title compound. 2.2 mg recovered. HPLC retention time: 2.18 minutes. MS ESI (m/z): 358.2 (M+H)⁺, calc. 357.

Example 43

Preparation of 6-(3,5-dimethylphenyl)-1-(1-methyl-1H-indol-5-yl)-1H-imidazo[4,5-b]pyrazin-2(3H)-one (Compound BG)

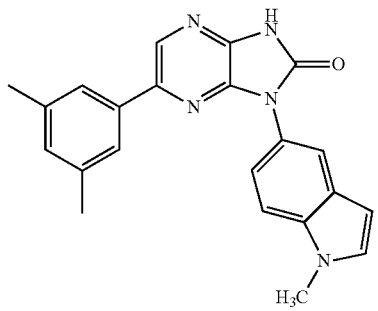 [SMILES: Cc1cc(C)cc(-c2cnc3[nH]c(=O)n(-c4ccc5c(ccn5C)c4)c3n2)c1]

Compound BG was prepared by a method analogous to that described in Example 3 by substituting 3,5-dimethylphenylboronic acid for 4-hydroxyphenylboronic acid in the reaction with 6-bromo-1-(1-methyl-1H-indol-5-yl)-1H-imidazo[4,5-b]pyrazin-2(3H)-one. 1.6 mg recovered. HPLC retention time: 3.04 minutes. MS ESI (m/z): 370.2 (M+H)⁺, calc. 369.

Example 44

Preparation of 1-(1H-indol-5-yl)-6-(pyridin-4-yl)-1H-imidazo[4,5-b]pyrazin-2(3H)-one (Compound BH)

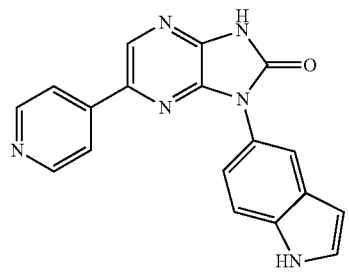 [SMILES: O=c1[nH]c2ncc(-c3ccncc3)nc2n1-c1ccc2[nH]ccc2c1]

Compound BH was prepared by a method analogous to that described in Example 1 by substituting pyridin-4-ylboronic acid for 3,4,5-trimethoxyphenylboronic acid in the reaction with Compound BC. 1.6 mg recovered. HPLC retention time: 1.10 minutes. MS ESI (m/z): 329.4 (M+H)⁺, calc. 328.

Example 45

Preparation of 6-(4-hydroxyphenyl)-1-(1H-indol-5-yl)-1H-imidazo[4,5-b]pyrazin-2(3H)-one (Compound BI)

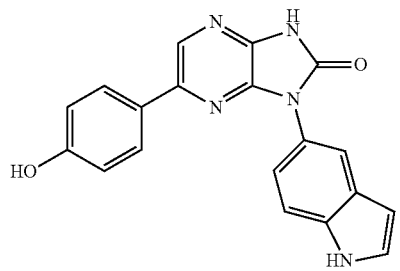 [SMILES: O=c1[nH]c2ncc(-c3ccc(O)cc3)nc2n1-c1ccc2[nH]ccc2c1]

Compound BI was prepared by a method analogous to that described in Example 1 by substituting by substituting 4-hydroxyphenylboronic acid for 3,4,5-trimethoxyphenylboronic acid in the reaction with Compound BC. 13.7 mg recovered. ¹H NMR (DMSO-d6, 300 MHz): δ 12.07 (s, 1H), 11.30 (s, 1H), 9.61 (s, 1H), 8.38 (s, 1H), 7.69 (m, 2H), 7.52 (d, J=8.4 Hz, 1H), 7.44 (m, 1H), 7.26 (dd, J=1.8, 8.7 Hz), 6.76 (dd, J=2.4, 12.9 Hz), 6.52 (m, 1H); HPLC retention time: 1.99 minutes. MS ESI (m/z): 344.2 (M+H)$^+$, calc. 343.

Example 46

Preparation of 6-(3,5-dimethylphenyl)-1-(1H-indol-5-yl)-1H-imidazo[4,5-b]pyrazin-2(3H)-one (Compound BJ)

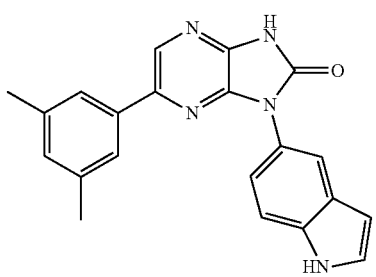 [SMILES: Cc1cc(C)cc(-c2cnc3[nH]c(=O)n(-c4ccc5[nH]ccc5c4)c3n2)c1]

Compound BJ was prepared by a method analogous to that described in Example 1 by substituting 3,5-dimethylphenylboronic acid for 3,4,5-trimethoxyphenylboronic acid in the reaction with Compound BC. 4.3 mg recovered. HPLC retention time: 2.80 minutes. MS ESI (m/z): 356.2 (M+H)$^+$, calc. 355.

Examples 47-119

Examples 47-119, shown in Table 3 below, were synthesized in parallel according to procedures given below in Schemes 7 and 8, using the reagents in Tables 1 and 2.

Examples 47-67

Scheme 7

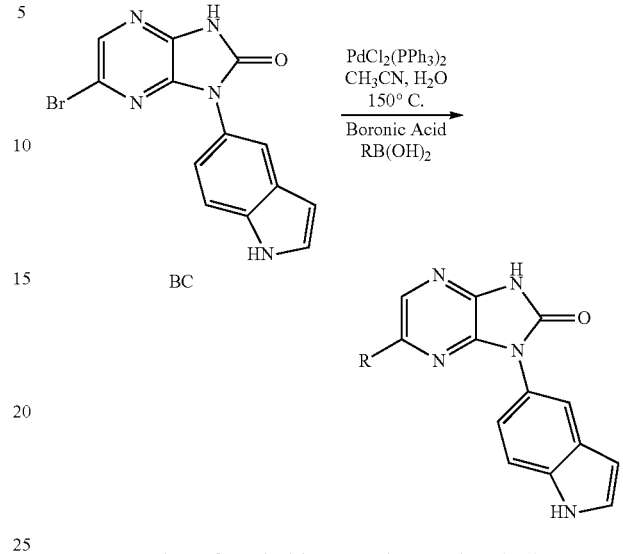

Preparation of 1H-imidazo[4,5-b]pyrazin-2(3H)-one compounds in Table 1

To a solution of 6-bromo-1-(1H-indol-5-yl)-1H-imidazo[4,5-b]pyrazin-2(3H)-one (27 mg, 0.08 mmol) in CH$_3$CN (1 mL) in a Personal Chemistry microwave reaction vial was added 3,4,5-trimethoxyphenylboronic acid (17 mg, 0.08 mmol), bis(triphenylphosphine)-palladium(II) dichloride (6.0 mg, 0.008 mmol), and 1 M Na$_2$CO$_3$ (1 mL). The resulting mixture was de-gassed with Ar for 10 min, after which it was heated at 150° C. for 10 min in a Personal Chemistry Optimizer. The organic layer was separated, filtered, and concentrated in vacuo. The residue was purified by preparatory HPLC to yield the title compounds (>3 mg) in table 1, isolated as amorphous solids.

TABLE 1

| Ex. | Boronic Acid | Purified Compound Isolated |
|---|---|---|
| 47 | 3,4-dimethoxyphenyl boronic acid | 6-(3,4-dimethoxyphenyl)-1-(1H-indol-5-yl)-1H-imidazo[4,5-b]pyrazin-2(3H)-one |
| 48 | 3,5-dichlorophenyl boronic acid | 6-(3,5-dichlorophenyl)-1-(1H-indol-5-yl)-1H-imidazo[4,5-b]pyrazin-2(3H)-one |
| 49 | 3-fluoro-4-methoxyphenyl boronic acid | 6-(3-fluoro-4-methoxyphenyl)-1-(1H-indol-5-yl)-1H-imidazo[4,5-b]pyrazin-2(3H)-one |
| 50 | 3-amino-4-methoxyphenyl boronic acid | 6-(3-amino-4-methoxyphenyl)-1-(1H-indol-5-yl)-1H-imidazo[4,5-b]pyrazin-2(3H)-one |
| 51 | 4-methoxy-3,5-dimethylphenyl boronic acid | 1-(1H-indol-5-yl)-6-(4-methoxy-3,5-dimethylphenyl)-1H-imidazo[4,5-b]pyrazin-2(3H)-one |
| 52 | 4-morpholinophenyl boronic acid | 1-(1H-indol-5-yl)-6-(4-morpholinophenyl)-1H-imidazo[4,5-b]pyrazin-2(3H)-one |
| 53 | Indole-5-boronic acid | 1,6-di(1H-indol-5-yl)-1H-imidazo[4,5-b]pyrazin-2(3H)-one |
| 54 | 3-hydroxyphenyl boronic acid | 6-(3-hydroxyphenyl)-1-(1H-indol-5-yl)-1H-imidazo[4,5-b]pyrazin-2(3H)-one |
| 55 | 4-hydroxy-3-methoxyphenyl | 6-(4-hydroxy-3-methoxyphenyl)-1-(1H-indol-5-yl)-1H-imidazo[4,5-b]pyrazin-2(3H)-one |
| 56 | indole-6-boronic | 1-(1H-indol-5-yl)-6-(1H-indol-6-yl)-1H-imidazo[4,5-b]pyrazin-2(3H)-one |
| 57 | 3-methoxy-4-(2-morpholinoethoxy)phenyl boronic acid | 1-(1H-indol-5-yl)-6-(3-methoxy-4-(2-morpholinoethoxy)phenyl)-1H-imidazo[4,5-b]pyrazin-2(3H)-one |

TABLE 1-continued

| Ex. | Boronic Acid | Purified Compound Isolated |
|---|---|---|
| 58 | 2,5-difluoro-4-hydroxyphenyl boronic acid | 6-(2,5-difluoro-4-hydroxyphenyl)-1-(1H-indol-5-yl)-1H-imidazo[4,5-b]pyrazin-2(3H)-one |
| 59 | 3,5-difluoro-4-hydroxyphenyl boronic acid | 6-(3,5-difluoro-4-hydroxyphenyl)-1-(1H-indol-5-yl)-1H-imidazo[4,5-b]pyrazin-2(3H)-one |
| 60 | 4-amino-3-methoxyphenyl boronic acid | 6-(4-amino-3-methoxyphenyl)-1-(1H-indol-5-yl)-1H-imidazo[4,5-b]pyrazin-2(3H)-one |
| 61 | 3,5-difluorophenyl boronic acid | 6-(3,5-difluorophenyl)-1-(1H-indol-5-yl)-1H-imidazo[4,5-b]pyrazin-2(3H)-one |
| 62 | 4-hydroxy-3,5-dimethoxyphenyl boronic acid | 6-(4-hydroxy-3,5-dimethoxyphenyl)-1-(1H-indol-5-yl)-1H-imidazo[4,5-b]pyrazin-2(3H)-one |
| 63 | 2,3-dihydrobenzo[b][1,4]dioxin-6-boronic acid | 6-(2,3-dihydrobenzo[b][1,4]dioxin-6-yl)-1-(1H-indol-5-yl)-1H-imidazo[4,5-b]pyrazin-2(3H)-one |
| 64 | 4-hydroxy-3,5-dimethylphenyl boronic acid | 6-(4-hydroxy-3,5-dimethylphenyl)-1-(1H-indol-5-yl)-1H-imidazo[4,5-b]pyrazin-2(3H)-one |
| 65 | 3,5-dimethoxyphenyl boronic acid | 6-(3,5-dimethoxyphenyl)-1-(1H-indol-5-yl)-1H-imidazo[4,5-b]pyrazin-2(3H)-one |
| 66 | 2-(4-methylpiperazin-1-yl)pyridin-4-boronic acid | 1-(1H-indol-5-yl)-6-(2-(4-methylpiperazin-1-yl)pyridin-4-yl)-1H-imidazo[4,5-b]pyrazin-2(3H)-one |
| 67 | (3-methoxy-4-(2-(piperazin-1-yl)ethoxy)phenyl | 1-(1H-indol-5-yl)-6-(3-methoxy-4-(2-(piperazin-1-yl)ethoxy)phenyl)-1H-imidazo[4,5-b]pyrazin-2(3H)-one |

Examples 68-118

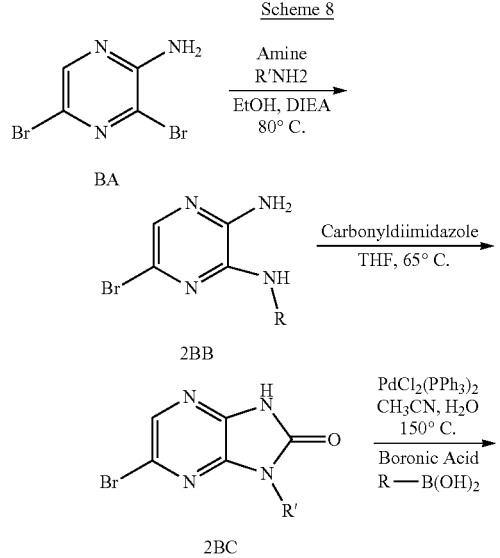

Preparation of Intermediates 2BB

To a stirred suspension of 3,5-dibromopyrazin-2-amine (3.48 g, 13.7 mmol) and the corresponding alkyl, aryl, or heteroaryl amine (15.0 mmol) in EtOH (3.5 mL) was added diisopropylethylamine [DIEA] (2.60 mL, 15.0 mmol). The resulting mixture was stirred for 48 hr at 80° C., after which it was partitioned between EtOAc and $H_2O$. The organic layer was separated, after which it was washed with brine, dried over $Na_2SO_4$, filtered, and evaporated in vacuo to yield a residue that was purified by automated medium pressure silica gel chromatography eluting with 1:1 EtOAc:hexanes to yield the intermediates as amorphous solids.

Preparation of Intermediates 2BC

Intermediates 2BB (0.450 g, 1.5 mmol) were dissolved in THF (5 mL) and treated with carbonyldiimidazole (1.20 g, 7.40 mmol). The resulting mixture was heated at 65° C. for 48 hr, after which it was concentrated in vacuo and partitioned between EtOAc and $H_2O$. The organic layer was separated, dried over $MgSO_4$, filtered, and concentrated in vacuo to yield a residue that was purified via automated silica gel chromatography eluting with hexane/EtOAc to yield the intermediates 2BC as amorphous solids.

Preparation of 1H-imidazo[4,5-b]pyrazin-2(3H)-one compounds in Table 2

Individual solutions of intermediates 2BC (0.08 mmol) in $CH_3CN$ (1 mL) in a Personal Chemistry microwave reaction vial was added the corresponding boronic acid (0.08 mmol), bis(triphenylphosphine)-palladium(II) dichloride (6.0 mg, 0.008 mmol), and 1 M $Na_2CO_3$ (1 mL). The resulting mixture was de-gassed with Ar for 10 min, after which it was heated at 150° C. for 10 min in a Personal Chemistry Optimizer. The organic layer was separated, filtered, and concentrated in vacuo. The residue was purified by preparatory HPLC to yield the title compounds in table 2 (>3 mg) as amorphous solids.

| Ex. | Boronic Acid | Amine | Purified Compound Isolated |
|---|---|---|---|
| 68 | 3,4,5-trimethoxyphenyl boronic acid | 4-methoxy-aniline | 1-(4-methoxyphenyl)-6-(3,4,5-trimethoxyphenyl)-1H-imidazo[4,5-b]pyrazin-2(3H)-one |
| 69 | 3,4-dimethoxyphenyl boronic acid | 4-methoxy-aniline | 6-(3,4-dimethoxyphenyl)-1-(4-methoxyphenyl)-1H-imidazo[4,5-b]pyrazin-2(3H)-one |
| 70 | 3,4-dimethoxyphenyl boronic acid | 4-methoxy-aniline | 6-(3,4-dimethoxyphenyl)-1-(4-methoxyphenyl)-1H-imidazo[4,5-b]pyrazin-2(3H)-one |
| 71 | pyridin-4-boronic acid boronic acid | 4-methoxy-aniline | 1-(4-methoxyphenyl)-6-(pyridin-4-yl)-1H-imidazo[4,5-b]pyrazin-2(3H)-one |
| 72 | 3,4,5-trimethoxyphenyl boronic acid | 2-methyl-5-amino-indole | 1-(2-methyl-1H-indol-5-yl)-6-(3,4,5-trimethoxyphenyl)-1H-imidazo[4,5-b]pyrazin-2(3H)-one |
| 73 | 3,5-dichlorophenyl boronic acid | 2-methyl-5-amino-indole | 6-(3,5-dichlorophenyl)-1-(2-methyl-1H-indol-5-yl)-1H-imidazo[4,5-b]pyrazin-2(3H)-one |
| 74 | 3,4,5-trimethoxyphenyl boronic acid | 1-amino-cyclopentane | 1-cyclopentyl-6-(3,4,5-trimethoxyphenyl)-1H-imidazo[4,5-b]pyrazin-2(3H)-one |
| 75 | 3,4-dimethoxyphenyl boronic acid | 1-amino-cyclopentane | 1-cyclopentyl-6-(3,4-dimethoxyphenyl)-1H-imidazo[4,5-b]pyrazin-2(3H)-one |
| 76 | 4-hydroxyphenyl boronic acid | 1-amino-cyclopentane | 1-cyclopentyl-6-(4-hydroxyphenyl)-1H-imidazo[4,5-b]pyrazin-2(3H)-one |
| 77 | pyridin-4-boronic acid | 1-amino-cyclopentane | 1-cyclopentyl-6-(pyridin-4-yl)-1H-imidazo[4,5-b]pyrazin-2(3H)-one |
| 78 | 3,4,5-trimethoxyphenyl boronic acid | Cyclopropane-methylamine | 1-(cyclopropylmethyl)-6-(3,4,5-trimethoxyphenyl)-1H-imidazo[4,5-b]pyrazin-2(3H)-one |
| 79 | 3,4-dimethoxyphenyl boronic acid | Cyclopropane-methylamine | 1-(cyclopropylmethyl)-6-(3,4-dimethoxyphenyl)-1H-imidazo[4,5-b]pyrazin-2(3H)-one |
| 80 | 3,5-dichlorophenyl boronic acid | Cyclopropane-methylamine | 1-(cyclopropylmethyl)-6-(3,5-dichlorophenyl)-1H-imidazo[4,5-b]pyrazin-2(3H)-one |
| 81 | 4-hydroxyphenyl boronic acid | Cyclopropane-methylamine | 1-(cyclopropylmethyl)-6-(4-hydroxyphenyl)-1H-imidazo[4,5-b]pyrazin-2(3H)-one |
| 82 | 4-aminopyridine boronic acid | Cyclopropane-methylamine | 1-(cyclopropylmethyl)-6-(pyridin-4-yl)-1H-imidazo[4,5-b]pyrazin-2(3H)-one |
| 83 | 3,4,5-trimethoxyphenyl boronic acid | 1H-Indazol-5-amine | 1-(1H-indazol-5-yl)-6-(3,4,5-trimethoxyphenyl)-1H-imidazo[4,5-b]pyrazin-2(3H)-one |
| 84 | 4-hydroxypheny boronic acid | 2-methyl-5-amino-indole | 6-(4-hydroxyphenyl)-1-(2-methyl-1H-indol-5-yl)-1H-imidazo[4,5-b]pyrazin-2(3H)-one |
| 85 | pyridin-4-boronic acid boronic acid | 2-methyl-5-amino-indole | 1-(2-methyl-1H-indol-5-yl)-6-(pyridin-4-yl)-1H-imidazo[4,5-b]pyrazin-2(3H)-one |
| 86 | 4-morpholinophenyl boronic acid | Cyclopropane-methylamine | 1-(cyclopropylmethyl)-6-(4-morpholinophenyl)-1H-imidazo[4,5-b]pyrazin-2(3H)-one |

-continued

| Ex. | Boronic Acid | Amine | Purified Compound Isolated |
|---|---|---|---|
| 87 | 3,4-dimethoxyphenyl boronic acid | 1H-Indazol-5-amine | 6-(3,4-dimethoxyphenyl)-1-(1H-indazol-5-yl)-1H-imidazo[4,5-b]pyrazin-2(3H)-one |
| 88 | 4-aminopyridine boronic acid | 1H-Indazol-5-amine | 1-(1H-indazol-5-yl)-6-(pyridin-4-yl)-1H-imidazo[4,5-b]pyrazin-2(3H)-one |
| 89 | 4-morpholinophenyl boronic acid | 1H-Indazol-5-amine | 1-(1H-indazol-5-yl)-6-(4-morpholinophenyl)-1H-imidazo[4,5-b]pyrazin-2(3H)-one |
| 90 | 3,4,5-trimethoxyphenyl boronic acid | 1H-Indazol-5-amine | 1-(1H-indazol-6-yl)-6-(3,4,5-trimethoxyphenyl)-1H-imidazo[4,5-b]pyrazin-2(3H)-one |
| 91 | 3,4-dimethoxyphenyl boronic acid | 1H-Indazol-5-amine | 6-(3,4-dimethoxyphenyl)-1-(1H-indazol-6-yl)-1H-imidazo[4,5-b]pyrazin-2(3H)-one |
| 92 | 4-hydroxyphenyl boronic acid | 1H-Indazol-5-amine | 6-(4-hydroxyphenyl)-1-(1H-indazol-6-yl)-1H-imidazo[4,5-b]pyrazin-2(3H)-one |
| 93 | 4-aminopyridine boronic acid | 1H-Indazol-5-amine | 1-(1H-indazol-6-yl)-6-(pyridin-4-yl)-1H-imidazo[4,5-b]pyrazin-2(3H)-one |
| 94 | 2,4,6-trimethoxyphenyl | 1-amino-cyclopentane | 1-cyclopentyl-6-(2,4,6-trimethoxyphenyl)-1H-imidazo[4,5-b]pyrazin-2(3H)-one |
| 95 | 3,5-dimethylphenyl boronic acid | 1H-Indazol-5-amine | 6-(3,5-dimethylphenyl)-1-(1H-indazol-6-yl)-1H-imidazo[4,5-b]pyrazin-2(3H)-one |
| 96 | 3,4,5-trimethoxyphenyl boronic acid | benzo[d]thiazol-5-amine | 1-(benzo[d]thiazol-5-yl)-6-(3,4,5-trimethoxyphenyl)-1H-imidazo[4,5-b]pyrazin-2(3H)-one |
| 97 | 4-hydroxyphenyl boronic acid | benzo[d]thiazol-5-amine | 1-(benzo[d]thiazol-5-yl)-6-(4-hydroxyphenyl)-1H-imidazo[4,5-b]pyrazin-2(3H)-one |
| 98 | 4-aminopyridine boronic acid | benzo[d]thiazol-5-amine | 1-(benzo[d]thiazol-5-yl)-6-(pyridin-4-yl)-1H-imidazo[4,5-b]pyrazin-2(3H)-one |
| 99 | 3,5-dimethylphenyl boronic acid | benzo[d]thiazol-5-amine | 1-(benzo[d]thiazol-5-yl)-6-(3,5-dimethylphenyl)-1H-imidazo[4,5-b]pyrazin-2(3H)-one |
| 100 | 4-morpholinophenyl boronic acid | benzo[d]thiazol-5-amine | 1-(benzo[d]thiazol-5-yl)-6-(4-morpholinophenyl)-1H-imidazo[4,5-b]pyrazin-2(3H)-one |
| 101 | 3,4,5-trimethoxyphenyl boronic acid | 2,3-dihydro-1H-inden-1-amine | 1-(2,3-dihydro-1H-inden-1-yl)-6-(3,4,5-trimethoxyphenyl)-1H-imidazo[4,5-b]pyrazin-2(3H)-one |
| 102 | 3,4,5-trimethoxyphenyl boronic acid | 1H-benzo[d]imidazol-5-amine | 1-(1H-benzo[d]imidazol-5-yl)-6-(3,4,5-trimethoxyphenyl)-1H-imidazo[4,5-b]pyrazin-2(3H)-one |
| 103 | 3,4-dimethoxyphenyl boronic acid | 1H-benzo[d]imidazol-5-amine | 1-(1H-benzo[d]imidazol-5-yl)-6-(3,4-dimethoxyphenyl)-1H-imidazo[4,5-b]pyrazin-2(3H)-one |
| 104 | 4-morpholinophenyl boronic acid | 1H-benzo[d]imidazol-5-amine | 1-(1H-benzo[d]imidazol-5-yl)-6-(4-morpholinophenyl)-1H-imidazo[4,5-b]pyrazin-2(3H)-one |

-continued

| Ex. | Boronic Acid | Amine | Purified Compound Isolated |
|---|---|---|---|
| 105 | 3,4,5-trimethoxyphenyl boronic acid | aniline | 1-phenyl-6-(3,4,5-trimethoxyphenyl)-1H-imidazo[4,5-b]pyrazin-2(3H)-one |
| 106 | 3,4-dimethoxyphenyl boronic acid | aniline | 6-(3,4-dimethoxyphenyl)-1-phenyl-1H-imidazo[4,5-b]pyrazin-2(3H)-one |
| 107 | 3-methoxy-4-(2-morpholinoethoxy) phenyl boronic acid | Cyclopropane-methylamine | 1-(cyclopropylmethyl)-6-(3-methoxy-4-(2-morpholinoethoxy)phenyl)-1H-imidazo[4,5-b]pyrazin-2(3H)-one |
| 108 | 3-methoxy-4-(2-morpholinoethoxy) phenyl | 1-amino-cyclopentane | 1-cyclopentyl-6-(3-methoxy-4-(2-morpholinoethoxy)phenyl)-1H-imidazo[4,5-b]pyrazin-2(3H)-one |
| 109 | 3,4,5-trimethoxyphenyl boronic acid | 6-morpholinopyridin-3-amine | 1-(6-morpholinopyridin-3-yl)-6-(3,4,5-trimethoxyphenyl)-1H-imidazo[4,5-b]pyrazin-2(3H)-one |
| 110 | 3,4,5-trimethoxyphenyl boronic acid | 2,3-dihydro-1H-inden-2-amine | 1-(2,3-dihydro-1H-inden-2-yl)-6-(3,4,5-trimethoxyphenyl)-1H-imidazo[4,5-b]pyrazin-2(3H)-one |
| 111 | 3,4-dimethoxyphenyl boronic acid | 1H-pyrrolo[2,3-b]pyridin-5-amine | 6-(3,4-dimethoxyphenyl)-1-(1H-pyrrolo[2,3-b]pyridin-5-yl)-1H-imidazo[4,5-b]pyrazin-2(3H)-one |
| 112 | 3,4,5-trimethoxyphenyl boronic acid | 1H-pyrrolo[2,3-b]pyridin-5-amine | 1-(1H-pyrrolo[2,3-b]pyridin-5-yl)-6-(3,4,5-trimethoxyphenyl)-1H-imidazo[4,5-b]pyrazin-2(3H)-one |
| 113 | 3,4,5-trimethoxyphenyl boronic acid | 1H-indol-6-amine | 1-(1H-indol-6-yl)-6-(3,4,5-trimethoxyphenyl)-1H-imidazo[4,5-b]pyrazin-2(3H)-one |
| 114 | 3,4,5-trimethoxyphenyl boronic acid | 4-aminophenol | 1-(4-hydroxyphenyl)-6-(3,4,5-trimethoxyphenyl)-1H-imidazo[4,5-b]pyrazin-2(3H)-one |
| 115 | 3,4-dimethoxyphenyl boronic acid | 4-aminophenol | 6-(3,4-dimethoxyphenyl)-1-(4-hydroxyphenyl)-1H-imidazo[4,5-b]pyrazin-2(3H)-one |
| 116 | 4-morpholinophenyl boronic acid | 4-aminophenol | 1-(4-hydroxyphenyl)-6-(4-morpholinophenyl)-1H-imidazo[4,5-b]pyrazin-2(3H)-one |
| 117 | 6-aminopyridin-3-boronic acid | 1-amino-cyclopentane | 6-(6-aminopyridin-3-yl)-1-cyclopentyl-1H-imidazo[4,5-b]pyrazin-2(3H)-one |
| 118 | 4-amino-3-methoxyphenyl boronic acid | 1-amino-cyclopentane | 6-(4-amino-3-methoxyphenyl)-1-cyclopentyl-1H-imidazo[4,5-b]pyrazin-2(3H)-one |

Examples 47-118 were physically characterized by electrospray ionization mass spectrometry. Structures and molecular masses are given below in Table 3.

TABLE 3

| Ex. | Structure | IUPAC Name | MW |
|---|---|---|---|
| 47 | 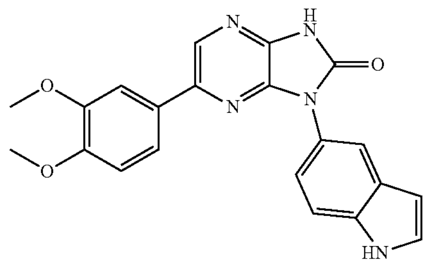 [SMILES: COc1ccc(-c2cnc3[nH]c(=O)n(-c4ccc5[nH]ccc5c4)c3n2)cc1OC] | 6-(3,4-dimethoxyphenyl)-1-(1H-indol-5-yl)-1H-imidazo[4,5-b]pyrazin-2(3H)-one | 387.13 |
| 48 | 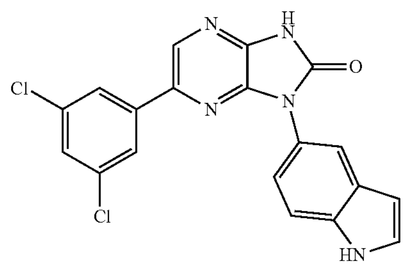 [SMILES: O=c1[nH]c2ncc(-c3cc(Cl)cc(Cl)c3)nc2n1-c1ccc2[nH]ccc2c1] | 6-(3,5-dichlorophenyl)-1-(1H-indol-5-yl)-1H-imidazo[4,5-b]pyrazin-2(3H)-one | 395.03 |
| 49 | 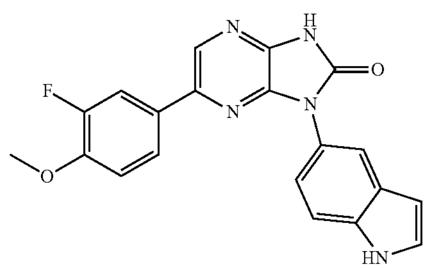 | 6-(3-fluoro-4-methoxyphenyl)-1-(1H-indol-5-yl)-1H-imidazo[4,5-b]pyrazin-2(3H)-one | 375.11 |
| 50 | 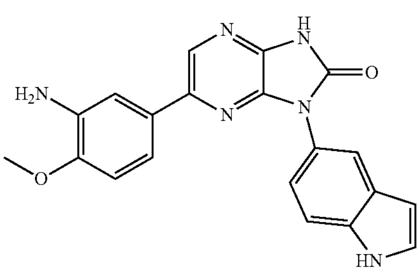 [SMILES: COc1ccc(-c2cnc3[nH]c(=O)n(-c4ccc5[nH]ccc5c4)c3n2)cc1N] | 6-(3-amino-4-methoxyphenyl)-1-(1H-indol-5-yl)-1H-imidazo[4,5-b]pyrazin-2(3H)-one | 372.13 |
| 51 | 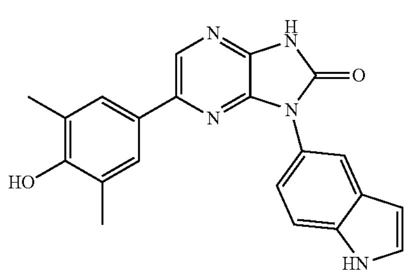 [SMILES: Cc1cc(-c2cnc3[nH]c(=O)n(-c4ccc5[nH]ccc5c4)c3n2)cc(C)c1O] | 1-(1H-indol-5-yl)-6-(4-methoxy-3,5-dimethylphenyl)-1H-imidazo[4,5-b]pyrazin-2(3H)-one | 371.40 |

TABLE 3-continued

| Ex. | Structure | IUPAC Name | MW |
|---|---|---|---|
| 52 | 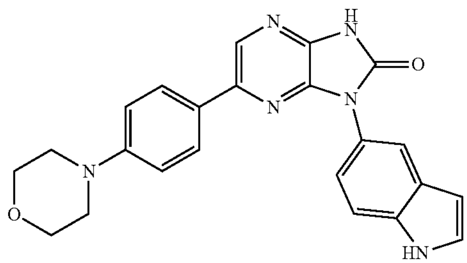 [SMILES: O=c1[nH]c2ncc(-c3ccc(N4CCOCC4)cc3)nc2n1-c1ccc2[nH]ccc2c1] | 1-(1H-indol-5-yl)-6-(4-morpholinophenyl)-1H-imidazo[4,5-b]pyrazin-2(3H)-one | 412.45 |
| 53 | 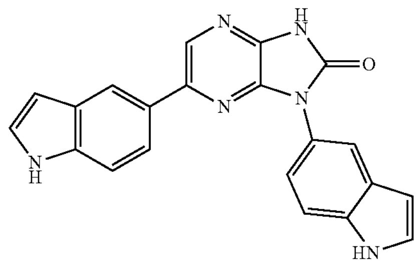 [SMILES: O=c1[nH]c2ncc(-c3ccc4[nH]ccc4c3)nc2n1-c1ccc2[nH]ccc2c1] | 1,6-di(1H-indol-5-yl)-1H-imidazo[4,5-b]pyrazin-2(3H)-one | 366.39 |
| 54 | 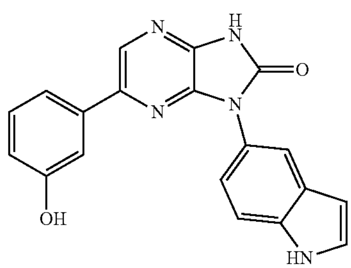 [SMILES: O=c1[nH]c2ncc(-c3cccc(O)c3)nc2n1-c1ccc2[nH]ccc2c1] | 6-(3-hydroxyphenyl)-1-(1H-indol-5-yl)-1H-imidazo[4,5-b]pyrazin-2(3H)-one | 343.35 |
| 55 | 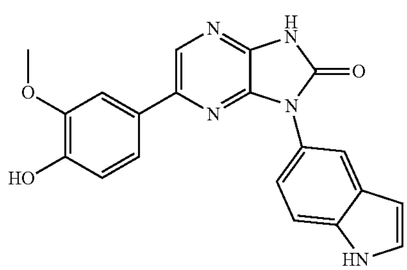 [SMILES: COc1cc(-c2cnc3[nH]c(=O)n(-c4ccc5[nH]ccc5c4)c3n2)ccc1O] | 6-(4-hydroxy-3-methoxyphenyl)-1-(1H-indol-5-yl)-1H-imidazo[4,5-b]pyrazin-2(3H)-one | 373.37 |
| 56 | 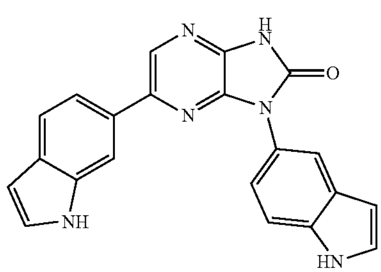 [SMILES: O=c1[nH]c2ncc(-c3ccc4cc[nH]c4c3)nc2n1-c1ccc2[nH]ccc2c1] | 1-(1H-indol-5-yl)-6-(1H-indol-6-yl)-1H-imidazo[4,5-b]pyrazin-2(3H)-one | 366.39 |
| 57 | 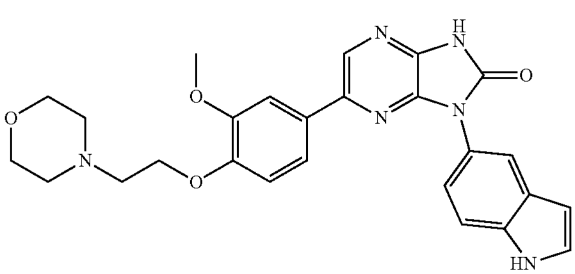 [SMILES: COc1cc(-c2cnc3[nH]c(=O)n(-c4ccc5[nH]ccc5c4)c3n2)ccc1OCCN1CCOCC1] | 1-(1H-indol-5-yl)-6-(3-methoxy-4-(2-morpholinoethoxy)phenyl)-1H-imidazo[4,5-b]pyrazin-2(3H)-one | 486.53 |

TABLE 3-continued

| Ex. | Structure | IUPAC Name | MW |
|---|---|---|---|
| 58 | 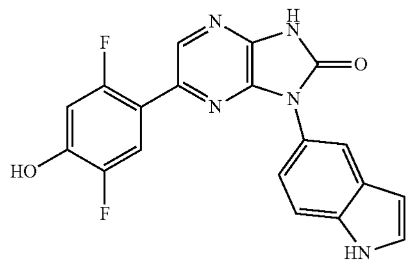 [SMILES: O=c1[nH]c2ncc(-c3cc(F)c(O)cc3F)nc2n1-c1ccc2[nH]ccc2c1] | 6-(2,5-difluoro-4-hydroxyphenyl)-1-(1H-indol-5-yl)-1H-imidazo[4,5-b]pyrazin-2(3H)-one | 379.33 |
| 59 | 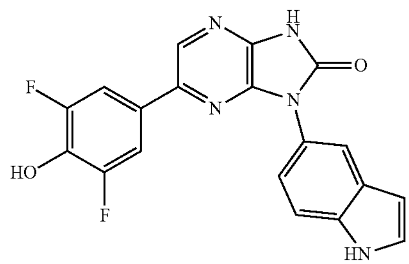 [SMILES: O=c1[nH]c2ncc(-c3cc(F)c(O)c(F)c3)nc2n1-c1ccc2[nH]ccc2c1] | 6-(3,5-difluoro-4-hydroxyphenyl)-1-(1H-indol-5-yl)-1H-imidazo[4,5-b]pyrazin-2(3H)-one | 379.33 |
| 60 | 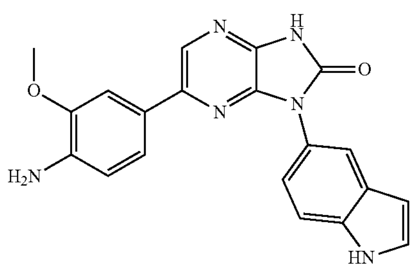 [SMILES: COc1cc(-c2cnc3[nH]c(=O)n(-c4ccc5[nH]ccc5c4)c3n2)ccc1N] | 6-(4-amino-3-methoxyphenyl)-1-(1H-indol-5-yl)-1H-imidazo[4,5-b]pyrazin-2(3H)-one | 372.39 |
| 61 | 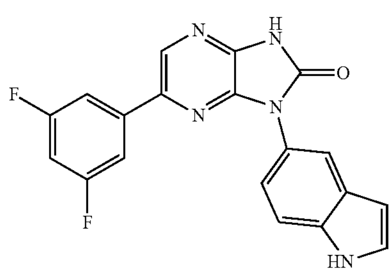 [SMILES: O=c1[nH]c2ncc(-c3cc(F)cc(F)c3)nc2n1-c1ccc2[nH]ccc2c1] | 6-(3,5-difluorophenyl)-1-(1H-indol-5-yl)-1H-imidazo[4,5-b]pyrazin-2(3H)-one | 363.33 |
| 62 | 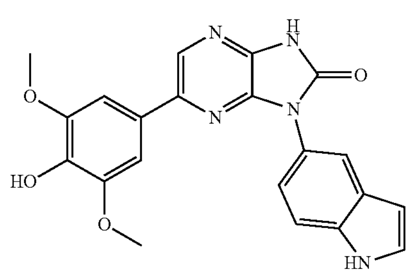 [SMILES: COc1cc(-c2cnc3[nH]c(=O)n(-c4ccc5[nH]ccc5c4)c3n2)cc(OC)c1O] | 6-(4-hydroxy-3,5-dimethoxyphenyl)-1-(1H-indol-5-yl)-1H-imidazo[4,5-b]pyrazin-2(3H)-one | 403.40 |

TABLE 3-continued

| Ex. | Structure | IUPAC Name | MW |
|---|---|---|---|
| 63 | 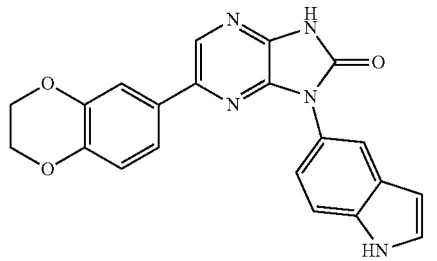 [SMILES: O=c1[nH]c2ncc(-c3ccc4c(c3)OCCO4)nc2n1-c1ccc2[nH]ccc2c1] | 6-(2,3-dihydrobenzo[b][1,4]dioxin-6-yl)-1-(1H-indol-5-yl)-1H-imidazo[4,5-b]pyrazin-2(3H)-one | 385.39 |
| 64 | 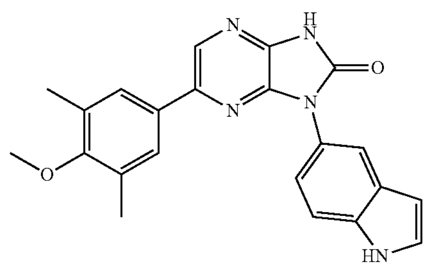 [SMILES: COc1c(C)cc(-c2cnc3[nH]c(=O)n(-c4ccc5[nH]ccc5c4)c3n2)cc1C] | 6-(4-hydroxy-3,5-dimethylphenyl)-1-(1H-indol-5-yl)-1H-imidazo[4,5-b]pyrazin-2(3H)-one | 385.43 |
| 65 | 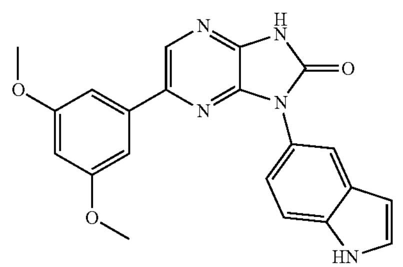 [SMILES: COc1cc(OC)cc(-c2cnc3[nH]c(=O)n(-c4ccc5[nH]ccc5c4)c3n2)c1] | 6-(3,5-dimethoxyphenyl)-1-(1H-indol-5-yl)-1H-imidazo[4,5-b]pyrazin-2(3H)-one | 387.40 |
| 66 | 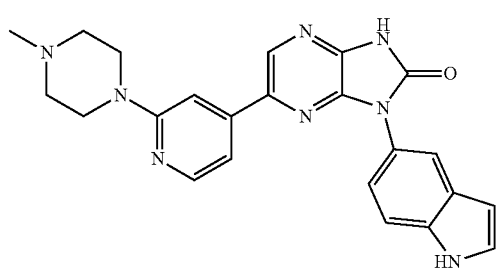 [SMILES: CN1CCN(c2cc(-c3cnc4[nH]c(=O)n(-c5ccc6[nH]ccc6c5)c4n3)ccn2)CC1] | 1-(1H-indol-5-yl)-6-(2-(4-methylpiperazin-1-yl)pyridin-4-yl)-1H-imidazo[4,5-b]pyrazin-2(3H)-one | 426.50 |
| 67 | 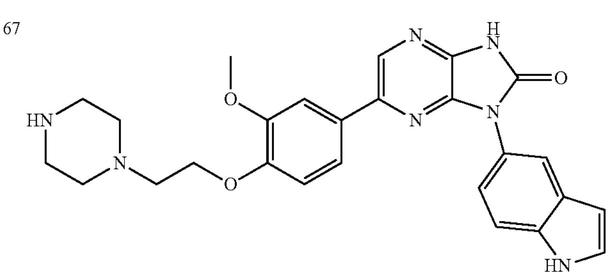 | 1-(1H-indol-5-yl)-6-(3-methoxy-4-(2-(piperazin-1-yl)ethoxy)phenyl)-1H-imidazo[4,5-b]pyrazin-2(3H)-one | 485.55 |

TABLE 3-continued

| Ex. | Structure | IUPAC Name | MW |
|---|---|---|---|
| 68 | 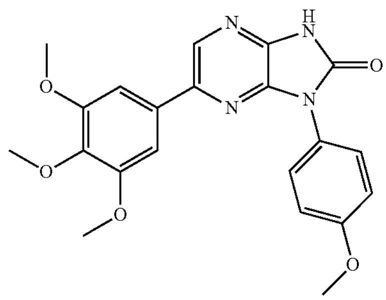 [SMILES: COc1ccc(-n2c(=O)[nH]c3ncc(-c4cc(OC)c(OC)c(OC)c4)nc32)cc1] | 1-(4-methoxyphenyl)-6-(3,4,5-trimethoxyphenyl)-1H-imidazo[4,5-b]pyrazin-2(3H)-one | 408.42 |
| 69 | 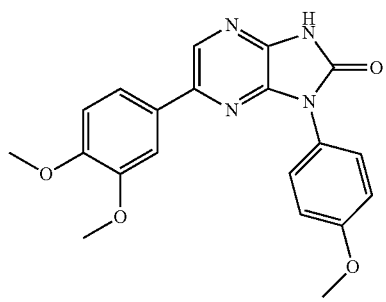 [SMILES: COc1ccc(-n2c(=O)[nH]c3ncc(-c4ccc(OC)c(OC)c4)nc32)cc1] | 6-(3,4-dimethoxyphenyl)-1-(4-methoxyphenyl)-1H-imidazo[4,5-b]pyrazin-2(3H)-one | 378.39 |
| 70 | 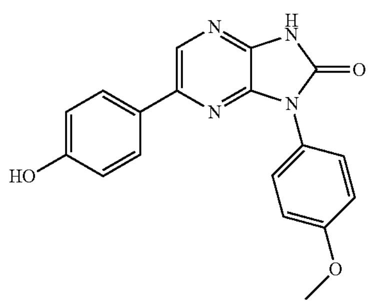 [SMILES: COc1ccc(-n2c(=O)[nH]c3ncc(-c4ccc(O)cc4)nc32)cc1] | 6-(4-hydroxyphenyl)-1-(4-methoxyphenyl)-1H-imidazo[4,5-b]pyrazin-2(3H)-one | 334.34 |
| 71 | 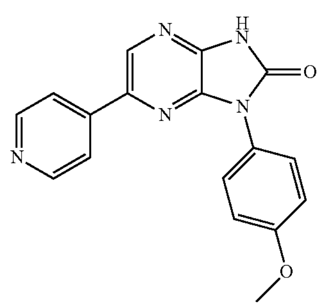 [SMILES: COc1ccc(-n2c(=O)[nH]c3ncc(-c4ccncc4)nc32)cc1] | 1-(4-methoxyphenyl)-6-(pyridin-4-yl)-1H-imidazo[4,5-b]pyrazin-2(3H)-one | 319.33 |
| 72 | 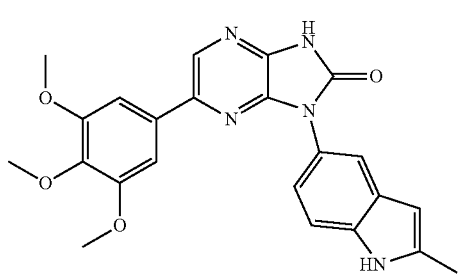 | 1-(2-methyl-1H-indol-5-yl)-6-(3,4,5-trimethoxyphenyl)-1H-imidazo[4,5-b]pyrazin-2(3H)-one | 431.45 |

TABLE 3-continued

| Ex. | Structure | IUPAC Name | MW |
|---|---|---|---|
| 73 | 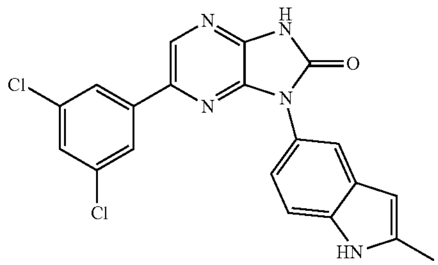 [SMILES: Cc1cc2cc(-n3c(=O)[nH]c4ncc(-c5cc(Cl)cc(Cl)c5)nc43)ccc2[nH]1] | 6-(3,5-dichlorophenyl)-1-(2-methyl-1H-indol-5-yl)-1H-imidazo[4,5-b]pyrazin-2(3H)-one | 410.27 |
| 74 | 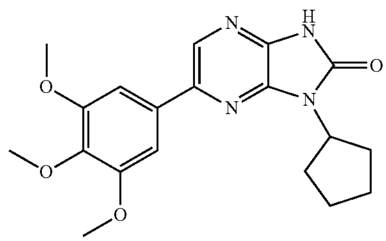 [SMILES: COc1cc(-c2cnc3[nH]c(=O)n(C4CCCC4)c3n2)cc(OC)c1OC] | 1-cyclopentyl-6-(3,4,5-trimethoxyphenyl)-1H-imidazo[4,5-b]pyrazin-2(3H)-one | 370.41 |
| 75 | 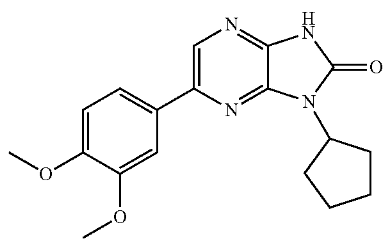 [SMILES: COc1ccc(-c2cnc3[nH]c(=O)n(C4CCCC4)c3n2)cc1OC] | 1-cyclopentyl-6-(3,4-dimethoxyphenyl)-1H-imidazo[4,5-b]pyrazin-2(3H)-one | 340.39 |
| 76 | 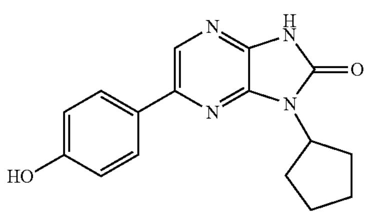 [SMILES: O=c1[nH]c2ncc(-c3ccc(O)cc3)nc2n1C1CCCC1] | 1-cyclopentyl-6-(4-hydroxyphenyl)-1H-imidazo[4,5-b]pyrazin-2(3H)-one | 296.33 |
| 77 | 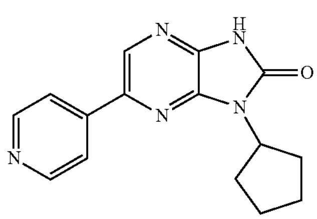 [SMILES: O=c1[nH]c2ncc(-c3ccncc3)nc2n1C1CCCC1] | 1-cyclopentyl-6-(pyridin-4-yl)-1H-imidazo[4,5-b]pyrazin-2(3H)-one | 281.32 |
| 78 | 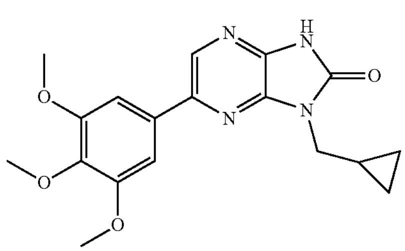 | 1-(cyclopropylmethyl)-6-(3,4,5-trimethoxyphenyl)-1H-imidazo[4,5-b]pyrazin-2(3H)-one | 356.38 |

TABLE 3-continued

| Ex. | Structure | IUPAC Name | MW |
|---|---|---|---|
| 79 | 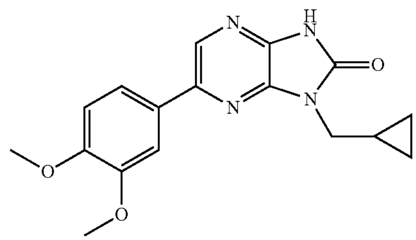 [SMILES: COc1ccc(-c2cnc3[nH]c(=O)n(CC4CC4)c3n2)cc1OC] | 1-(cyclopropylmethyl)-6-(3,4-dimethoxyphenyl)-1H-imidazo[4,5-b]pyrazin-2(3H)-one | 326.36 |
| 80 | 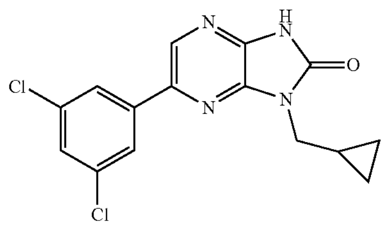 [SMILES: O=c1[nH]c2ncc(-c3cc(Cl)cc(Cl)c3)nc2n1CC1CC1] | 1-(cyclopropylmethyl)-6-(3,5-dichlorophenyl)-1H-imidazo[4,5-b]pyrazin-2(3H)-one | 335.20 |
| 81 | 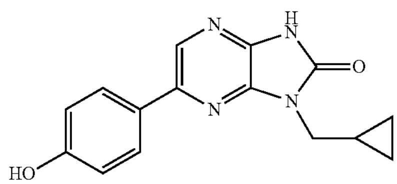 [SMILES: O=c1[nH]c2ncc(-c3ccc(O)cc3)nc2n1CC1CC1] | 1-(cyclopropylmethyl)-6-(4-hydroxyphenyl)-1H-imidazo[4,5-b]pyrazin-2(3H)-one | 282.30 |
| 82 | 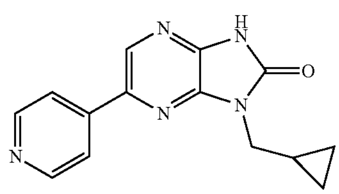 [SMILES: O=c1[nH]c2ncc(-c3ccncc3)nc2n1CC1CC1] | 1-(cyclopropylmethyl)-6-(pyridin-4-yl)-1H-imidazo[4,5-b]pyrazin-2(3H)-one | 267.29 |
| 83 | 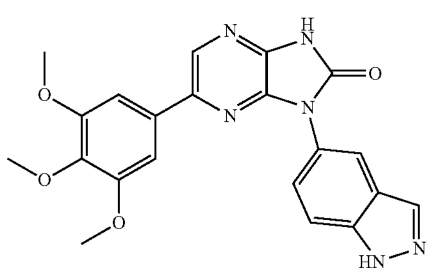 [SMILES: COc1cc(-c2cnc3[nH]c(=O)n(-c4ccc5[nH]ncc5c4)c3n2)cc(OC)c1OC] | 1-(1H-indazol-5-yl)-6-(3,4,5-trimethoxyphenyl)-1H-imidazo[4,5-b]pyrazin-2(3H)-one | 418.42 |
| 84 | 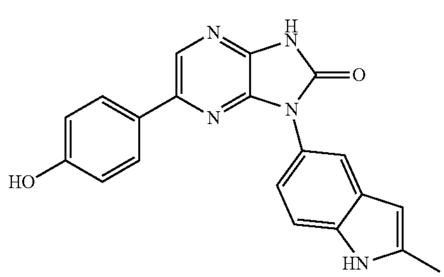 [SMILES: Cc1cc2cc(-n3c(=O)[nH]c4ncc(-c5ccc(O)cc5)nc43)ccc2[nH]1] | 6-(4-hydroxyphenyl)-1-(2-methyl-1H-indol-5-yl)-1H-imidazo[4,5-b]pyrazin-2(3H)-one | 357.37 |

TABLE 3-continued

| Ex. | Structure | IUPAC Name | MW |
|---|---|---|---|
| 85 | 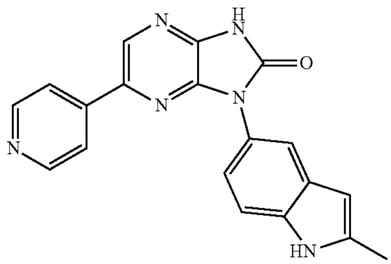 [SMILES: Cc1cc2cc(-n3c(=O)[nH]c4ncc(-c5ccncc5)nc43)ccc2[nH]1] | 1-(2-methyl-1H-indol-5-yl)-6-(pyridin-4-yl)-1H-imidazo[4,5-b]pyrazin-2(3H)-one | 342.36 |
| 86 | 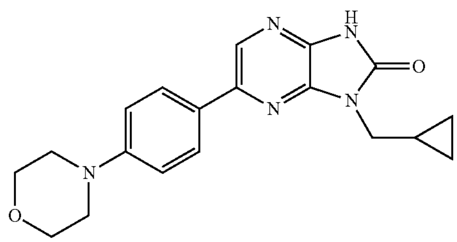 [SMILES: O=c1[nH]c2ncc(-c3ccc(N4CCOCC4)cc3)nc2n1CC1CC1] | 1-(cyclopropylmethyl)-6-(4-morpholinophenyl)-1H-imidazo[4,5-b]pyrazin-2(3H)-one | 351.41 |
| 87 | 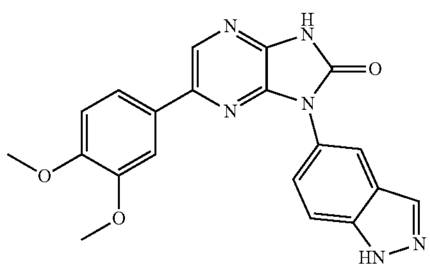 [SMILES: COc1ccc(-c2cnc3[nH]c(=O)n(-c4ccc5[nH]ncc5c4)c3n2)cc1OC] | 6-(3,4-dimethoxyphenyl)-1-(1H-indazol-5-yl)-1H-imidazo[4,5-b]pyrazin-2(3H)-one | 388.39 |
| 88 | 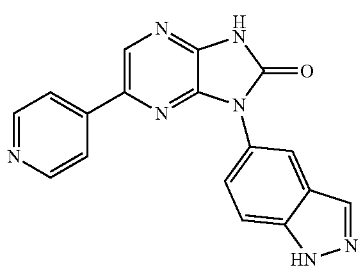 [SMILES: O=c1[nH]c2ncc(-c3ccncc3)nc2n1-c1ccc2[nH]ncc2c1] | 1-(1H-indazol-5-yl)-6-(pyridin-4-yl)-1H-imidazo[4,5-b]pyrazin-2(3H)-one | 329.32 |
| 89 | 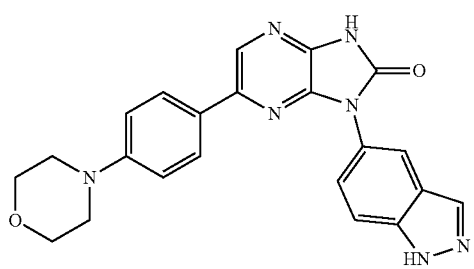 [SMILES: O=c1[nH]c2ncc(-c3ccc(N4CCOCC4)cc3)nc2n1-c1ccc2[nH]ncc2c1] | 1-(1H-indazol-5-yl)-6-(4-morpholinophenyl)-1H-imidazo[4,5-b]pyrazin-2(3H)-one | 413.44 |
| 90 | 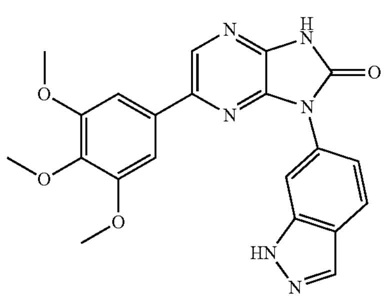 [SMILES: COc1cc(-c2cnc3[nH]c(=O)n(-c4ccc5cn[nH]c5c4)c3n2)cc(OC)c1OC] | 1-(1H-indazol-6-yl)-6-(3,4,5-trimethoxyphenyl)-1H-imidazo[4,5-b]pyrazin-2(3H)-one | 418.42 |

TABLE 3-continued
| Ex. | Structure | IUPAC Name | MW |
|---|---|---|---|
| 91 | 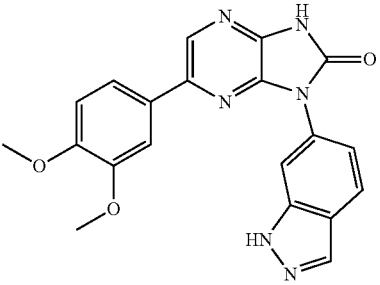 [SMILES: COc1ccc(-c2cnc3[nH]c(=O)n(-c4ccc5cn[nH]c5c4)c3n2)cc1OC] | 6-(3,4-dimethoxyphenyl)-1-(1H-indazol-6-yl)-1H-imidazo[4,5-b]pyrazin-2(3H)-one | 388.39 |
| 92 | 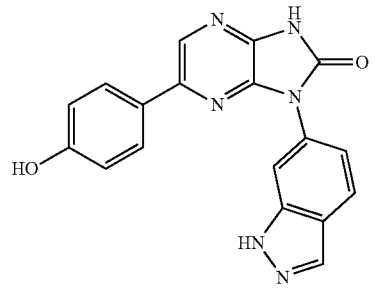 [SMILES: O=c1[nH]c2ncc(-c3ccc(O)cc3)nc2n1-c1ccc2cn[nH]c2c1] | 6-(4-hydroxyphenyl)-1-(1H-indazol-6-yl)-1H-imidazo[4,5-b]pyrazin-2(3H)-one | 344.34 |
| 93 | 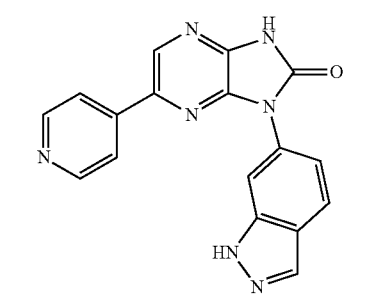 [SMILES: O=c1[nH]c2ncc(-c3ccncc3)nc2n1-c1ccc2cn[nH]c2c1] | 1-(1H-indazol-6-yl)-6-(pyridin-4-yl)-1H-imidazo[4,5-b]pyrazin-2(3H)-one | 329.32 |
| 94 | 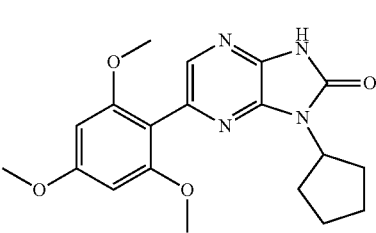 [SMILES: COc1cc(OC)c(-c2cnc3[nH]c(=O)n(C4CCCC4)c3n2)c(OC)c1] | 1-cyclopentyl-6-(2,4,6-trimethoxyphenyl)-1H-imidazo[4,5-b]pyrazin-2(3H)-one | 370.41 |
| 95 | 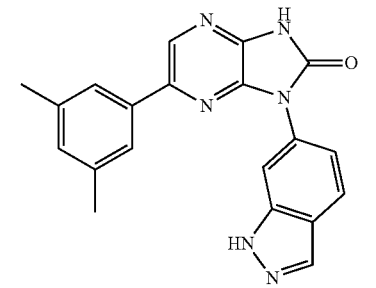 [SMILES: Cc1cc(C)cc(-c2cnc3[nH]c(=O)n(-c4ccc5cn[nH]c5c4)c3n2)c1] | 6-(3,5-dimethylphenyl)-1-(1H-indazol-6-yl)-1H-imidazo[4,5-b]pyrazin-2(3H)-one | 356.39 |

TABLE 3-continued

| Ex. | Structure | IUPAC Name | MW |
|---|---|---|---|
| 96 | 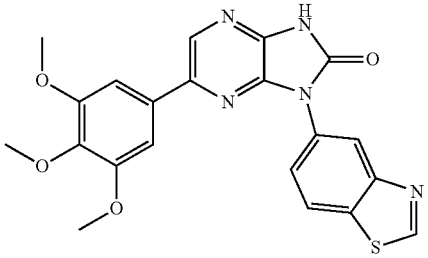 [SMILES: COc1cc(-c2cnc3[nH]c(=O)n(-c4ccc5scnc5c4)c3n2)cc(OC)c1OC] | 1-(benzo[d]thiazol-5-yl)-6-(3,4,5-trimethoxyphenyl)-1H-imidazo[4,5-b]pyrazin-2(3H)-one | 435.46 |
| 97 | 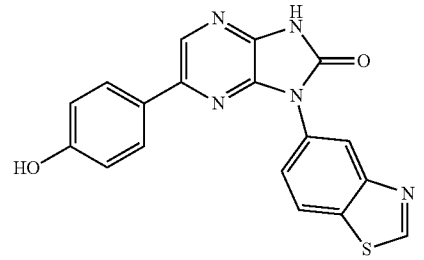 [SMILES: O=c1[nH]c2ncc(-c3ccc(O)cc3)nc2n1-c1ccc2scnc2c1] | 1-(benzo[d]thiazol-5-yl)-6-(4-hydroxyphenyl)-1H-imidazo[4,5-b]pyrazin-2(3H)-one | 361.38 |
| 98 | 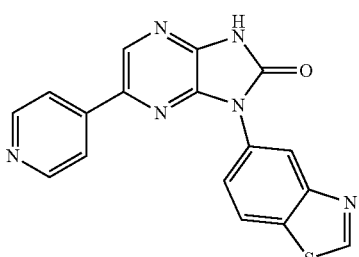 | 1-(benzo[d]thiazol-5-yl)-6-(pyridin-4-yl)-1H-imidazo[4,5-b]pyrazin-2(3H)-one | 346.37 |
| 99 | 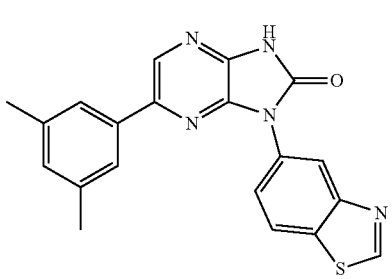 [SMILES: Cc1cc(C)cc(-c2cnc3[nH]c(=O)n(-c4ccc5scnc5c4)c3n2)c1] | 1-(benzo[d]thiazol-5-yl)-6-(3,5-dimethylphenyl)-1H-imidazo[4,5-b]pyrazin-2(3H)-one | 373.44 |
| 100 | 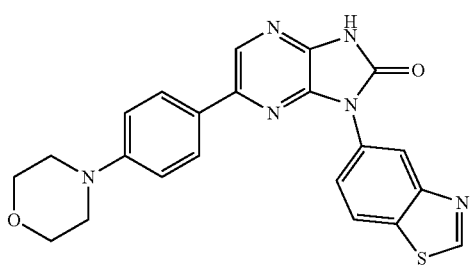 [SMILES: O=c1[nH]c2ncc(-c3ccc(N4CCOCC4)cc3)nc2n1-c1ccc2scnc2c1] | 1-(benzo[d]thiazol-5-yl)-6-(4-morpholinophenyl)-1H-imidazo[4,5-b]pyrazin-2(3H)-one | 430.49 |
| 101 | 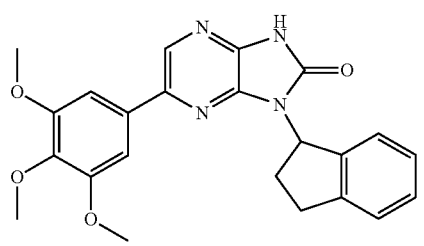 [SMILES: COc1cc(-c2cnc3[nH]c(=O)n(C4CCc5ccccc54)c3n2)cc(OC)c1OC] | 1-(2,3-(dihydro-1H-inden-1-yl)-6-(3,4,5-trimethoxyphenyl)-1H-imidazo[4,5-b]pyrazin-2(3H)-one | 418.46 |

TABLE 3-continued

| Ex. | Structure | IUPAC Name | MW |
|---|---|---|---|
| 102 | 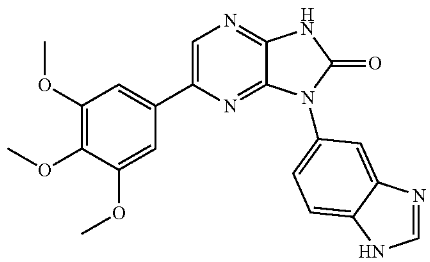 [SMILES: COc1cc(-c2cnc3[nH]c(=O)n(-c4ccc5[nH]cnc5c4)c3n2)cc(OC)c1OC] | 1-(1H-benzo[d]imidazol-5-yl)-6-(3,4,5-trimethoxyphenyl)-1H-imidazo[4,5-b]pyrazin-2(3H)-one | 418.42 |
| 103 | 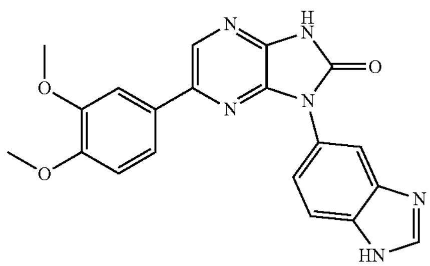 [SMILES: COc1ccc(-c2cnc3[nH]c(=O)n(-c4ccc5[nH]cnc5c4)c3n2)cc1OC] | 1-(1H-benzo[d]imidazol-5-yl)-6-(3,4-dimethoxyphenyl)-1H-imidazo[4,5-b]pyrazin-2(3H)-one | 388.39 |
| 104 | 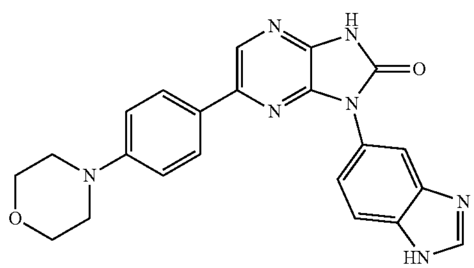 | 1-(1H-benzo[d]imidazol-5-yl)-6-(4-morpholinophenyl)-1H-imidazo[4,5-b]pyrazin-2(3H)-one | 413.44 |
| 105 | 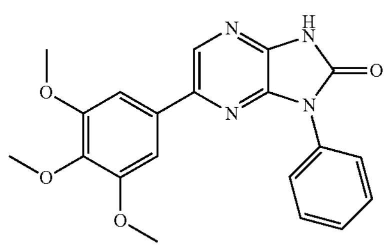 [SMILES: COc1cc(-c2cnc3[nH]c(=O)n(-c4ccccc4)c3n2)cc(OC)c1OC] | 1-phenyl-6-(3,4,5-trimethoxyphenyl)-1H-imidazo[4,5-b]pyrazin-2(3H)-one | 378.39 |
| 106 | 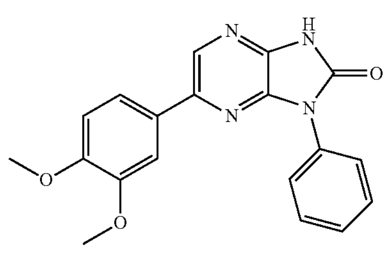 [SMILES: COc1ccc(-c2cnc3[nH]c(=O)n(-c4ccccc4)c3n2)cc1OC] | 6-(3,4-dimethoxyphenyl)-1-phenyl-1H-imidazo[4,5-b]pyrazin-2(3H)-one | 348.36 |
| 107 | 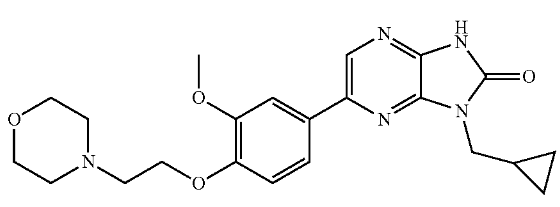 [SMILES: COc1cc(-c2cnc3[nH]c(=O)n(CC4CC4)c3n2)ccc1OCCN1CCOCC1] | 1-(cyclopropylmethyl)-6-(3-methoxy-4-(2-morpholinoethoxy)phenyl)-1H-imidazo[4,5-b]pyrazin-2(3H)-one | 425.49 |

TABLE 3-continued

| Ex. | Structure | IUPAC Name | MW |
|---|---|---|---|
| 108 | 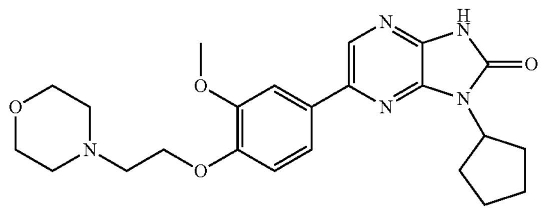 [SMILES: COc1cc(-c2cnc3[nH]c(=O)n(C4CCCC4)c3n2)ccc1OCCN1CCOCC1] | 1-cyclopentyl-6-(3-methoxy-4-(2-morpholinoethoxy)phenyl)-1H-imidazo[4,5-b]pyrazin-2(3H)-one | 439.52 |
| 109 | 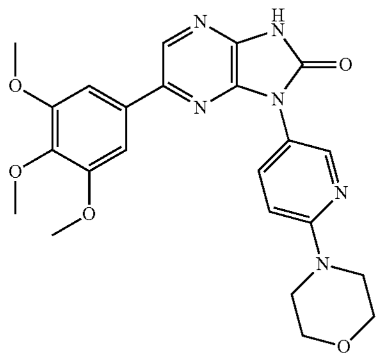 [SMILES: COc1cc(-c2cnc3[nH]c(=O)n(-c4ccc(N5CCOCC5)nc4)c3n2)cc(OC)c1OC] | 1-(6-morpholinopyridin-3-yl)-6-(3,4,5-trimethoxyphenyl)-1H-imidazo[4,5-b]pyrazin-2(3H)-one | 464.48 |
| 110 | 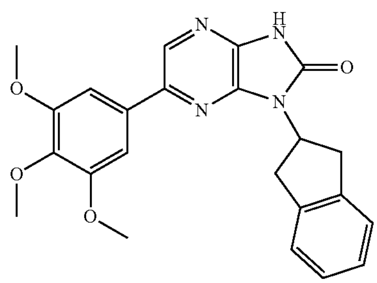 [SMILES: COc1cc(-c2cnc3[nH]c(=O)n(C4Cc5ccccc5C4)c3n2)cc(OC)c1OC] | 1-(2,3-dihydro-1H-inden-2-yl)-6-(3,4,5-trimethoxyphenyl)-1H-imidazo[4,5-b]pyrazin-2(3H)-one | 418.46 |
| 111 | 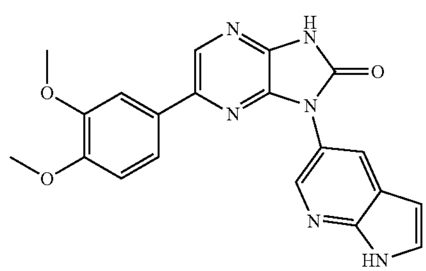 [SMILES: COc1ccc(-c2cnc3[nH]c(=O)n(-c4cnc5[nH]ccc5c4)c3n2)cc1OC] | 6-(3,4-dimethoxyphenyl)-1-(1H-pyrrolo[2,3-b]pyridin-5-yl)-1H-imidazo[4,5-b]pyrazin-2(3H)-one | 388.39 |
| 112 | 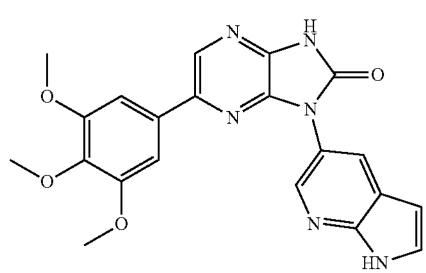 [SMILES: COc1cc(-c2cnc3[nH]c(=O)n(-c4cnc5[nH]ccc5c4)c3n2)cc(OC)c1OC] | 1-(1H-pyrrolo[2,3-b]pyridin-5-yl)-6-(3,4,5-trimethoxyphenyl)-1H-imidazo[4,5-b]pyrazin-2(3H)-one | 418.42 |

TABLE 3-continued

| Ex. | Structure | IUPAC Name | MW |
|---|---|---|---|
| 113 | 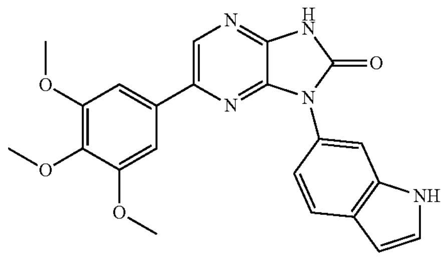 [SMILES: COc1cc(-c2cnc3[nH]c(=O)n(-c4ccc5cc[nH]c5c4)c3n2)cc(OC)c1OC] | 1-(1H-indol-6-yl)-6-(3,4,5-trimethoxyphenyl)-1H-imidazo[4,5-b]pyrazin-2(3H)-one | 418.42 |
| 114 | 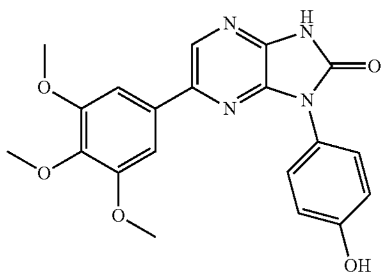 [SMILES: COc1cc(-c2cnc3[nH]c(=O)n(-c4ccc(O)cc4)c3n2)cc(OC)c1OC] | 1-(4-hydroxyphenyl)-6-(3,4,5-trimethoxyphenyl)-1H-imidazo[4,5-b]pyrazin-2(3H)-one | 394.50 |
| 115 | 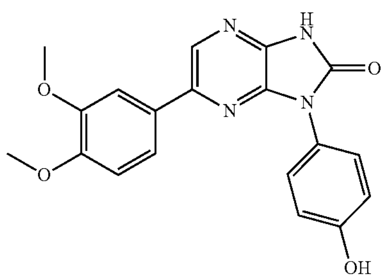 [SMILES: COc1ccc(-c2cnc3[nH]c(=O)n(-c4ccc(O)cc4)c3n2)cc1OC] | 6-(3,4-dimethoxyphenyl)-1-(4-hydroxyphenyl)-1H-imidazo[4,5-b]pyrazin-2(3H)-one | 364.50 |
| 116 | 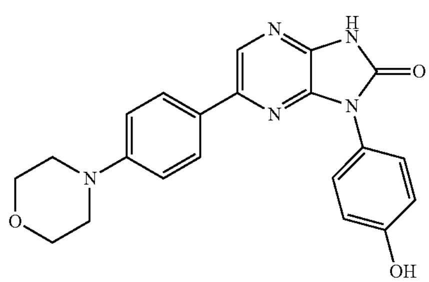 [SMILES: O=c1[nH]c2ncc(-c3ccc(N4CCOCC4)cc3)nc2n1-c1ccc(O)cc1] | 1-(4-hydroxyphenyl)-6-(4-morpholinophenyl)-1H-imidazo[4,5-b]pyrazin-2(3H)-one | 389.50 |
| 117 | 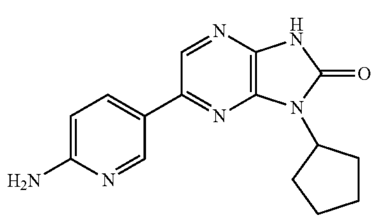 [SMILES: Nc1ccc(-c2cnc3[nH]c(=O)n(C4CCCC4)c3n2)cn1] | 6-(6-aminopyridin-3-yl)-1-cyclopentyl-1H-imidazo[4,5-b]pyrazin-2(3H)-one | 296.33 |
| 118 | 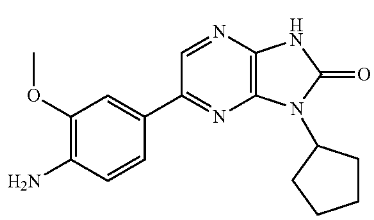 [SMILES: COc1cc(-c2cnc3[nH]c(=O)n(C4CCCC4)c3n2)ccc1N] | 6-(4-amino-3-methoxyphenyl)-1-cyclopentyl-1H-imidazo[4,5-b]pyrazin-2(3H)-one | 325.37 |

Example 119

Preparation of 5-chloro-1-(cyclopropylmethyl)-6-(3,4,5-trimethoxyphenyl)-1H-imidazo[4,5-b]pyrazin-2(3H)-one

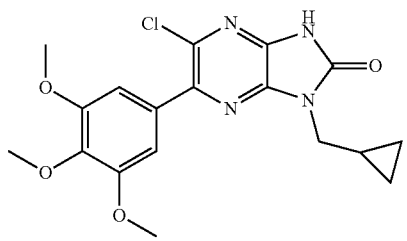 [SMILES: COc1cc(-c2nc3c(nc2Cl)[nH]c(=O)n3CC2CC2)cc(OC)c1OC]

Example 119 was prepared by a method analogous to that described in Examples 68-118 by substituting 6 chloro-3,5-dibromopyrazin-2-amine for 3,5-dibromopyrazin-2-amine in the reaction with aminomethylcyclopropane. MS ESI (m/z): 390.83 calc

Example 120

Scheme 8

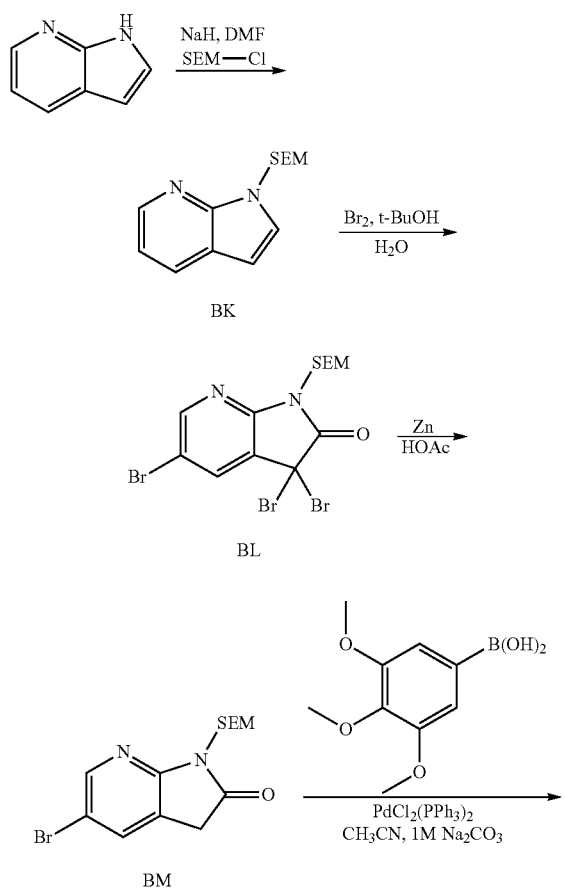

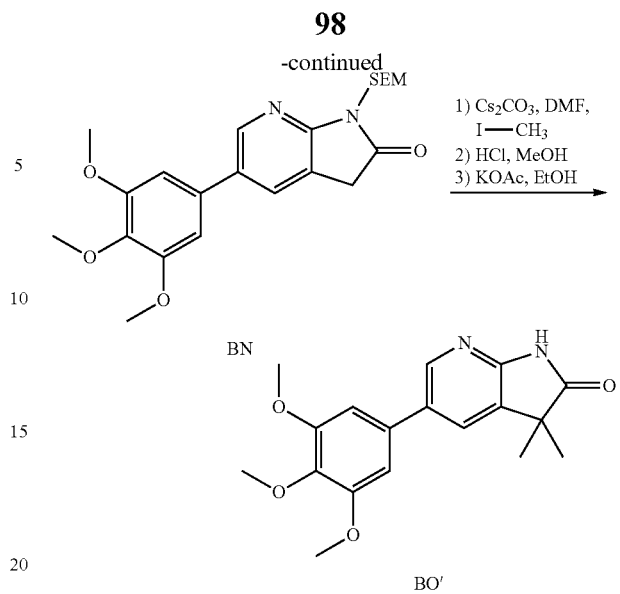

Preparation of 1-((2-(trimethylsilyl)ethoxy)methyl)-1H-pyrrolo[2,3-b]pyridine (Intermediate BK)

To a stirred solution of 7-azaindole (1.18 g, 10.0 mmol) in anhydrous dimethylformamide (10 mL) cooled to 0° C. was added NaH [60% dispersion in mineral oil] (0.480 g, 12.0 mmol) in portions over 15 min. The resulting mixture was allowed to stir for 1 hr at 0° C., after which (2-(chloromethoxy)ethyl)trimethylsilane [SEM-Cl] (2.12 mL, 12.0 mmol) was added over 15 min. The resulting mixture was stirred for 1 hr, after which it was quenched with $H_2O$ (50 mL), and partioned between EtOAc and $H_2O$. The organic layer was separated, washed with brine, dried over $MgSO_4$, filtered, and evaporated in vacuo to yield a yellow oil (2.50 g, 100%). HPLC retention time: 2.66 minutes; MS ESI (m/z): 249.4 (M+1)$^+$, calc. 248.

Preparation of 3,3,5-tribromo-1-((2-(trimethylsilyl)ethoxy)methyl)-1H-pyrrolo[2,3-b]pyridin-2(3H)-one (Compound BL)

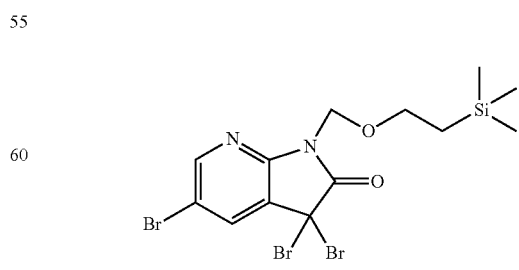

To a solution of 1-((2-(trimethylsilyl)ethoxy)methyl)-1H-pyrrolo[2,3-b]pyridine (2.50 g, 10.0 mmol) in 1:1 tert-butanol/H₂O (140 mL) at room temperature was added bromine (6.40 mL, 126 mmol). After stirring for 3.5 hr at room temperature, an additional portion of bromine was added (6.40 mL, 126 mmol) and the resulting mixture was stirred for 18 hr. The resulting mixture was concentrated in vacuo to yield the title compound, which was used without any further purification. HPLC retention time: 2.97 minutes; MS ESI (m/z): 441.0/443.0/445.2 (Fragment+1)⁺, calc. 498.

Preparation of 5-bromo-1-((2-(trimethylsilyl)ethoxy)methyl)-1H-pyrrolo[2,3-b]pyridin-2(3H)-one (Compound BM)

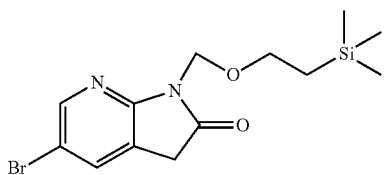 [SMILES: C[Si](C)(C)CCOCN1C(=O)Cc2cc(Br)cnc21]

To a solution of 3,3,5-tribromo-1-((2-(trimethylsilyl)ethoxy)methyl)-1H-pyrrolo[2,3-b]pyridin-2(3H)-one (4.98 g, 10.0 mmol) in AcOH (50 mL) was added zinc dust (1.28 g, 20.0 mmol). The resulting mixture was stirred at room temperature for 2 hr, after which it was filtered thru Celite and concentrated in vacuo. The resulting residue was purified via silica gel chromatography eluting with 1:1 Hexanes:EtOAc to yield the title compound as a yellow oil (0.85 g, 25% over three steps). HPLC retention time: 2.60 minutes; MS ESI (m/z): 287.2 (Fragment+1)₊, calc. 342.

Preparation of 5-(3,4,5-trimethoxyphenyl)-1-((2-(trimethylsilyl)ethoxy)-methyl)-1H-pyrrolo[2,3-b]pyridin-2(3H)-one (Compound BN)

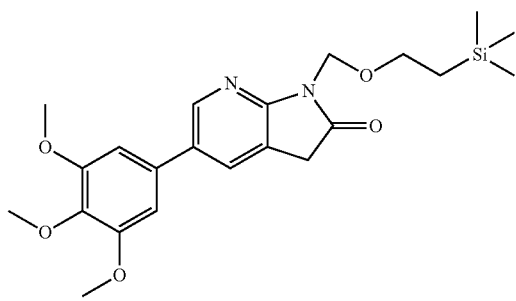

To a solution of 5-bromo-1-((2-(trimethylsilyl)ethoxy)methyl)-1H-pyrrolo[2,3-b]pyridin-2(3H)-one (0.85 g, 2.5 mmol) in CH₃CN (5 mL) was added 3,4,5-trimethoxyphenylboronic acid (525 mg, 2.5 mmol), bis(triphenylphosphine)palladium(II) dichloride (250 mg, 0.35 mmol), and 1 M Na₂CO₃ (5 mL). The resulting mixture was de-gassed with Ar for 10 min, after which it was heated at 80° C. for 2 hr. The reaction mixture was partitioned between EtOAc and H₂O, and the organic layer was separated, filtered, and concentrated in vacuo. The residue was purified by silica gel chromatography eluting with 3:1 EtOAc:Hexanes to yield the title compound (640 mg, 60%). HPLC retention time: 2.51 minutes; MS ESI (m/z): 431.4 (M+1)⁺, calc. 430.

Preparation of 3,3-dimethyl-5-(3,4,5-trimethoxyphenyl)-1H-pyrrolo[2,3-b]pyridin-2(3H)-one (Compound BO)

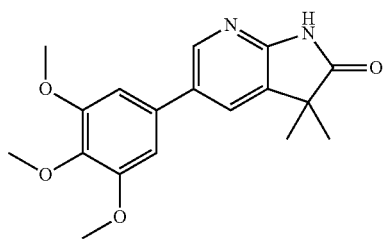 [SMILES: COc1cc(-c2cnc3c(c2)C(C)(C)C(=O)N3)cc(OC)c1OC]

To a solution of 5-(3,4,5-trimethoxyphenyl)-1-((2-(trimethylsilyl)ethoxy)-methyl)-1H-pyrrolo[2,3-b]pyridin-2(3H)-one (43 mg, 0.10 mmol) in DMF (2 mL) was added cesium carbonate (0.17 g, 0.50 mmol) and methyl iodide (19 μL, 0.30 mmol). The resulting solution was stirred for 48 hr at room temperature, after which it was partitioned between EtOAc and H₂O. The organic layer was separated, dried over MgSO₄, filtered, and concentrated in vacuo. The residue was dissolved in 6 N HCl (10 mL) and MeOH (5 mL), and the resulting mixture was stirred at room temperature overnight, after which it was partitioned between EtOAc and H₂O. The organic layer was concentrated in vacuo, and the residue was dissolved in EtOH (2 mL). Potassium acetate (100 mg) was then added, and the reaction was stirred for 2 hr. The resulting solution was purified via preparatory HPLC to give the title compound (24 mg, 73%). ¹H NMR (CDCl₃, 300 MHz): δ 9.72 (s, 1H), 8.35 (d, J=2.1 Hz, 1H), 7.60 (d, J=1.8 Hz, 1H), 6.71 (s, 2H), 3.95 (s, 6H), 3.90 (s, 3H), 1.49 (s, 6H). HPLC retention time: 1.80 minutes; MS ESI (m/z): 329.4 (M+1)₊, calc. 328.

Example 121

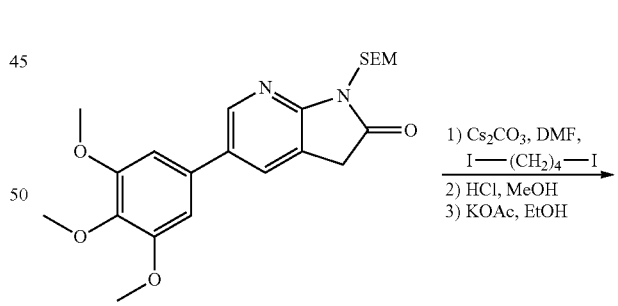

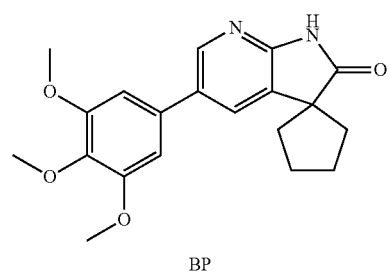

101

Preparation of 5'-(3,4,5-trimethoxyphenyl)spiro [cyclopentane-1,3'-pyrrolo[2,3-b]pyridin]-2'(1'H)-one (Compound BP)

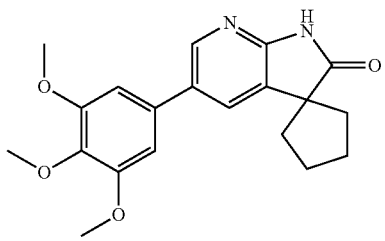 [SMILES: COc1cc(-c2cnc3c(c2)C2(CCCC2)C(=O)N3)cc(OC)c1OC]

To a solution of 5-(3,4,5-trimethoxyphenyl)-1-((2-(trimethylsilyl)ethoxy)-methyl)-1H-pyrrolo[2,3-b]pyridin-2(3H)-one (Compound BN, 43 mg, 0.10 mmol) in DMF (2 mL) was added cesium carbonate (0.17 g, 0.50 mmol) and 1,4-diiodobutane (13 µL, 0.10 mmol). The resulting solution was stirred for 4 hr at room temperature, after which it was partitioned between EtOAc and H$_2$O. The organic layer was separated, dried over MgSO$_4$, filtered, and concentrated in vacuo. The residue was dissolved in 6 N HCl (10 mL) and MeOH (5 mL), and the resulting mixture was stirred at room temperature overnight, after which it was partitioned between EtOAc and H$_2$O. The organic layer was concentrated in vacuo, and the residue was dissolved in EtOH (2 mL). Potassium acetate (100 mg) was then added, and the reaction was stirred for 2 hr. The resulting solution was purified via preparatory HPLC to give the title compound (18 mg, 51%). $^1$H NMR (CDCl$_3$, 300 MHz): δ 9.53 (s, 1H), 8.32 (d, J=2.1 Hz, 1H), 7.56 (s, 1H), 6.69 (s, 2H), 3.95 (s, 6H), 3.90 (s, 3H), 2.28 (m, 2H), 2.24 (m, 2H), 1.97 (m, 4H). HPLC retention time: 2.00 minutes; MS ESI (m/z): 355.4 (M+1)$^+$, calc. 354.

Examples 122 and 123

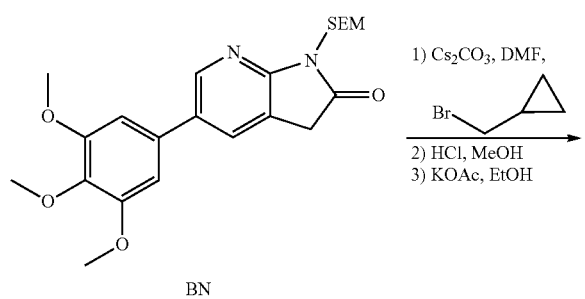

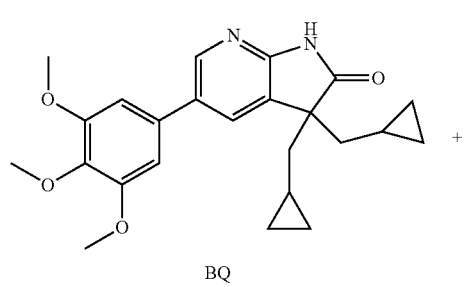

Preparation of 3,3-bis(cyclopropylmethyl)-5-(3,4,5-trimethoxyphenyl)-1H-pyrrolo[2,3-b]pyridin-2(3H)-one (Example 22, Compound BQ) and 3-(cyclopropylmethyl)-5-(3,4,5-trimethoxyphenyl)-1H-pyrrolo[2,3-b]pyridin-2(3H)-one (Example 23, Compound BR)

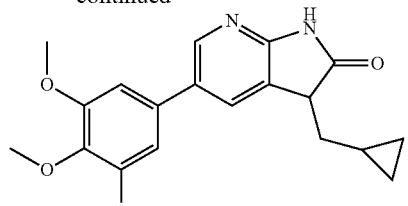

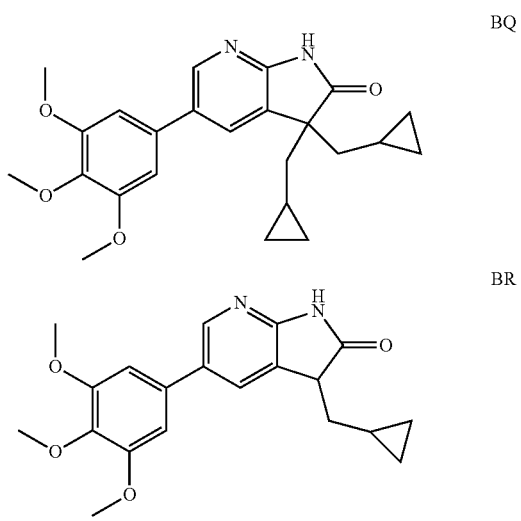

To a solution of 5-(3,4,5-trimethoxyphenyl)-1-((2-(trimethylsilyl)ethoxy)-methyl)-1H-pyrrolo[2,3-b]pyridin-2(3H)-one (43 mg, 0.10 mmol) in DMF (2 mL) was added cesium carbonate (0.17 g, 0.50 mmol), (bromomethyl)cyclopropane (10 µL, 0.10 mmol), and potassium iodide (83 mg, 0.50 mmol). The resulting solution was stirred for 4 hr at room temperature, after which it was partitioned between EtOAc and H$_2$O. The organic layer was separated, dried over MgSO$_4$, filtered, and concentrated in vacuo. The residue was dissolved in 6 N HCl (10 mL) and MeOH (5 mL), and the resulting mixture was stirred at room temperature overnight, after which it was partitioned between EtOAc and H$_2$O. The organic layer was concentrated in vacuo, and the residue was dissolved in EtOH (2 mL). Potassium acetate (100 mg) was then added, and the reaction was stirred for 2 hr. The resulting solution was purified via preparatory HPLC to give the Compound Q (11.4 mg) and Compound R (4.1 mg). Compound BQ: $^1$H NMR (CDCl$_3$, 300 MHz): δ 8.37 (d, J=2.1 Hz, 1H), 7.71 (s, 1H), 6.72 (s, 2H), 3.96 (s, 6H), 3.91 (s, 3H), 2.04 (m, 2H), 1.69 (m, 2H), 1.26 (m, 2H), 0.88 (m, 2H), 0.40 (m, 2H), 0.29 (m, 2H), −0.07 (m, 2H). HPLC retention time: 2.49 minutes; MS ESI (m/z): 409.4 (M+1)$^+$, calc. 408. Compound BR: $^1$H NMR (CDCl$_3$, 300 MHz): δ 8.31 (s, 1H), 7.92 (s, 1H), 6.69 (s, 2H), 3.95 (s, 6H), 3.91 (s, 3H), 3.50 (m, 1H), 2.18 (m, 1H), 1.78 (m, 1H), 1.26 (m, 1H), 0.83 (m, 2H), 0.25 (m, 2H). HPLC retention time: 2.32 minutes; MS ESI (m/z): 355.0 (M+1)+, calc. 354.

Example 124

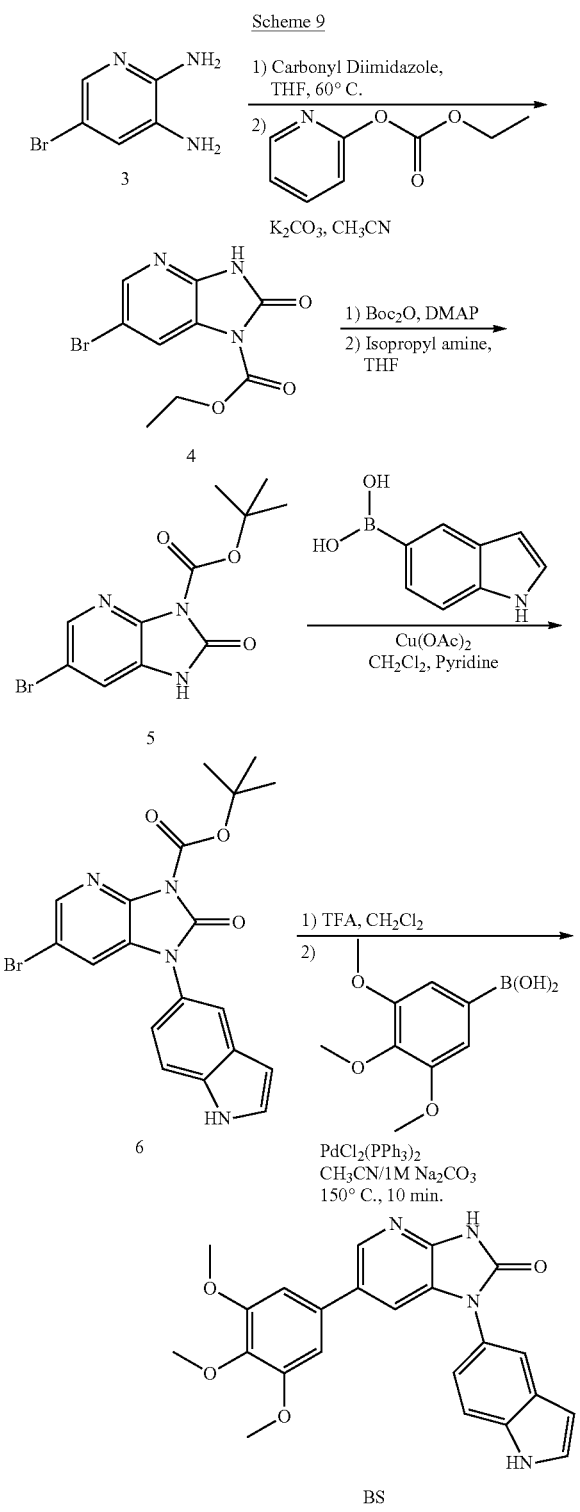

Preparation of 1-(1H-indol-5-yl)-6-(3,4,5-trimethoxyphenyl)-1H-imidazo[4,5-b]pyridin-2(3H)-one (Compound BS)

Commercially available 5-bromopyridine-2,3-diamine 3 was converted to 6-bromo-1H-imidazo[4,5-b]pyridin-2(3H)-one via treatment with carbonyl diimidazole in THF at 60° C., which was then protected as the monoethoxy carbonyl derivative 4 in a fashion similar to that described in *J. Org. Chem.*, 1995, 1565-1582. Intermediate 4 was subjected to an NOE analysis, and interactions between the 7-position hydrogen and the carbamate ethyl group were apparent, supporting the structure that is shown above. Following protection of the 3-position amine with a tert-butyl carboxylate group and deprotection of the ethyl carboxylate group using isopropyl amine, intermediate 6 was coupled to indole-5-boronic acid using copper acetate in a mixture of DCM/pyridine, after which it was deprotected using TFA/CH$_2$Cl$_2$. To the resulting 6-bromo-1-(1H-indol-5-yl)-1H-imidazo[4,5-b]pyridin-2(3H)-one in CH$_3$CN (1 mL) in a microwave reaction vial was added 3,4,5-trimethoxyphenylboronic acid (30 mg, 0.14 mmol), bis(triphenylphosphine)-palladium(II) dichloride (7.0 mg, 0.010 mmol), and 1 M Na$_2$CO$_3$ (1 mL). The resulting mixture was de-gassed with Ar for 10 min, after which it was heated at 150° C. for 10 min in a Personal Chemistry Optimizer. The resulting mixture was partitioned between EtOAc and 1 M NaOH. The organic layer was separated, dried over MgSO$_4$, filtered, and stripped to give a residue that was purified via preparatory HPLC to give 1.8 mg of the title compound. HPLC retention time: 2.36 minutes; MS ESI (m/z): 417.4 (M+1)+, calc. 416.

Example 125

Preparation of 1-(cyclopropylmethyl)-6-(3,4,5-trimethoxyphenyl)-1H-imidazo[4,5-b]pyridin-2(3H)-one

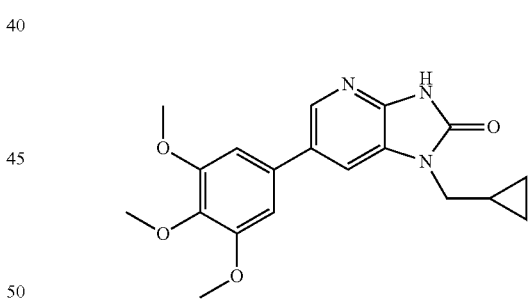

Intermediate 5 from Example 124 was alkylated with (bromomethyl)cyclopropane using K$_2$CO$_3$ in acetone, after which it was deprotected using TFA/CH$_2$Cl$_2$. To the resulting 6-bromo-1-(cyclopropylmethyl)-1H-imidazo[4,5-b]pyridin-2(3H)-one in CH$_3$CN (1 mL) in a microwave reaction vial was added 3,4,5-trimethoxyphenylboronic acid (30 mg, 0.14 mmol), bis(triphenylphosphine)-palladium(II) dichloride (7.0 mg, 0.010 mmol), and 1 M Na$_2$CO$_3$ (1 mL). The resulting mixture was de-gassed with Ar for 10 min, after which it was heated at 150° C. for 10 min in a Personal Chemistry Optimizer. The resulting mixture was partitioned between EtOAc and 1 M NaOH. The organic layer was separated, dried over MgSO$_4$, filtered, and stripped to give a residue that was purified via preparatory HPLC to give 3.7 mg of the title compound. HPLC retention time: 1.90 minutes; MS ESI (m/z): 356.2 (M+1)+, calc. 355.

Example 126

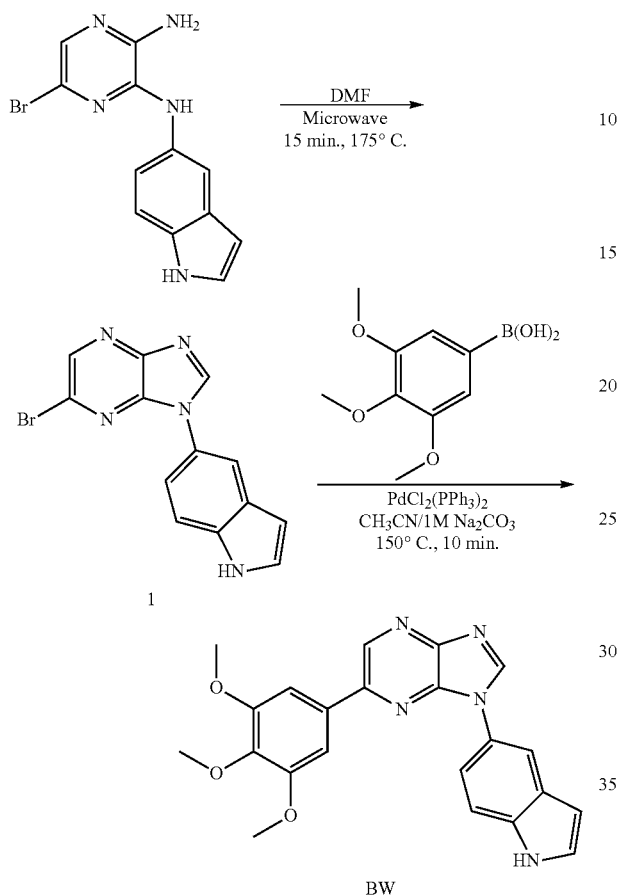

BW

Preparation of 1-(1H-indol-5-yl)-6-(3,4,5-trimethoxyphenyl)-1H-imidazo[4,5-b]pyrazine (Compound BW)

Following a method described in *Pteridines,* 2002, Vol. 13, 65-72, Intermediate BB was heated in anhydrous DMF at 175° C. for 15 min. in a Personal Chemistry Optimizer. To the resulting 6-bromo-1-(1H-indol-5-yl)-1H-imidazo[4,5-b] pyrazine 1 in CH$_3$CN (1 mL) in a microwave reaction vial was added 3,4,5-trimethoxyphenylboronic acid (30 mg, 0.14 mmol), bis(triphenylphosphine)-palladium(II) dichloride (7.0 mg, 0.010 mmol), and 1 M Na$_2$CO$_3$ (1 mL). The resulting mixture was de-gassed with Ar for 10 min, after which it was heated at 150° C. for 10 min in a Personal Chemistry Optimizer. The resulting mixture was partitioned between EtOAc and 1 M NaOH. The organic layer was separated, dried over MgSO$_4$, filtered, and stripped to give a residue that was purified via preparatory HPLC to give 4.7 mg of the title compound. HPLC retention time: 2.43 minutes; MS ESI (m/z): 402.8 (M+1)$^+$, calc. 401.

Example 127

Preparation of 1-(cyclopropylmethyl)-6-(3,4,5-trimethoxyphenyl)-1H-imidazo[4,5-b]pyrazine-2(3H)-thione (Compound BX)

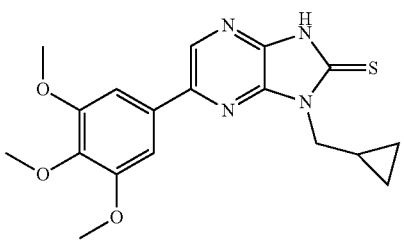 [SMILES: COc1cc(-c2cnc3[nH]c(=S)n(CC4CC4)c3n2)cc(OC)c1OC]

Compound BX was prepared by reacting Example 78 with Lawesson's reagent in refluxing toluene. The resulting mixture was partitioned between EtOAc and 1 M NaHCO$_3$. The organic layer was separated, dried over MgSO$_4$, filtered, and stripped to give a residue that was purified via preparatory HPLC to give 2.0 mg of the title compound. HPLC retention time: 2.29 minutes; MS ESI (m/z): 373.2 (M+1)$^+$, calc. 372.

Example 128

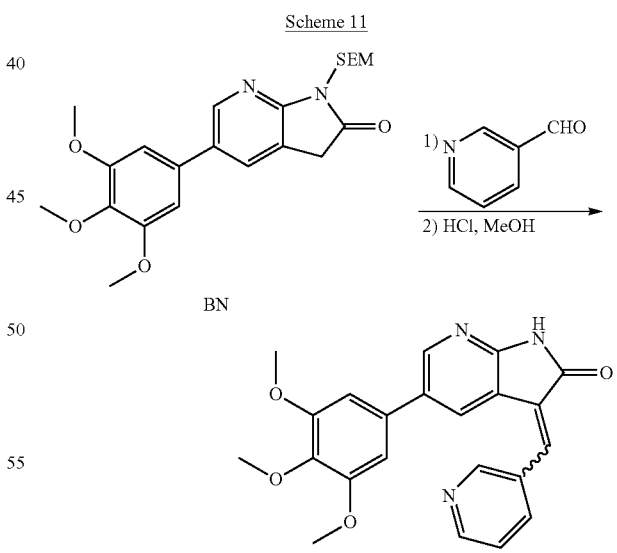

Preparation of 3-pyridin-3-ylmethylene-5-(3,4,5-trimethoxy-phenyl)-1,3-dihydro-pyrrolo[2,3-b]pyridin-2-one To a solution of 5-(3,4,5-trimethoxy-phenyl)-1-(2-trimethylsilanyl-ethoxymethyl)-1,3-dihydro-pyrrolo[2,3-b]pyridin-2-one (157 mg, 0.365 mmol) in toluene (2 mL) was added triethylamine (56 μl, 0.365 mmol), molecular sieves 4 Å (100 mg), and 3-pyridinecarboxaldehyde (38 μl, 0.401 mmol). The resulting mixture was stirred overnight at room temperature, after which it was filtered and partitioned between DCM and H₂O. The organic layer was separated, dried over MgSO₄, filtered, and concentrated in vacuo. The residue was purified by silica gel chromatography eluting with 40-70% EtOAc: Hexanes to yield the SEM-protected precursor as a mixture of cis and trans isomers (101 mg, 53%). 41 mg (0.079 mmol) of this material was dissolved in MeOH (1.5 ml), 6 N HCl (3 ml) was added, and the mixture was stirred for 3 hours at 45° C. The reaction was quenched with 1 N NaOH (15 ml), neutralized by the addition of saturated NaHCO₃ and extracted with DCM. Silica gel chromatography eluting with 0-5% MeOH: DCM yielded the title compound (22 mg, 72%) as a cis/trans-mixture. ¹H NMR (CDCl₃, 300 MHz): δ 9.15 (d, J=4.8 Hz, 1H), 9.11 (bs, 1H), 9.02 (d, J=1.2 Hz, 1H), 8.98 (d, J=1.1, 1H), 8.69 (dd, J=0.9, 2.9 Hz, 1H), 8.66 (dd, J=0.9, 2.8 Hz, 1H), 8.39 (d, J=1.2 Hz, 1H), 8.37 (d, J=1.2 Hz, 1H), 7.95 (m, 1H), 7.93 (s, 1H), 7.87 (d, J=1.1 Hz, 1H), 7.44 (m, 1H), 6.75 (s, 2H), 6.59 (s, 2H), 3.97 (s, 6H), 3.91 (s, 3H), 3.90 (s, 6H), 3.86 (s, 3H).

Example 129

Preparation of (E)- and (Z)-3-pyridin-4-ylmethylene-5-(3,4,5-trimethoxy-phenyl)-1,3-dihydro-pyrrolo[2,3-b]pyridin-2-one

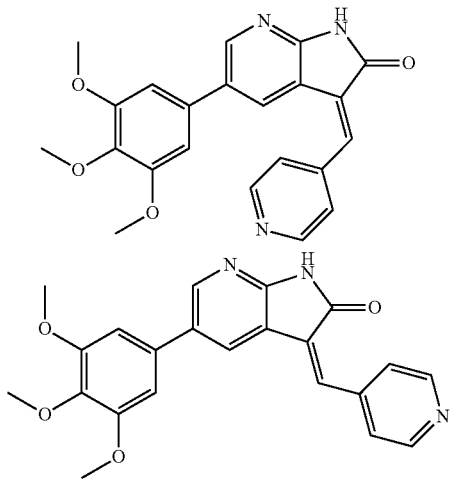

(E)- and (Z)-3-pyridin-4-ylmethylene-5-(3,4,5-trimethoxy-phenyl)-1,3-dihydro-pyrrolo[2,3-b]pyridin-2-one were prepared by a method analogous to that described in Example 128 by substituting 3-pyridinecarboxaldehyde for 4-pyridinecarboxaldehyde in the reaction with Compound BN. The isomers were separated using silica gel chromatography eluting with 0-5% MeOH:DCM. Assignment of stereochemistry is tentatively based on the ¹H NMR spectra. ¹H NMR (CDCl₃, 300 MHz): E-isomer: δ 8.91 (s, 1H), 8.76 (d, (J=3.6 Hz, 1H), 8.39 (d, J=1.2 Hz, 1H), 8.02 (d, J=3.7 Hz, 1H), 7.91 (d, J=1.2 Hz, 1H), 7.52 (s, 1H), 6.74 (s, 2H), 3.96 (s, 6H), 3.91 (s, 3H). Z-isomer: δ 9.01 (s, 1H), 8.78 (d, (J=3.5 Hz, 1H), 8.38 (d, J=1.2 Hz, 1H), 7.87 (s, 1H), 7.81 (d, J=1.2 Hz, 1H), 7.52 (d, J=6.1 Hz, 1H), 6.56 (s, 2H), 3.89 (s, 6H), 3.88 (s, 3H).

Example 130

Preparation of 3-benzylidene-5-(3,4,5-trimethoxy-phenyl)-1,3-dihydro-pyrrolo[2,3-b]pyridin-2-one

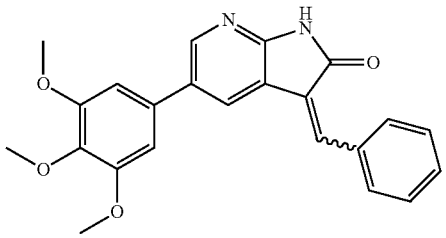 [SMILES: COc1cc(-c2cnc3c(c2)C(=Cc2ccccc2)C(=O)N3)cc(OC)c1OC]

3-Benzylidene-5-(3,4,5-trimethoxy-phenyl)-1,3-dihydro-pyrrolo[2,3-b]pyridin-2-one was prepared by a method analogous to that described in Example 128 by substituting 3-pyridinecarboxaldehyde for benzaldehyde in the reaction with Compound BN. 15 mg (33%) of the title compound were obtained.

Example 131

Preparation of 4-[2-oxo-5-(3,4,5-trimethoxy-phenyl)-1,2-dihydro-pyrrolo[2,3-b]pyridin-3-ylidenemethyl]-benzamide

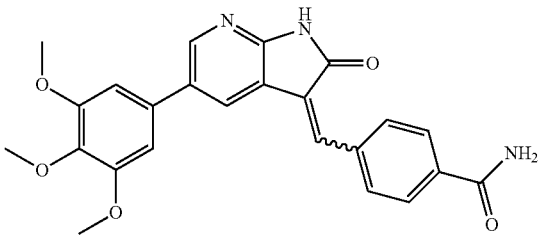 [SMILES: COc1cc(-c2cnc3c(c2)C(=Cc2ccc(C(N)=O)cc2)C(=O)N3)cc(OC)c1OC]

4-[2-Oxo-5-(3,4,5-trimethoxy-phenyl)-1,2-dihydro-pyrrolo[2,3-b]pyridin-3-ylidenemethyl]-benzamideone was prepared by a method analogous to that described in Example 128 by substituting 3-pyridinecarboxaldehyde for 4-formyl-benzamide in the reaction with Compound BN. 25 mg (50%) of the title compound were obtained.

Example 132

Preparation of 3-[2-oxo-5-(3,4,5-trimethoxy-phenyl)-1,2-dihydro-pyrrolo[2,3-b]pyridin-3-ylidenemethyl]-benzamide

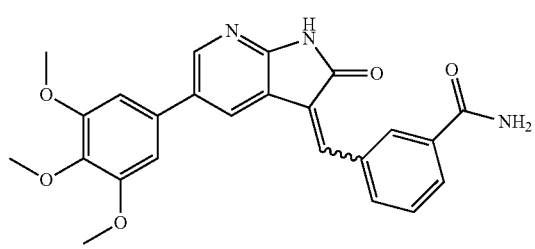 [SMILES: COc1cc(-c2cnc3c(c2)C(=Cc2cccc(C(N)=O)c2)C(=O)N3)cc(OC)c1OC]

3-[2-Oxo-5-(3,4,5-trimethoxy-phenyl)-1,2-dihydro-pyrrolo[2,3-b]pyridin-3-ylidenemethyl]-benzamideone was prepared by a method analogous to that described in Example 128 by substituting 3-pyridinecarboxaldehyde for 3-formylbenzamide in the reaction with Compound BN. 26 mg (52%) of the title compound were obtained.

Example 133

Scheme 12

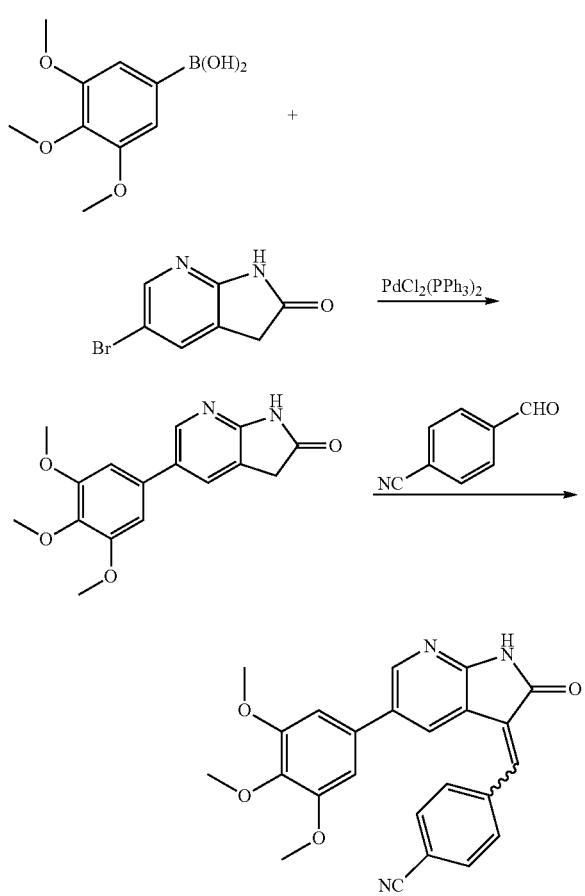

Preparation of 5-(3,4,5-trimethoxy-phenyl)-1,3-dihydro-pyrrolo[2,3-b]pyridin-2-one (Intermediate BY)

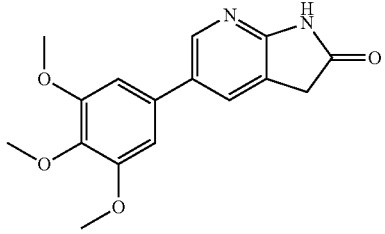 [SMILES: COc1cc(-c2cnc3c(c2)CC(=O)N3)cc(OC)c1OC]

A mixture of 5-bromo-1,3-dihydro-pyrrolo[2,3-b]pyridin-2-one (200 mg, 0.939 mmol), 3,4,5-trimethoxyphenylboronic acid (239 mg, 1.127 mmol) and dichlorobis(triphenylphosphine)palladium (II) (33 mg, 0.047 mmol) in CH₃CN (5 ml) and 1 M Na₂CO₃ (5 ml) was heated in a microwave reactor for 10 min at 150° C. The reaction mixture was filtered, evaporated, partitioned between water and DCM and purified by silica gel chromatography with 0-10% MeOH:DCM to obtain 85 mg (30%) of compound #. ¹H NMR (CDCl₃/DMSO-d6, 300 MHz): δ 10.19 (bs, 1H), 8.18 (d, J=1.1 Hz, 1H), 7.54 (s, 1H), 6.57 (s, 2H), 3.80 (s, 6H), 3.75 (s, 3H), 3.47 (s, 2H).

Preparation of 4-[2-oxo-5-(3,4,5-trimethoxy-phenyl)-1,2-dihydro-pyrrolo[2,3-b]pyridin-3-ylidenemethyl]-benzonitrile

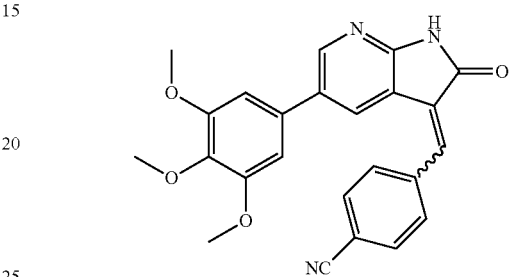

A mixture of 5-(3,4,5-trimethoxy-phenyl)-1,3-dihydro-pyrrolo[2,3-b]pyridin-2-one (Intermediate BY, 42 mg, 0.14 mmol), 4-cyanobenzaldehyde (22 mg, 0.168 mmol), triethylamine (22 µl, 0.168 mmol) and molecular sieves 4 Å (100 mg) in toluene (2 ml) was reacted at 80° C. for 1 d. The mixture was partitioned between DCM and water, the aqueous phase extracted with DCM, combined organic phases dried, evaporated and purified by silica gel chromatography (0-5% MeOH:DCM) to obtain 31 mg (54%) of the title compound as a mixture of (E)- and (Z)-isomers.

Example 134

Preparation of 3-[2-oxo-5-(3,4,5-trimethoxy-phenyl)-1,2-dihydro-pyrrolo[2,3-b]pyridin-3-ylidenemethyl]-benzonitrile

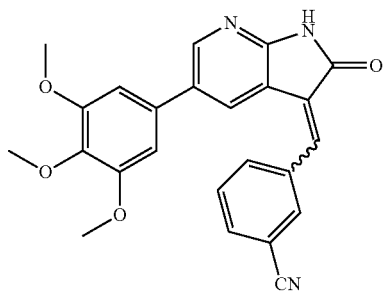 [SMILES: COc1cc(-c2cnc3c(c2)C(=Cc2cccc(C#N)c2)C(=O)N3)cc(OC)c1OC]

3-[2-oxo-5-(3,4,5-trimethoxy-phenyl)-1,2-dihydro-pyrrolo[2,3-b]pyridin-3-ylidenemethyl]-benzonitrile was prepared by a method analogous to that described in Example 133 by substituting 4-cyanobenzaldehyde for 3-cyanobenzaldehyde in the reaction with Intermediate BY. 36 mg (62%) of the title compound were obtained as a mixture of cis- and trans-isomers.

Example 135

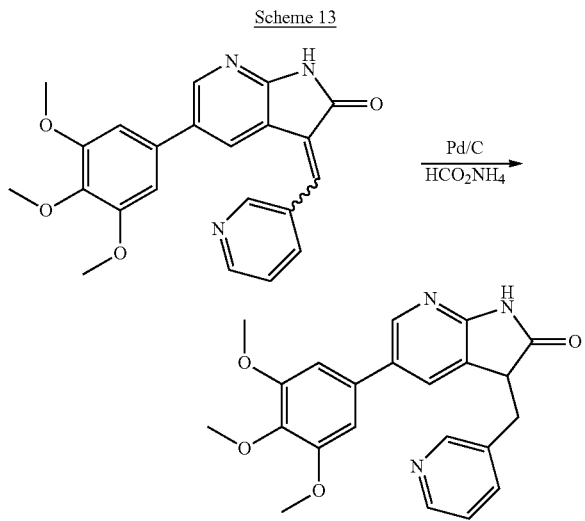

Preparation of 3-pyridin-3-ylmethyl-5-(3,4,5-trimethoxy-phenyl)-1,3-dihydro-pyrrolo[2,3-b]pyridin-2-one To a solution of 3-pyridin-4-ylmethylene-5-(3,4,5-trimethoxy-phenyl)-1,3-dihydro-pyrrolo[2,3-b]pyridin-2-one (50 mg, 0.128 mmol) in MeOH (4 ml) was added ammonium formate (245 mg, 3.85 mmol) and Pd/C (10%, 30 mg). The mixture was stirred at room temperature for 3 hrs after which it was filtered, evaporated, and partitioned between water and DCM. The title compound (33 mg, 66%) was obtained after silica gel chromatography eluting with 0-10% MeOH:DCM. $^1$H NMR (CDCl$_3$, 300 MHz): δ 10.05 (s, 1H), 8.60 (d, J=2.6 Hz, 1H), 8.45 (d, J=1.1 Hz, 1H), 8.38 (d, J=1.2 Hz, 1H), 7.62 (d, J=4.7 Hz, 1H), 7.35 (dd, J=2.9, 4.7 Hz, 1H), 6.53 (d, J=1.2 Hz, 1H), 6.38 (s, 1H), 3.95 (m, 1H), 3.90 (m, 1H), 3.85 (s, 6H), 3.84 (s, 3H), 3.84 (m, 1H).

Example 136

Preparation of 3-pyridin-4-ylmethyl-5-(3,4,5-trimethoxy-phenyl)-1,3-dihydro-pyrrolo[2,3-b]pyridin-2-one

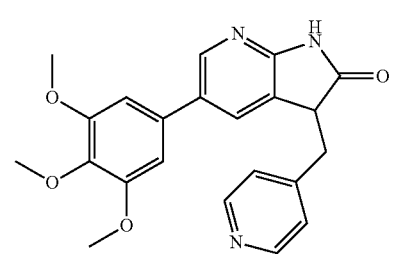 [SMILES: COc1cc(-c2cnc3c(c2)C(Cc2ccncc2)C(=O)N3)cc(OC)c1OC]

3-Pyridin-4-ylmethyl-5-(3,4,5-trimethoxy-phenyl)-1,3-dihydro-pyrrolo[2,3-b]pyridin-2-one was prepared by a method analogous to that described in Example 135. The title compound (14 mg, 61%) was obtained after silica gel chromatography eluting with 0-8% MeOH:DCM. $^1$H NMR (CDCl$_3$, 300 MHz): δ 9.52 (bs, 1H), 8.54 (d, J=3.5 Hz, 1H), 8.32 (d, J=1.1 Hz, 1H), 7.18 (d, J=3.6 Hz, 1H), 7.12 (m, 1H), 6.54 (s, 1H), 3.91 (s, 6H), 3.89 (m, 1H), 3.88 (s, 3H), 3.54 (dd, J=3.1, 8.3 Hz, 1H), 3.03 (dd, J=5.6, 8.3 Hz, 1H).

Example 137

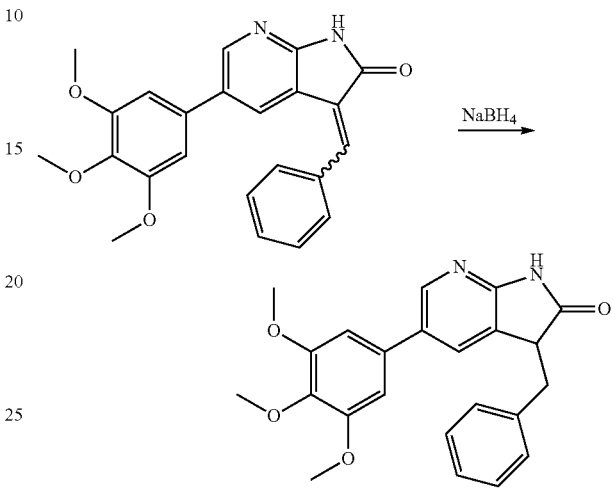

Preparation of 3-benzyl-5-(3,4,5-trimethoxy-phenyl)-1,3-dihydro-pyrrolo[2,3-b]pyridin-2-one To a solution of 3-benzylidene-5-(3,4,5-trimethoxy-phenyl)-1,3-dihydro-pyrrolo[2,3-b]pyridin-2-one (41 mg, 0.106 mmol) in a mixture of MeOH (2 ml), THF (1 ml) and water (0.3 ml) was added sodium borohydride (40 mg, 1.06 mmol). The reaction was stirred at room temperature for 10 min after which it was quenched by the addition of 1 N HCl and partitioned between water and DCM. The residue was purified by preparatory HPLC to yield the title compound (5.2 mg, 13%).

Example 138

Preparation of 4-[2-oxo-5-(3,4,5-trimethoxy-phenyl)-2,3-dihydro-1H-pyrrolo[2,3-b]pyridin-3-ylmethyl]-benzamide

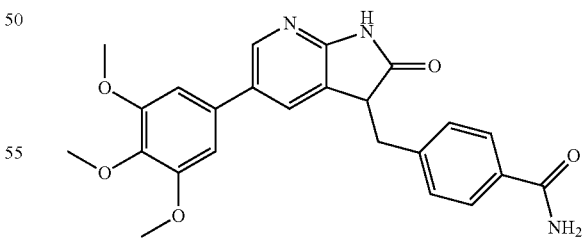

4-[2-Oxo-5-(3,4,5-trimethoxy-phenyl)-2,3-dihydro-1H-pyrrolo[2,3-b]pyridin-3-ylmethyl]-benzamide was prepared from 4-[2-oxo-5-(3,4,5-trimethoxy-phenyl)-1,2-dihydro-pyrrolo[2,3-b]pyridin-3-ylidenemethyl]-benzamideone by a method analogous to that described in Example 137. The title compound (12 mg, 54%) was obtained after silica gel chromatography eluting with 0-10% MeOH:DCM. $^1$H NMR (DMSO-d6, 300 MHz): δ 11.06 (s, 1H), 8.34 (d, J=1.5 Hz, 1H), 7.88 (s, 1H), 7.75 (d, J=5.0 Hz, 2H), 7.41 (d, J=0.5 Hz, 1H), 7.30 (s, 1H), 7.28 (d, J=5.0 Hz, 2H), 6.74 (s, 2H), 4.03 (m, 1H), 3.82 (s, 6H), 3.67 (s, 3H), 3.44 (dd, J=3.4, 8.2 Hz, 1H), 3.11 (dd, J=4.6, 8.2 Hz, 1H).

Example 139

Preparation of 3,3-dibenzyl-5-(3,4,5-trimethoxy-phenyl)-1,3-dihydro-pyrrolo[2,3-b]pyridin-2-one

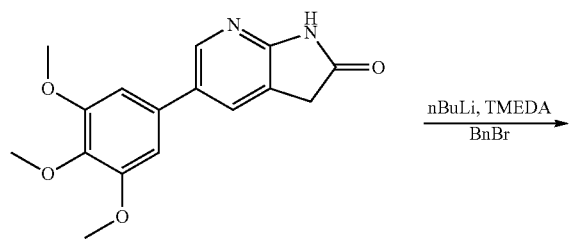

5-(3,4,5-Trimethoxy-phenyl)-1,3-dihydro-pyrrolo[2,3-b]pyridin-2-one (95 mg, 0.316 mmol) and TMEDA (96 µl, 0.623 mmol) were dissolved in anhydrous THF (4 ml) and cooled to −78° C. n-BuLi (1.6 M in hexanes, 415 µl, 0.664 mmol) was added dropwise. After completed addition stirring was continued for 1 hr at −78° C. Benzyl bromide (41.3 µl, 0.348 mmol) was added dropwise as a 10% solution in anh. THF. After completed addition the reaction was allowed to warm up to room temperature while stirring overnight. The reaction was quenched by the addition of MeOH, evaporated and partitioned between water and DCM. Silica gel chromatography eluting with 0-50% EtOAc:Hexanes yielded the title compound (47 mg, 38%). $^1$H NMR (CDCl$_3$, 300 MHz): δ 8.83 (s, 1H), 8.18 (d, J=1.2 Hz, 1H), 7.19 (d, J=1.2 Hz, 1H), 7.14 (m, 6H), 6.99 (m, 4H), 6.61 (s, 2H), 3.96 (s, 6H), 3.90 (s, 3H), 3.30 (d, J=8.0 Hz, 2H), 3.26 (d, J=8.0 Hz, 2H).

Example 140

Preparation of 1-(4-{4-[3-(1H-indol-5-yl)-1H-pyrrolo[2,3-b]pyridin-5-yl]-benzyl}-piperazin-1-yl)-ethanone

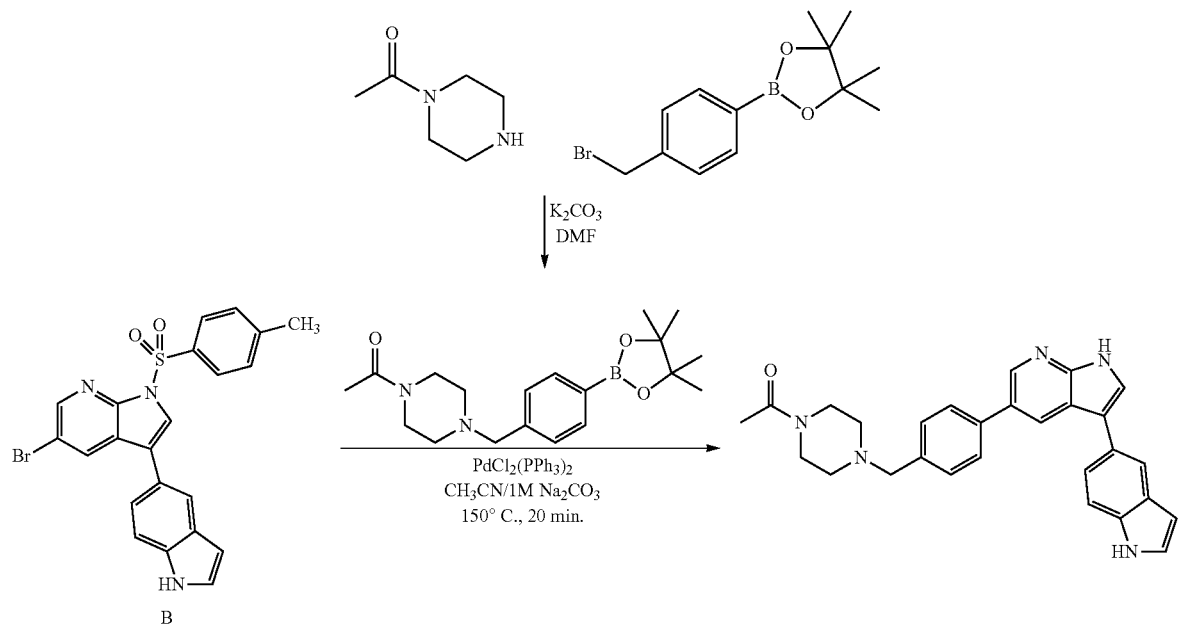

-continued

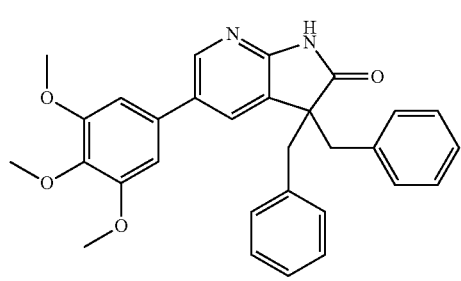

2-(4-Bromomethyl-phenyl)-4,4,5,5-tetramethyl-[1,3,2]dioxaborolane (100 mg, 0.337 mmol), N-acetylpiperazine (47 mg, 0.37 mmol) and K$_2$CO$_3$ (93 mg, 0.675 mmol) were combined in DMF (2.5 ml) and stirred overnight at room temperature. The reaction was quenched by the addition of water, extracted with DCM and dried. The residue was taken up in CH$_3$CN (2 ml), Intermediate B (120 mg, 0.275 mmol) and dichlorobis(triphenylphosphine)palladium (II) (10 mg, 0.013 mmol) were added and the reaction was heated to 150° C. in a microwave reactor for 20 min. The mixture was partitioned between water and DCM, the organic phase dried, evaporated and purified by silica gel chromatography using 0-5% MeOH:DCM. 53 mg (46%) of the title compound were obtained. MS ESI (m/z): 450.4 (M+1)$^+$, calc. 449.

Example 141

Preparation of 4-{4-[3-(1H-indol-5-yl)-1H-pyrrolo[2,3-b]pyridin-5-yl]-benzyl}-1-methyl-piperazin-2-one

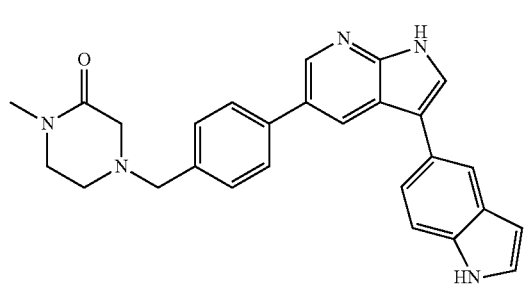 [SMILES: CN1CCN(Cc2ccc(-c3cnc4[nH]cc(-c5ccc6[nH]ccc6c5)c4c3)cc2)CC1=O]

4-{4-[3-(1H-Indol-5-yl)-1H-pyrrolo[2,3-b]pyridin-5-yl]-benzyl}-1-methyl-piperazin-2-one was prepared by a method analogous to that described in Example 140 by substituting N-acetylpiperazine for 1-methyl-piperazin-2-one. The title compound (14 mg, 28%) was obtained after silica gel chromatography eluting with 0-10% MeOH:DCM. MS ESI (m/z): 435.9 (M+1)$^+$, calc. 435.

Example 142

Preparation of 4-{4-[3-(1H-indol-5-yl)-1H-pyrrolo[2,3-b]pyridin-5-yl]-benzyl}-piperazin-2-one

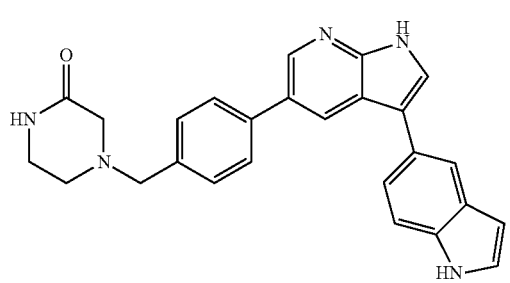 [SMILES: O=C1CN(Cc2ccc(-c3cnc4[nH]cc(-c5ccc6[nH]ccc6c5)c4c3)cc2)CCN1]

4-{4-[3-(1H-Indol-5-yl)-1H-pyrrolo[2,3-b]pyridin-5-yl]-benzyl}-piperazin-2-one was prepared by a method analogous to that described in Example 140 by substituting N-acetylpiperazine for piperazin-2-one. The title compound (22 mg, 45%) was obtained after silica gel chromatography eluting with 0-10% MeOH:DCM. MS ESI (m/z): 422.2 (M+1)$^+$, calc. 421.

Example 143

Preparation of 4-{3-[3-(1H-indol-5-yl)-1H-pyrrolo[2,3-b]pyridin-5-yl]-benzyl}-1-methyl-piperazin-2-one

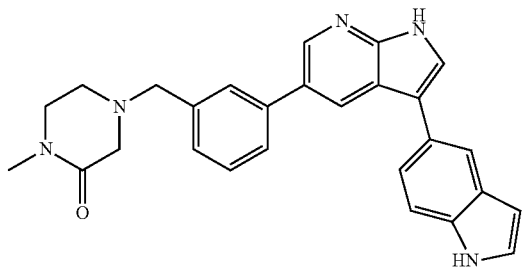 [SMILES: CN1CCN(Cc2cccc(-c3cnc4[nH]cc(-c5ccc6[nH]ccc6c5)c4c3)c2)CC1=O]

4-{3-[3-(1H-Indol-5-yl)-1H-pyrrolo[2,3-b]pyridin-5-yl]-benzyl}-1-methyl-piperazin-2-one was prepared by a method analogous to that described in Example 140 by substituting N-acetylpiperazine for 1-methyl-piperazin-2-one and 2-(4-bromomethyl-phenyl)-4,4,5,5-tetramethyl-[1,3,2]dioxaborolane for 3-(bromomethyl)phenylboronic acid. The title compound (22 mg, 45%) was obtained after silica gel chromatography eluting with 0-10% MeOH:DCM. MS ESI (m/z): 436.4 (M+1)$^+$, calc. 435.

Example 144

Preparation of 4-{4-[3-(1H-indol-5-yl)-1H-pyrrolo[2,3-b]pyridin-5-yl]-benzyl}-piperazine-1-carboxylic acid tert-butyl ester

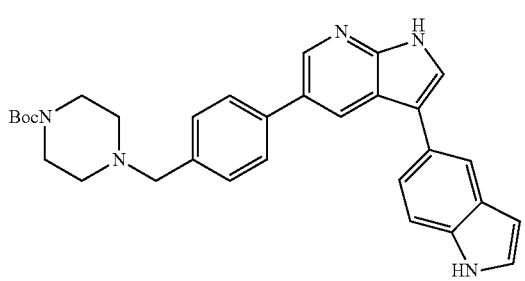 [SMILES: CC(C)(C)OC(=O)N1CCN(Cc2ccc(-c3cnc4[nH]cc(-c5ccc6[nH]ccc6c5)c4c3)cc2)CC1]

4-{4-[3-(1H-Indol-5-yl)-1H-pyrrolo[2,3-b]pyridin-5-yl]-benzyl}-piperazine-1-carboxylic acid tert-butyl ester was prepared by a method analogous to that described in Example 140 by substituting N-acetylpiperazine for N-Boc-piperazine. The title compound (20 mg, 33%) was obtained after silica gel chromatography eluting with 0-3% MeOH:DCM. MS ESI (m/z): 508.2 (M+1)$^+$, calc. 507.

Example 145

Scheme 15

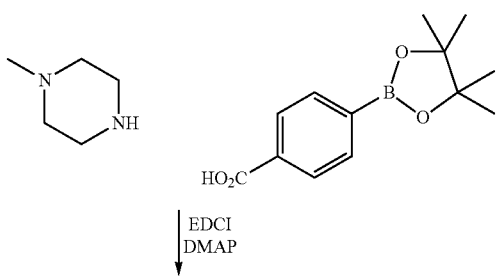

EDCI
DMAP

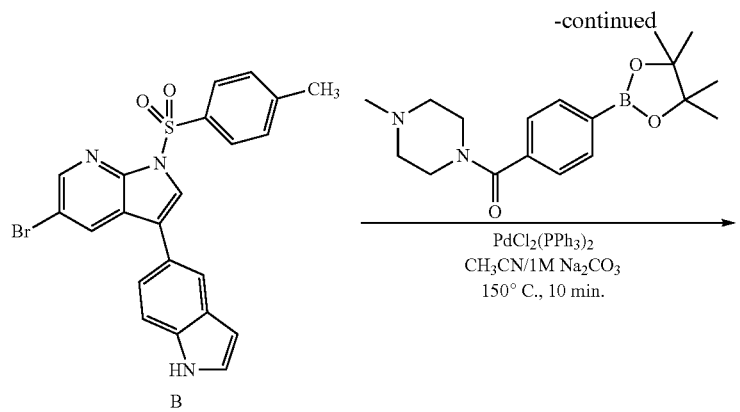

B

Preparation of {4-[3-(1H-indol-5-yl)-1H-pyrrolo[2,3-b]pyridin-5-yl]-phenyl}-(4-methyl-piperazin-1-yl)-methanone 4-(4,4,5,5-Tetramethyl-[1,3,2]dioxaborolan-2-yl)-benzoic acid (100 mg, 0.403 mmol), EDCI (97 mg, 0.504 mmol) and DMAP (catalytic amount) were combined in CH₃CN, stirred for 10 min and treated with N-methylpiperazine (54 µl, 0.484 mmol). The mixture was stirred overnight at room temperature. An aliquot of 650 µl was taken, combined with Intermediate B (50 mg, 0.107 mmol) and dichlorobis(triphenylphosphine)palladium (II) (10 mg, 0.013 mmol) and heated to 150° C. in a microwave reactor for 20 min. The mixture was partitioned between water and DCM, the organic phase dried, evaporated and purified by silica gel chromatography using 0-6% MeOH:DCM. 13 mg (28%) of the title compound were obtained. ¹H NMR (DMSO-d6, 300 MHz): δ 11.88 (d, J=1.5 Hz, 1H), 11.08 (s, 1H), 8.57 (d, J=2.1 Hz, 1H), 8.45 (d, J=1.8 Hz, 1H), 7.90 (s, 1H), 7.82 (d, J=8.4 Hz, 1H), 7.77 (d, J=2.4 Hz, 1H), 7.47 (m, 4H), 7.34 (t, J=2.6 Hz, 1H), 6.47 (t, J=2.4 Hz, 1H), 3.58 (bs, 4H), 2.3 (bs, 4H), 2.18 (s, 3H).

Example 146
Preparation of 1-(4-{4-[3-(1H-indol-5-yl)-1H-pyrrolo[2,3-b]pyridin-5-yl]-benzoyl}-piperazin-1-yl)-ethanone

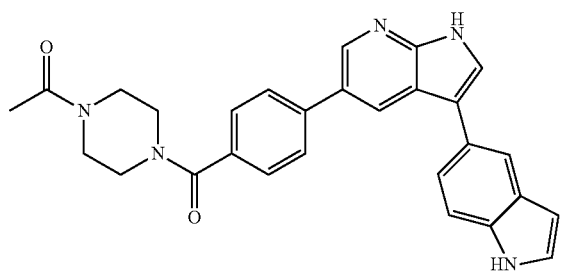 [SMILES: CC(=O)N1CCN(C(=O)c2ccc(-c3cnc4[nH]cc(-c5ccc6[nH]ccc6c5)c4c3)cc2)CC1]

1-(4-{4-[3-(1H-Indol-5-yl)-1H-pyrrolo[2,3-b]pyridin-5-yl]-benzoyl}-piperazin-1-yl)-ethanone was synthesized by a method analogous to that described in Example 144 by substituting N-methylpiperazine for N-acetylpiperazine. The title compound (13 mg, 26%) was obtained after silica gel chromatography eluting with 0-5% MeOH:DCM. MS ESI (m/z): 464.2 (M+1)⁺, calc. 463.

Example 147
Preparation of {3-[3-(1H-indol-5-yl)-1H-pyrrolo[2,3-b]pyridin-5-yl]-phenyl}-(4-methyl-piperazin-1-yl)-methanone

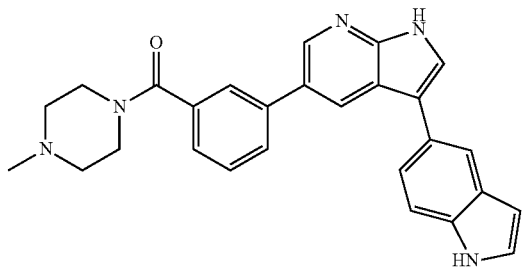 [SMILES: CN1CCN(C(=O)c2cccc(-c3cnc4[nH]cc(-c5ccc6[nH]ccc6c5)c4c3)c2)CC1]

{3-[3-(1H-Indol-5-yl)-1H-pyrrolo[2,3-b]pyridin-5-yl]-phenyl}-(4-methyl-piperazin-1-yl)-methanone was synthesized by a method analogous to that described in Example 144 by substituting 4-(4,4,5,5-tetramethyl-dioxaborolan-2-yl)-benzoic acid for 3-carboxyphenylboronic acid. The title compound (23 mg, 49%) was obtained after silica gel chromatography eluting with 5-10% MeOH:DCM. MS ESI (m/z): 436.4 (M+1)⁺, calc. 435.

Example 148

Scheme 16

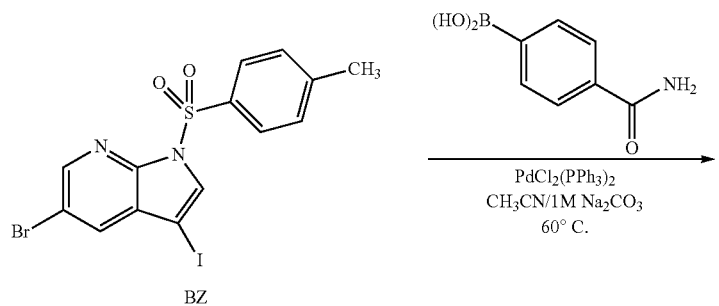

BZ

-continued

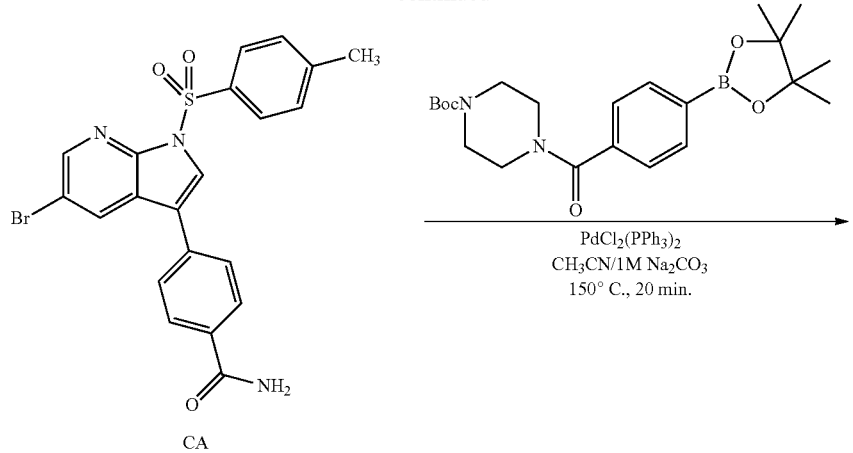

Preparation of 4-[5-bromo-1-(toluene-4-sulfonyl)-1H-pyrrolo[2,3-b]pyridin-3-yl]-benzamide (Intermediate CA)

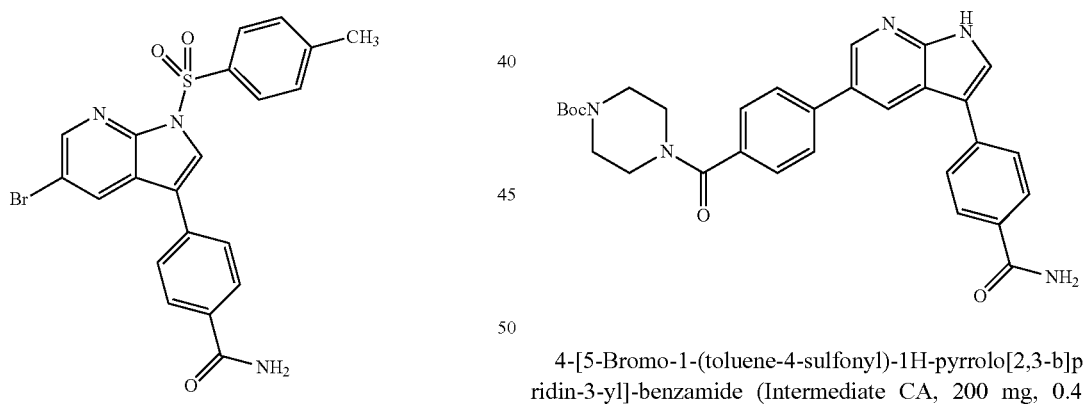

Preparation of 4-{4-[3-(4-carbamoyl-phenyl)-1H-pyrrolo[2,3-b]pyridin-5-yl]-benzoyl}-piperazine-1-carboxylic acid tert-butyl ester 5-Bromo-3-iodo-1-(toluene-4-sulfonyl)-1H-pyrrolo[2,3-b]pyridine (Intermediate BZ, 483 mg, 1.01 mmol), 4-aminocarbonylphenylboronic acid (196 mg, 1.22 mmol) and dichlorobis(triphenylphosphine)palladium (II) (71 mg, 0.1 mmol) were combined in $CH_3CN$ (10 ml) and 1 M $Na_2CO_3$ (10 ml) and stirred at 60° C. for 3 hrs. Water was added and the mixture was extracted with DCM and purified by silica gel chromatography using 0-30% EtOAc/Hexanes. The title compound was obtained in 79% yield (373 mg). $^1$H NMR ($CDCl_3$, 300 MHz): δ 8.51 (d, J=1.2 Hz, 1H), 8.20 (d, J=1.2 Hz, 1H), 8.11 (d, J=5.1 Hz, 2H), 7.96 (s, 1H), 7.93 (d, J=5.0 Hz, 2H), 7.64 (d, J=5.1 Hz, 2H), 7.31 (d, J=4.8 Hz, 2H), 6.1 (bs, 1H), 5.7 (bs, 1H), 2.39 (s, 3H).

4-[5-Bromo-1-(toluene-4-sulfonyl)-1H-pyrrolo[2,3-b]pyridin-3-yl]-benzamide (Intermediate CA, 200 mg, 0.425 mmol), 4-[4-(4,4,5,5-tetramethyl-dioxaborolan-2-yl)-benzoyl]-piperazine-1-carboxylic acid tert-butyl ester (212 mmg, 0.51 mmol) and dichlorobis(triphenylphosphine)palladium (II) (15 mg, 0.021 mmol) were combined in $CH_3CN$ (5 ml) and 1 M $Na_2CO_3$ (5 ml) and reacted in a microwave reactor at 150° C. for 10 min. The mixture was filtered, water was added, extracted with EtOAc and purified by silica gel chromatography using 0-8% MeOH:DCM. The title compound was obtained in 46% yield (102 mg). $^1$H NMR (DMSO-d6, 300 MHz): δ 12.2 (bs, 1H), 8.63 (d, J=1.1 Hz, 1H), 8.54 (d, J=1.1 Hz, 1H), 8.08 (s, 1H), 7.98 (bs, 1H), 7.96 (d, J=5.1 Hz, 2H), 7.89 (m, 4H), 7.54 (d, J=4.9 Hz, 2H), 7.32 (bs, 1H), 3.6 (bs, 2H), 3.4 (bs), 1.41 (s, 9H).

Example 149

Preparation of 4-{5-[4-(piperazine-1-carbonyl)-phenyl]-1H-pyrrolo[2,3-b]pyridin-3-yl}-benzamide, hydrochloride salt

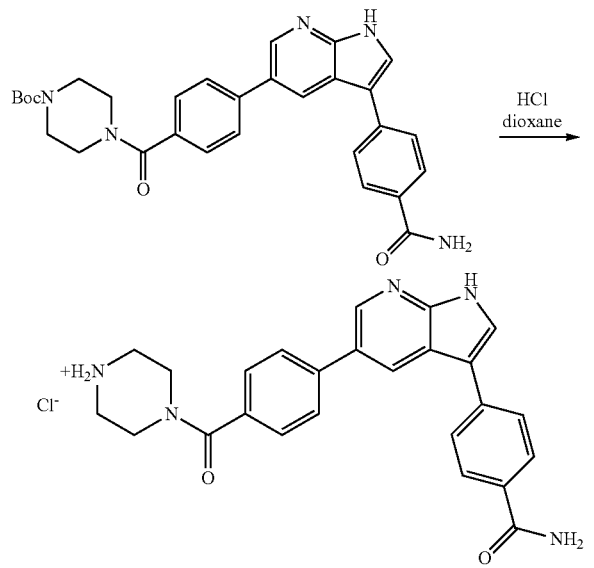

A solution of 4-{4-[3-(4-carbamoyl-phenyl)-1H-pyrrolo[2,3-b]pyridin-5-yl]-benzoyl}-piperazine-1-carboxylic acid tert-butyl ester (100 mg, 0.19 mmol) in MeOH (3 ml) was treated with 4 N HCl in dioxane (2.5 ml) and stirred at room temperature for 1 hr. The mixture was evaporated, taken up in MeOH and evaporated again. This was repeated twice to give 102 mg (116%) of the title compound. MS ESI (m/z): MS ESI (m/z): 426.4 (M+1)$^+$, calc. 425.

Example 150

Preparation of 4-{5-[4-(4-acetyl-piperazine-1-carbonyl)-phenyl]-1H-pyrrolo[2,3-b]pyridin-3-yl}-benzamide

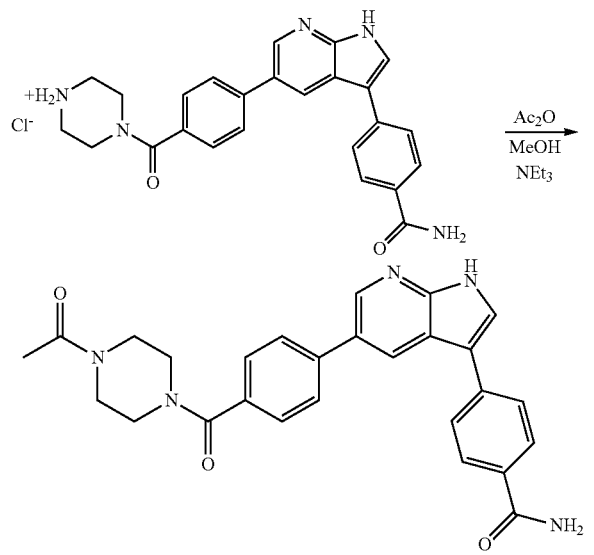

To a solution of 4-{5-[4-(piperazine-1-carbonyl)-phenyl]-1H-pyrrolo[2,3-b]pyridin-3-yl}-benzamide, hydrochloride salt (19 mg, 0.041 mmol) in MeOH (2 ml) was added triethylamine (400 µl, 2.88 mmol) and acetic anhydride (100 µl, 1.06 mmol). The mixture was stirred for 1 hr at room temperature. EtOAc was added and washed with saturated aqu. NaHCO$_3$, water, brine and dried and evacuated. Purification on silica gel employing 0-10% MeOH:DCM provided 4.7 mg (25%) of the title compound. MS ESI (m/z): 468.3 (M+1)$_+$, calc. 467.

Example 151

Preparation of 4-{3-[3-(4-carbamoyl-phenyl)-1H-pyrrolo[2,3-b]pyridin-5-yl]-benzoyl}-piperazine-1-carboxylic acid tert-butyl ester

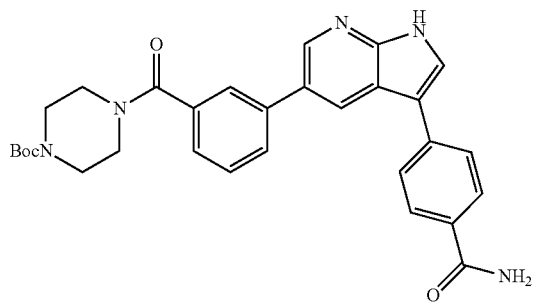 [SMILES: CC(C)(C)OC(=O)N1CCN(C(=O)c2cccc(-c3cnc4[nH]cc(-c5ccc(C(N)=O)cc5)c4c3)c2)CC1]

4-{3-[3-(4-Carbamoyl-phenyl)-1H-pyrrolo[2,3-b]pyridin-5-yl]-benzoyl}-piperazine-1-carboxylic acid tert-butyl ester was prepared by a method analogous to that described in Example 148 by substituting 4-[4-(4,4,5,5-tetramethyl-[1,3,2]dioxaborolan-2-yl)-benzoyl]-piperazine-1-carboxylic acid tert-butyl ester for 4-[3-(4,4,5,5-Tetramethyl-[1,3,2]dioxaborolan-2-yl)-benzoyl]-piperazine-1-carboxylic acid tert-butyl ester. The title compound (109 mg, 49%) was obtained after silica gel chromatography eluting with 0-8% MeOH:DCM. $^1$H NMR (DMSO-d6, 300 MHz): δ 12.18 (bs, 1H), 8.61 (d, J=1.2 Hz, 1H), 8.52 (d, J=1.2 Hz, 1H), 8.07 (s, 1H), 7.96 (m, 3H), 7.89 (m, 3H), 7.80 (s, 1H), 7.57 (t, J=4.6 Hz, 1H), 7.41 (d, J=4.6 Hz, 1H), 7.32 (s, 1H), 3.63 (bs, 2H), 3.4 (bs, 2H), 1.40 (s, 9H).

Example 152

Preparation of 4-{5-[3-(piperazine-1-carbonyl)-phenyl]-1H-pyrrolo[2,3-b]pyridin-3-yl}-benzamide, hydrochloride salt

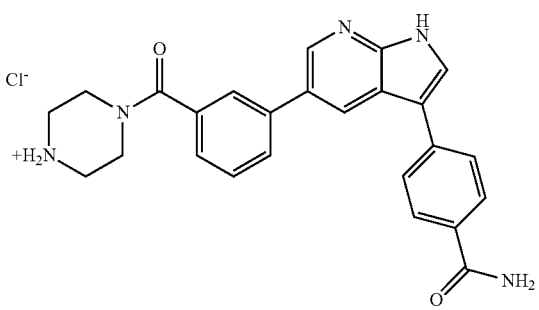 [SMILES: [Cl-] ; NC(=O)c1ccc(-c2c[nH]c3ncc(-c4cccc(C(=O)N5CC[NH2+]CC5)c4)cc23)cc1]

The hydrochloride salt of 4-{5-[3-(piperazine-1-carbonyl)-phenyl]-1H-pyrrolo[2,3-b]pyridin-3-yl}-benzamide was prepared by a method analogous to that described in Example 149 by substituting 4-{4-[3-(4-carbamoyl-phenyl)-1H-pyrrolo[2,3-b]pyridin-5-yl]-benzoyl}-piperazine-1-carboxylic acid tert-butyl ester for 4-{3-[3-(4-carbamoyl-phenyl)-1H-pyrrolo[2,3-b]pyridin-5-yl]-benzoyl}-piperazine-1-carboxylic acid tert-butyl ester. 105 mg (128%) of the title compound were obtained. $^1$H NMR (DMSO-d6, 300 MHz): δ 12.32 (s, 1H), 9.52 (s, 2H), 8.66 (d, J=1.8 Hz, 1H), 8.59 (d, J=1.8 Hz, 1H), 8.11 (d, J=2.7 Hz, 1H), 7.95 (m, 5H), 7.60 (t, J=7.8 Hz, 1H), 7.52 (d, J=7.2 Hz, 1H), 7.36 (bs, 1H), 3.6-4.0 (bs, 8H).

Example 153

Preparation of 4-{5-[3-(4-acetyl-piperazine-1-carbonyl)-phenyl]-1H-pyrrolo[2,3-b]pyridin-3-yl}-benzamide

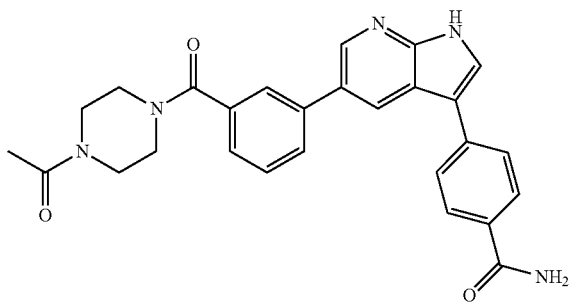 [SMILES: CC(=O)N1CCN(C(=O)c2cccc(-c3cnc4[nH]cc(-c5ccc(C(N)=O)cc5)c4c3)c2)CC1]

4-{5-[3-(4-Acetyl-piperazine-1-carbonyl)-phenyl]-1H-pyrrolo[2,3-b]pyridin-3-yl}-benzamide was prepared by a method analogous to that described in Example 150 by substituting 4-{5-[4-(piperazine-1-carbonyl)-phenyl]-1H-pyrrolo[2,3-b]pyridin-3-yl}-benzamide, hydrochloride salt for 4-{5-[3-(piperazine-1-carbonyl)-phenyl]-1H-pyrrolo[2,3-b]pyridin-3-yl}-benzamide, hydrochloride salt. 3.1 mg (14%) of the title compound were obtained. $^1$H NMR (CD$_3$OD, 300 MHz): δ 8.56 (d, J=1.2 Hz, 1H), 8.55 (d, J=1.2 Hz, 1H), 7.99 (d, J=4.2 Hz, 2H), 7.86 (m, 4H), 7.81 (d, J=1.8 Hz, 1H), 7.62 (t, J=4.6 Hz, 1H), 7.47 (dd, J=0.7, 3.8 Hz, 1H), 3.5-3.9 (m, 8H), 2.14 (bd, 3H).

Example 154

Preparation of 4-[7-oxy-5-(3,4,5-trimethoxy-phenyl)-1H-pyrrolo[2,3-b]pyridin-3-yl]-benzamide

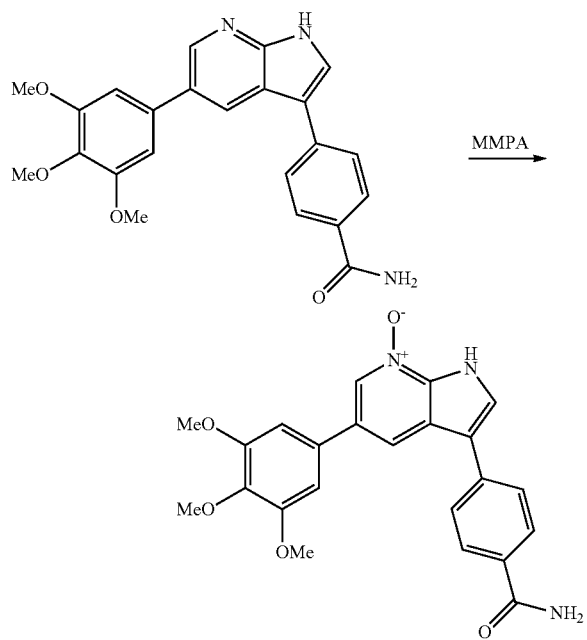

4-[5-(3,4,5-Trimethoxy-phenyl)-1H-pyrrolo[2,3-b]pyridin-3-yl]-benzamide (50 mg, 0.124 mmol), magnesium monoperoxyphthalic acid (80%, 300 mg, 0.46 mmol) and acetic acid (10 drops were combined in EtOH (3 ml) and stirred at 50° C. for 1 hr. After adding EtOAc the mixture was washed with saturated NaHCO$_3$, dried and purified by silica gel chromatography using 0-8% MeOH:DCM to provide 18 mg (33%) of the title compound. $^1$H NMR (DMSO-d6, 300 MHz): δ 12.9 (bs, 1H), 8.62 (s, 1H), 8.14 (s, 1H), 8.0 (bs, 2H), 7.97 (d, J=5.0 Hz, 2H), 7.89 (d, J=5.0 Hz, 2H), 7.34 (bs, 1H), 7.04 (s, 2H), 3.89 (s, 6H), 3.70 (s, 3H).

Example 155

Preparation of 4-{5-[4-(4-methyl-piperazin-1-ylmethyl)-phenyl]-1H-pyrrolo[2,3-b]pyridin-3-yl}-benzamide

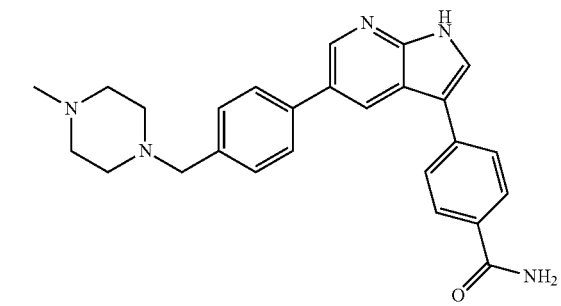 [SMILES: CN1CCN(Cc2ccc(-c3cnc4[nH]cc(-c5ccc(C(N)=O)cc5)c4c3)cc2)CC1]

4-{5-[4-(4-Methyl-piperazin-1-ylmethyl)-phenyl]-1H-pyrrolo[2,3-b]pyridin-3-yl}-benzamide was prepared by a method analogous to that described in Example 148 by substituting 4-[4-(4,4,5,5-tetramethyl-[1,3,2]dioxaborolan-2-yl)-benzoyl]-piperazine-1-carboxylic acid tert-butyl ester for 1-methyl-4-[4-(4,4,5,5-tetramethyl-[1,3,2]dioxaborolan-2-yl)-benzyl]-piperazine. The title compound (24 mg, 44%) was obtained by precipitation from DCM. $^1$H NMR (DMSO-d6, 300 MHz): δ 12.1 (s, 1H), 8.57 (d, J=1.2 Hz, 1H), 8.48 (d, J=1.2 Hz, 1H), 8.05 (d, J=1.3 Hz, 1H), 7.98 (bs, 1H), 7.96 (d, J=5.0 Hz, 2H), 7.88 (d, J=5.1 Hz, 2H), 7.73 (d, J=4.5 Hz, 2H), 7.40 (d, J=4.5 Hz, 2H), 7.31 (bs, 1H), 3.50 (s, 2H), 2.2-2.45 (bs, 8H), 2.15 (s, 3H).

Example 156

Preparation of 4-{5-[3-(4-methyl-piperazin-1-ylmethyl)-phenyl]-1H-pyrrolo[2,3-b]pyridin-3-yl}-benzamide

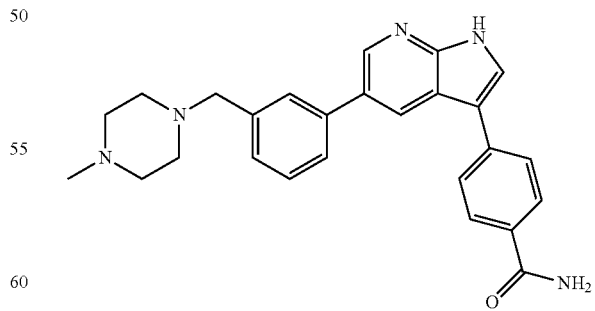

4-{5-[3-(4-Methyl-piperazin-1-ylmethyl)-phenyl]-1H-pyrrolo[2,3-b]pyridin-3-yl}-benzamide was prepared by a method analogous to that described in Example 148 by substituting 4-[4-(4,4,5,5-tetramethyl-[1,3,2]dioxaborolan-2-yl)-benzoyl]-piperazine-1-carboxylic acid tert-butyl ester for 1-methyl-4-[3-(4,4,5,5-tetramethyl-[1,3,2]dioxaborolan-2-yl)-benzyl]-piperazine. The title compound (8 mg, 15%) was obtained by precipitation from DCM. ¹H NMR (DMSO-d6, 300 MHz): δ 12.1 (s, 1H), 8.56 (d, J=1.2 Hz, 1H), 8.46 (d, J=1.2 Hz, 1H), 8.05 (d, J=1.3 Hz, 1H), 7.96 (m, 3H), 7.88 (d, J=5.1 Hz, 2H), 7.66 (m, 2H), 7.45 (m, 1H), 7.31 (m, 2H), 3.55 (s, 2H), 2.2-2.45 (bs, 8H), 2.14 (s, 3H).

Example 157

Preparation of 4-{5-[4-(4-acetyl-piperazin-1-ylmethyl)-phenyl]-1H-pyrrolo[2,3-b]pyridin-3-yl}-benzamide

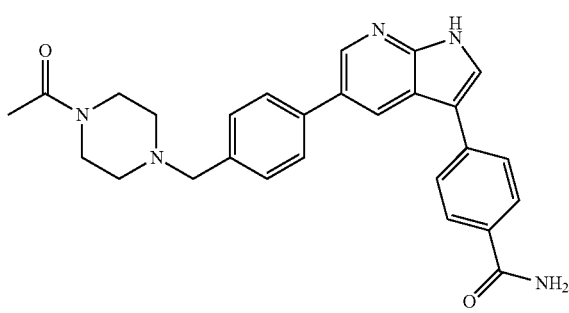 [SMILES: CC(=O)N1CCN(Cc2ccc(-c3cnc4[nH]cc(-c5ccc(C(N)=O)cc5)c4c3)cc2)CC1]

4-{5-[4-(4-Acetyl-piperazin-1-ylmethyl)-phenyl]-1H-pyrrolo[2,3-b]pyridin-3-yl}-benzamide was prepared by a method analogous to that described in Example 140 by substituting Intermediate B with Intermediate CA. Purification by silica gel chromatography using 4-5% MeOH:DCM yielded the title compound (13 mg, 30%). MS ESI (m/z): 454.1 (M+1)⁺, calc. 453.

Example 158

Preparation of 4-{5-[4-(4-methyl-3-oxo-piperazin-1-ylmethyl)-phenyl]-1H-pyrrolo[2,3-b]pyridin-3-yl}-benzamide

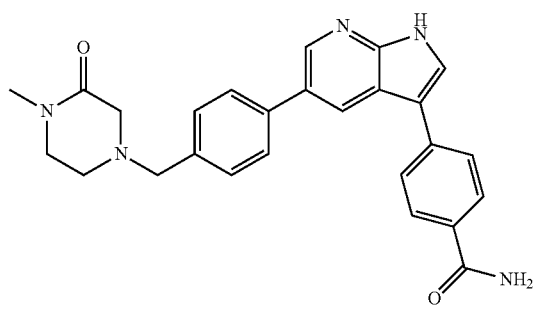 [SMILES: CN1CCN(Cc2ccc(-c3cnc4[nH]cc(-c5ccc(C(N)=O)cc5)c4c3)cc2)CC1=O]

4-{5-[4-(4-Methyl-3-oxo-piperazin-1-ylmethyl)-phenyl]-1H-pyrrolo[2,3-b]pyridin-3-yl}-benzamide was prepared by a method analogous to that described in Example 140 by substituting Intermediate B with Intermediate CA and N-acetylpiperazine for 1-methyl-piperazin-2-one. Purification by silica gel chromatography using 4-5% MeOH:DCM yielded the title compound (4 mg, 10%). MS ESI (m/z): 440.3 (M+1)⁺, calc. 439.

Example 159

Scheme 17

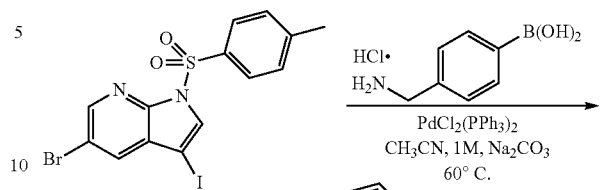

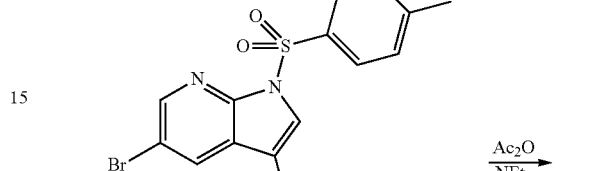

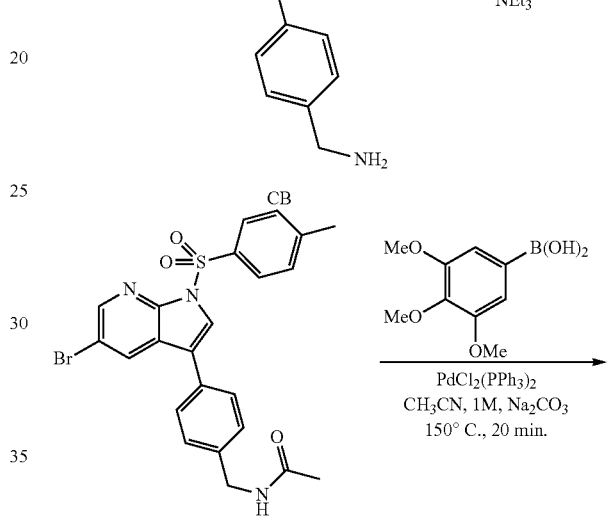

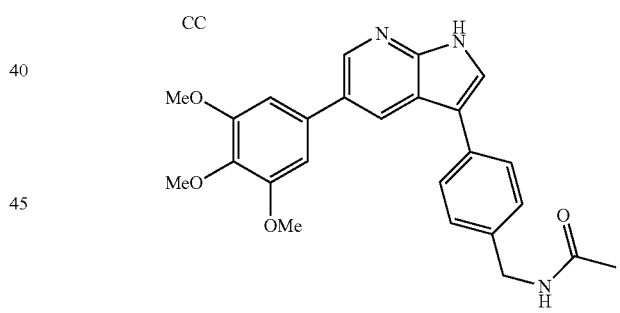

Preparation of 4-[5-bromo-1-(toluene-4-sulfonyl)-1H-pyrrolo[2,3-b]pyridin-3-yl]-benzylamine (Intermediate CB)

CB

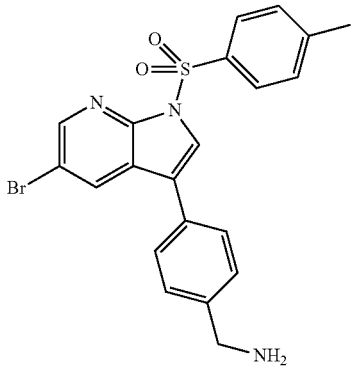

5-Bromo-3-iodo-1-(toluene-4-sulfonyl)-1H-pyrrolo[2,3-b]pyridine (200 mg, 0.419 mmol), 4-aminomethylphenylboronic acid hydrochloride (95 mg, 0.503 mmol) and dichlorobis(triphenylphosphine)palladium (II) (29 mg, 0.042 mmol) were combined in $CH_3CN$ (5 ml) and 1 M $Na_2CO_3$ (5 ml) and stirred at 60° C. for 3 hrs. EtOAc was added, the organic phase was washed with water, dried and evaporated. to yield 136 mg (71%) of the title compound. MS ESI (m/z): 455.9/458.1 $(M+1)_+$, calc. 455/457.

Preparation of N-{4-[5-bromo-1-(toluene-4-sulfonyl)-1H-pyrrolo[2,3-b]pyridin-3-yl]-benzyl}-acetamide (Intermediate CC)

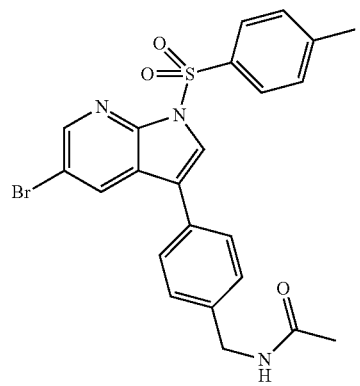

CC

4-[5-Bromo-1-(toluene-4-sulfonyl)-1H-pyrrolo[2,3-b]pyridin-3-yl]-benzylamine (Intermediate CB, 45 mg, 0.1 mmol) was combined with triethylamine (45 µl, 0.3 mmol) and acetic anhydride (11 µl, 0.11 mmol) in anh. DCM (2 ml). The mixture was stirred for 2 hrs, EtOAc, was added and washed with 0.5 N HCl, saturated $NaHCO_3$, water and brine. Evaporation yielded the title compound (48 mg, 96%). MS ESI (m/z): 498.1/500.1 $(M+1)_+$, calc. 497/499.

Preparation of N-{4-[5-(3,4,5-Trimethoxy-phenyl)-1H-pyrrolo[2,3-b]pyridin-3-yl]-benzyl}-acetamide

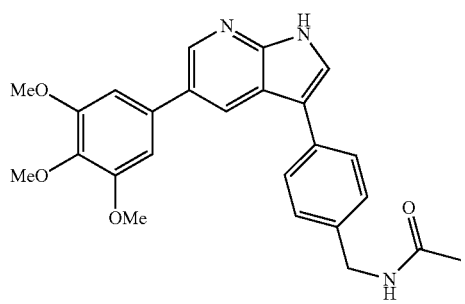 [SMILES: COc1cc(-c2cnc3[nH]cc(-c4ccc(CNC(C)=O)cc4)c3c2)cc(OC)c1OC]

N-{4-[5-Bromo-1-(toluene-4-sulfonyl)-1H-pyrrolo[2,3-b]pyridin-3-yl]-benzyl}-acetamide (Intermediate CC, 24 mg, 0.048 mmol), 3,4,5-trimethoxyphenyl boronic acid (13 mg, 0.058 mmol) and dichlorobis(triphenylphosphine)palladium (II) (2 mg, 0.002 mmol) were combined in $CH_3CN$ (1 ml) and 1 M $Na_2CO_3$ (2 ml) and heated in a microwave reactor at 150° C. for 20 min. EtOAc was added, washed with water, dried and purified by silica gel chromatography eluting with 0-4% MeOH:DCM to give 11 mg (53%) of the title compound. MS ESI (m/z): 432.2 $(M+1)^+$, calc. 431.

Example 160

Preparation of 2-phenyl-N-{4-[5-(3,4,5-trimethoxy-phenyl)-1H-pyrrolo[2,3-b]pyridin-3-yl]-benzyl}-acetamide

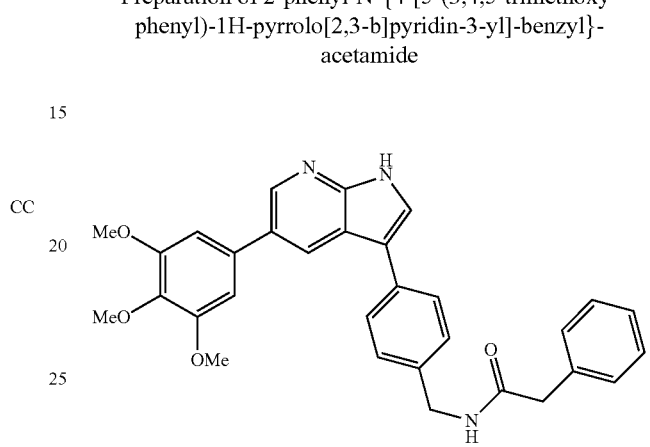

2-Phenyl-N-{4-[5-(3,4,5-trimethoxy-phenyl)-1H-pyrrolo[2,3-b]pyridin-3-yl]-benzyl}-acetamide was prepared by a method analogous to that described in Example 159 by substituting acetic anhydride for phenacetyl chloride. Purification by silica gel chromatography using 0-4% MeOH:DCM yielded the title compound (9 mg, 38%). MS ESI (m/z): 508.3 $(M+1)^+$, calc. 507.

Example 161

Preparation of 3-phenyl-N-{4-[5-(3,4,5-trimethoxy-phenyl)-1H-pyrrolo[2,3-b]pyridin-3-yl]-benzyl}-propionamide

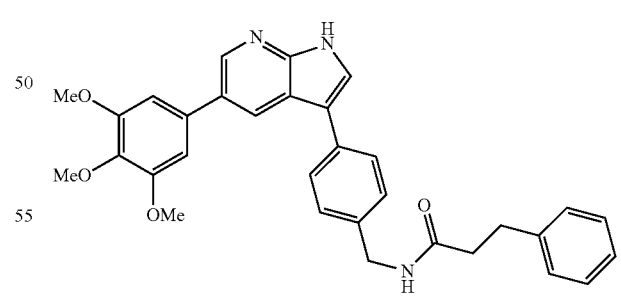

3-Phenyl-N-{4-[5-(3,4,5-trimethoxy-phenyl)-1H-pyrrolo[2,3-b]pyridin-3-yl]-benzyl}-propionamide was prepared by a method analogous to that described in Example 159 by substituting acetic anhydride for phenylpropionyl chloride. Purification by silica gel chromatography using 0-4% MeOH:DCM yielded the title compound (13 mg, 54%). MS ESI (m/z): 522.4 $(M+1)^+$, calc. 521.

Example 162

Scheme 18

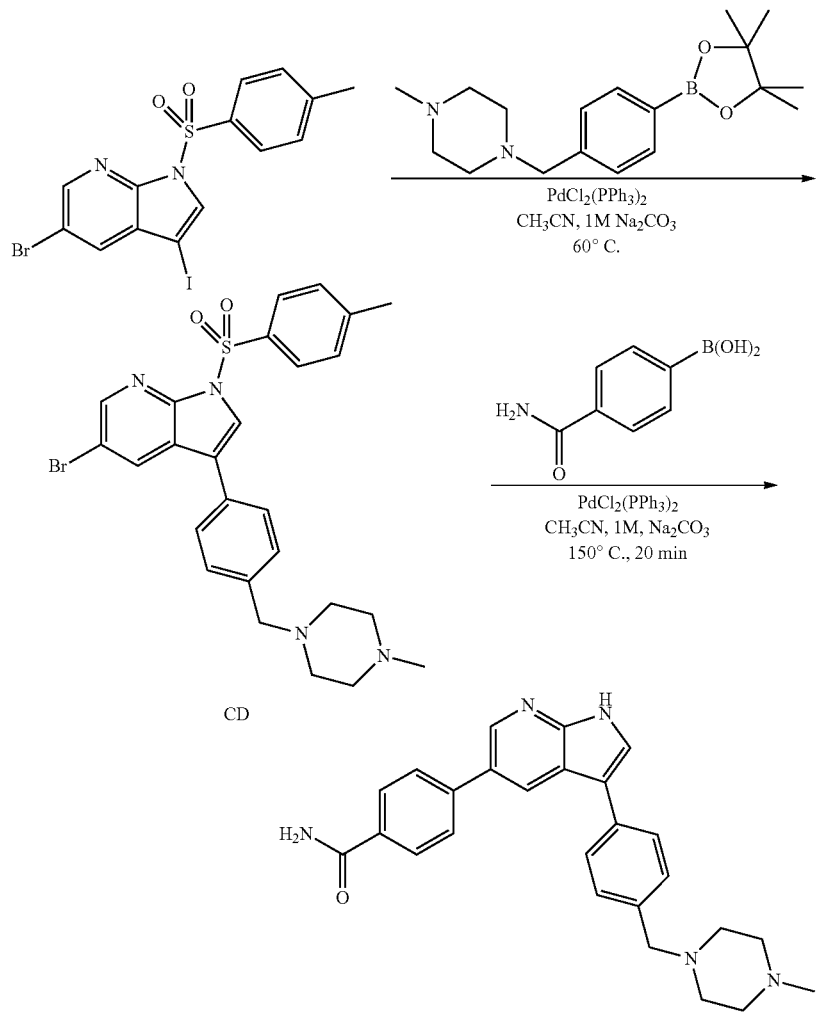

Preparation of 5-bromo-3-[4-(4-methyl-piperazin-1-ylmethyl)-phenyl]-1-(toluene-4-sulfonyl)-1H-pyrrolo[2,3-b]pyridine (Intermediate CD)

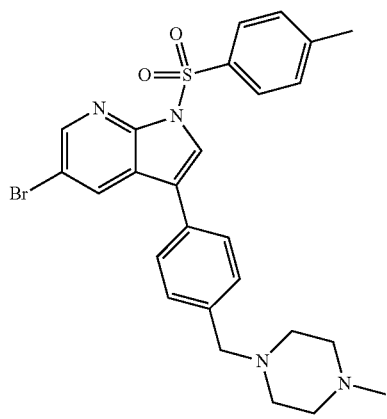 [SMILES: Cc1ccc(S(=O)(=O)n2cc(-c3ccc(CN4CCN(C)CC4)cc3)c3cc(Br)cnc32)cc1]

5-Bromo-3-iodo-1-(toluene-4-sulfonyl)-1H-pyrrolo[2,3-b]pyridine (200 mg, 0.419 mmol), 1-methyl-4-[4-(4,4,5,5-tetramethyl-[1,3,2]dioxaborolan-2-yl)-benzyl]-piperazine (160 mg, 0.503 mmol) and dichlorobis(triphenylphosphine)palladium (II) (30 mg, 0.042 mmol) were combined in CH$_3$CN (5 ml) and 1 M Na$_2$CO$_3$ (5 ml) and stirred at 60° C. for 2 hrs. EtOAc was added and the organic phase was washed with water, dried and evaporated.

Purification by silica gel chromatography using 0-20% MeOH:DCM yielded 235 mg (104%) of the title compound. MS ESI (m/z): 539.0/541.2 (M+1)$^+$, calc. 538/540.

Preparation of 4-{3-[4-(4-methyl-piperazin-1-ylmethyl)-phenyl]-1H-pyrrolo[2,3-b]pyridin-5-yl}-benzamide

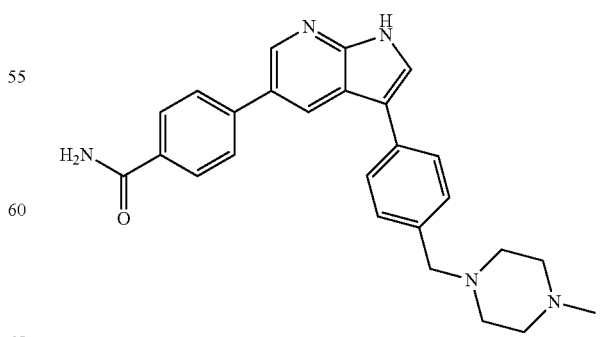

5-Bromo-3-[4-(4-methyl-piperazin-1-ylmethyl)-phenyl]-1-(toluene-4-sulfonyl)-1H-pyrrolo[2,3-b]pyridine (Intermediate CD, 70 mg, 0.13 mmol), aminocarbonylphenylboronic acid (26 mg, 0.156 mmol) and dichlorobis(triphenylphosphine)palladium (II) (5 mg, 0.0065 mmol) were combined in CH₃CN (2 ml) and 1 M Na₂CO₃ (2 ml) and reacted in a microwave reactor for 20 min at 150° C. Water was added and the aqueous phase was extracted with DCM, dried and evaporated. Purification by reversed phase chromatography using 0-100% MeOH:water yielded 6 mg (11%) of the title compound. MS ESI (m/z): 426.7 (M+1)$^+$, calc. 425.

Example 163

Preparation of 5-(1H-indol-5-yl)-3-[4-(4-methyl-piperazin-1-ylmethyl)-phenyl]-1H-pyrrolo[2,3-b]pyridine

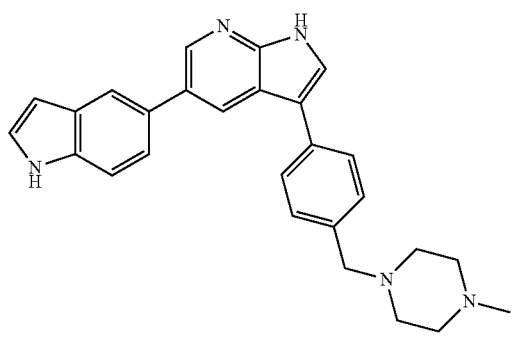 [SMILES: CN1CCN(Cc2ccc(-c3c[nH]c4ncc(-c5ccc6[nH]ccc6c5)cc34)cc2)CC1]

5-(1H-Indol-5-yl)-3-[4-(4-methyl-piperazin-1-ylmethyl)-phenyl]-1H-pyrrolo[2,3-b]pyridine was prepared by a method analogous to that described in Example 162 by substituting aminocarbonylphenylboronic acid for indole-5-boronic acid. Purification by silica gel chromatography using 0-10% MeOH:DCM yielded the title compound (28 mg, 60%). MS ESI (m/z): 422.4 (M+1)$^+$, calc. 421.

Example 164

Scheme 19

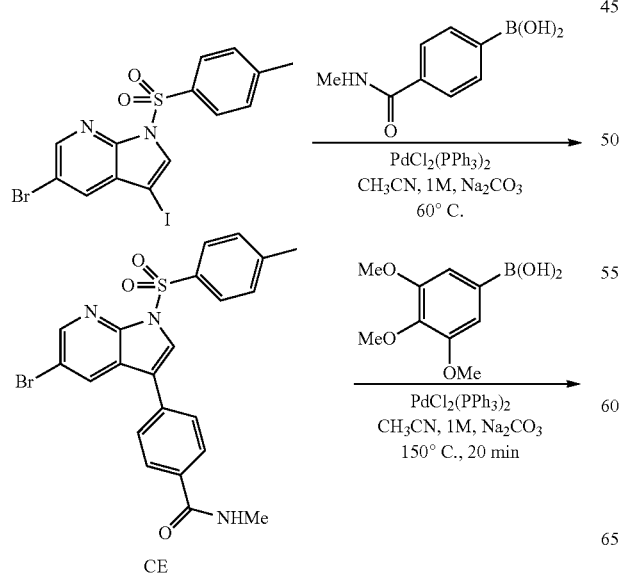

Preparation of 4-[5-bromo-1-(toluene-4-sulfonyl)-1H-pyrrolo[2,3-b]pyridin-3-yl]-N-methyl-benzamide (Intermediate CE)

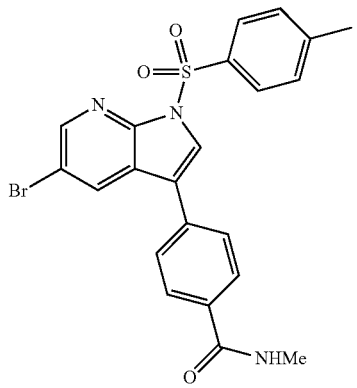

5-Bromo-3-iodo-1-(toluene-4-sulfonyl)-1H-pyrrolo[2,3-b]pyridine (350 mg, 0.73 mmol), 4-(N-methylaminocarbonyl)phenylboronic acid (160 mg, 0.88 mmol) and dichlorobis(triphenylphosphine)palladium (II) (52 mg, 0.073 mmol) were combined in CH₃CN (10 ml) and 1 M Na₂CO₃ (10 ml) and stirred at 60° C. for 5 hrs. Water was added and the mixture was extracted with DCM, combined organic phases were dried and evaporated to yield 428 mg (121%) of the title compound. $^1$H NMR (CDCl₃, 300 MHz): δ 8.50 (d, J=1.3 Hz, 1H), 8.20 (d, J=1.2 Hz, 1H), 8.09 (d, J=5.1 Hz, 2H), 7.94 (s, 1H), 7.87 (d, J=5.1, 2H), 7.61 (d, J=5.0 Hz, 2H), 7.31 (d, J=5.0 Hz, 2H), 6.21 (bd, J=2.5 Hz, 1H), 3.06, (d, J=2.9 Hz, 3H), 2.39 (s, 3H).

Preparation of N-methyl-4-[5-(3,4,5-trimethoxyphenyl)-1H-pyrrolo[2,3-b]pyridin-3-yl]-benzamide

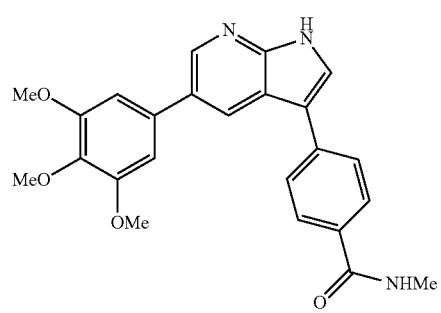 [SMILES: CNC(=O)c1ccc(-c2c[nH]c3ncc(-c4cc(OC)c(OC)c(OC)c4)cc23)cc1]

4-[5-Bromo-1-(toluene-4-sulfonyl)-1H-pyrrolo[2,3-b]pyridin-3-yl]-N-methyl-benzamide (Intermediate CE, 100 mg,

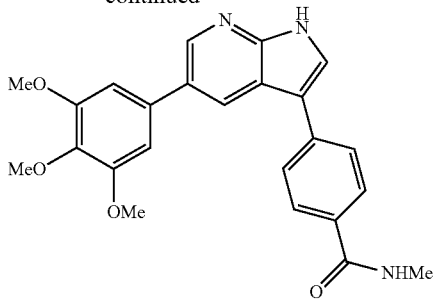

0.206 mmol), 3,4,5-trimethoxyphenylboronic acid (53 mg, 0.248 mmol) and dichlorobis(triphenylphosphine)palladium (II) (9 mg, 0.012 mmol) were combined in CH₃CN (2 ml) and 1 M Na₂CO₃ (2 ml) and reacted in a microwave reactor for 20 min at 150° C. Water was added, the aqueous phase was extracted with DCM and the organic phase was dried and evaporated. Purification by silica gel chromatography using 0-8% MeOH:DCM yielded 40 mg (47%) of the title compound. $^1$H NMR (CDCl₃, 300 MHz): δ 12.09 (s, 1H), 8.59 (d, J=1.2 Hz, 1H), 8.48 (d, J=1.2 Hz, 1H), 8.43 (q, J=2.7 Hz, 1H), 8.04 (s, 1H), 7.94 (d, J=4.0, 2H), 7.91 (d, J=4.0 Hz, 2H), 7.00 (s, 2H), 3.89 (s, 6H), 3.70 (s, 3H), 2.80, (d, J=4.5 Hz, 3H).

Example 165

Preparation of N-methyl-4-{5-[4-(4-methyl-piperazin-1-ylmethyl)-phenyl]-1H-pyrrolo[2,3-b]pyridin-3-yl}-benzamide

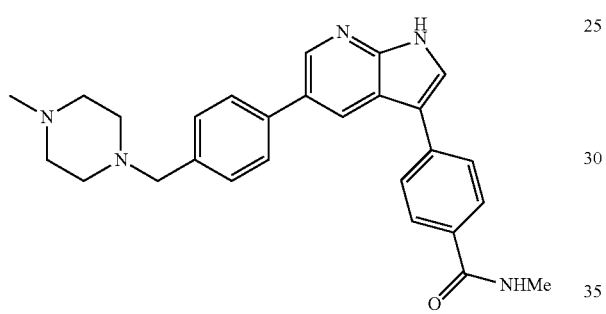

N-Methyl-4-{5-[4-(4-methyl-piperazin-1-ylmethyl)-phenyl]-1H-pyrrolo[2,3-b]pyridin-3-yl}-benzamide was prepared by a method analogous to that described in Example 164 by substituting 3,4,5-trimethoxyphenylboronic acid for 1-methyl-4-[4-(4,4,5,5-tetramethyl-[1,3,2]dioxaborolan-2-yl)-benzyl]-piperazine. Purification by precipitation from hot DCM yielded the title compound (46 mg, 51%). $^1$H NMR (CDCl₃, 300 MHz): δ 12.09 (s, 1H), 8.57 (d, J=1.2 Hz, 1H), 8.48 (d, J=1.2 Hz, 1H), 8.43 (q, J=2.7 Hz, 1H), 8.05 (d, J=1.5 Hz, 1H), 7.92 (d, J=5.2 Hz, 2H), 7.89 (d, J=5.2 Hz, 2H), 7.73 (d, J=4.9 Hz, 2H), 7.40 (d, J=4.9 Hz, 2H), 3.50 (s, 2H), 2.81, (d, J=2.7 Hz, 3H), 2.2-2.45 (bs. 8H), 2.15 (s, 3H).

Example 166

Scheme 20

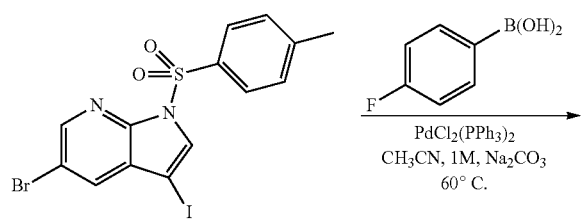

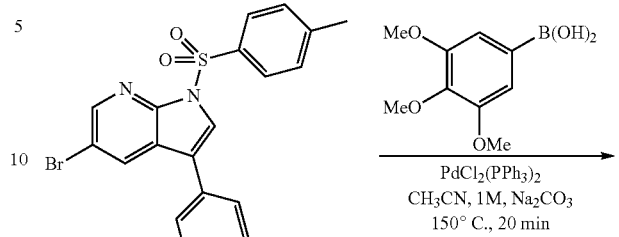

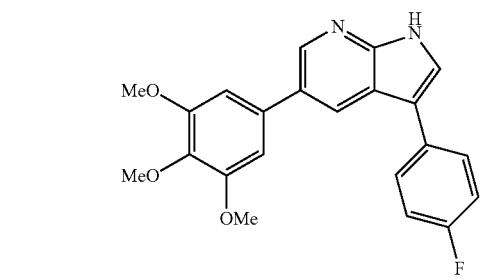

Preparation of 5-bromo-3-(4-fluoro-phenyl)-1-(toluene-4-sulfonyl)-1H-pyrrolo[2,3-b]pyridine (Intermediate CF)

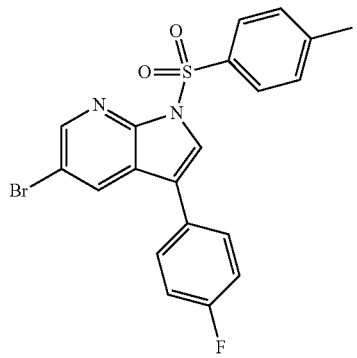 [SMILES: Cc1ccc(S(=O)(=O)n2cc(-c3ccc(F)cc3)c3cc(Br)cnc32)cc1]

5-Bromo-3-iodo-1-(toluene-4-sulfonyl)-1H-pyrrolo[2,3-b]pyridine (70 mg, 0.147 mmol), 4-fluorophenylboronic acid (25 mg, 0.176 mmol) and dichlorobis(triphenylphosphine) palladium (II) (10 mg, 0.015 mmol) were combined in CH₃CN (2 ml) and 1 M Na₂CO₃ (2 ml) and stirred at 60° C. for 3 hrs. EtOAc was added and the mixture was washed with water, dried and evaporated to yield 73 mg (112%) of the title compound. MS ESI (m/z): 445.1/447.2 (M+1)⁺, calc. 444/446.

135

Preparation of 3-(4-fluoro-phenyl)-5-(3,4,5-tri-methoxy-phenyl)-1H-pyrrolo[2,3-b]pyridine

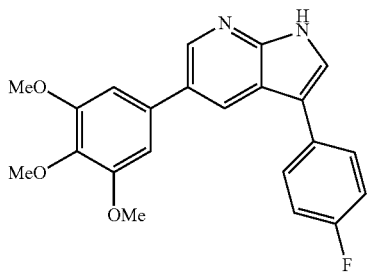 [SMILES: COc1cc(-c2cnc3[nH]cc(-c4ccc(F)cc4)c3c2)cc(OC)c1OC]

5-Bromo-3-(4-fluoro-phenyl)-1-(toluene-4-sulfonyl)-1H-pyrrolo[2,3-b]pyridine (37 mg, 0.083 mmol), 3,4,5-trimethoxyphenylboronic acid (21 mg, 0.1 mmol) and dichlorobis(triphenylphosphine)palladium (II) (3 mg, 0.004 mmol) were combined in CH$_3$CN (1.5 ml) and 1 M Na$_2$CO$_3$ (2 ml) and reacted in a microwave reactor for 20 min at 150° C. EtOAc was added and the mixture was washed with water, dried, evaporated and purified by silica gel chromatography using 0-2% MeOH:DCM to yield 9 mg (29%) of the title compound. MS ESI (m/z): 379.2 (M+1)$^+$, calc. 378.

Example 167

Scheme 21

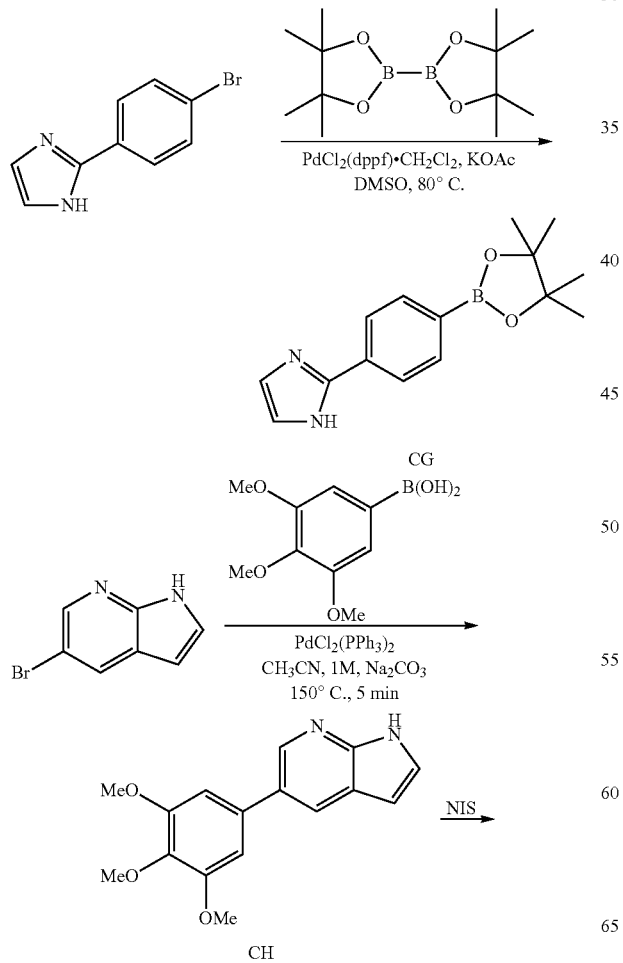

136

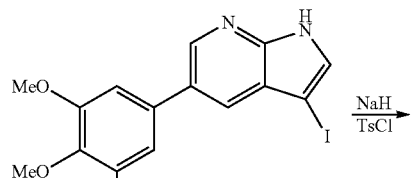

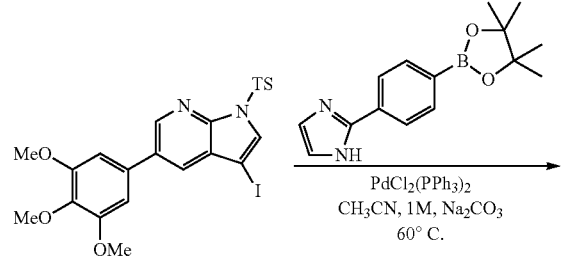

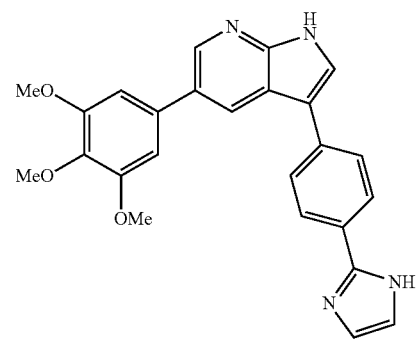 [SMILES: COc1cc(-c2cnc3[nH]cc(-c4ccc(-c5ncc[nH]5)cc4)c3c2)cc(OC)c1OC]

Preparation of 2-[4-(4,4,5,5-tetramethyl-[1,3,2]dioxaborolan-2-yl)-phenyl]-1H-imidazole (Intermediate CG)

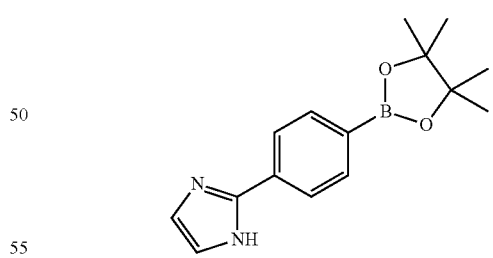

2-(4-Bromo-phenyl)-1H-imidazole (300 mg, 1.3 mmol), bis(pinacolato)diboron (376 mg, 1.48 mmol), KOAc (400 mg, 4.03 mmol) and PdCl$_2$(dppf)-CH$_2$Cl$_2$ (50 mg, 0.067 mmol) were combined in DMSO (8 ml) and stirred t 80° C. overnight. EtOAc was added, washed with water, dried, evaporated and purified by silica gel chromatography eluting with 0-5% MeOH:DCM to give 116 mg (36%) of the title compound. $^1$H NMR (CDCl$_3$, 300 MHz): δ 7.86 (s, 4H), 7.18 (s, 2H), 1.36 (s, 12H).

Preparation of 5-(3,4,5-trimethoxy-phenyl)-1H-pyrrolo[2,3-b]pyridine (Intermediate CH)

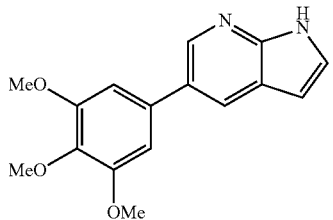 [SMILES: COc1cc(-c2cnc3[nH]ccc3c2)cc(OC)c1OC]

5-Bromo-1H-pyrrolo[2,3-b]pyridine (1.54 g, 7.83 mmol), 3,4,5-trimethoxyphenylboronic acid (1.83 g, 8.61 mmol) and dichlorobis(triphenylphosphine)palladium (II) (275 mg, 0.39 mmol) were combined in CH$_3$CN (10 ml) and 1 M Na$_2$CO$_3$ (10 ml) and reacted in a microwave reactor for 5 min at 150° C. EtOAc was added and the mixture was washed with water, brine, dried, evaporated and purified by silica gel chromatography using 0-2% MeOH:DCM to yield 1.86 g (84%) of the title compound. $^1$H NMR (CDCl$_3$, 300 MHz): δ 9.9 (bs, 1H), 8.54 (d, J=2.1 Hz, 1H), 8.11 (d. J=2.1 Hz, 1H), 7.41 (t, J=2.1 Hz, 1H), 6.82 (s, 2H), 6.58 (t, J=1.5 Hz, 1H), 3.96 (s, 6H), 3.92 (s, 3H).

Preparation of 3-iodo-5-(3,4,5-trimethoxy-phenyl)-1H-pyrrolo[2,3-b]pyridine (Intermediate CI)

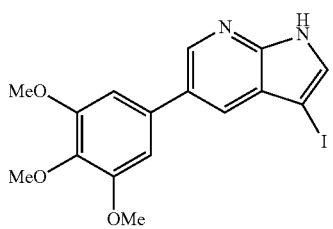 [SMILES: COc1cc(-c2cnc3[nH]cc(I)c3c2)cc(OC)c1OC]

To a solution of 5-(3,4,5-trimethoxy-phenyl)-1H-pyrrolo[2,3-b]pyridine (510 mg, 1.79 mmol) in acetone (100 ml) was added N-iodosuccinimide (444 mg, 1.97 mmol) under stirring. After 1 hr the mixture was evaporated and purified by silica gel chromatography using 0-2% MeOH:DCM to give the title compound (870 mg, 118%). MS ESI (m/z): 411.1 (M+1)$^+$, calc. 410.

Preparation of 3-iodo-1-(toluene-4-sulfonyl)-5-(3,4,5-trimethoxy-phenyl)-1H-pyrrolo[2,3-b]pyridine (Intermediate CJ)

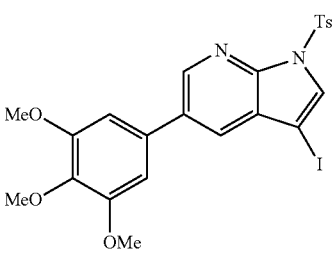 [SMILES: COc1cc(-c2cnc3c(c2)c(I)cn3S(=O)(=O)c2ccc(C)cc2)cc(OC)c1OC]

A solution of 3-iodo-5-(3,4,5-trimethoxy-phenyl)-1H-pyrrolo[2,3-b]pyridine (870 mg, 2.12 mmol) in anh. THF (10 ml) was cooled to 0° C. and NaH (60% dispersion, 130 mg, 3.18 mmol) was added. After 20 min tosyl chloride (450 mg, 2.33 mmol) was added and the mixture was allowed to warm to room temperature. After 3 hrs the mixture was cooled to 0° C. and quenched by the addition of 0.5 N HCl. The product was extracted with DCM and purified by silica gel chromatography using DCM as an eluent affording 648 mg (54%). $^1$H NMR (CDCl$_3$, 300 MHz): δ 8.61 (d, J=2.4 Hz, 1H), 8.12 (d. J=8.4 Hz, 1H), 7.91 (s, 1H), 7.74 (d, J=2.1 Hz, 1H), 7.31 (d, J=8.4 Hz, 2H), 6.73 (s, 2H), 3.94 (s, 6H), 3.90 (s, 3H), 2.39 (s, 3H).

Preparation of 3-[4-(1H-imidazol-2-yl)-phenyl]-5-(3,4,5-trimethoxy-phenyl)-1H-pyrrolo[2,3-b]pyridine

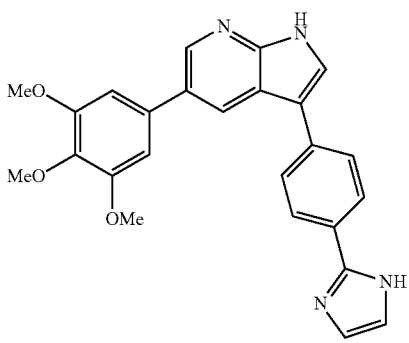

3-Iodo-1-(toluene-4-sulfonyl)-5-(3,4,5-trimethoxy-phenyl)-1H-pyrrolo[2,3-b]pyridine (Intermediate CJ, 30 mg, 0.053 mmol), 2-[4-(4,4,5,5-tetramethyl-[1,3,2]dioxaborolan-2-yl)-phenyl]-1H-imidazole (Intermediate CG, 18 mg, 0.064 mmol) and dichlorobis(triphenylphosphine)palladium (II) (2 mg, 0.003 mmol) were combined in CH$_3$CN (1 ml) and 1 M Na$_2$CO$_3$ (1 ml) and stirred at 60° C. for 2 d. Additional Intermediate CG (18 mg, 0.064 mmol) was added and stirring was continued for another day. EtOAc was added and the mixture was washed with water, dried, evaporated and purified by silica gel chromatography using 0-5% MeOH:DCM to yield 5 mg (22%) of the title compound. MS ESI (m/z): 427.2 (M+1)$_+$, calc. 426.

Biological Activity

The activity of the compounds in Examples 1-138 as MLK inhibitors is illustrated in the following assays. The other compounds listed above, which have not yet been made and/or tested, are predicted to have activity in these assays as well.

Radiometric Filter Plate MLK3 Assay 200 ng (130 nM) MLK3 (Dundee, DU8313) was incubated with 1 µM inactive MKK7b (Dundee, DU703) in the presence of 2 µM cold ATP (K$_m$) and 0.5 µCi/assay $^{33}$P ATP and appropriate concentrations of compounds. After a twenty minute incubation, the reactions were washed through filter plates and read on a scintillation counter. Results are shown in Table 4 below, in which +++ indicates ≤0.1 µM, ++ indicates >0.1 µM and ≤1 µM, and + indicates >1 µM.

TABLE 4

| Ex. | MK3 IC$_{50}$ | MW |
|---|---|---|
| 1 | ++ | 399.45 |
| 2 | ++ | 369.43 |
| 3 | +++ | 366.50 |
| 4 | +++ | 325.50 |
| 5 | +++ | 354.50 |

TABLE 4-continued

| Ex. | MK3 IC$_{50}$ | MW |
|---|---|---|
| 6 | ++ | 340.39 |
| 7 | +++ | 408.50 |
| 8 | +++ | 324.50 |
| 9 | +++ | 326.36 |
| 10 | ++ | 394.48 |
| 11 | +++ | 402.50 |
| 12 | ++ | 348.41 |
| 13 | ++ | 353.43 |
| 14 | ++ | 309.13 |
| 15 | +++ | 375.43 |
| 16 | +++ | 417.47 |
| 17 | +++ | 377.41 |
| 18 | +++ | 376.42 |
| 19 | +++ | 404.47 |
| 20 | + | 304.32 |
| 21 | ++ | 358.45 |
| 22 | + | 366.83 |
| 23 | ++ | 301.35 |
| 24 | +++ | 413.48 |
| 25 | +++ | 403.44 |
| 26 | +++ | 373.14 |
| 27 | ++ | 358.14 |
| 28 | ++ | 329.13 |
| 29 | + | 338.77 |
| 30 | +++ | 339.15 |
| 31 | ++ | 422.54 |
| 32 | +++ | 421.55 |
| 33 | +++ | 366.47 |
| 34 | +++ | 467.58 |
| 35 | + | 426.52 |
| 36 | +++ | 400.44 |
| 37 | +++ | 370.41 |
| 38 | +++ | 355.40 |
| 39 | +++ | 469.55 |
| 40 | +++ | 417.43 |
| 41 | ++ | 431.16 |
| 42 | + | 357.12 |
| 43 | + | 369.16 |
| 44 | + | 328.11 |
| 45 | ++ | 343.11 |
| 46 | + | 355.14 |
| 47 | ++ | 387.13 |
| 48 | + | 395.03 |
| 49 | + | 375.11 |
| 50 | ++ | 372.13 |
| 51 | ++ | 371.40 |
| 52 | ++ | 412.45 |
| 53 | ++ | 366.39 |
| 54 | ++ | 343.35 |
| 55 | +++ | 373.37 |
| 56 | + | 366.39 |
| 57 | +++ | 486.53 |
| 58 | ++ | 379.33 |
| 59 | +++ | 379.33 |
| 60 | +++ | 372.39 |
| 61 | + | 363.33 |
| 62 | +++ | 403.40 |
| 63 | ++ | 385.39 |
| 64 | + | 385.43 |
| 65 | + | 387.40 |
| 66 | + | 426.50 |
| 67 | ++ | 485.55 |
| 68 | ++ | 408.42 |
| 69 | + | 378.39 |
| 70 | + | 334.34 |
| 71 | + | 319.33 |
| 72 | +++ | 431.45 |
| 73 | + | 410.27 |
| 74 | +++ | 370.41 |
| 75 | + | 340.39 |
| 76 | ++ | 296.33 |
| 77 | + | 281.32 |
| 78 | ++ | 356.38 |
| 79 | ++ | 326.36 |
| 80 | + | 335.20 |
| 81 | + | 282.30 |
| 82 | + | 267.29 |
| 83 | ++ | 418.42 |
| 84 | ++ | 357.37 |
| 85 | + | 342.36 |
| 86 | + | 351.41 |
| 87 | + | 388.39 |
| 88 | + | 329.32 |
| 89 | + | 413.44 |
| 90 | ++ | 418.42 |
| 91 | ++ | 388.39 |
| 92 | + | 344.34 |
| 93 | ++ | 329.32 |
| 94 | + | 370.41 |
| 95 | + | 356.39 |
| 96 | ++ | 435.46 |
| 97 | ++ | 361.38 |
| 98 | + | 346.37 |
| 99 | + | 373.44 |
| 100 | + | 430.49 |
| 101 | + | 418.46 |
| 102 | +++ | 418.42 |
| 103 | ++ | 388.39 |
| 104 | ++ | 413.44 |
| 105 | ++ | 378.39 |
| 106 | ++ | 348.36 |
| 107 | ++ | 425.49 |
| 108 | ++ | 439.52 |
| 109 | + | 464.48 |
| 110 | +++ | 418.46 |
| 111 | ++ | 388.39 |
| 112 | +++ | 418.42 |
| 113 | +++ | 418.42 |
| 114 | ++ | 394.50 |
| 115 | ++ | 364.50 |
| 116 | ++ | 389.50 |
| 117 | + | 296.33 |
| 118 | ++ | 325.37 |
| 119 | + | 390.83 |
| 120 | ++ | 328.37 |
| 121 | ++ | 354.41 |
| 122 | + | 413.40 |
| 123 | ++ | 354.41 |
| 124 | ++ | 416.44 |
| 125 | + | 355.40 |
| 126 | + | 401.43 |
| 127 | + | 372.45 |
| 128 | ++ | 389.40 |
| 129 | + | 389.40 |
| 130 | + | 388.42 |
| 131 | ++ | 431.44 |
| 132 | + | 431.44 |
| 133 | + | 413.43 |
| 134 | + | 413.43 |
| 135 | + | 391.42 |
| 136 | + | 391.42 |
| 137 | + | 390.44 |
| 138 | + | 433.46 |
| 139 | ++ | 480.55 |
| 140 | + | 449.55 |
| 141 | +++ | 435.52 |
| 142 | +++ | 421.49 |
| 143 | +++ | 435.52 |
| 144 | +++ | 507.63 |
| 145 | ++ | 435.52 |
| 146 | +++ | 463.53 |
| 147 | +++ | 435.52 |
| 148 | +++ | 525.60 |
| 149 | +++ | 425.48 |
| 150 | ++ | 467.52 |
| 151 | +++ | 525.60 |
| 152 | ++ | HCl-salt: 461.94 |
| 153 | ++ | 467.52 |
| 154 | ++ | 419.43 |
| 155 | ++ | 425.53 |
| 156 | +++ | 425.53 |
| 157 | +++ | 453.54 |
| 158 | +++ | 439.51 |
| 159 | +++ | 431.48 |
| 160 | ++ | 507.58 |

TABLE 4-continued

| Ex. | MK3 IC$_{50}$ | MW |
|---|---|---|
| 161 | ++ | 521.61 |
| 162 | +++ | 425.53 |
| 163 | + | 421.54 |
| 164 | + | 417.46 |
| 165 | +++ | 439.55 |
| 166 | ++ | 378.40 |
| 167 | ++ | 426.47 |

Pharmacokinetic Studies

Compounds disclosed herein may be evaluated in pharmacokinetic assays and models to determine absorption, distribution, metabolism, and excretion parameters. The choice and tailoring of in vitro and ex vivo assays and in vivo models will vary according to the route of administration/formulation, indication under study, properties of test compounds, etc., as well as according to such factors as costs, availability of technology and resources, etc. Such parameters are well known in the fields of pharmacology and drug development. It is within the capacity of one skilled in the art to design and carry out, such work, or to outsource it to a capable third party.

Pharmacokinetic Evaluation in Mice

Several compounds disclosed herein were evaluated in a standard murine pharmacokinetic model. Compounds were selected that exhibited reasonable solubility and metabolic stability, and good predicted blood brain barrier penetration, based on low molecular weight, a low number of hydrogen bond donors, log D within a range of 2-4, and low polar surface area.

Compounds were dissolved in either 5% DMSO, 40% PEG400, and 55% saline (pH=8) or % DMSO, 40% PEG400, and 55% (20% HP-β-CD in deionized water; pH=8) to yield a nominal concentration of 2 mg/mL for intravenous administration. Compounds were administered via a single intravenous (IV) injection in CL57 BL/6 mice at 10 mg/kg in DMSO/PEG400 solution. Three mice in each group were used for blood and brain collection at each time point. Blood samples (300 µL) were collected via the retro-orbital vein predose and at 5 min, 0.25, 0.50, 1, 2, 4, 6, 8, and 24 hours postdose. Blood samples were placed into tubes containing sodium heparin and centrifuged under refrigerated conditions at 8000 rpm for 6 minutes to separate plasma from the samples. The brain of each animal was collected after the final blood collection. The whole tissue was harvested, excised and rinsed by saline, dried by filter paper, and then placed into one tube per tissue per animal. All samples were stored at −20° C. until bioanalysis.

Compound concentrations in plasma and brain homogenate were determined using a high performance liquid chromatography/mass spectrometry (HPLC/MS/MS) method (Agilent 1100 series HPLC, AB Inc. API4000 triple-quadrupole with an ESI interface and Analyst 1.4 software).

Results in the form of area under the time-versus-concentration curve (AUC) are given below in Table 5. Additional compounds disclosed herein can be tested according to this method and are expected to exhibit similar results.

TABLE 5

| Ex. | AUC Plasma<br>+ indicates ≥1500<br>− indicates <1500 | AUC Brain<br>+ indicates ≥500<br>− indicates <500 |
|---|---|---|
| 1 | + | + |
| 4 | − | − |
| 9 | + | + |
| 17 | + | − |
| 18 | + | − |
| 32 | + | + |

Animal Models of Efficacy

Compounds disclosed herein may be tested in any number of well-known and publicly available animal models of efficacy for diseases in which MLK3 inhibition may play a therapeutic role. It is within the capacity of one skilled in the art to select and tailor such a model.

Testing of Compounds for Efficacy in Established HIV-1-Encephalitic (HIVE) Mouse Model For example, compounds disclosed herein can be ranked for in vivo efficacy in a mouse model relevant to NeuroAids (D. Eggert, The Journal of Immunology, in press, November 2009.) Test compounds selected may be prioritized based on MLK3 potency and favorable exposure in the brain, but this is not an absolute requirement. Four-week-old male CB-17/IcrCrl-SCIDbr (CB17/SCID) mice may be purchased from Charles River Laboratory. HIV-1ADA-infected MDM (1.5× $10^5$ cells infected at an MOI of 0.1 in 5 ml) is stereotactically injected intracranially after 1 day of viral infection and referred to as HIVE mice. The test compound is then administered i.p. daily for 7 days at doses 0.5, 1.0, 1.5, 5.0, and 15.0 mg/kg/d (where, e.g., n=4 mice/treatment group). Vehicle only serves as the control. CB17/SCID mice receive intracranial (i.c.) injections of media (sham-operated) and serve as additional controls. Animals are treated with vehicle or test compound (i.e., a compound as disclosed herein) starting 1 d post-i.c. injection and for 7 d after MDM injections and test compound treatments. Dosing parameters, number per group, etc. may be varied as needed, and such variations are within the skill of one skilled in the art.

Histopathology and Image Analysis

Brain tissue is collected at necropsy, fixed in 4% phosphate-buffered paraformaldehyde, and embedded in paraffin. Paraffin blocks are cut until the injection site of the human MDM is identified. HIV-1 p24 Ag (cloneKal-1; Dako, Carpinteria, Calif.) is used to test for virus-infected human MDM. For each mouse, 30-100 serial (5-mm-thick) sections are cut from the injection site and three to seven sections (10 sections apart) analyzed. Abs to vimentin intermediate filaments (clone VIM 3B4; Boehringer Mannheim, Indianapolis, Ind.) are used for detection of human cells in mouse brains. Mouse microglia are detected by Abs to Iba-1 (WAKO, Osaka, Japan), and astrocytes are detected by Abs for glial fibrillaryacidic protein ([GFAP] Dako). NeuN, MAP-2 (both from Chemicon International), and H chain (200 kDa) neurofilaments (Dako) are used for detection of neurons. All sections are counterstained with Mayer's hematoxylin. The numbers of human MDM and HIV-1 p24 Ag-positive cells are counted with a Nikon Microphot-FXA microscope. All obtained images are imported into Image-Pro Plus, v. 4.0 (Media Cybernetics, Silver Spring, Md.) for quantifying area (%) of GFAP, Iba-1, MAP-2, and NeuN positive staining. Efficacious MLK inhibitors will exhibit a dose-dependent reduction in microgliosis and restoration of normal synaptic architecture relative to control animals. Compounds disclosed herein can be tested according to this method and are expected to exhibit similar results.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. A compound having Formula (IX):

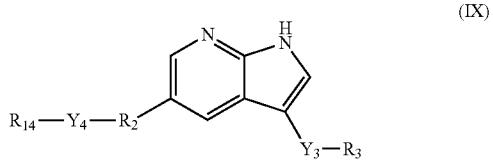

(IX)

or a pharmaceutically acceptable salt thereof, wherein:
$Y_3$ is chosen from a bond or $CH_2$;
$R_3$ is chosen from lower cycloalkyl and bicyclic heteroaryl, any of which are unsubstituted or substituted with one or more substituents chosen from halogen, hydroxy, lower amino, lower amido, lower phenylamido, lower phenylalkylamido, lower heterocycloalkyl, and lower alkylheterocycloalkyl;
the moiety $R_{14}$—$Y_4$—$R_2$ is chosen from

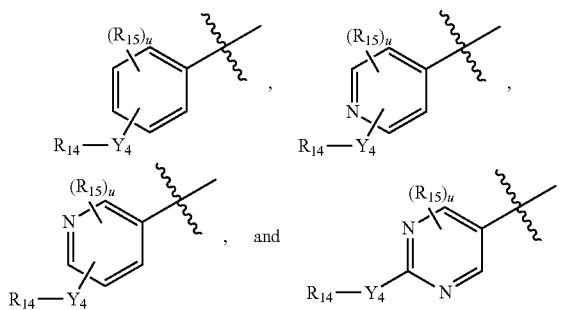

wherein
u is 0, 1, or 2;
wherein each $R_{15}$ is independently chosen from halogen, hydroxy, $C_1$-$C_4$ alkyl, $C_2$-$C_4$ alkenyl, $C_2$-$C_4$ alkynyl, $C_1$-$C_4$ haloalkyl, $C_1$-$C_3$ alkoxy, $C_1$-$C_3$ haloalkoxy, lower amino, lower amido, lower sulfonamido, and lower sulfonyl,
$Y_4$ is —$CH_2$—; and
wherein $R_{14}$ is chosen from lower cycloalkyl and lower heterocycloalkyl, any of which are unsubstituted or substituted with lower alkyl, lower alkenyl, lower alkynyl, lower alkanoyl, lower heteroalkyl, lower heterocycloalkyl, lower haloalkyl, lower cycloalkyl, phenyl, aryl, aryloxy, lower alkoxy, lower haloalkoxy, oxo, lower acyloxy, carboxy, lower alkylcarbonyl, lower carboxyester, lower carboxamido, halogen, hydroxy, amino, lower alkylamino, arylamino, amido, nitro, thiol, lower alkylthio, lower haloalkylthio, sulfonate, or sulfonic acid.

2. The compound as recited in claim 1, wherein $Y_3$ is a bond.

3. The compound as recited in claim 1, wherein $R_3$ is chosen from benzothiazolyl, pyrrolopyridinyl, and indolyl, any of which is optionally substituted.

4. The compound as recited in claim 1, wherein $R_3$ is substituted with one or more substituents chosen from hydroxy, $NH_2$, $NH(CH_3)$, $N(CH_3)_2$, $C(O)NH_2$, $C(O)NHCH_3$, morpholino, piperazinyl, methylpiperazinyl, acetamido, methylacetamido, methylpropionamido, phenylacetamidomethylene, benzamidomethylene, and phenylpropanamidomethylene.

5. The compound as recited in claim 1, wherein $Y_3$ is $CH_2$ and $R_3$ is lower cycloalkyl optionally substitute with one or more substituents chosen from halogen, hydroxyl, lower amino, lower amino, lower phenylamido, lower pdenylalkylamido, lower heterocycloalkyl, and lower alkylheterocycloalky.

6. The compound as recited in claim 1, wherein
u is 1 or 2; and
each $R_{15}$ is independently chosen from fluorine, hydroxy, $NH_2$, $NH(CH_3)$, $N(CH_3)_2$, $NHS(O)_2CH_3$, methoxy, and methyl.

7. The compound as recited in claim 1, wherein u is 0.

8. The compound as recited in claim 1, wherein
$R_3$ is optionally substituted 5/6-fused bicyclic heteroaryl; and
$R_{14}$ is substituted or unsubstituted monocyclic heterocycloalkyl.

9. The compound as recited in claim 1, wherein $R_{14}$ is substituted or unsubstituted lower heterocycloalkyl.

10. The compound as recited in claim 1, wherein $R_{14}$ is substituted or unsubstituted piperazinyl.

11. A pharmaceutical composition comprising a compound as recited in claim 1 together with a pharmaceutically acceptable carrier.

12. A method of inhibiting mixed lineage kinase-3 activity in a patient, comprising the step of administering to said patient a therapeutically effective amount of a compound as recited in claim 1.

13. The method as recited in claim 12, wherein the patient has depression, bipolar disorder, or post-traumatic stress disorder.

14. The method as recited in claim 12, wherein the patient has traumatic brain injury.

15. The method as recited in claim 12, wherein the patient has Alzheimer's disease, Parkinson's disease, or human immunodeficiency virus associated neurocognitive disorder.

16. The method as recited in claim 12 wherein the patient has a neurologic disorder of hearing or vision.

17. The method as recited in claim 12, wherein said disorder is chosen from ototoxicity, hearing loss, acute injury to the inner ear, acoustic trauma, and injury resulting from blast noise.

* * * * *